US009249234B2

(12) United States Patent
Deisseroth et al.

(10) Patent No.: US 9,249,234 B2
(45) Date of Patent: *Feb. 2, 2016

(54) LIGHT-SENSITIVE ION-PASSING MOLECULES

(71) Applicant: The Board of Trustees of the Leland Stanford Junior University, Palo Alto, CA (US)

(72) Inventors: Karl Deisseroth, Palo Alto, CA (US); Feng Zhang, Cambridge, MA (US); Viviana Gradinaru, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/622,809

(22) Filed: Sep. 19, 2012

(65) Prior Publication Data

US 2013/0090454 A1 Apr. 11, 2013

Related U.S. Application Data

(63) Continuation of application No. 13/577,565, filed as application No. PCT/US2011/028893 on Mar. 17, 2011, now Pat. No. 9,079,940.

(60) Provisional application No. 61/314,969, filed on Mar. 17, 2010.

(51) Int. Cl.
| | |
|---|---|
| C07H 21/04 | (2006.01) |
| C07K 14/195 | (2006.01) |
| C12N 15/86 | (2006.01) |
| C07K 19/00 | (2006.01) |
| A01K 67/027 | (2006.01) |
| C07K 14/00 | (2006.01) |

(52) U.S. Cl.
CPC ............. *C07K 19/00* (2013.01); *A01K 67/0271* (2013.01); *A01K 67/0275* (2013.01); *C07K 14/00* (2013.01); *A01K 2207/05* (2013.01); *A01K 2227/105* (2013.01); *A01K 2267/0393* (2013.01); *C12N 2799/025* (2013.01)

(58) Field of Classification Search
CPC ................. C07K 14/195; C07K 19/00; C12N 2799/021; C12N 15/00; C07H 21/04
USPC .......................... 536/23.4; 435/320.1; 530/350
See application file for complete search history.

(56) References Cited

U.S. PATENT DOCUMENTS

| | | |
|---|---|---|
| 2,968,302 A | 1/1961 | Fry et al. |
| 3,131,690 A | 5/1964 | Innis et al. |
| 3,499,437 A | 3/1970 | Balamuth et al. |
| 3,567,847 A | 3/1971 | Price |
| 4,343,301 A | 8/1982 | Indech |
| 4,559,951 A | 12/1985 | Dahl et al. |
| 4,616,231 A | 10/1986 | Autrey et al. |
| 4,865,042 A | 9/1989 | Umemura et al. |
| 4,879,284 A | 11/1989 | Lang et al. |
| 5,032,123 A | 7/1991 | Katz et al. |
| 5,041,224 A | 8/1991 | Ohyama et al. |
| 5,082,670 A | 1/1992 | Gage et al. |
| 5,249,575 A | 10/1993 | Di Mino et al. |
| 5,267,152 A | 11/1993 | Yang et al. |
| 5,290,280 A | 3/1994 | Daikuzono et al. |
| 5,330,515 A | 7/1994 | Rutecki et al. |
| 5,382,516 A | 1/1995 | Bush |
| 5,445,608 A | 8/1995 | Chen et al. |
| 5,460,950 A | 10/1995 | Barr et al. |
| 5,460,954 A | 10/1995 | Lee et al. |
| 5,470,307 A | 11/1995 | Lindall |
| 5,495,541 A | 2/1996 | Murray et al. |
| 5,520,188 A | 5/1996 | Hennige et al. |
| 5,527,695 A | 6/1996 | Hodges et al. |
| 5,550,316 A | 8/1996 | Mintz |
| 5,641,650 A | 6/1997 | Turner et al. |
| 5,703,985 A | 12/1997 | Owyang et al. |
| 5,722,426 A | 3/1998 | Kolff |
| 5,738,625 A | 4/1998 | Gluck |
| 5,739,273 A | 4/1998 | Engelman et al. |
| 5,755,750 A | 5/1998 | Petruska et al. |
| 5,756,351 A | 5/1998 | Isacoff et al. |
| 5,782,896 A | 7/1998 | Chen et al. |
| 5,795,581 A | 8/1998 | Segalman et al. |
| 5,807,285 A | 9/1998 | Vaitekunas et al. |
| 5,816,256 A | 10/1998 | Kissinger et al. |

(Continued)

FOREIGN PATENT DOCUMENTS

| | | |
|---|---|---|
| EP | 1 334 748 | 8/2003 |
| EP | 1873566 | 1/2008 |

(Continued)

OTHER PUBLICATIONS

Gradinaru et al. (2008) Brain Cell Biology, vol. 36, 129-139.*
Lanyi et al. (1990) J. Biol. Chem., vol. 265(3), 1253-1260.*
Hofherr et al. (2005) Journal of Cell Science, vol. 118, 1935-1943.*
Zhang et al. (2007) Nature, vol. 446, 633-641.*
Aebischer, et al. "Long-Term Cross-Species Brain Transplantation of a Polymer-Encapsulated Dopamine-Secreting Cell Line", Experimental Neurology, 1991, vol. 111, pp. 269-275.
Ahmad, et al. "The *Drosophila rhodopsin* cytoplasmic tail domain is required for maintenance of rhabdomere structure." The FASEB Journal, 2007, vol. 21, p. 449-455.
Airan, et al., "Temporally Precise in vivo Control of Intracellular Signaling", 2009, Nature, vol. 458, No. 7241, pp. 1025-1029.
Akirav, et al. "The role of the medial prefrontal cortex-amygdala circuit in stress effects on the extinction of fear", Neural Plasticity, 2007: vol. 2007 Article ID:30873, pp. 1-11.
Ang, et at. "Hippocampal CA1 Circuitry Dynamically Gates Direct Cortical Inputs Preferentially at Theta Frequencies." The Journal of Neurosurgery, 2005, vol. 25, No. 42, pp. 9567-9580.

(Continued)

*Primary Examiner* — Anne Marie S Wehbe
(74) *Attorney, Agent, or Firm* — Bozicevic, Field & Francis LLP; Paula A. Borden

(57) ABSTRACT

The invention provides polynucleotides and methods for expressing light-activated proteins in animal cells and altering an action potential of the cells by optical stimulation. The invention also provides animal cells and non-human animals comprising cells expressing the light-activated proteins.

13 Claims, 33 Drawing Sheets

(56) References Cited

U.S. PATENT DOCUMENTS

| | | |
|---|---|---|
| 5,898,058 A | 4/1999 | Nichols |
| 5,939,320 A | 8/1999 | Littman et al. |
| 6,057,114 A | 5/2000 | Akong |
| 6,134,474 A | 10/2000 | Fischell et al. |
| 6,161,045 A | 12/2000 | Fischell et al. |
| 6,253,109 B1 | 6/2001 | Gielen |
| 6,303,362 B1 | 10/2001 | Kay et al. |
| 6,334,846 B1 | 1/2002 | Ishibashi et al. |
| 6,336,904 B1 | 1/2002 | Nikolchev |
| 6,364,831 B1 | 4/2002 | Crowley |
| 6,377,842 B1 | 4/2002 | Pogue et al. |
| 6,436,708 B1 | 8/2002 | Leone et al. |
| 6,473,639 B1 | 10/2002 | Fischell et al. |
| 6,480,743 B1 | 11/2002 | Kirkpatrick et al. |
| 6,489,115 B2 | 12/2002 | Lahue et al. |
| 6,497,872 B1 | 12/2002 | Weiss et al. |
| 6,506,154 B1 | 1/2003 | Ezion et al. |
| 6,536,440 B1 | 3/2003 | Dawson |
| 6,551,346 B2 | 4/2003 | Crossley |
| 6,567,690 B2 | 5/2003 | Giller et al. |
| 6,597,954 B1 | 7/2003 | Pless et al. |
| 6,609,020 B2 | 8/2003 | Gill |
| 6,615,080 B1 | 9/2003 | Unsworth et al. |
| 6,631,283 B2 | 10/2003 | Storrie et al. |
| 6,632,672 B2 | 10/2003 | Calos |
| 6,647,296 B2 | 11/2003 | Fischell et al. |
| 6,685,656 B1 | 2/2004 | Duarte et al. |
| 6,686,193 B2 | 2/2004 | Maher et al. |
| 6,721,603 B2 | 4/2004 | Zabara et al. |
| 6,729,337 B2 | 5/2004 | Dawson |
| 6,780,490 B1 | 8/2004 | Tanaka et al. |
| 6,790,652 B1 | 9/2004 | Terry et al. |
| 6,790,657 B1 | 9/2004 | Arya |
| 6,805,129 B1 | 10/2004 | Pless et al. |
| 6,810,285 B2 | 10/2004 | Pless et al. |
| 6,889,085 B2 | 5/2005 | Dawson |
| 6,921,413 B2 | 7/2005 | Mahadevan-Jansen et al. |
| 6,969,449 B2 | 11/2005 | Maher et al. |
| 6,974,448 B2 | 12/2005 | Petersen |
| 7,045,344 B2 | 5/2006 | Kay et al. |
| 7,091,500 B2 | 8/2006 | Schnitzer |
| 7,144,733 B2 | 12/2006 | Miesenbock et al. |
| 7,175,596 B2 | 2/2007 | Vitek et al. |
| 7,191,018 B2 | 3/2007 | Gielen et al. |
| 7,211,054 B1 | 5/2007 | Francis et al. |
| 7,220,240 B2 | 5/2007 | Struys et al. |
| 7,298,143 B2 | 11/2007 | Jaermann et al. |
| 7,313,442 B2 | 12/2007 | Velasco et al. |
| 7,603,174 B2 | 10/2009 | De Ridder |
| 7,610,100 B2 | 10/2009 | Jaax et al. |
| 7,613,520 B2 | 11/2009 | De Ridder |
| 7,686,839 B2 | 3/2010 | Parker |
| 7,824,869 B2 | 11/2010 | Hegemann et al. |
| 7,988,688 B2 | 8/2011 | Webb et al. |
| 8,386,312 B2 | 2/2013 | Pradeep et al. |
| 8,398,692 B2 | 3/2013 | Deisseroth et al. |
| 8,815,582 B2 | 8/2014 | Deisseroth et al. |
| 2002/0094516 A1 | 7/2002 | Calos et al. |
| 2002/0155173 A1 | 10/2002 | Chopp et al. |
| 2002/0164577 A1 | 11/2002 | Tsien et al. |
| 2003/0009103 A1 | 1/2003 | Yuste et al. |
| 2003/0026784 A1 | 2/2003 | Koch et al. |
| 2003/0040080 A1 | 2/2003 | Miesenbock et al. |
| 2003/0050258 A1 | 3/2003 | Calos |
| 2003/0088060 A1 | 5/2003 | Benjamin et al. |
| 2003/0097122 A1 | 5/2003 | Ganz et al. |
| 2003/0104512 A1 | 6/2003 | Freeman et al. |
| 2003/0125719 A1 | 7/2003 | Furnish |
| 2003/0204135 A1 | 10/2003 | Bystritsky |
| 2003/0232339 A1 | 12/2003 | Shu et al. |
| 2004/0023203 A1 | 2/2004 | Miesenbock et al. |
| 2004/0034882 A1 | 2/2004 | Vale et al. |
| 2004/0039312 A1 | 2/2004 | Hillstead et al. |
| 2004/0068202 A1 | 4/2004 | Hansson et al. |
| 2004/0076613 A1 | 4/2004 | Mazarakis et al. |
| 2004/0122475 A1 | 6/2004 | Myrick et al. |
| 2004/0203152 A1 | 10/2004 | Calos |
| 2005/0058987 A1 | 3/2005 | Shi et al. |
| 2005/0107753 A1 | 5/2005 | Rezai et al. |
| 2005/0119315 A1 | 6/2005 | Fedida et al. |
| 2005/0124897 A1 | 6/2005 | Chopra |
| 2005/0153885 A1 | 7/2005 | Yun et al. |
| 2005/0197679 A1 | 9/2005 | Dawson |
| 2005/0202398 A1 | 9/2005 | Hegemann et al. |
| 2005/0215764 A1 | 9/2005 | Tuszynski et al. |
| 2005/0240127 A1 | 10/2005 | Seip et al. |
| 2005/0267011 A1 | 12/2005 | Deisseroth et al. |
| 2005/0267454 A1 | 12/2005 | Hissong et al. |
| 2006/0025756 A1 | 2/2006 | Francischelli et al. |
| 2006/0034943 A1 | 2/2006 | Tuszynski |
| 2006/0057192 A1 | 3/2006 | Kane |
| 2006/0057614 A1 | 3/2006 | Heintz |
| 2006/0058671 A1 | 3/2006 | Vitek et al. |
| 2006/0058678 A1 | 3/2006 | Vitek et al. |
| 2006/0100679 A1 | 5/2006 | DiMauro et al. |
| 2006/0106543 A1 | 5/2006 | Deco et al. |
| 2006/0155348 A1 | 7/2006 | deCharms |
| 2006/0161227 A1 | 7/2006 | Walsh et al. |
| 2006/0184069 A1 | 8/2006 | Vaitekunas |
| 2006/0190044 A1 | 8/2006 | Libbus et al. |
| 2006/0206172 A1 | 9/2006 | DiMauro et al. |
| 2006/0216689 A1 | 9/2006 | Maher et al. |
| 2006/0236525 A1 | 10/2006 | Sliwa et al. |
| 2006/0241697 A1 | 10/2006 | Libbus et al. |
| 2006/0253177 A1 | 11/2006 | Taboada et al. |
| 2006/0271024 A1 | 11/2006 | Gertner et al. |
| 2007/0031924 A1 | 2/2007 | Li et al. |
| 2007/0053996 A1 | 3/2007 | Boyden et al. |
| 2007/0054319 A1 | 3/2007 | Boyden et al. |
| 2007/0060915 A1 | 3/2007 | Kucklick |
| 2007/0135875 A1 | 6/2007 | Demarais et al. |
| 2007/0156180 A1 | 7/2007 | Jaax et al. |
| 2007/0191906 A1 | 8/2007 | Lyer et al. |
| 2007/0196838 A1 | 8/2007 | Chesnut et al. |
| 2007/0197918 A1 | 8/2007 | Vitek et al. |
| 2007/0219600 A1 | 9/2007 | Gertner et al. |
| 2007/0220628 A1 | 9/2007 | Glassman et al. |
| 2007/0239080 A1 | 10/2007 | Schaden et al. |
| 2007/0239210 A1 | 10/2007 | Libbus et al. |
| 2007/0253995 A1 | 11/2007 | Hildebrand et al. |
| 2007/0261127 A1 | 11/2007 | Boyden et al. |
| 2007/0282404 A1 | 12/2007 | Cottrell et al. |
| 2007/0295978 A1 | 12/2007 | Coushaine et al. |
| 2008/0020465 A1 | 1/2008 | Padidam |
| 2008/0027505 A1 | 1/2008 | Levin et al. |
| 2008/0033569 A1 | 2/2008 | Ferren et al. |
| 2008/0046053 A1 | 2/2008 | Wagner et al. |
| 2008/0050770 A1 | 2/2008 | Zhang et al. |
| 2008/0051673 A1 | 2/2008 | Kong et al. |
| 2008/0060088 A1 | 3/2008 | Shin et al. |
| 2008/0065158 A1 | 3/2008 | Ben-Ezra et al. |
| 2008/0065183 A1 | 3/2008 | Whitehurst et al. |
| 2008/0077200 A1 | 3/2008 | Bendett et al. |
| 2008/0085265 A1 | 4/2008 | Schneider et al. |
| 2008/0103551 A1 | 5/2008 | Masoud |
| 2008/0119421 A1 | 5/2008 | Tuszynski et al. |
| 2008/0125836 A1 | 5/2008 | Streeter et al. |
| 2008/0167261 A1 | 7/2008 | Sclimenti |
| 2008/0175819 A1 | 7/2008 | Kingsman et al. |
| 2008/0176076 A1 | 7/2008 | Van Veggel et al. |
| 2008/0200749 A1 | 8/2008 | Zheng et al. |
| 2008/0221452 A1 | 9/2008 | Njemanze |
| 2008/0227139 A1 | 9/2008 | Deisseroth et al. |
| 2008/0228244 A1 | 9/2008 | Pakhomov et al. |
| 2008/0262411 A1 | 10/2008 | Dobak |
| 2008/0287821 A1 | 11/2008 | Jung et al. |
| 2008/0290318 A1 | 11/2008 | Van Veggel et al. |
| 2009/0030930 A1 | 1/2009 | Pradeep et al. |
| 2009/0054954 A1 | 2/2009 | Foley et al. |
| 2009/0088680 A1 | 4/2009 | Aravanis et al. |
| 2009/0093403 A1 | 4/2009 | Zhang et al. |
| 2009/0099038 A1 | 4/2009 | Deisseroth et al. |
| 2009/0112133 A1 | 4/2009 | Deisseroth et al. |
| 2009/0118800 A1 | 5/2009 | Deisseroth et al. |

(56) References Cited

U.S. PATENT DOCUMENTS

| | | | |
|---|---|---|---|
| 2009/0148861 | A1 | 6/2009 | Pegan et al. |
| 2009/0157145 | A1 | 6/2009 | Cauller |
| 2009/0254134 | A1 | 10/2009 | Nikolov et al. |
| 2009/0268511 | A1 | 10/2009 | Birge et al. |
| 2009/0269751 | A1 | 10/2009 | Zhang et al. |
| 2009/0319008 | A1 | 12/2009 | Mayer |
| 2009/0326603 | A1 | 12/2009 | Boggs |
| 2010/0009444 | A1 | 1/2010 | Herlitze et al. |
| 2010/0016783 | A1 | 1/2010 | Bourke et al. |
| 2010/0145418 | A1 | 6/2010 | Zhang et al. |
| 2010/0146645 | A1 | 6/2010 | Vasar et al. |
| 2010/0190229 | A1 | 7/2010 | Zhang et al. |
| 2010/0234273 | A1 | 9/2010 | Deisseroth et al. |
| 2011/0021970 | A1 | 1/2011 | Vo-Dinh et al. |
| 2011/0092800 | A1 | 4/2011 | Yoo et al. |
| 2011/0105998 | A1 | 5/2011 | Zhang et al. |
| 2011/0112179 | A1 | 5/2011 | Deisseroth et al. |
| 2011/0125077 | A1 | 5/2011 | Denison et al. |
| 2011/0125078 | A1 | 5/2011 | Denison et al. |
| 2011/0159562 | A1 | 6/2011 | Deisseroth et al. |
| 2011/0165681 | A1 | 7/2011 | Boyden et al. |
| 2011/0166632 | A1 | 7/2011 | Delp et al. |
| 2011/0172653 | A1 | 7/2011 | Deisseroth et al. |
| 2011/0301529 | A1 | 12/2011 | Zhang et al. |
| 2011/0311489 | A1 | 12/2011 | Deisseroth et al. |
| 2012/0093772 | A1 | 4/2012 | Horsager et al. |
| 2012/0165904 | A1 | 6/2012 | Deisseroth et al. |
| 2012/0253261 | A1 | 10/2012 | Poletto et al. |
| 2013/0030275 | A1 | 1/2013 | Seymour et al. |
| 2013/0144359 | A1 | 6/2013 | Kishawi et al. |

FOREIGN PATENT DOCUMENTS

| | | |
|---|---|---|
| JP | 2006-295350 | 10/1994 |
| JP | 2010227537 A | 10/2010 |
| WO | WO 96/32076 | 10/1996 |
| WO | WO 00/27293 | 5/2000 |
| WO | WO 01-25466 | 4/2001 |
| WO | WO 03/106486 A2 | 2/2003 |
| WO | WO 2013/016486 | 2/2003 |
| WO | WO 03-040323 | 5/2003 |
| WO | WO 03-084994 | 10/2003 |
| WO | WO 03-102156 | 12/2003 |
| WO | WO 2004/033647 | 4/2004 |
| WO | WO 2007-024391 | 3/2007 |
| WO | WO 2007-131180 | 11/2007 |
| WO | WO 2008/086470 | 7/2008 |
| WO | WO 2008/106694 | 9/2008 |
| WO | WO 2009/025819 | 2/2009 |
| WO | WO2009/119782 | 10/2009 |
| WO | WO 2009-131837 | 10/2009 |
| WO | WO 2010/011404 A3 | 1/2010 |
| WO | WO 2010/056970 | 5/2010 |
| WO | WO-2010123993 | 10/2010 |
| WO | WO 2011/066320 A3 | 6/2011 |
| WO | WO 2011-116238 A2 | 9/2011 |
| WO | WO 2011/127088 A3 | 10/2011 |
| WO | WO 2012/032103 | 3/2012 |
| WO | WO 2012/061676 | 5/2012 |
| WO | WO2012/061681 | 5/2012 |
| WO | WO2012/061684 | 5/2012 |
| WO | WO2012/061688 | 5/2012 |
| WO | WO2012/061690 | 5/2012 |
| WO | WO 2012/061741 | 5/2012 |
| WO | WO 2012/061744 | 5/2012 |
| WO | 2012/106407 | 8/2012 |
| WO | WO 2012/134704 A2 | 10/2012 |
| WO | WO 2013/126521 | 8/2013 |
| WO | WO 2013/142196 | 9/2013 |

OTHER PUBLICATIONS

Araki, et al. "Site-Directed Integration of the cre Gene Mediated by Cre Recombinase Using a Combination of Mutant lox Sites", Nucleic Acids Research, 2002, vol. 30, No. 19, pp. 1-8.

Aravanis, et al. "An optical neural interface: in vivo control of rodent motor cortex with integrated fiberoptic and optogenetic technology," J. Neural. Eng., 2007, vol. 4(3):S143-S156.

Argos, et al. "The integrase family of site-specific recombinases: regional similarities and global diversity", The EMBO Journal, 1986, vol. 5, No. 2, pp. 433-440.

Bamberg et al. "Light-driven proton or chloride pumping by halorhodopsin." Proc. Natl. Academy Science USA, 1993, vol. 90, No. 2, p. 639-643.

Banghart, et al. "Light-activated ion channels for remote control of neuronal firing". Nature Neuroscience, 2004, vol. 7, No. 12 pp. 1381-1386.

Basil et al. "Is There Evidence for Effectiveness of Transcranial Magnetic Stimulation in the Treatment of Psychiatric Disorders?" Psychiatry, 2005, pp. 64-69.

Bebbington et al., "The use of vectors based on gene amplification for the expression of cloned genes in mammalian cells in DNA cloning" vol. 3, Academic Press, New York, 1987.

Benabid "Future strategies to restore brain functions," Conference proceedings from Medicine Meets Millennium: World Congress of Medicine and Health, 2000, 6 pages.

Benoist et al. "In vivo sequence requirements of the SV40 early promotor region" Nature (London), 1981, vol. 290(5804): pp. 304-310.

Berges et al., "Transduction of Brain by Herpes Simplex Virus Vectors", Molecular Therapy, 2007, vol. 15, No. 1: pp. 20-29.

Berridge et al., "The Versatility and Universality of Calcium Signaling", Nature Reviews: Molecular Cell Biology, 2000, vol. 1: pp. 11-21.

Bocquet et al. "A prokaryotic proton-gated ion channel from the nicotinic acetylcholine receptor family." Nature Letters, 2007, vol. 445, p. 116-119.

Boyden, et al. "Millisecond-timescale, genetically targeted optical control of neural activity" Nature Neuroscience, 2005, vol. 8, No. 9: pp. 1263-1268.

Bi, et al. "Ectopic Expression of a Microbial-Type Rhodopsin Restores Visual Responses in Mice with Photoreceptor Degeneration", Neuron, 2006, vol. 50, No. 1: pp. 23-33.

Bi, et al. "Synaptic Modifications in Cultured Hippocampal Neurons: Dependence on Spike Timing, Synaptic Strength, and Postsynaptic Cell Type", Journal of Neuroscience, 1998, vol. 18, No. 24: pp. 10464-10472.

Blomer et al., "Highly Efficient and Sustained Gene Transfer in Adult Neurons with Lentivirus Vector", Journal of Virology,1997, vol. 71, No. 9: pp. 6641-6649.

Braun, "Two Light-activated Conductances in the Eye of the Green Alga Volvox carteri", 1999, Biophys J., vol. 76, No. 3, pp. 1668-1678.

Brinton, et al. "Preclinical analyses of the therapeutic potential of allopregnanolone to promote neurogenesis in vitro and in vivo in transgenic mouse model of Alzheimer's disease." Current Alzheimer Research, 2006, vol. 3, No. 1: pp. 11-17.

Brosenitsch et al, "Physiological Patterns of Electrical Stimulation Can Induce Neuronal Gene Expression by Activating N-Type Calcium Channels," Journal of Neuroscience, 2001, vol. 21, No. 8, pp. 2571-2579.

Brown, et al. "Long-term potentiation induced by θ frequency stimulation is regulated by a protein phosphate-operated gate." The Journal of Neuroscience, 2000, vol. 20, No. 21, pp. 7880-7887.

Callaway, et al. "Photostimulation using caged glutamate reveals functional circuitry in living brain slices", Proc. Natl. Acad. Sci. USA., 1993, vol. 90: pp. 7661-7665.

Campagnola et al. "Fiber-coupled light-emitting diode for localized photostimulation of neurons expressing channelrhodopsin-2." Journal of Neuroscience Methods , 2008, vol. 169, Issue 1. Abstract only.

Cardin, et al. "Driving Fast spiking Cells Induces Gamma Rhythm and Controls Sensory Responses", 2009, Nature, vol. 459, vol. 7247, pp. 663-667.

Cenatiempo "Prokaryotic gene expression in vitro: transcription-translation coupled systems", Biochimie, 1986, vol. 68(4): pp. 505-515.

Claudio et al. "Nucleotide and deduced amino acid sequences of Torpedo californica acetylcholine receptor gamma subunit." PNAS USA,1983, vol. 80, p. 1111-1115.

(56) References Cited

OTHER PUBLICATIONS

Collingridge et al. "Inhibitory post-synaptic currents in rat hippocampal CA1 neurones." J. Physiol., 1984, vol. 356, pp. 551-564.
Covington, et al. "Antidepressant Effect of Optogenetic Stimulation of the Medial Prefrontal Cortex." Journal of Neuroscience, 2010, vol. 30(48), pp. 16082-16090.
Crouse, et al. "Expression and amplification of engineered mouse dihydrofolate reductase minigenes" Mol. Cell. Biol., 1983, vol. 3(2): pp. 257-266.
Cucchiaro et al., "Phaseolus vulgaris leucoagglutinin (PHA-L): a neuroanatomical tracer for electron microscopic analysis of synaptic circuitry in the cat's dorsal lateral geniculate nucleus" J. Electron. Microsc. Tech., 1990, 15 (4):352-368.
Cucchiaro et al., "Electron-Microsoft Analysis of Synaptic Input from the Perigeniculate Nucleus to A-Lamine of the Lateral Geniculate Nucleus in Cats", The Journal of Comparitive Neurology, 1991, vol. 310, pp. 316-336.
Cui, et al., "Electrochemical deposition and characterization of conducting polymer polypyrrole/PSS on multichannel neural probes," Sensors and Actuators, 2001, vol. 93(1): pp. 8-18.
Date, et al. "Grafting of Encapsulated Dopamine-Secreting Cells in Parkinson's Disease: Long-Term Primate Study", Cell Transplant, 2000, vol. 9, pp. 705-709.
Dalva, et al. "Rearrangements of Synaptic Connections in Visual Cortex Revealed by Laser Photostimulation", Science, 1994, vol. 265, pp. 255-258.
Dederen, et al. "Retrograde neuronal tracing with cholera toxin B subunit: comparison of three different visualization methods", Histochemical Journal, 1994, vol. 26, pp. 856-862.
De Foubert et al. "Fluoxetine-Induced Change in Rat Brain Expression of Brain-Derived Neurotrophic Factor Varies Depending on Length of Treatment," Neuroscience, 2004, vol. 128, pp. 597-604.
Deisseroth et al., "Signaling from Synapse to Nucleus: Postsynaptic CREB Phosphorylation During Multiple Forms of Hippocampal Synaptic Plasticity", Neuron, 1996, vol. 16, pp. 89-101.
Deisseroth et al., "Translocation of Calmodulin to the Nucleus Supports CREB Phosphorylation in Hippocampal Neurons", Nature, 1998, vol. 392, pp. 198-202.
Deisseroth et al., "Signaling from Synapse to Nucleus: the logic Behind the Mechanisms", Currrent Opinion in Neurobiology, 2003, vol. 13, pp. 354-365.
Deisseroth et al., "Excitation-neurogenesis Coupling in Adult Neural Stem/Progenitor Cells", 2004, Neuron, vol. 42, pp. 535-552.
Deisseroth "Next-generation optical technologies for illuminating genetically targeted brain circuits," The Journal of Neuroscience, 2006, vol. 26, No. 41, pp. 10380-10386.
Denk, W., et al. "Anatomical and functional imaging of neurons using 2-photon laser scanning microscopy", Journal of Neuroscience Methods, 1994, vol. 54, pp. 151-162.
Ditterich, et al. "Microstimulation of visual cortex affects the speed of perceptual decisions", 2003, Nature Neuroscience, vol. 6, No. 8, pp. 891-898.
Dittgen, et al. "Lentivirus-based genetic manipulations of cortical neurons and their optical and electrophysiological monitoring in vivo", PNAS, 2004, vol. 101, No. 52, pp. 18206-18211.
Emerich, et al. "A Novel Approach to Neural Transplantation in Parkinson's Disease: Use of Polymer-Encapsulated Cell Therapy", Neuroscience and Biobehavioral Reviews, 1992, vol. 16, pp. 437-447.
Ensell, et al. "Silicon-based microelectrodes for neurophysiology, micromachined from silicon-on-insulator wafers," Med. Biol. Eng. Comput., 2000, vol. 38, pp. 175-179.
Eisen, "Treatment of amyotrophic lateral sclerosis", Drugs Aging, 1999; vol. 14, No. 3, pp. 173-196.
Ernst, et al. "Photoactivation of Channelrhodopsin", 2008, vol. 283, No. 3, pp. 1637-1643.
Evanko "Optical excitation yin and yang" Nature Methods, 2007, 4:384.

Esposito et al. "The integrase family of tyrosine recombinases: evolution of a conserved active site domain", Nucleic Acids Research, 1997, vol. 25, No. 18, pp. 3605-3614.
Fabian et al. "Transneuronal transport of lectins" Brain Research, 1985, vol. 344, pp. 41-48.
Falconer et al. "High-throughput screening for ion channel modulators," Journal of Biomolecular Screening, 2002, vol. 7, No. 5, pp. 460-465.
Farber, et al. "Identification of Presynaptic Neurons by Laser Photostimulation", Science, 1983, vol. 222, pp. 1025-1027.
Feng, et al. "Imaging Neuronal Subsets in Transgenic Mice Expressing Multiple Spectral Variants of GFP", Neuron, 2000, vol. 28, pp. 41-51.
Fisher, J. et al. "Spatiotemporal Activity Patterns During Respiratory Rhythmogenesis in the Rat Ventrolateral Medulla," The Journal of Neurophysiol, 2006, vol. 95, pp. 1982-1991.
Fitzsimons et al., "Promotors and Regulatory Elements that Improve Adeno-Associated Virus Transgene Expression in the Brain", 2002, Methods, vol. 28, pp. 227-236.
Foster, "Bright blue times", Nature, 2005, vol. 433, pp. 698-699.
Genbank Accession No. DQ094781 (Jan. 15, 2008).
Gelvich et al. "Contact flexible microstrip applicators (CFMA) in a range from microwaves up to short waves," IEEE Transactions on Biomedical Engineering, 2002, vol. 49, Issue 9: 1015-1023.
Gigg, et al. "Glutamatergic hippocampal formation projections to prefrontal cortex in the rat are regulated by GABAergic inhibition and show convergence with glutamatergic projections from the limbic thalamus," Hippocampus, 1994, vol. 4, No. 2, pp. 189-198.
Gilman, et al. "Isolation of sigma-28-specific promoters from *Bacillus subtilis* DNA" Gene, 1984, vol. 32(1-2): pp. 11-20.
Glick et al."Factors affecting the expression of foreign proteins in *Escherichia coli*", Journal of Industrial Microbiology, 1987, vol. 1(5): pp. 277-282.
Goekoop, R. et al. "Cholinergic challenge in Alzheimer patients and mild cognitive impairment differentially affects hippocampal activation—a pharmacological fMRI study." Brain, 2006, vol. 129, pp. 141-157.
Gold, et al. "Representation of a perceptual decision in developing oculomotor commands", Nature, 2000, vol. 404, pp. 390-394.
Gordon, et al. "Regulation of Thy-1 Gene Expression in Transgenic Mice", Cell, 1987, vol. 50, pp. 445-452.
Gorelova et al., "The course of neural projection from the prefrontal cortex to the nucleus accumbens in the rat ", Neuroscience, 1997, vol. 76, No. 3, pp. 689-706.
Gottesman et al."Bacterial regulation: global regulatory networks," Ann. Rev. Genet. , 1984, vol. 18, pp. 415-441.
Gradinaru, et al. "ENpHR: a Natronomonas Halorhodopsin Enhanced for Optogenetic Applications", 2008, Brain Cell Biol., vol. 36 (1-4), pp. 129-139.
Greenberg, et al. "Three-year outcomes in deep brain stimulation for highly resistant obsessive-compulsive disorder," Neuropsychopharmacology, 2006, vol. 31, pp. 2384-2393.
Gregory, et al. "Integration site for *Streptomyces* phage φBT1 and development of site-specific integrating vectors", Journal of Bacteriology, 2003, vol. 185, No. 17, pp. 5320-5323.
Groth et al. "Phage integrases: biology and applications," Journal of Molecular Biology, 2004, vol. 335, pp. 667-678.
Groth, et al. "A phage integrase directs efficient site-specific integration in human cells", PNAS, 2000, vol. 97, No. 11, pp. 5995-6000.
Guatteo, et al. "Temperature sensitivity of dopaminergic neurons of the substantia nigra pars compacta: Involvement of transient receptor potential channels," Journal of Neurophysiol. , 2005, vol. 94, pp. 3069-3080.
Gulick, et al. "Transfection using DEAE-Dextran" Supplement 40, Current Protocols in Molecular Biology, 1997, Supplement 40, 9.2.1-9.2.10.
Gur et al., "A Dissociation Between Brain Activity and Perception: Chromatically Opponent Cortical Neurons Signal Chromatic Flicker that is not Perceived", Vision Research, 1997, vol. 37, No. 4, pp. 377-382.

(56) References Cited

OTHER PUBLICATIONS

Hallet et al. "Transposition and site-specific recombination: adapting DNA cut-and-paste mechanisms to a variety of genetic rearrangements," FEMS Microbiology Reviews, 1997, vol. 21, No. 2, pp. 157-178.
Hamer, et al. "Regulation In Vivo of a cloned mammalian gene: cadmium induces the transcription of a mouse metallothionein gene in SV40 vectors," Journal of Molecular Applied Genetics, 1982, vol. 1, No. 4, pp. 273-288.
Hausser, et al. "Tonic Synaptic Inhibition Modulates Neuronal Output Pattern and Spatiotemporal Synaptic Integration", Neuron, 1997, vol. 19, pp. 665-678.
Hegemann et al., "All-trans Retinal Constitutes the Functional Chromophore in *Chlamydomonas* rhodopsin", Biophys. J., 1991, vol. 60, pp. 1477-1489.
Herlitze, et al., "New Optical Tools for Controlling Neuronal Activity", 2007, Curr Opin Neurobiol, vol. 17, No. 1, pp. 87-94.
Herry, et al. "Switching on and off fear by distinct neuronal circuits," Nature, 2008, vol. 454, pp. 600-606.
Hildebrandt et al, "Bacteriorhodopsin expressed in *Schizosaccharomyces pombe* pumps protons through the plasma membrane, " PNAS, 1993, vol. 90, pp. 3578-3582.
Hirase, et al. "Multiphoton stimulation of neurons", J Neurobiol, 2002, vol. 51, No. 3: pp. 237-247.
Hodaie, et al., "Chronic Anterior Thalamus Stimulation for Intractable Epilepsy," Epilepsia, 2002, vol. 43, pp. 603-608.
Hoffman et al., "K+ Channel Regulation of Signal Propagation in Dendrites of Hippocampal Pyramidal Neurons", 1997, Nature, vol. 387: pp. 869-874.
Hosokawa, T. et al. "Imaging spatio-temporal patterns of long-term potentiation in mouse hippocampus." Philos. Trans. R. Soc. Lond. B., 2003, vol. 358, pp. 689-693.
Hynynen, et al. "Clinical applications of focused ultrasound—The brain." Int. J. Hyperthermia, 2007, vol. 23, No. 2: pp. 193-202.
International Search Report for International Application No. PCT/US2009/053474, dated Oct. 8, 2009.
Isenberg et al. "Cloning of a Putative Neuronal Nicotinic Aceylcholine Receptor Subunit," Journal of Neurochemistry, 1989, pp. 988-991.
Jekely, "Evolution of Phototaxis", 2009, Phil. Trans. R. Soc. B, vol. 364, pp. 2795-2808.
Johansen, et al., "Optical Activation of Lateral Amygdala Pyramidal Cells Instructs Associative Fear Learning", 2010, PNAS, vol. 107, No. 28, pp. 12692-12697.
Johnston et al. "Isolation of the yeast regulatory gene *GAL4* and analysis of its dosage effects on the galactose/melibiose regulon," PNAS, 1982, vol. 79, pp. 6971-6975.
Kandel, E.R., et al. "Electrophysiology of Hippocampal Neurons: I. Sequential Invasion and Synaptic Organization," J Neurophysiol, 1961, vol. 24, pp. 225-242.
Kandel, E.R., et al. "Electrophysiology of Hippocampal Neurons: II. After-Potentials and Repetitive Firing", J Neurophysiol., 1961, vol. 24, pp. 243-259.
Karreman et al. "On the use of double FLP recognition targets (FRTs) in the LTR of retroviruses for the construction of high producer cell lines", Nucleic Acids Research, 1996, vol. 24, No. 9: pp. 1616-1624.
Kato et al. "Present and future status of noninvasive selective deep heating using RF in hyperthermia." Med & Biol. Eng. & Comput 31 Supp: S2-11, 1993. Abstract. p. S2 only.
Katz, et al. "Scanning laser photostimulation: a new approach for analyzing brain circuits," Journal of Neuroscience Methods, 1994, vol. 54, pp. 205-218.
Khodakaramian, et al. "Expression of Cre Recombinase during Transient Phage Infection Permits Efficient Marker Removal in *Streptomyces*," Nucleic Acids Research, 2006, vol. 34, No. 3:e20, pp. 1-5.
Khossravani et al., "Voltage-Gated Calcium Channels and Idiopathic Generalized Epilepsies", Physiol. Rev., 2006, vol. 86: pp. 941-966.
Kianianmomeni, et al. "Channelrhodopsins of Volvox carteri are Photochromic Proteins that are Specifically Expressed in Somatic Cells under Control of Light, Temperature, and the Sex Inducer", 2009, Plant Physiology, vol. 151, No. 1, pp. 347-366.
Kim et al., "Light-Driven Activation of β2-Adrenergic Receptor Signaling by a Chimeric Rhodopsin Containing the β2-Adrenergic Receptor Cytoplasmic Loops," Biochemistry, 2005, vol. 44, No. 7, pp. 2284-2292.
Kingston et al. "Transfection of DNA into Eukaryotic Cells," Supplement 63, Current Protocols in Molecular Biology, 1996, 9.1.1-9.1.11, 11 pages.
Kingston et al. "Transfection and Expression of Cloned DNA," Supplement 31, Current Protocols in Immunology, 1999, 10.13.1-10.13.9.
Kita, H. et al. "Effects of dopamine agonists and antagonists on optical responses evoked in rat frontal cortex slices after stimulation of the subcortical white matter," Exp. Brain Research, 1999, vol. 125, pp. 383-388.
Kitayama, et al. "Regulation of neuronal differentiation by $N$-methyl-D-aspartate receptors expressed in neural progenitor cells isolated from adult mouse hippocampus," Journal of Neurosci Research, 2004, vol. 76, No. 5: pp. 599-612.
Klausberger, et al. "Brain-state- and cell-type-specific firing of hippocampal interneurons in vivo", Nature, 2003, vol. 421: pp. 844-848.
Kocsis et al., "Regenerating Mammalian Nerve Fibres: Changes in Action Potential Waveform and Firing Characteristics Following Blockage of Potassium Conductance", 1982, Proc. R. Soc. Lond., vol. B 217: pp. 77-87.
Knopfel, et al. "Optical Probin of Neuronal Circuit Dynamics: Gentically Encoded Versus Classical Fluorescent Sensors", 2006, Trends Neurosci, vol. 29, No. 3, pp. 160-166.
Kuhlman et al. (2008) "High-Resolution Labeling and Functional Manipulation of Specific Neuron Types in Mouse Brain by Cre-Activated Viral Gene Expression" PLoS One, 2005, vol. 3, No. 4, pp. 1-11.
Kunkler, P. et at. "Optical Current Source Density Analysis in Hippocampal Organotypic Culture Shows that Spreading Depression Occurs with Uniquely Reversing Current," The Journal of Neuroscience, 2005, vol. 25, No. 15, pp. 3952-3961.
Landy, A. "Mechanistic and structural complexity in the site-specific recombination pathways of Int and FLP", Current Opinion in Genetics and Development, 1993, vol. 3, pp. 699-707.
Lee et al. "Sterotactic Injection of Adenoviral Vectors that Target Gene Expression to Specific Pituitary Cell Types: Implications for Gene Therapy", Neurosurgery, 2000, vol. 46, No. 6: pp. 1461-1469.
Lee et al., "Potassium Channel Gone Therapy Can Prevent Neuron Deatch Resulting from Necrotic and Apoptotic Insults", Journal of Neurochemistry, 2003, vol. 85: pp. 1079-1088.
Levitan et al. "Surface Expression of Kv1 Voltage-Gated K+ Channels is Governed by a C-terminal Motif," Trends Cardiovasc. Med., 2000, vol. 10, No. 7, pp. 317-320.
Li et al. "Fast noninvasive activation and inhibition of neural and network activity by vertebrate rhodopsin and green algae channelrhodopsin." PNAS, 2005, vol. 102, No. 49, p. 17816-17821.
Lim et al., "A Novel Targeting Signal for Proximal Clustering of the Kv2.1K+ Channel in Hippocampal Neurons", Neuron, 2000, vol. 25: pp. 385-397.
Lima, et al. "Remote Control of Behavior through Genetically Targeted Photostimulation of Neurons", Cell, 2005, vol. 121: pp. 141-152.
Liman, et al. "Subunit Stoichiometry of a Mammalian K+ Channel Determined by Construction of Multimeric cDNAs," Neuron, 1992, vol. 9, pp. 861-871.
Louis et al. "Cloning and sequencing of the cellular-viral junctions from the human adenovirus type 5 transformed 293 cell line," Virology, 1997, vol. 233, pp. 423-429.
Luecke, et al. "Structural Changes in Bacteriorhodopsin During Ion Transport at 2 Angstrom Resolution," Science, 1999, vol. 286, pp. 255-260.
Lyznik, et al. "FLP-mediated recombination of *FRT* sites in the maize genome," Nucleic Acids Research, 1996, vol. 24, No. 19: pp. 3784-3789.
Ma et al. "Role of ER Export Signals in Controlling Surface Potassium Channel Numbers," Science, 2001, vol. 291, pp. 316-319.

(56) References Cited

OTHER PUBLICATIONS

Mann et at. "Perisomatic Feedback Inhibition Underlies Cholinergically Induced Fast Network Oscillations in the Rat Hippocampus in Vitro," Neuron, 2005, vol. 45, 2005, pp. 105-117.

Mattson, "Apoptosis in Neurodegenerative Disorders", Nature Reviews, 2000, vol. 1: pp. 120-129.

Mayberg et al. "Deep Brain Stimulation for Treatment-Resistant Depression," Focus, 2008, vol. VI, No. 1, pp. 143-154.

McAllister, "Cellular and Molecular Mechanisms of Dendrite Growth", 2000, Cereb Cortex, vol. 10, No. 10, pp. 963-973.

McKnight "Functional relationships between transcriptional control signals of the thymidine kinase gene of herpes simplex virus", Cell, 1982, vol. 31 pp. 355-365.

Melyan, Z., et al. "Addition of human melanopsin renders mammalian cells Photoresponsive", Nature, 2005, vol. 433: pp. 741-745.

Mermelstein, et al. "Critical Dependence of cAMP Response Element-Binding Protein Phosphorylation on L-Type Calcium Channels Supports a Selective Response to EPSPs in Preference to Action Potentials", The Journal of Neuroscience, 2000, vol. 20, No. 1, pp. 266-273.

Meyer, et al. "High density interconnects and flexible hybrid assemblies for active biomedical implants," IEEE Transactions on Advanced Packaging, 2001, vol. 24, No. 3, pp. 366-372.

Monje et al., "Irradiation Induces Neural Precursor-Cell Dysfunction", Natural Medicine, 2002, vol. 8, No. 9, pp. 955-962.

Mortensen et al. "Selection of Transfected Mammalian Cells," Supplement 86, Current Protocols in Molecular Biology, 1997, 9.5.1-09.5.19.

Nacher, et al. "NMDA receptor antagonist treatment increases the production of newneurons in the aged rat hippocampus", Neurobiology of Aging, 2003,vol. 24, No. 2: pp. 273-284.

Nagel et al."Functional Expression of Bacteriorhodopsin in Oocytes Allows Direct Measurement of Voltage Dependence of Light Induced H+ Pumping," FEBS Letters, 1995, vol. 377, pp. 263-266.

Nagel, et al. "Channelrhodopsin-I: a light-gated proton channel in green algae", Science, 2002, vol. 296: pp. 2395-2398.

Nagel, et al. "Channelrhodopsin-2, a directly light-gated cation-selective membrane channel", PNAS, 2003, vol. 100, No. 24: pp. 13940-13945.

Nakagami, et al. "Optical Recording of Trisynaptic Pathway in Rat Hippocampal Slices with a Voltage-Sensitive Dye" Neuroscience, 1997, vol. 81, No. 1, pp. 1-8.

Naqvi, et al. "Damage to the insula disrupts addiction to cigarette smoking," Science; 2007, vol. 315 pp. 531-534.

Nirenberg, et al. "The Light Response of Retinal Ganglion Cells is Truncated by a Displaced Amacrine Circuit", Neuron, 1997, vol. 18: pp. 637-650.

Nunes-Duby, et al. "Similarities and differences among 105 members of the Int family of site-specific recombinases", Nucleic Acids Research, 1998, vol. 26, No. 2: pp. 391-406.

O'Gorman et al. "Recombinase-mediated gene activation and site-specific integration in mammalian cells", Science, 1991, 251(4999): pp. 1351-1355.

Olivares (2001) "Phage R4 integrase mediates site-specific integration in human cells", Gene, 2001, vol. 278, pp. 167-176.

Ory, et al. "A stable human-derived packaging cell line for production of high titer retrovirus/vesicular stomatitis virus G pseudotypes," PNAS, 1996, vol. 93: pp. 11400-11406.

Palmer et al., "The Adult Rat Hippocampus Contains Primordial Neural Stem Cells", Molecular and Cellular Neuroscience, 1997, vol. 8, pp. 389-404.

Palmer et al., "Fibroblast Growth Factor-2 Activates a Latent Neurogenic Program in Neural Stem Cells from Diverse Regions of the Adult CNS", The Journal of Neuroscience, 1999, vol. 19, pp. 8487-8497.

Pan et al. "Functional Expression of a Directly Light-Gated Membrane Channel in Mammalian Retinal Neurons: A Potential Strategy for Restoring Light Sensitivity to the Retina After Photoreceptor Degeneration,"Investigative Opthalmology & Visual Science, 2005, 46 E-Abstract 4631. Abstract only.

Panda, et al. "Illumination of the Melanopsin Signaling Pathway", Science, 2005, vol. 307: pp. 600-604.

Pape, et al., "Plastic Synaptic Networks of the Amygdala for the Acquisition, Expression, and Extinction of Conditioned Fear", 2010, Physiol Rev, vol. 90, pp. 419-463.

Paulhe et al. "Specific Endoplasmic Reticulum Export Signal Drives Transport of Stem Cell Factor (Kitl) to the Cell Surface," The Journal of Biological Chemistry, 2004, vol. 279, No. 53, p. 55545-55555.

Pear "Transient Transfection Methods for Preparation of High-Titer Retroviral Supernatants" Supplement 68, Current Protocols in Molecular Biology, 1996, 9.1 1 .I -9.1 1 .I 8.

Petersen et al. "Spatiotemporal Dynamics of Sensory Responses in Layer ⅔ of Rat Barrel Cortex Measured In Vivo by Voltage-Sensitive Dye Imaging Combined with Whole-Cell Voltage Recordings and Neuron Reconstructions," The Journal of Neuroscience, 2003, vol. 23, No. 3, pp. 1298-1309.

Petrecca, et al. "Localization and Enhanced Current Density of the Kv4.2 Potassium Channel by Interaction with the Actin-Binding Protein Filamin," The Journal of Neuroscience, 2000, vol. 20, N. 23, pp. 8736-8744.

Pettit, et al. "Local Excitatory Circuits in the Intermediate Gray Layer of the Superior Colliculus", J Neurophysiol., 1999, vol. 81, No. 3: pp. 1424-1427.

Potter, "Transfection by Electroporation." Supplement 62, Current Protocols in Molecular Biology, 1996, 9.3.1-9.3.6.

Pouille, et al. "Routing of spike series by dynamic circuits in the hippocampus", Nature, 2004, vol. 429: pp. 717-723.

Qiu et al. "Induction of photosensitivity by heterologous expression of melanopsin", Nature, 2005, vol. 433: pp. 745-749.

Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2546.

Randic, et al. "Long-term Potentiation and Long-term Depression of Primary Afferent Neurotransmission in the Rat Spinal Cord", 1993, Journal of Neuroscience, vol. 13, No. 12, pp. 5228-5241.

Rathnasingham et al., "Characterization of implantable microfabricated fluid delivery devices," IEEE Transactions on Biomedical Engineering, 2004, vol. 51, No. 1: pp. 138-145.

Ritter, et al., "Monitoring Light-induced Structural Changes of Channelrhodopsin-2 by UV-Visible and Fourier Transform Infared Spectroscopy", 2008, The Journal of Biological Chemistry, vol. 283, No. 50, pp. 35033-35041.

Rivera et al., "BDNF-Induced TrkB Activation Down-Regulates the K+-Cl-cotransporter KCC2 and Impairs Neuronal Cl-Extrusion", The Journal of Cell Biology, 2002, vol. 159: pp. 747-752.

Rosenkranz, et al. "The prefrontal cortex regulates lateral amygdala neuronal plasticity and responses to previously conditioned stimuli", J. Neurosci., 2003, vol. 23, No. 35: pp. 11054-11064.

Rousche, et al., "Flexible polyimide-based intracortical electrode arrays with bioactive capability," IEEE Transactions on Biomedical Engineering, 2001, vol. 48, No. 3, pp. 361-371.

Rubinson et at. "A lentivirus-based system to functionally silence genes in primary mammalian cells, stem cells and transgenic mice by RNA interference," Nature Genetics, 2003, vol. 33, p. 401-406.

Rudiger et at. "Specific arginine and threonine residues control anion binding and transport in the light-driven chloride pump halorhodopsin," The EMBO Journal, 1997, vol. 16, No. 13, pp. 3813-3821.

Salzman, et al. "Cortical microstimulation influences perceptual judgements of motion direction", Nature, 1990, vol. 346, pp. 174-177.

Sajdyk, et al., "Excitatory Amino Acid Receptors in the Basolateral Amygdala Regulate Anxiety Responses in the Social Interaction Test", Brain Research, 1997, vol. 764, pp. 262-264.

Sato et al. "Role of Anion-binding Sites in cytoplasmic and extracellular channels of *Natronomonas pharaonis* halorhodopsin," Biochemistry, 2005. vol. 44, pp. 4775-4784.

Sauer "Site-specific recombination: developments and applications," Current Opinion in Biotechnology, 1994, vol. 5, No. 5: pp. 521-527.

Schiff, et al. "Behavioral improvements with thalamic stimulation after severe traumatic brain injury," Nature, 2007, vol. 448, pp. 600-604.

(56) References Cited

OTHER PUBLICATIONS

Schlaepfer et al. "Deep Brain stimulation to Reward Circuitry Alleviates Anhedonia in Refractory Major Depresion," Neuropsychopharmacology, 2008,vol. 33, pp. 368-377.

Sclimenti, et al. "Directed evolution of a recombinase for improved genomic integration at a native human sequence," Nucleic Acids Research, 2001, vol. 29, No. 24: pp. 5044-5051.

Shepherd, et al. "Circuit Analysis of Experience-Dependent Plasticity in the Developing Rat Barrel Cortex", Neuron, 2003, vol. 38: pp. 277-289.

Shibasaki et al. "Effects of body temperature on neural activity in the hippocampus: Regulation of resting membrane potentials by transient receptor potential vanilloid 4," The Journal of Neuroscience, 2007, vol. 27, No. 7: pp. 1566-1575.

Silver, et al. "Amino terminus of the yeast *GAL4* gene product is sufficient for nuclear localization" PNAS, 1984, vol. 81, No. 19: pp. 5951-5955.

Singer et al. "Elevated Intrasynaptic Dopamine Release in Tourette's Syndrome Measured by PET," American Journal of Psychiatry, 2002, vol. 159: pp. 1329-1336.

Slimko et al., "Selective Electrical Silencing of Mammalian Neurons In Vitro by the use of Invertebrate Ligand-Gated Chloride Channels", The Journal of Neuroscience, 2002, vol. 22, No. 17: pp. 7373-7379.

Smith et al. "Diversity in the serine recombinases", Molecular Microbiology, 2002, vol. 44, No. 2: pp. 299-307.

Song et al. "Differential Effect of TEA on Long-Term Synaptic Modification in Hippocampal CA1 and Dentate Gyms in vitro." Neurobiology of Learning and Memory, 2001, vol. 76, No. 3, pp. 375-387.

Song, "Genes responsible for native depolarization-activated K+ currents in neurons," Neuroscience Research, 2002, vol. 42, pp. 7-14.

Stark, et al. "Catalysis by site-specific recombinases," Trends Genet., 1992, vol. 8, No. 12: pp. 432-439.

Stockklausner et al. "A sequence motif responsible for ER export and surface expression of Kir2.0 inward rectifier K+ channels," FEBS Letters, 2001, vol. 493, pp. 129-133.

Stoll, et al. "Phage TP901-I site-specific integrase functions in human cells," Journal of Bacteriology, 2002, vol. 184, No. 13: pp. 3657-3663.

Swanson, "Lights, Opsins, Action! Optogenetics Brings Complex Neuronal Circuits into Sharper Focus", 2009, The Dana Foundation, [URL: http://www.dana.org/news/features/detail.aspx?id=24236], PDF File, pp. 1-3.

Swiss-Prot_Q2QCJ4, Opsin 1, Oct. 31, 2006, URL: http://www.ncbi.nlm.nig.gov/protein/Q2QCJ4.

Takahashi, et al."Diversion of the Sign of Phototaxis in a *Chlamydomonas reinhardtii* Mutant Incorporated with Retinal and Its Analogs," FEBS Letters, 1992, vol. 314, No. 3, pp. 275-279.

Tatarkiewicz, et al. "Reversal of Hyperglycemia in Mice After Subcutaneous Transplantation of Macroencapsulated Islets", Transplantation, 1999, vol. 67, No. 5: pp. 665-671.

Tottene et al., "Familial Hemiplegic Migraine Mutations Increase $Ca^{2+}$ Influx Through Single Human $Ca_v2.1$ Current Density in Neurons", PNAS USA, 2002, vol. 99, No. 20: pp. 13284-13289.

Tsau et al. "Distributed Aspects of the Response to Siphon Touch in *Aplysia*: Spread of Stimulus Information and Cross-Correlation Analysis," The Journal of Neuroscience, 1994, vol. 14, No. 7, pp. 4167-4184.

[No Authors Listed] "Two bright new faces in gene therapy," Nature Biotechnology, 1996, vol. 14: p. 556.

Tye et. al., "Amygdala circuitry mediating reversible and bidirectional control of anxiety", Nature, 2011, vol. 471(7338): pp. 358-362.

Tye et. al., Supplementary Materials: "An optically-resolved microcircuit for bidirectional anxiety control", Nature, 2011, vol. 471(7338): pp. 358-362.

"SubName: Full=Channelrhodopsin-1", retrieved from EBI accession No. UNIPROT: B4Y103. Database accession No. B4Y103. Sep. 23, 2008.

Ulmanen, et al. "Transcription and translation of foreign genes in *Bacillus subtilis* by the aid of a secretion vector," Journal of Bacteriology, 1985, vol. 162, No. 1: pp. 176-182.

Van Der Linden, "Functional brain imaging and pharmacotherapy in social phobia: single photon emission computed tomography before and after Treatment with the selective serotonin reuptake inhibitor citalopram," Prog Neuro-psychopharmacol Biol Psychiatry, 2000, vol. 24, No. 3: pp. 419-438.

Vanin, et al. "Development of high-titer retroviral producer cell lines by using Cre-mediated recombination," Journal of Virology, 1997, vol. 71, No. 10: pp. 7820-7826.

Vetter, et al. "Development of a Microscale Implantable Neural Interface (MINI) Probe System," Proceedings of the 2005 IEEE, Engineering in Medicine and Biology 27th Annual Conference, Shanghai, China, Sep. 1-4, 2005.

Wagner, "Noninvasive Human Brain Stimulation", Annual Rev. Biomed. Eng. 2007. 9:19.1-19.39.

Ward, et al. "Construction and characterisation of a series of multicopy promoter-probe plasmid vectors for *Streptomyces* using the aminoglycoside phosphotransferase gene from Tn5 as indicator", 1986, Mol. Gen. Genet., vol. 203: pp. 468-478.

Watson, et al. "Targeted transduction patterns in the mouse brain by lentivirus vectors pseudotyped with VSV, Ebola, Mokola, LCMV, or MuLV envelope proteins," Molecular Therapy, 2002, vol. 5, No. 5, pp. 528-537.

Wang et al. "Direct-current Nanogenerator Driven by Ultrasonic Waves," Science, 2007, vol. 316, pp. 102-105.

Wang et. al., "High-speed mapping of synaptic connectivity using photostimulation in Channelrhodopsin-2 transgenic mice", PNAS, 2007, vol. 104, No. 19, pp. 8143-8148.

Weick et al. "Interactions with PDZ Proteins are Required for L-Type Calcium Channels to Activate cAMP Response Element-Binding Protein-Dependent Gene Expression," The Journal of Neuroscience, 2003, vol. 23, No. 8, pp. 3446-3456.

Wells et al. "Application of Infrared light for in vivo neural stimulation," Journal of Biomedical Optics, 2005, vol. 10(6), pp. 064003-1-064003-12.

Witten et. al., Supporting Online Material for: "Cholinergic Interneurons Control Local Circuit Activity and Cocaine Conditioning", Science, 2010, vol. 330: 17 pages.

Witten et. al., "Cholinergic Interneurons Control Local Circuit Activity and Cocaine Conditioning", Science, 2010, vol. 330, No. 6011: pp. 1677-1681.

Yamazoe, et al. "Efficient generation of dopaminergic neurons from mouse embryonic stem cells enclosed in hollow fibers", Biomaterials, 2006, vol. 27, pp. 4871-4880.

Yan et al., "Cloning and Characterization of a Human β,β-Carotene-15, 15'-Dioxygenase that is Highly Expressed in the Retinal Pigment Epithelium", Genomics, 2001, vol. 72: pp. 193-202.

Yizhar et. al., "Neocortical excitation/inhibition balance in information processing and social dysfunction", Nature, 2011, vol. 477, pp. 171-178; and Supplemental Materials; 41 pages.

Yoon, et al., "A micromachined silicon depth probe for multichannel neural recording," IEEE Transactions Biomedical Engineering, 2000, vol. 47, No. 8, pp. 1082-1087.

Yoshimura, et al. "Excitatory cortical neurons form fine-scale functional networks", Nature, 2005, vol. 433: pp. 868-873.

Zacharias et al. "Recent advances in technology for measuring and manipulating cell signals," Current Opinion in Neurobiology, 2000, vol. 10: pp. 416-421.

Zemelman, et al. "Selective Photostimulation of Genetically ChARGed Neurons", Neuron, 2002, vol. 33: pp. 15-22.

Zemelman, et al. "Photochemical gating of heterologous ion channels: Remote control over genetically designated populations of neurons", PNAS, 2003, vol. 100, No. 3: pp. 1352-1357.

Zhang, et al. "Channelrhodopsin-2 and optical control of excitable cells," Nature Methods,2006, vol. 3, No. 10, pp. 785-792.

Zhang, et al. "Red-Shifted Optogenetic Excitation: a Tool for Fast Neural Control Derived from *Volvox carteri*", Nature Neurosciences, 2008,vol. 11, No. 6, pp. 631-633.

Zhang "Multimodal fast optical interrogation of neural circuitry," Nature, 2007, vol. 446, pp. 633-641.

(56) References Cited

OTHER PUBLICATIONS

Zrenner, E., "Will Retinal Implants Restore Vision?" Science, 2002, vol. 295, No. 5557, pp. 1022-1025.
Zufferey, et al. "Self-Inactivating Lentivirus Vector for Safe and Efficient In Vivo Gene Delivery", Journal of Virology, 1998, vol. 72, No. 12, pp. 9873-9880.
Kingston et al. "Transfection and Expression of Cloned DNA," Supplement 31, Current Protocols in Immunology, 1999, 10.13.1 -1 0.13.9.
Pear "Transient Transfection Methods for Preparation of High-Titer Retroviral Supernatants" Supplement 68, Current Protocols in Molecular Biology, 1996, 9.1 1 .I-9.1 1 .I 8.
Rammes, et al., "Synaptic Plasticity in the Basolateral Amygdala in Transgenic Mice Expressing Dominant-Negative cAMP Response Element-binding Protein (CREB) in Forebrain", Eur J. Neurosci, 2000, vol. 12, No. 7, pp. 2534-2556.
Song et al. "Differential Effect of TEA on Long-Term Synaptic Modification in Hippocampal CA1 and Dentate Gyrus in vitro." Neurobiology of Learning and Memory, 2001, vol. 76, No. 3, pp. 375-387.
Tye, et al. "Optogenetic investigation of neural circuits underlying brain disease in animal models," Nature Reviews Neuroscience (Mar. 2012), 13(4):251-266.
U.S. Appl. No. 13/577,565, filed Sep. 14, 2012, Deisseroth, et at.
U.S. Appl. No. 13/623,612, filed Sep. 20, 2012, Deisseroth, et at.
Cazillis et al., "VIP and PACAP induce selective neuronal differentiation of mouse embryonic stem cells", Eur J Neurosci, 2004, 19(4):798-808.
Morelli et al., "Neuronal and glial cell type-specific promoters within adenovirus recombinants restrict the expression of the apoptosis-inducing molecule Fas ligand to predetermined brain cell types, and abolish peripheral liver toxicity", Journal of General Virology, 1999, 80:571-583.
Berke, et al. "Addiction, Dopamine, and the Molecular Mechanisms of Memory", Molecular Plasticity, 2000, vol. 25: pp. 515-532.
Goshen et al. "Dynamics of Retrieval Strategies for Remote Memories", Cell, 2011, vol. 147: pp. 678-589.
Jimenez S.A & Maren S. et al/ "Nuclear disconnection within the amygdala reveals a direct pathway to fear", Learning Memory, 2009, vol. 16: pp. 766-768.
Ehrlich I. et al. "Amygdala inhibitory circuits and the control of fear memory", Neuron, 2009. Friedrich Meischer Institute, vol. 62: pp. 757-771.
Berndt et al. "Bi-stable neural state switches", Nature Neuroscience, 2009, vol. 12, No. 2: pp. 229-234.
Simmons et al. "Localization and function of NK3 subtype Tachykinin receptors of layer pyramidal neurons of the guinea-pig medial prefrontal cortex", Neuroscience, 2008, vol. 156, No. 4: pp. 987-994.
Loetterle, et al., "Cerebellar Stimulation: Pacing the Brain", American Journal of Nursing, 1975, vol. 75, No. 6, pp. 958-960.
Takahashi, et al., "Induction of Pluripotent Stem Cells from Mouse Embryonic and Adult Fibroblast Cultures by Defined Factors", 2006, Cell, vol. 126, pp. 663-676.
Adamantidis, et al., "Optogenetic Interrogation of Dopaminergic Modulation of the Multiple Phases of Reward-Seeking Behavior", J. Neurosci, 2011, vol. 31, No. 30, pp. 10829-10835.
Han, et al., "Multiple-Color Optical Activation, Silencing, and Desynchronization of Neural Activity with Single-Spike Temporal Resolution", PLoS One, 2007, vol. 2, No. 3, pp. 1-12.
Kinoshita, et al., "Optogenetically Induced Supression of Neural Activity in the Macaque Motor Cortex", Poster Sessions Somatomotor System, Others,2010, pp. 141-154.
Rein, et al., "The Optogenetic (r)evolution", Mol. Genet. Genomics, 2012, vol. 287, No. 2, pp. 95-109.
Remy, et al., "Depression in Parkinson's Disease: Loss of Dopamine and Noradrenaline Innervation in the Limbic System", Brain, 2005, vol. 128 (Pt 6), pp. 1314-1322.
Tsai, et al., "Phasic Firing in Dopaminergic Neurons in Sufficient for Behavioral Conditioning", Science, 2009, vol. 324, pp. 1080-1084.
Zhao, et al., "Improved Expression of Halorhodopsin for Light-Induced Silencing of Neuronal Activity", Brain Cell Biology, 2008, vol. 36 (1-4), pp. 141-154.
Wang, et al., "Molecular Determinants Differentiating Photocurrent Properties of Two Channelrhodopsins from Chlamydomonas", 2009, The Journal of Biological Chemistry, vol. 284, No. 9, pp. 5685-5696.
Gradinaru, et al., Molecular and Cellular Approaches for Diversifying and Extending Optogenetics, Cell, 2010, vol. 141, No. 1, pp. 154-165.
Delaney et al., "Evidence for a long-lived 13-cis-containing intermediate in the photocycle of the leu 93 → ala bacteriorhodopsin mutant", J. Physical Chemistry B, 1997, vol. 101, No. 29, pp. 5619-5621.
Fenno et al., "The development and application of optogenetics", Annual Review of Neuroscience, 2011, vol. 34, No. 1, pp. 389-412.
Gunaydin et al., "Ultrafast optogenetic control", Nature Neuroscience, 2010, vol. 13, No. 3, pp. 387-392.
Hira et al., "Transcranial optogenetic stimulation for functional mapping of the motor cortex", J Neurosci Methods, 2009, vol. 179, pp. 258-263.
Lalumiere, R., "A new technique for controlling the brain: optogenetics and its potential for use in research and the clinic", Brain Stimulation, 2011, vol. 4, pp. 1-6.
Lin, "A user's guide to channelrhodopsin variants: features, limitations and future developments", Exp Physiol, 2010, vol. 96, No. 1, pp. 19-25.
Mancuso et al., "Optogenetic probing of functional brain circuitry", Experimental Physiology, 2010, vol. 96.1, pp. 26-33.
Peralvarez-Marin et al., "Inter-helical hydrogen bonds are essential elements for intra-protein signal transduction: The role of Asp115 in bacteriorhodopsin transport function", J. Mol. Biol., 2007, vol. 368, pp. 666-676.
Pinkham et al., "Neural bases for impaired social cognition in schizophrenia and autism spectrum disorders", Schizophrenia Research, 2008, vol. 99, pp. 164-175.
Sohal et al., "Parvalbumin neurons and gamma rhythms enhance cortical circuit performance", Nature, 2009, vol. 459, No. 7247, pp. 698-702.
Yizhar et al., "Optogenetics in neural systems", Neuron Primer, 2011, vol. 71, No. 1, pp. 9-34.
Li et al., "Surface Expression of Kv1 Channels is Governed by a C-Terminal Motif", J. Bioi. Chem. (2000), 275(16):11597-11602.
Lonnerberg et al. "Regulatory Region in Choline Acetyltransferase Gene Directs Developmental and Tissue-Specific Expression in Transgenic mice", Proc. Natl. Acad. Sci. USA (1995), 92(9):4046-4050.
Varo et al.,"Light-Driven Chloride Ion Transport by Halorhodopsin from Natronobacterium pharaonis. 2. Chloride Release and Uptake, Protein Conformation Change, and Thermodynamics", Biochemistry (1995), 34(44):14500-14507.
Deisseroth, et al., "Controlling the Brain with Light", Scientific American, 2010, vol. 303, pp. 48-55.
Douglass, et al., "Escape Behavior Elicited by Single, Channelrhodopsin-2-evoked Spikes in Zebrafish Somatosensory Neurons", Curr Biol., 2008, vol. 18, No. 15, pp. 1133-1137.
Sineshchekov, et al., "Two Rhodopsins Mediate Phototaxis to Low and High Intensity Light in Chlamydomas Reinhardtil", PNAS, 2002, vol. 99, No. 13, pp. 8689-8694.
Tønnese, et al., "Optogenetic Control of Epileptiform Activity", PNAS, 2009, vol. 106, No. 29, pp. 12162-12167.
Shibasaki et al., "Effects of body temperature on neural activity in the hippocampus: Regulation of resting membrane potentials by transient receptor potential vanilloid 4," The Journal of Neuroscience, 2007, 27(7):1566-1575.
Hikida et al., "Increased sensitivity to cocaine by cholinergic cell ablation in nucleus accumbens", PNAS, Nov. 2001, 98(23): 13351-13354.
Hikida et al., "Acetylcholine enhancement in the nucleus accumbens prevents addictive behaviors of cocaine and morphine", PNAS, May 2003, 100(10):6169-6173.
Kitabatake et al., "Impairment of reward-related learning by cholinergic cell ablation in the striatum", PNAS, Jun. 2003, 100(13):7965-7970.

(56) References Cited

OTHER PUBLICATIONS

Tamai, "Progress in Pathogenesis and Therapeutic Research in Retinitis Pigmentosa and Age Related Macular Degeneration", Nippon Ganka Gakkai Zasshi, vol. 108, No. 12, Dec. 2004, pp. 750-769.
RecName: Full=Halorhodopsin; Short=HR; Alt Name: Full=NpHR; XP002704922, retrieved from EBI accession No. UNIPROT: P15647. Database accession No. P15647. Apr. 1, 1990.
"N. pharaonis halorhodopsin (hop) gene, complete cds.", XP002704883, retrieved from EBI accession No. EMBL: J05199. Database accession No. J05199. Nov. 22, 1990.
"Subname: Fluu= Bacteriorhodopsin"; XP002704863, retrieved from EBI accession No. UNIPROT: B0R5N9. Database accession No. B0R5N9. Apr. 8, 2008.
Zhang, et al., "The Microbial Opsin Family of Optogenetic Tools", Cell, 2011, vol. 147, No. 7, pp. 1146-1457.
Tam, B. et al., "Identification of an Outer Segment Targeting Signal in the COOH Terminus of Rhodopsin Using Transgenic Xenopus laevis", The Journal of Cell Biology, 2000, vol. 151, No. 7, pp. 1369-1380.
Gradinaru et al., "Targeting and readout strategies for fast optical neural control in vitro and in vivo", J Neuroscience, 2007, 27(52):14231-14238.
Berndt et al., "Structure-Guided Transformation of Channelrhodopsin into a Light-Activated Chloride Channel", Science (Apr. 2014), 344(6182):420-424.
Chow et al., "Optogenetics and Translational Medicine", Science Translational Medicine (Mar. 2013), 5(177):177ps5.
Eijkelkamp, et al. "Neurological perspectives on voltage-gated sodium channels", Brain (Sep. 2012), 135(Pt 9):2585-2612.
Garrido et al., "A targeting motif involved in sodium channel clustering at the axonal initial segment", Science (Jun. 2003), 300(5628):2091-4.
Han; et al., "Two-color, bi-directional optical voltage control of genetically-targeted neurons", CoSyne (2007), Abstract Presentation, Poster III-67, p. 269, Presented Feb. 24, 2007.
Hustler; et al., "Acetylcholinesterase staining in human auditory and language cortices: regional variation of structural features", Cereb Cortex (Mar.-Apr. 1996), 6(2):260-70.
Iyer et al., "Virally mediated optogenetic excitation and inhibition of pain in freely moving nontransgenic mice", Nat Biotechnol., (Mar. 2014), 32(3):274-8.
Ji et al., "Light-evoked Somatosensory Perception of Transgenic Rats that Express Channelrhodopsin-2 in Dorsal Root Ganglion Cells", PLoS One (2012), 7(3):e32699.
Jennings et al., "Distinct extended amygdala circuits for divergent motivational states," Nature (Apr. 2013), 496 (7444):224-8.
Kim et al., "PDZ domain proteins of synapses", Nature Reviews Neuroscience, (Oct. 2004), 5(10):771-81.
Kim et al., "Diverging neural pathways assemble a behavioural state from separable features in anxiety" Nature (Apr. 2013), 496(7444):219-23.
Kokel et al., "Photochemical activation of TRPA1 channels in neurons and animals", Nat Chem Biol (Apr. 2013), 9 (4):257-63.
Lammel et al., "Input-specific control of reward and aversion in the ventral tegmental area", Nature (Nov. 2012), 491 (7423): 212-7.
Liske et al., "Optical inhibition of motor nerve and muscle activity in vivo", Muscle Nerve (Jun. 2013), 47(6):916-21.
Llewellyn et al., "Orderly recruitment of motor units under optical control in vivo", Nature Medicine, (Oct. 2010), 16 (10):1161-5.
Mattis et al., "Principles for applying optogenetic tools derived from direct comparative analysis of microbial opsins", Nat Methods (Dec. 2011), 9(2):159-72.
Mourot et al., "Rapid Optical Control of Nociception with an Ion Channel Photoswitch", Nat Methods (Feb. 2012), 9 (4):396-402.
Nieh et al., "Optogenetic dissection of neural circuits underlying emotional valence and motivated behaviors", Brain Research, (May 2012), 1511:73-92.
Slamovits et al., "A bacterial proteorhodopsin proton pump in marie eukaryotes", Nature Communications (Feb. 2011), 2:183.

Towne et al., "Efficient transduction of non-human primate motor neurons after intramuscular delivery of recombinant AAV serotype 6", Gene Ther. (Jan. 2010), 17(1):141-6.
Towne et al., "Optogenetic control of targeted peripheral axons in freely moving animals", PLoS One (Aug. 2013), 8 (8):e72691.
Towne et al., "Recombinant adeno-associated virus serotype 6 (rAAV2/6)-mediated gene transfer to nociceptive neurons through different routes of delivery", Mol Pain (Sep. 2009), 5:52.
Wang et al., "Mrgprd-Expressing Polymodal Nociceptive Neurons Innervate Most Known Classes of Substantia Gelatinosa Neurons", J Neurosci (Oct. 2009), 29(42):13202-13209.
Williams et al., "From optogenetic technologies to neuromodulation therapies", Sci Transl Med. (Mar. 2013), 5 (177):177ps6.
Babin et al., "Zebrafish Models of Human Motor Neuron Diseases: Advantages and Limitations", Progress in Neurobiology (2014), 118:36-58.
Santana et al., "Can Zebrafish be Used as Animal Model to Study Alzheimer's Disease?" Am. J. Neurodegener. Dis. (2012), 1(1):32-48.
Sheikh et al., "Neurodegenerative Diseases: Multifactorial Conformational Diseases and Their Therapeutic Interventions", Journal of Neurodegenerative Diseases (2013), Article ID 563481:1-8.
Suzuki et al., "Stable Transgene Expression from HSV Amplicon Vectors in the Brain: Potential Involvement of Immunoregulatory Signals", Molecular Therapy (2008), 16(10):1727-1736.
Thomas et al., "Progress and Problems with the Use of Viral Vectors for Gene", Nat. Rev. Genet. (2003), 4(5):346-358.
Ageta-Ishihara et al., "Chronic overload of SEPT4, a parkin substrate that aggregates in Parkinson's disease, cause behavioral alterations but not neurodegeneration in mice", Molecular Brain, 2013, vol. 6, 14 pages.
Axoclamp-28 Microelectrode claim theory and operation. Accessed from https://physics.ucsd.edu/neurophysics/Manuals/Axon%20Instruments/Axoclamp-2B_Manual.pdf on Dec. 12, 2014.
Cowan et al., "Targeting gene expression to endothelium in transgenic animals: a comparison of the human ICAM-2, PECAM-1, and endoglin promoters", Xenotransplantation, 2003, vol. 10, pp. 223-231.
Definition of Psychosis (2015).
Ebert et al., "A Moloney MLV-rat somatotropin fusion gene produces biologically active somatotropin in a transgenic pig", Mol. Endocrinology, 1988, vol. 2, pp. 277-283.
Hammer et al., "Spontaneous inflammatory disease in transgenic rats expressing HLA-B27 and Human $\beta_2$m: an animal model of HLA-B27-associated human disorders", Cell, 1990, vol. 63, pp. 1099-1112.
Karra, et al. "Transfection Techniques for Neuronal Cells", The Journal of Neuroscience, 2010, vol. 30, No. 18, pp. 6171-6177.
Kelder et al., "Glycoconjugates in human and transgenic animal milk", Advances in Exp. Med. and Biol., 2001, vol. 501, pp. 269-278.
Mullins et al., "Fulminant hypertension in transgenic rats harbouring the mouse *Ren-2* gene", Nature, 1990, vol. 344, pp. 541-544.
Mullins et al., "Expression of the DBA/2J *Ren-2* gene in the adrenal gland of transgenic mice", EMBO, 1989, vol. 8, pp. 4065-4072.
Taurog et al., "HLA-B27 in inbred and non-inbred transgenic mice", J. Immunol., 1988, vol. 141, pp. 4020-4023.
Wall, "Transgenic livestock: Progress and prospects for the future", Theriogenology, 1996, vol. 45, pp. 57-68.
Wang, et al., "High-speed mapping of synaptic connectivity using photostimulation in Channelrhodopsin-2 transgenic mice", Proceedings of the National Academy of Sciences, 2007, vol. 104, No. 19, pp. 8143-8148.
Written opinion of PCT Application No. PCT/US2011/059383 (May 9, 2012).
Fox et al., "A gene neuron expression fingerprint of C. elegans embryonic motor neurons", BMC Genomics, 2005, 6(42):1-23.
Nonet, "Visualization of synaptic specializations in live C. elegans with synaptic vesicle protein-GFP fusions", J. Neurosci. Methods, 1999, 89:33-40.
Synapse, Chapter 13, http://michaeldmann.net/mann13.html, downloaded Apr. 2014.

(56) References Cited

OTHER PUBLICATIONS

Balint, et al., "The Nitrate Transporting Photochemical Reaction Cycle of the Pharaonis Halorhodopsin", Biophysical Journal, 2004, vol. 86, pp. 1655-1663.
Fiala et al., "Optogenetic approaches in neuroscience", Current Biology, Oct. 2010, 20(20): R897-R903.
Gradinaru et al., "Optical deconstruction of parkinsonian neural circuitry", Science, Apr. 2009, 324(5925):354-359.
Liu et al., "Optogenetics 3.0", Cell, Apr. 2010, 141(1):22-24.
Malin et al., "Involvement of the rostral anterior cingulate cortex in consolidation of inhibitory avoidance memory: Interaction with the basolateral amygdala", Neurobiol Learning Mem, 2007,87(2):295-302.
Mayford et al., "Control of memory formation through regulated expression of CAMKII Transgene", Science, Dec. 1996, 274:1678-1683.
Schroll et al., "Light-induced activation of distinct modulatory neurons triggers appetitive or aversive learning in *Drosphila* larvae", Current Biology, Sep. 2006, 16(17):1741-1747.
Xiong et al., "Interregional connectivity to primary motor cortex revealed using MRI resting state images", Hum Brain Mapp, 1999, 8(2-3):151-156.
Arenkiel, et al. "In vivo light-induced activation of neural circuitry in transgenic mice expressing Channelrhodopsin-2", Neuron, 2007, 54:205-218.
Milella et al. "Opposite roles of dopamine and orexin in quinpirole-induced excessive drinking: a rat model of psychotic polydipsia" Psychopharmacology, 2010, 211:355-366.
Marin, et al., The Amino Terminus of the Fourth Cytoplasmic Loop of Rhodopsin Modulates Rhodopsin-Transduction Interaction, The Journal of Biological Chemistry, 2000, vol. 275, pp. 1930-1936.
Gonzalez, et al., "Cell-Based Assays and Instrumentation for Screening Ion-Channel Targets", DDT, 1999, vol. 4, No. 9, pp. 431-439.
Natochin, et al. "Probing rhodopsin-transducin interaction using *Drosophila* Rh1-bovine rhodopsin chimeras," Vision Res., 2006, vol. 46, No. 27: pp. 4575-4581.
Peterlin, et al. "Optical probing of neuronal circuits with calcium indicators," PNAS, 2000, vol. 97, No. 7: pp. 3619-3624.
Ibbini, et al.; "A Field Conjugation Method for Direct Synthesis of Hyperthermia Phased-Array Heating Patterns"; IEEE Transactions on Ultrasonics, Ferroelectrics, and Frequency Control; vol. 36, No. 1, pp. 3-9 (Jan. 1989).
Han, et a.; "Virogenetic and optogenetic mechanisms to define potential therapeutic targets in psychiatric disorders"; Neuropharmacology; vol. 62, pp. 89-100 (2012).
Zhang, et al.; "Optogenetic interrogation of neural circuits: Technology for probing mammalian brain structures"; Nature Protocols; vol. 5, No. 3, pp. 439-456 (Mar. 1, 2010).
Han, et al., "Millisecond-Timescale Optical Control of Neural Dynamics in the Nonhuman Primate Brain"; Neuron; vol. 62, pp. 191-198 (Apr. 30, 2009).

\* cited by examiner

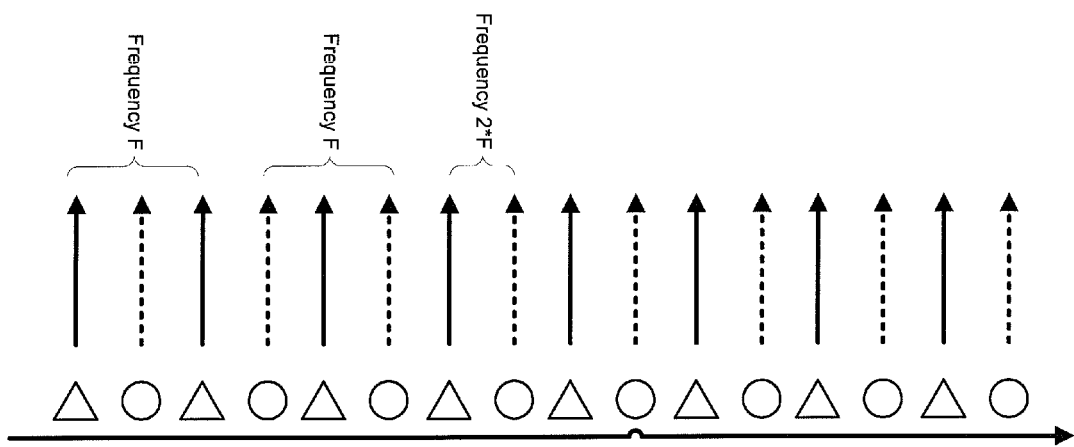
Example 3
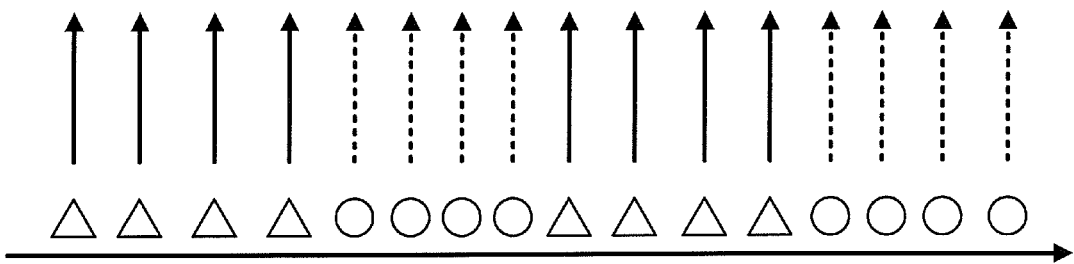
Example 4
Figure 2B

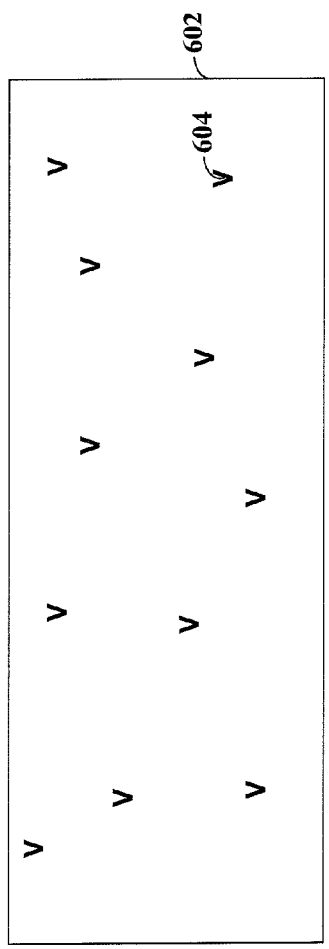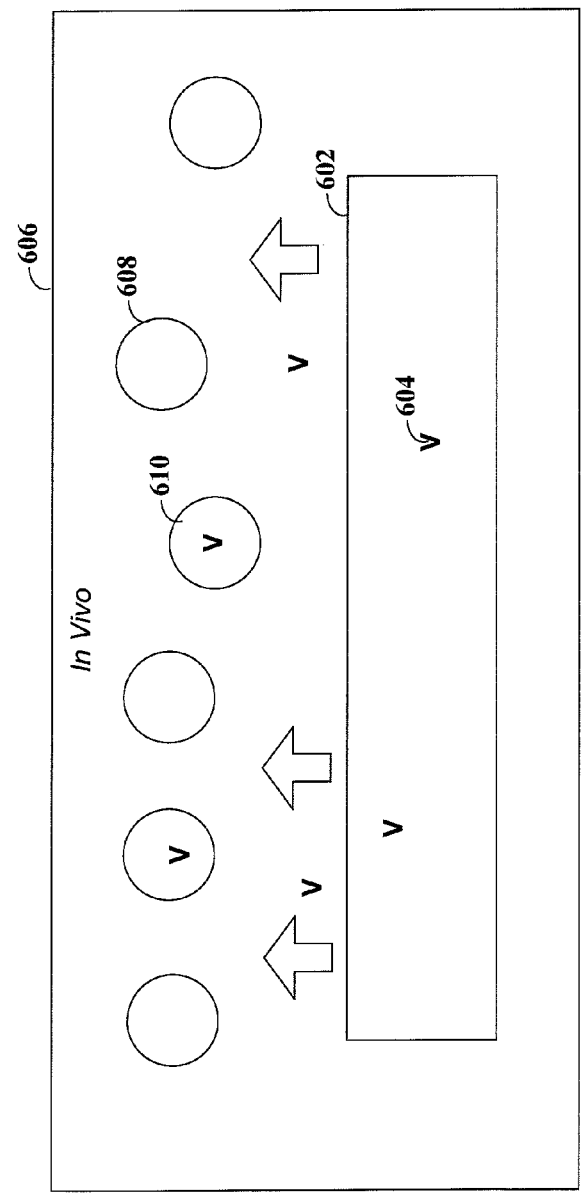
FIG. 8A
FIG. 8B

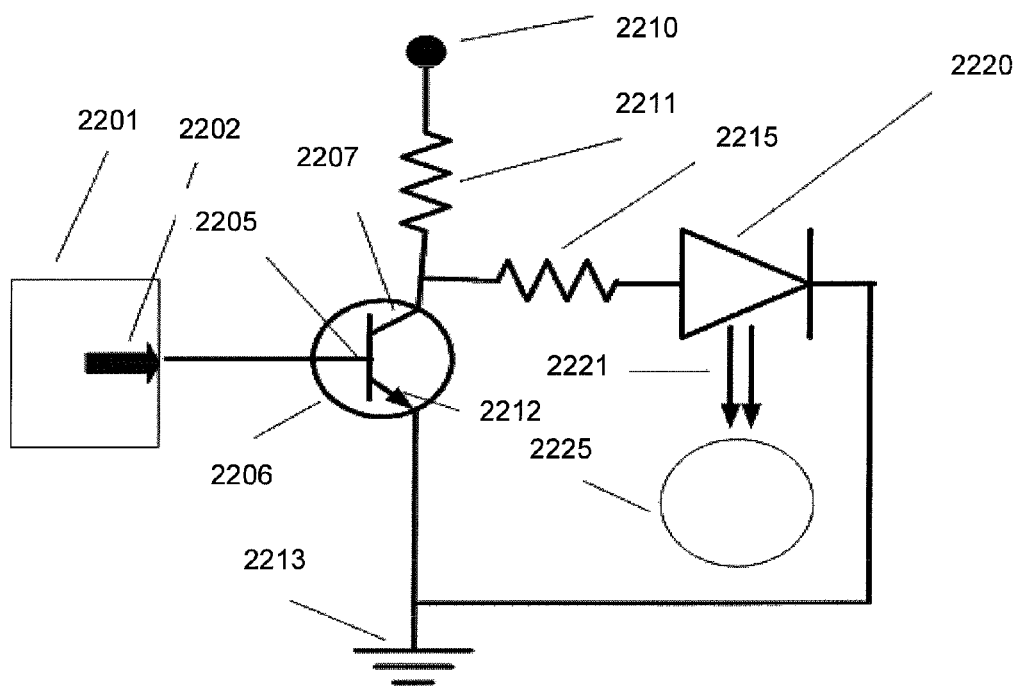
Figure 21A
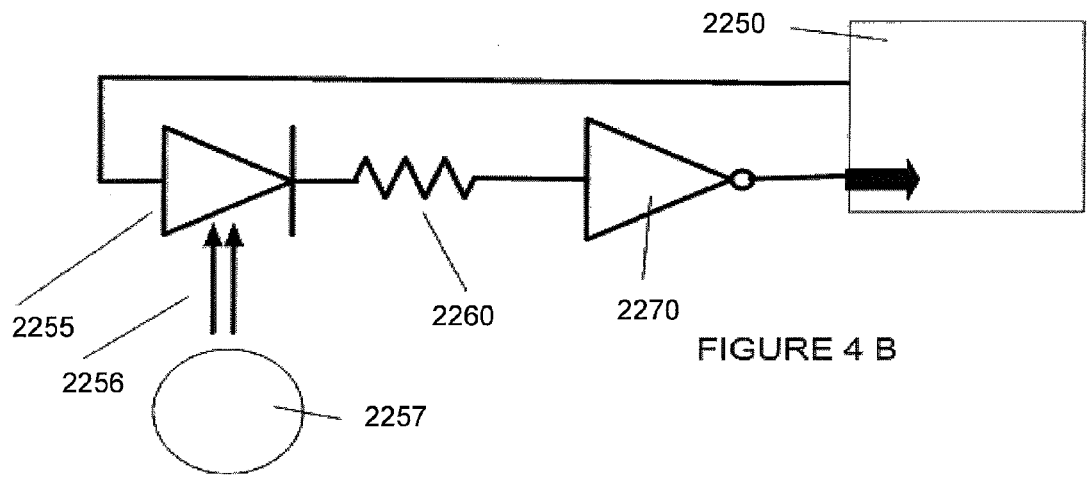
FIGURE 4 B
Figure 21B

LIGHT-SENSITIVE ION-PASSING MOLECULES

RELATED PATENT DOCUMENT

This patent document claims the benefit, under 35 U.S.C. §119(e), of U.S. Provisional Patent Application Ser. No. 61/314,969 filed on Mar. 17, 2010, and entitled "Light-Sensitive Ion-Passing Molecules;" this patent document and the Appendices filed in the underlying provisional application are fully incorporated herein by reference.

OVERVIEW AND SUMMARY

Aspects of the present disclosure relate generally to systems and approaches for stimulating target cells, and more particularly to using optics to stimulate the target cells. The stimulation of various cells of the body has been used to produce a number of beneficial effects. One method of stimulation involves the use of electrodes to introduce an externally generated signal into cells. One problem faced by electrode-based brain stimulation techniques is the distributed nature of neurons responsible for a given mental process. Conversely, different types of neurons reside close to one another such that only certain cells in a given region of the brain are activated while performing a specific task. Alternatively stated, not only do heterogeneous nerve tracts move in parallel through tight spatial confines, but the cell bodies themselves may exist in mixed, sparsely embedded configurations. This distributed manner of processing seems to defy the best attempts to understand canonical order within the CNS, and makes neuromodulation a difficult therapeutic endeavor. This architecture of the brain poses a problem for electrode-based stimulation because electrodes are relatively indiscriminate with regards to the underlying physiology of the neurons that they stimulate. Instead, physical proximity of the electrode poles to the neuron is often the single largest determining factor as to which neurons will be stimulated. Accordingly, it is generally not feasible to absolutely restrict stimulation to a single class of neuron using electrodes.

Another issue with the use of electrodes for stimulation is that because electrode placement dictates which neurons will be stimulated, mechanical stability is frequently inadequate, and results in lead migration of the electrodes from the targeted area. Moreover, after a period of time within the body, electrode leads frequently become encapsulated with glial cells, raising the effective electrical resistance of the electrodes, and hence the electrical power delivery required to reach targeted cells. Compensatory increases in voltage, frequency or pulse width, however, may spread the electrical current and increase the unintended stimulation of additional cells.

Another method of stimulus uses photosensitive bio-molecular structures to stimulate target cells in response to light. For instance, light activated proteins can be used to control the flow of ions through cell membranes. By facilitating or inhibiting the flow of positive or negative ions through cell membranes, the cell can be briefly depolarized, depolarized and maintained in that state, or hyperpolarized. Neurons are an example of a type of cell that uses the electrical currents created by depolarization to generate communication signals (i.e., nerve impulses). Other electrically excitable cells include skeletal muscle, cardiac muscle, and endocrine cells. Neurons use rapid depolarization to transmit signals throughout the body and for various purposes, such as motor control (e.g., muscle contractions), sensory responses (e.g., touch, hearing, and other senses) and computational functions (e.g., brain functions). Thus, the control of the depolarization of cells can be beneficial for a number of different purposes, including (but not limited to) psychological therapy, muscle control and sensory functions.

Various aspects of the present invention are directed toward a blue-light sensing opsin capable of inhibiting neural activity. The opsin comes from cryptophytes *Guillardia theta* (*G. theta*). The opsin of interest is the third opsin isolated from *G. theta*, and is abbreviated GtR3. GtR3 is capable of mediating a hyperpolarizing current when illuminated with light. Characterization of the action spectra for GtR3 suggests that the absorption maxima are around 490 nm, and GtR3 is not activated by yellow light.

Various aspects of the present invention are directed to a blue-light sensing channelrhodopsin capable of exciting neural activity. The channelrhodopsin is derived from *Dunaliella salina*. The channelrhodopsin of interest is abbreviated as DChR. DChR can be heterologously expressed in mammalian neurons and mediates a robust depolarizing current when illuminated with blue light. The action maxima for DChR are around 500 nm.

Consistent with an embodiment of the present disclosure, an inhibitory current flow is created by engineering a protein derived from *Guillardia theta* that responds to light by producing an inhibitory current to dissuade depolarization of a neuron. The protein is delivered to a neuron of interest and the neuron is exposed to light.

Consistent with another embodiment of the present disclosure, a method of optical stimulation of a cell expressing a GtR3 proton pump comprises providing a sequence of stimuli to the cell, each stimulus increasing the probability of a depolarizing event occurring in the cell. Light is provided to the cell to activate the expression of the GtR3 proton pump, thereby decreasing the probability of the depolarizing event occurring in the cell. In certain specific embodiments the light provided is in the blue light spectrum.

Consistent with another embodiment of the present disclosure, a system for controlling an action potential of a neuron or other cell in vivo is disclosed. The system comprises a delivery device that introduces a protein responsive to blue light to the neuron or cell. The protein responsive to blue light produces an inhibitory current in response to blue light. The system includes a blue light source that generates light for stimulation of the blue light responsive protein and a control device that controls the generation of light by the light source.

Consistent with another embodiment of the present disclosure, a method for providing a light responsive protein for mammalian expression is disclosed. A light responsive protein is isolated from *G. theta*. The isolated protein has a C-terminus and an N-terminus. An endoplasmic reticulum (ER) export signal is added to the C-terminus of the isolated protein to create an enhanced light responsive protein. The enhanced protein is placed in an empty virus vector for delivery to a cell of interest. The virus vector with the enhanced protein is then delivered to the cell of interest.

Consistent with an embodiment of the present disclosure an animal cell is provided. The animal cell includes an integrated exogenous molecule which expresses a proton pump responsive to blue light. The exogenous molecule is derived from *G. theta*. In certain embodiments the animal cell is a neural cell. The animal cell may also be a muscle cell or a cell line, for example.

The above discussion of the present disclosure is not intended to describe each illustrated embodiment or every implementation of the present invention. The figures and detailed description that follow more particularly exemplify these embodiments.

BRIEF DESCRIPTION OF THE DRAWINGS

The invention may be more completely understood in consideration of the detailed description of various embodiments of the invention that follows in connection with the accompanying drawings as follows:

FIG. 2B shows a stimulus profile for use with certain embodiments in which two or more light responsive proteins are introduced into the same cell population;

FIG. 8A and FIG. 8B show a diagram of a viral matrix, according to an example embodiment of the present invention;

FIGS. 21A and 21B depict an electronic circuit mechanism for activating the LED emitters used within the emitter/detector units, according to an example embodiment of the present invention;

Figure 1A:
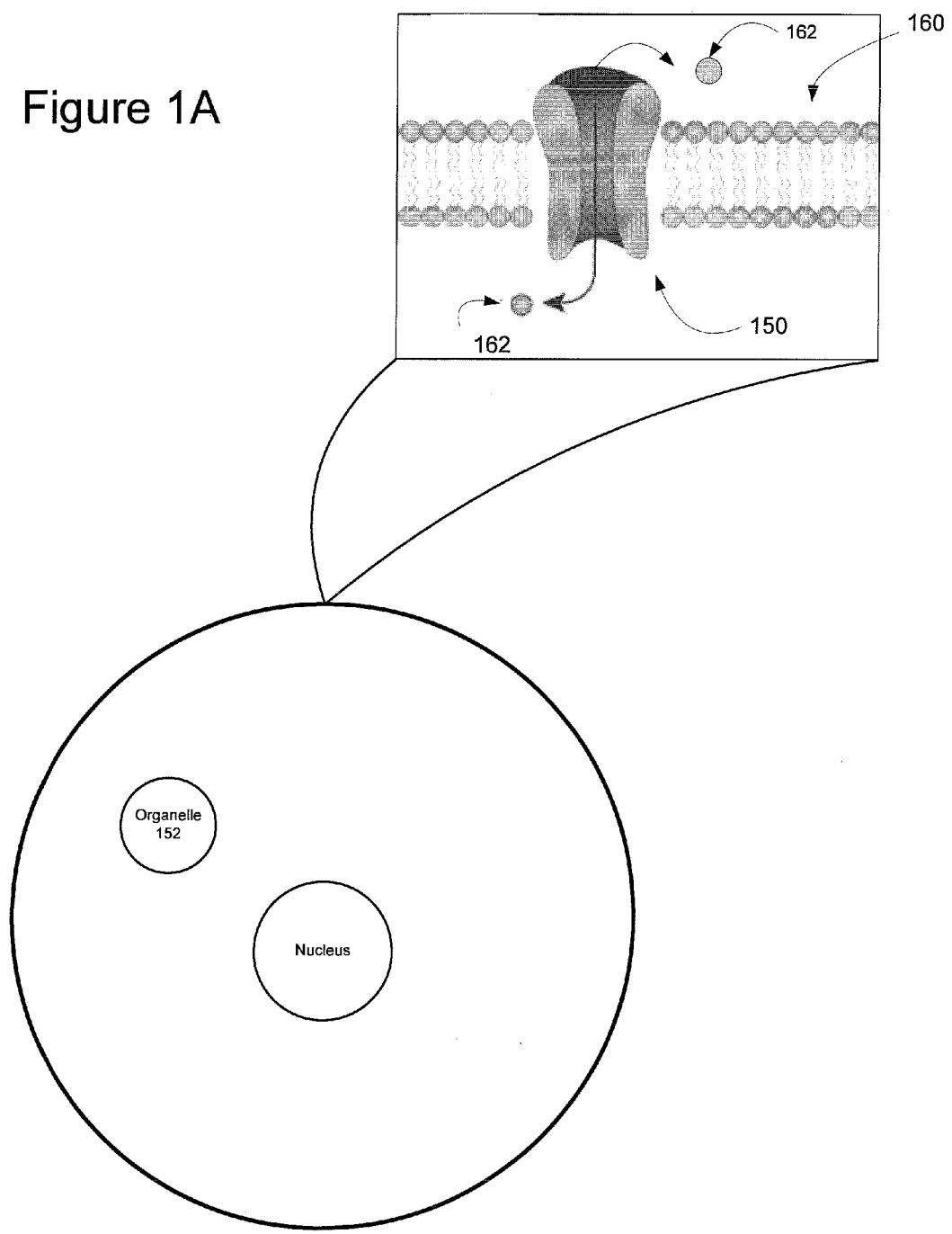
FIG. 1A shows an ion pump in an organelle membrane.

While the invention is amenable to various modifications and alternative forms, examples thereof have been shown by way of example in the drawings and will be described in detail. It should be understood, however, that the intention is not to limit the invention to the particular embodiments shown and/or described. On the contrary, the intention is to cover all modifications, equivalents, and alternatives falling within the spirit and scope of the invention.

DETAILED DESCRIPTION

The present invention is believed to be useful for facilitating practical application of a variety of photosensitive biomolecular structures, and the invention has been found to be particularly suited for use in arrangements and methods dealing with cellular membrane voltage control and stimulation. While the present invention is not necessarily limited to such applications, various aspects of the invention may be appreciated through a discussing of various examples using this context.

As used herein, stimulation of a target cell is generally used to describe modification of properties of the cell. For instance, the stimulus of a target cell may result in a change in the properties of the cell membrane that can lead to the depolarization or polarization of the target cell. In a particular instance, the target cell is a neuron and the stimulus affects the transmission of impulses by facilitating or inhibiting the generation of impulses by the neuron.

Consistent with one example embodiment of the present invention, a light-responsive protein is engineered in a cell. The protein affects a flow of ions (anions, cations or protons) across the cell membrane in response to light. This change in ion flow creates a corresponding change in the electrical properties of the cells including, for example, the voltage and current flow across the cell membrane. In one instance, the protein functions in vivo using an endogenous cofactor to modify ion flow across the cell membrane. In another instance, the protein changes the voltage across the cell membrane so as to dissuade or encourage action potential firing in the cell. In yet another instance, the protein is capable of changing the electrical properties of the cell within several milliseconds of the light being introduced.

An inhibitory protein dissuades firing of the action potential by moving the potential of the cell away from the action potential trigger level for the cell. In many neurons, this means that the protein increases the negative voltage seen across the cell membrane. In a specific instance, the protein acts as a proton pump that actively transfers protons out of the cell. In this manner, the protein generates an inhibitory current across the cell membrane. More specifically, the protein responds to light by lowering the voltage across the cell, thereby decreasing the probability that an action potential or depolarization will occur.

Certain aspects of the present invention are based on the identification and development of a molecule/protein that functions as a proton pump. This proton pump is derived from the cryptophyte *Guillardia theta* (*G. theta*) and has been developed for expression in target cells. In certain more specific embodiments the cell is a neuron. The engineered protein, GtR3, responds to blue light by producing an inhibitory current to dissuade depolarization of the cell. When expressed in neural cells the proton pump (GtR3) can be used to inhibit neural activity in response to blue light stimulation. The GtR3 pump responds to optical stimulus by creating an inhibitory current across the neural membrane. This current inhibits action potentials while the modified cell is exposed to (blue) light.

The present disclosure also provides for the modification of light-activated proteins expressed in a cell by the addition of one or more amino acid sequence motifs which enhance transport to the plasma membranes of mammalian cells. Light-activated proteins derived from evolutionarily simpler organisms may not be expressed or tolerated by mammalian cells or may exhibit impaired subcellular localization when expressed at high levels in mammalian cells. Consequently, in some embodiments, the light-activated protein expressed in a cell is fused to one or more amino acid sequence motifs selected from the group consisting of a signal peptide, an endoplasmic reticulum (ER) export signal, a membrane trafficking signal, and an N-terminal golgi export signal. The one or more amino acid sequence motifs which enhance light-activated protein transport to the plasma membranes of mammalian cells can be fused to the N-terminus, the C-terminus, or to both the N- and C-terminal ends of the light-activated protein. Optionally, the light-activated protein and the one or more amino acid sequence motifs may be separated by a linker. Additional protein motifs which can enhance light-activated protein transport to the plasma membrane of a cell are described in U.S. patent application Ser. No. 12/041,628 which is incorporated herein in its entirety.

The present disclosure additionally provides for light-activated proteins which contain amino acid substitutions, deletions, and insertions in the amino acid sequence of a native light-activated protein (such as, but not limited to, native GtR3, NpHR, DChR, and BR). Light-activated proteins include those in which one or more amino acid residues have undergone an amino acid substitution while retaining the ability to respond to light and the ability to control the polarization state of a plasma membrane. For example, light-activated proteins can be made by substituting one or more amino acids into the native or wild type amino acid sequence of the protein. In some embodiments, the invention includes proteins comprising altered amino acid sequences in comparison with a native amino acid sequence, wherein the altered light-activated protein retains the characteristic light-activated nature and/or the ability to regulate ion flow across plasma membranes of the precursor protein but may have altered properties in some specific aspects (for example, an increased or decreased sensitivity to light, an increased or decreased sensitivity to particular wavelengths of light, and/or an increased or decreased ability to regulate the polarization state of the plasma membrane of a mammalian cell, as compared to the native protein). Amino acid substitutions in a native protein sequence may be conservative or non-conservative and such substituted amino acid residues may or may not be one encoded by the genetic code. The standard twenty amino acid "alphabet" is divided into chemical families based on chemical properties of their side chains. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and side chains having aromatic groups (e.g., tyrosine, phenylalanine, tryptophan, histidine). A "conservative amino acid substitution" is one in which the amino acid residue is replaced with an amino acid residue having a chemically similar side chain (i.e., replacing an amino acid possessing a basic side chain with another amino acid with a basic side chain). A "non-conservative amino acid substitution" is one in which the amino acid residue is replaced with an amino acid residue having a chemically different side chain (i.e., replacing an amino acid having a basic side chain with an amino acid having an aromatic side chain).

Certain aspects of the present invention are directed to an animal cell expressing the GtR3 molecule. In this manner, the animal cell includes an integrated exogenous molecule which expresses a proton pump responsive to blue light. In certain non-limiting embodiments the animal cell can be a neural cell, a muscle cell, a rod or cone cell or a cell line. In some embodiments, the animal cell is a mammalian cell.

Provided herein is an animal cell comprising a light-activated protein expressed on the cell membrane, wherein the protein is responsive to blue light and is derived from *Guillardia theta*, wherein the protein is capable of mediating a hyperpolarizing current in the cell when the cell is illuminated with light. In some embodiments the light has a wavelength between about 450 and 495 nm. In some embodiments, the light has a wavelength about 490 nm. In some embodiments, the light-activated protein comprises an amino acid sequence at least 95% identical to the sequence shown in SEQ ID NO: 1. In some embodiments, the light-activated protein comprises an amino acid sequence at least 90%, 91%, 92%, 93%, 94%, 95%, 96%, 97%, 98%, 99%, or 100% identical to the sequence shown in SEQ ID NO: 1. In some embodiments, the light-activated protein comprises substitutions, deletions, and/or insertions introduced into a native amino acid sequence to increase or decrease sensitivity to light, increase or decrease sensitivity to particular wavelengths of light, and/or increase or decrease the ability of the light-activated protein to regulate the polarization state of the plasma membrane of the cell. In some embodiments, the light-activated protein contains one or more conservative amino acid substitutions. In some embodiments, the light-activated protein contains one or more non-conservative amino acid substitutions. The light-activated protein comprising substitutions, deletions, and/or insertions introduced into the native amino acid sequence suitably retains the ability to hyperpolarize the plasma membrane of a neuronal cell in response to light.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 1 and an endoplasmic reticulum (ER) export signal. The ER export signal may be fused to the C-terminus of the core amino acid sequence or may be fused to the N-terminus of the core amino acid sequence. In some embodiments, the ER export signal is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal comprises the amino acid sequence FXYENE (SEQ ID NO: 14), where X can be any amino acid. In some embodiments, the ER export signal comprises the amino acid sequence VXXSL, where X can be any amino acid. In some embodiments, the ER export signal comprises the amino acid sequence FCYENEV (SEQ ID NO: 12).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 1 and a signal peptide (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the signal peptide comprises the amino acid sequence MDYGGALSAVGRELLFVTNPVVVNGSVLVPEDQCYCAGWIESRGTNG (SEQ ID NO: 10). In some embodiments, other signal peptides (such as signal peptides from other opsins) may be used.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 1 and a trafficking signal (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal is derived from the amino acid sequence of the human inward rectifier potassium channel Kir2.1. In some embodiments, the trafficking signal comprises the amino acid sequence KSRITSEGEYIPLDQIDINV (SEQ ID NO: 11).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 1 and two or more amino acid sequence motifs which enhance transport to the plasma membranes of mammalian cells selected from the group consisting of a signal peptide, an ER export signal, and a membrane trafficking signal. In some embodiments, the light activated protein comprises an N-terminal signal peptide and a C-terminal ER export signal. In some embodiments, the light activated protein comprises an N-terminal signal peptide and a C-terminal trafficking signal. In some embodiments, the light activated protein comprises an N-terminal signal peptide, a C-terminal ER Export signal, and a C-terminal trafficking signal. In some embodiments, the light activated protein comprises a C-terminal ER Export signal and a C-terminal trafficking signal. In some embodiments, the C-terminal ER Export signal and the C-terminal trafficking signal are linked by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the proteins described herein, such as a light-activated protein comprising a core amino acid sequence at least 90%, 91%, 92%, 93%, 94%, 95%, 96%, 97%, 98%, 99%, or 100% identical to the sequence shown in SEQ ID NO: 1. Also provided herein are expression vectors (such as a viral vector described herein) comprising a polynucleotide encoding any of the proteins described herein, such as a light-activated protein comprising a core amino acid sequence at least 90%, 91%, 92%, 93%, 94%, 95%, 96%, 97%, 98%, 99%, or 100% identical to the sequence shown in SEQ ID NO: 1. The polynucleotides may be used for expression of the light-activated protein in animal cells.

Provided herein is an animal cell comprising a light-activated protein expressed on the cell membrane, wherein the protein is responsive to blue light and is derived from *Dunaliella salina*, wherein the protein is capable of mediating a depolarizing current in the cell when the cell is illuminated with light. In some embodiments the light has a wavelength between about 450 and 495 nm. In some embodiments, the light has a wavelength about 490 nm. In some embodiments, the light-activated protein comprises an amino acid sequence at least 95% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2. In some embodiments, the light-activated protein comprises an amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2. In some embodiments, the light-activated protein comprises substitutions, deletions, and/or insertions introduced into a native amino acid sequence to increase or decrease sensitivity to light, increase or decrease sensitivity to particular wavelengths of light, and/or increase or decrease the ability of the light-activated protein to regulate the polarization state of the plasma membrane of the cell. In some embodiments, the light-activated protein contains one or more conservative amino acid substitutions. In some embodiments, the light-activated protein contains one or more non-conservative amino acid substitutions. The light-activated protein comprising substitutions, deletions, and/or insertions introduced into the native amino acid sequence suitably retains the ability to depolarize the plasma membrane of a neuronal cell in response to light.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2 and an endoplasmic reticulum (ER) export signal. The ER export signal may be fused to the C-terminus of the core amino acid sequence or may be fused to the N-terminus of the core amino acid sequence. In some embodiments, the ER export signal is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal comprises the amino acid sequence FXYENE (SEQ ID NO: 14), where X can be any amino acid. In some embodiments, the ER export signal comprises the amino acid sequence VXXSL, where X can be any amino acid. In some embodiments, the ER export signal comprises the amino acid sequence FCYENEV (SEQ ID NO: 12).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2 and a signal peptide (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the signal peptide comprises the amino acid sequence MDYGGALSAVGRELLFVTNPVVVNGSV-LVPEDQCYCAGWIESRGTNG (SEQ ID NO: 10). In some embodiments, other signal peptides (such as signal peptides from other opsins) may be used.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2 and a trafficking signal (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal is derived from the amino acid sequence of the human inward rectifier potassium channel Kir2.1. In some embodiments, the trafficking signal comprises the amino acid sequence KSRITSEGEYIPLD-QIDINV (SEQ ID NO: 11).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2 and two or more amino acid sequence motifs which enhance transport to the plasma membranes of mammalian cells selected from the group consisting of a signal peptide, an ER export signal, and a membrane trafficking signal. In some embodiments, the light activated protein comprises an N-terminal signal peptide and a C-terminal ER export signal. In some embodiments, the light activated protein comprises an N-terminal signal peptide and a C-terminal trafficking signal. In some embodiments, the light activated protein comprises an N-terminal signal peptide, a C-terminal ER Export signal, and a C-terminal trafficking signal. In some embodiments, the light activated protein comprises a C-terminal ER Export signal and a C-terminal trafficking signal. In some embodiments, the C-terminal ER Export signal and the C-terminal trafficking signal are linked by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein are isolated polynucleotides encoding any of the proteins described herein, such as a light-activated protein comprising a core amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2. Also provided herein are expression vectors (such as a viral vector described herein) comprising a polynucleotide encoding any of the proteins described herein, such as a light-activated protein comprising a core amino acid sequence at least 90%, 91%, 92%, 93%, 94%, 95%, 96%, 97%, 98%, 99%, or 100% identical to the sequence shown in residues 25-365, 24-365, 23-365, 22-365, 21-365, 20-365, 19-365, 18-365, 17-365, 16-365, 15-365, 14-365, 13-365, 13-365, 12-365, 11-365, 10-365, 9-365, 8-365, 7-365, 6-365, 5-365, 4-365, 3-365, 2-365, or 1-365 of SEQ ID NO: 2. The polynucleotides may be used for expression of the light-activated protein in animal cells.

Provided herein is an animal cell comprising a light-activated protein expressed on the cell membrane, wherein the protein is responsive to amber as well as red light and is derived from *Natronomonas pharaonis*, wherein the protein is capable of mediating a hyperpolarizing current in the cell when the cell is illuminated with light. In some embodiments the light has a wavelength between about 580 and 630 nm. In some embodiments, the light has a wavelength about 589 nm. In some embodiments, the light has a wavelength greater than about 630 nm (e.g. less than 740 nm). In some embodiments, the light has a wavelength around 630 nm. In some embodiments, the light-activated protein comprises an amino acid sequence at least 95% identical to the sequence shown in SEQ ID NO: 3. In some embodiments, the light-activated protein comprises an amino acid sequence at least 90%, 91%, 92%, 93%, 94%, 95%, 96%, 97%, 98%, 99%, or 100% identical to the sequence shown in SEQ ID NO: 3. In some embodiments, the light-activated protein comprises substitutions, deletions, and/or insertions introduced into a native amino acid sequence to increase or decrease sensitivity to light, increase or decrease sensitivity to particular wavelengths of light, and/or increase or decrease the ability of the light-activated protein to regulate the polarization state of the plasma membrane of the cell. In some embodiments, the light-activated protein contains one or more conservative amino acid substitutions. In some embodiments, the light-activated protein contains one or more non-conservative amino acid substitutions. The light-activated protein comprising substitutions, deletions, and/or insertions introduced into the native amino acid sequence suitably retains the ability to hyperpolarize the plasma membrane of a neuronal cell in response to light.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 3 and an endoplasmic reticulum (ER) export signal. The ER export signal may be fused to the C-terminus of the core amino acid sequence or may be fused to the N-terminus of the core amino acid sequence. In some embodiments, the ER export signal is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal comprises the amino acid sequence FXYENE (SEQ ID NO: 14), where X can be any amino acid. In some embodiments, the ER export signal comprises the amino acid sequence VXXSL, where X can be any amino acid. In some embodiments, the ER export signal comprises the amino acid sequence FCYENEV (SEQ ID NO: 12).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 3 and a trafficking signal (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal is derived from the amino acid sequence of the human inward rectifier potassium channel Kir2.1. In some embodiments, the trafficking signal comprises the amino acid sequence KSRITSEGEYIPLD-QIDINV (SEQ ID NO: 11).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 3 and two or more amino acid sequence motifs which enhance transport to the plasma membranes of mammalian cells selected from the group consisting of an ER export signal and a membrane trafficking signal. In some embodiments, the light activated protein comprises a C-terminal ER Export signal and a C-terminal trafficking signal. In some embodiments, the C-terminal ER Export signal and the C-terminal trafficking signal are linked by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 3, wherein the N-terminal signal peptide of SEQ ID NO:3 is deleted or substituted In some embodiments, the light-activated protein comprises an amino acid sequence at least 95% identical to the sequence shown in residues 40-291, 39-291, 38-291, 37-291, 36-291, 35-291, 34-291, 33-291, 32-291, 31-291, 30-291, 29-291, 28-291, 27-291, 26-291, 25-291, 24-291, 23-291, 22-291, 21-291, 20-291, 19-291, 18-291, 17-291, 16-291, 15-291, 14-291, 13-291, 13-291, 12-291, 11-291, 10-291, 9-291, 8-291, 7-291, 6-291, 5-291, 4-291, 3-291, 2-291, or 1-291 of SEQ ID NO:3. In some embodiments, other signal peptides (such as signal peptides from other opsins) may be used. The light-activated protein may further comprise an ER transport signal and a membrane trafficking signal described herein.

Also provided herein are polynucleotides encoding for any of the proteins described herein, such as a light-activated protein comprising a core amino acid sequence at least 90%, 91%, 92%, 93%, 94%, 95%, 96%, 97%, 98%, 99%, or 100% identical to the sequence shown in SEQ ID NO: 3, an ER export signal, and a membrane trafficking signal. The polynucleotides may be in an expression vector (such as a viral vector described herein). The polynucleotides may be used for expression of the light-activated protein in animal cells.

Provided herein is an animal cell comprising a light-activated protein expressed on the cell membrane, wherein the protein is responsive to green light and is derived from *Halobacterium salinarum* wherein the protein is capable of mediating a hyperpolarizing current in the cell when the cell is illuminated with light. In some embodiments the light has a wavelength between about 520 and 570 nm. In some embodiments, the light has a wavelength about 560 nm. In some embodiments, the light-activated protein comprises an amino acid sequence at least 95% identical to the sequence shown in SEQ ID NO: 4. In some embodiments, the light-activated protein comprises an amino acid sequence at least 90%, 91%, 92%, 93%, 94%, 95%, 96%, 97%, 98%, 99%, or 100% identical to the sequence shown in SEQ ID NO: 4. In some embodiments, the light-activated protein comprises substitutions, deletions, and/or insertions introduced into a native amino acid sequence to increase or decrease sensitivity to light, increase or decrease sensitivity to particular wavelengths of light, and/or increase or decrease the ability of the light-activated protein to regulate the polarization state of the plasma membrane of the cell. In some embodiments, the light-activated protein contains one or more conservative amino acid substitutions. In some embodiments, the light-activated protein contains one or more non-conservative amino acid substitutions. The light-activated protein comprising substitutions, deletions, and/or insertions introduced into the native amino acid sequence suitably retains the ability to hyperpolarize the plasma membrane of a neuronal cell in response to light.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 4 and an endoplasmic reticulum (ER) export signal. The ER export signal may be fused to the C-terminus of the core amino acid sequence or may be fused to the N-terminus of the core amino acid sequence. In some embodiments, the ER export signal is linked to the core amino acid sequence by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the ER export signal comprises the amino acid sequence FXYENE (SEQ ID NO: 14), where X can be any amino acid. In some embodiments, the ER export signal comprises the amino acid sequence VXXSL, where X can be any amino acid. In some embodiments, the ER export signal comprises the amino acid sequence FCYENEV (SEQ ID NO: 12).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% 25 identical to the sequence shown in SEQ ID NO: 4 and a trafficking signal (e.g., which enhances transport to the plasma membrane). The signal peptide may be fused to the C-terminus of the core amino acid sequence or may be fused to the N-terminus of the core amino acid sequence. In some embodiments, the signal peptide is linked to the core amino acid sequence by a linker. The linker can comprise any of 5, 10, 20, 30, 40, 50, 30 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments, the trafficking signal is derived from the amino acid sequence of the human inward rectifier potassium channel Kir2.1. In some embodiments, the trafficking signal comprises the amino acid sequence KSRIT-SEGEYIPLDQIDINV (SEQ ID NO: 11).

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 4 and two or more amino acid sequence motifs which enhance transport to the plasma membranes of mammalian cells selected from the group consisting of an ER export signal and a membrane trafficking signal. In some embodiments, the light activated protein comprises a C-terminal ER Export signal and a C-terminal trafficking signal. In some embodiments, the C-terminal ER Export signal and the C-terminal trafficking signal are linked by a linker. The linker can comprise any of 5, 10, 20, 30, 40, 50, 75, 100, 125, 150, 175, 200, 225, 250, 275, 300, 400, or 500 amino acids in length. The linker may further comprise a fluorescent protein, for example, but not limited to, a yellow fluorescent protein, a red fluorescent protein, a green fluorescent protein, or a cyan fluorescent protein. In some embodiments the ER Export signal is more C-terminally located than the trafficking signal. In some embodiments the trafficking signal is more C-terminally located than the ER Export signal.

Also provided herein is an animal cell comprising a light-activated protein expressed on the cell membrane, wherein the protein comprises a core amino acid sequence at least 90%, 91%, 92%, 93%, 94%, 95%, 96%, 97%, 98%, 99%, or 100% identical to the sequence shown in SEQ ID NO: 4, wherein the N-terminal signal peptide of SEQ ID NO:4 is deleted or substituted. In some embodiments, the light-activated protein comprises an amino acid sequence at least 95% identical to the sequence shown in residues 40-262, 39-262, 38-262, 37-262, 36-262, 35-262, 34-262, 33-262, 32-262, 31-262, 30-262, 29-262, 28-262, 27-262, 26-262, 25-262, 24-262, 23-262, 22-262, 21-262, 20-262, 19-262, 18-262, 17-262, 16-262, 15-262, 14-262, 13-262, 13-262, 12-262, 11-262, 10-262, 9-262, 8-262, 7-262, 6-262, 5-262, 4-262, 3-262, 2-262, or 1-262 of SEQ ID NO:4. In some embodiments, other signal peptides (such as signal peptides from other opsins) may be used. The light-activated protein may further comprise an ER transport signal and/or a membrane trafficking signal described herein.

Also provided herein are polynucleotides encoding for any of the proteins described herein, such as a light-activated protein comprising a core amino acid sequence at least 90%, 91%, 92%, 93%, 94%, 95%, 96%, 97%, 98%, 99%, or 100% identical to the sequence shown in SEQ ID NO: 4, an ER export signal, and a membrane trafficking signal. The polynucleotides may be in an expression vector (such as a viral vector described herein). The polynucleotides may be used for expression of the light-activated protein in animal cells.

In certain more particular embodiments, a method for providing a light responsive protein for mammalian expression is provided. A light responsive protein is isolated from *G. theta* (GtR3). GtR3 has a C-terminus and an N-terminus. A promoter is added to the C-terminus of GtR3. In certain embodiments the promoter is an endoplasmic reticulum (ER) export signal. For more specifics on optimizing GtR3 for expression in mammalian cells, see Appendix A as filed in the underlying provisional application and entitled, "Molecular and Cellular Approaches for Diversifying and Extending Optogenetics."

An excitatory protein encourages firing of the action potential by moving the potential of the cell toward the action potential trigger level for the cell. In many neurons, this means that the protein decreases the negative voltage seen across the cell membrane. In a specific instance, the protein acts an additional ion channel that transfers cations into the cell. In this manner, the protein generates an excitatory current across the cell membrane. More specifically, the protein responds to light by raising the voltage across the cell membrane, thereby increasing the probability that an action potential or depolarization will occur. In certain instances the voltage across the cell membrane can be increased to the action potential trigger level or higher, causing depolarization of the cell.

Certain aspects of the present invention are based on the identification and development of a channel (DChR) that is derived from *Dunaliella salina*. Channelrhodopsin DChR mediates a robust depolarizing current when illuminated with blue light. The depolarizing current may cause a cell to become excited in response to exposure to blue light. In certain embodiments DChR is expressed as an exogenous protein in a cell of interest. For neural cells, DChR can function as an excitatory protein that uses an endogenous cofactor when delivered to a cell of interest.

The introduction of GtR3 and DChR to the field of optogenetics opens the door for a variety of applications. For instance, GtR3 and DChR can be used in combination with other optogenetic ion-passing molecules, such as ChR2 (developed from *Chlamydomonas reinhardtii*). GtR3 and DChR have different operating parameters, relative to other light-responsive molecules. This facilitates the development of a cell or a cell population that has a precisely-tuned response to different wavelengths of light. The parameter that can be tuned include, but are not limited to, current density, hyperpolarization level, membrane conductance, stimulus frequency, resting potential, optical wavelength and/or optical intensity.

In another example embodiment, a method for controlling action potential of a neuron involves the following steps: engineering a first light responsive protein in the neuron; producing, in response to light, an inhibitory current in the neuron and from the first light responsive protein; engineering a second light responsive protein in the neuron; and producing, in response to light, an excitation current in the neuron from the second light responsive protein. The first light responsive protein and the second light responsive protein may be responsive to different wavelengths of light. In certain instances, the use of DChR or GtR3 can facilitate specific current densities for this excitation or inhibitory current and/or optical wavelength at which such current is generated.

In another example embodiment, a method for controlling action potential of a neuron involves the following steps: engineering a first light responsive protein in the neuron; producing, in response to light, an inhibitory current in the neuron and from the first light responsive protein; engineering a second light responsive protein in the neuron; and producing, in response to light, a second inhibitory current from the second light responsive protein, the combination of the two currents more strongly inhibiting the neuron than a single light responsive protein. For instance, the first light responsive protein could be NpHR and the second light responsive protein could be GtR3.

Another method for controlling a voltage level across a cell membrane of a cell includes measuring the voltage level of the cell membrane. A light responsive protein is engineered and introducing the light responsive protein into the cell, where it is expressed. A light of a particular wavelength is provided, which produces a reaction in the cell by the light responsive protein. The response by the light responsive protein produces a current across the cell membrane. The current is responsive to the measured voltage level.

Another aspect of the present invention is directed to a system for controlling an action potential of a neuron in vivo. The system includes a delivery device, a light source, and a control device. The delivery device introduces a light responsive protein to the neuron, with the light responsive protein producing an inhibitory current. The light source generates light for stimulating the light responsive protein, and the control device controls the generation of light by the light source. In other embodiments the light responsive protein introduced into the neuron produces an excitatory current.

In more detailed embodiments, such a system is further adapted such that the delivery device introduces the light responsive protein by one of transfection, transduction and microinjection, and/or such that the light source introduces light to the neuron via one of an implantable light generator and fiber-optics. For additional detail regarding method of delivery and expression of genes, see, PCT Publication No. WO2010/019619 A1 (PCT/US2009/053474), entitled "Method and Composition for Controlling Gene Expression," which is fully incorporated herein by reference.

Another aspect of the present disclosure is directed to a method for treatment of a disorder. The method targets a group of neurons associated with the disorder; and in this group, the method includes engineering inhibitory proteins to respond to light by producing an inhibitory current to dissuade depolarization of the neurons, and exposing the neurons to light, thereby dissuading depolarization of the neurons.

Yet another aspect of the present disclosure is directed to a further method for treatment of a disorder. The method targets a group of neurons associated with the disorder; and in this group, the method includes engineering excitatory proteins to respond to light by producing an excitatory current to encourage depolarization of the neurons, and exposing the neurons to light, thereby encouraging depolarization of the neurons. In other aspects of the present invention both inhibitory and excitatory proteins, responsive to different wavelengths of light, are introduced into a targeted group of neurons. The neurons are exposed alternatively to different wavelengths of light to excite, and inhibit the depolarization of the neurons.

More detailed embodiments expand on such techniques. For instance, another aspect of the present invention co-expresses GtR3 and DChR with other known opsins, such as NpHR and VChR1 in the species (e.g., a mouse and *C. elegans*). Also, opsins creating currents of opposite polarity and having different color sensitivity are integrated with calcium imaging in acute mammalian brain slices for bidirectional optical modulation and readout of neural activity. Likewise, the coupled opsins can be targeted to *C. elegans* muscle and cholinergic motoneurons to control locomotion bidirectionally. Together coupled opsins can be used as a complete and complementary optogenetic system for multimodal, high-speed, genetically-targeted, all-optical interrogation of living neural circuits. Further, more than one set of cells may be targeted with different couplings of opsins, allowing for precise control of multiple sets of cells independently from each other.

In addition to GtR3 and DChR, there are a number of channelrhodopsins, halorhodopsins, and microbial opsins that can be engineered to optically regulate ion flux or second messengers within cells. Various embodiments of the invention include codon-optimized, mutated, truncated, fusion proteins, targeted versions, or otherwise modified versions of such ion optical regulators. For example, GtR3 and DChR (e.g., Appendices B and C as filed in the underlying provisional application). The cited opsins are used as representative of a number of different embodiments. Discussions specifically identifying GtR3 and DChR are not meant to limit the invention to such specific examples of optical regulators unless specified. For further details regarding the above mentioned sequences, reference can be made to "Multimodal fast optical interrogation of neural circuitry" by Feng Zhang, et al, Nature (Apr. 5, 2007) Vol. 446: 633-639, which is fully incorporated herein by reference.

Table 1 shows identified opsins for inhibition of cellular activity across the visible spectrum:

TABLE 1

Fast optogenetics: inibition across the visible spectrum

| Opsin Type | Biological Origin | Wavelength Sensitivity | Defined action |
|---|---|---|---|
| NpHR | natronomonas pharaonis | 680 nm utility (with 3.0 series) 589 nm max | Inhibition (hyperpolarization) |
| BR | halobacterium helobium | 570 nm max | Inhibition (hyperpolarization) |
| AR | Acetabulaira acetabulum | 518 nm max | Inhibition (hyperpolarization) |
| GtR3 | Guillardia theta | 472 nm max | Inhibition (hyperpolarization) |

Table 2 shows identified opsins for excitation and modulation across the visible spectrum:

TABLE 2

Fast optogenetics: excitation and modulation across the visible spectrum

| Opsin Type | Biological Origin | Wavelength Sensitivity | Defined action |
|---|---|---|---|
| VChR1 | Volvox carteri | 589 nm utility 535 nm max | Excitation (depolarization) |
| optoXRs | Bos taurus | 505 nm max | Modulation (Gs, Gq pathways) |
| DChR | Dunaliella salina | 500 nm max | Excitation (depolarization) |
| SFOs | Chlamydomonas reinhardtii | 546 nm deactivate 470 nm activate | modulation (electrical up states) |
| ChR2 | Chlamydomonas reinhardtii | 470 nm max 380-405 nm utility | Excitation (depolarization) |

Opsins described in U.S. patent application Ser. Nos. 12/988,567 and 12/996,753, U.S. Patent Application Publication Nos: 2007/0054319, 2010/0234273, 2007/0261127, 2007/0053996, 2010/0145418, 2009/0093403, 2008/0085265, 2010/0190229, 2009/0099038, and PCT Publication No. PCT/US09/64355 are incorporated herein by reference in their entirety.

In certain embodiments of the present invention, various combinations of the listed opsins, for example, are delivered to a cell population. A second combination can be delivered to a different cell population. Using the defined action and the wavelength sensitivity information for each opsin, combinations of opsins may be chosen to excite certain cell populations while inhibiting others, for example.

Consistent with one example embodiment of the present invention, target cells are stimulated using an implantable arrangement. The implantable arrangement includes a biological portion that facilitates the stimulation of the target cells in response to receipt of light. The implantable arrangement also includes a light generator for creating light to trigger the stimulus of the target cells. In certain embodiments the implantable arrangement includes a microcontroller and a feedback loop. The color of light created by the light generator is dependent on the voltage of the cell. The target cell can include multiple light sensitive proteins which respond to different wavelengths of light to inhibit or encourage depolarization of the target cell.

Consistent with another example embodiment of the present invention, a method is implemented for stimulating target cells in vivo using gene transfer vectors (for example, viruses) capable of inducing photosensitive ion channel growth (for example, DChR ion channels) or photosensitive ion pumps (for example, GtR3 proton pumps). The vectors are implanted in the body, along with the electronic components of the apparatus. A light producing device is implanted near the target cells. The target cells are stimulated in response to light generated by the light producing device. In certain more specific embodiments, gene transfer vectors are capable of inducing growth of more than one ion channel or ion pump.

Consistent with a particular embodiment of the present invention, a protein is introduced to one or more target cells. When introduced into a cell, the protein changes the potential of the cell in response to light having a certain frequency. This may result in a change in resting potential that can be used to control (dissuade) action potential firing. In a specific example, the protein is GtR3 which acts as a membrane pump for transferring charge across the cell membrane in response to light. Membrane pumps are energy transducers which use electromagnetic or chemical bond energy for translocation of ions across the membrane. In other specific examples, the protein is a halorhodopsin which acts as the membrane pump. The halorhodopsin membrane pump moves specific ions across the membrane. For further information regarding halorhodopsin membrane pumps, reference can be made to "Halorhodopsin Is a Light-driven Chloride Pump" by Brigitte Schobert et al, The Journal of Biological Chemistry Vol. 257, No. 17. Sep. 10, 1982, pp. 10306-10313, which is fully incorporated herein by reference.

In specific embodiments GtR3 and NpHR may be introduced into different target cell populations, respectively. The two inhibitors are responsive to different wavelengths of light allowing the two proteins to be used to inhibit different target cell populations independently. GtR3 and NpHR may also be introduced into the same cell population for gradient control over the inhibition of a cell population. For instance, GtR3 and NpHR molecules within the same cell can be activated relatively independent from one another. Thus, a first level of inhibition can be implemented by activating the molecule type (GtR3 or NpHR) that provides the lowest current levels for the cell conditions. The next level could be implemented by deactivating this first molecule type and activating the other molecule type. A third level can be implemented by activating both molecules simultaneously. Further gradient control can be achieved by varying the wavelength of light, or by varying the light intensity at or near the maxima of each protein, for example.

The combination of multiple inhibitors can also lead to shunting inhibition, which combined with hyperpolarizing inhibition can lead to stronger hyperpolarization in the combination approach than from using a single inhibitor protein. In a cell membrane the reversal potential (also known as the Nernst potential) of an ion is the membrane potential at which there is no net (overall) flow of ions from one side of the membrane to the other. Each type of ion channel has a specific reversal potential. At the Nernst potential the outward and inward rates of ion movement are the same (the ion flux is in equilibrium for the ion type). A change of membrane potential on either side of the Nernst potential reverses the overall direction of ion flux. If the reversal potential of an ion channel is below the resting potential (or instant potential in the case where a light responsive protein ion channel been stimulated and changed the "resting" potential) of the cell membrane, the ion channel will contribute to inhibition through hyperpolarization of the cell. In contract, if the reversal potential for an ion channel is between the resting potential and the threshold for the generation of action potentials, the ion channel will have a shunting effect. The concentration gradient for any given ion (for example Cl−) is determined in part by the balance between the activity of the other ions (for example Na+ and K+). Shunting inhibition is termed "shunting" because the channel conductance short-circuits currents that are generated at adjacent excitatory channels. Accordingly, the addition of a light responsive protein channel with inhibitory characteristics can lower the membrane potential to a point where an existing ion channel reverses direction and "shunts" the current, creating an additional path which prevents the membrane potential from reaching the action potential.

Provided herein are populations of cells, tissues, and non-human animals comprising a cell expressing one or more of the light-activated proteins described herein on the cell membrane. Methods of using the cells, population of cells, tissues, and non-human animals are also provided.

FIG. 1A shows a light responsive ion-passing molecule (a pump or channel) 150 in a cell membrane 160. In general, ion channels allow flow toward the channel's reversal potential (or equilibrium potential for the channel); the direction is based on whether the membrane potential is above or below the channel's reversal potential. Ion channels do not require additional energy to transport the ion. Ion pumps transport ions against the equilibrium flow and require introduction of some form of energy, such as ATP, to transport the ion across the membrane. Ions 162 may be anions or cations. The hydrogen ion is a proton (as well as a cation). The direction the ions flow along with the ions polarity will determine whether the ion-passing molecule has a hyperpolarizing effect or a depolarizing effect on the cell. In certain embodiments, the ion-passing molecule 150 transports protons out of the cell, causing hyperpolarization of the cell and inhibition of the firing of the cell. The light responsive ion channel/pump 150 is not open/active unless light of the appropriate frequency is present.

Figure 1B:
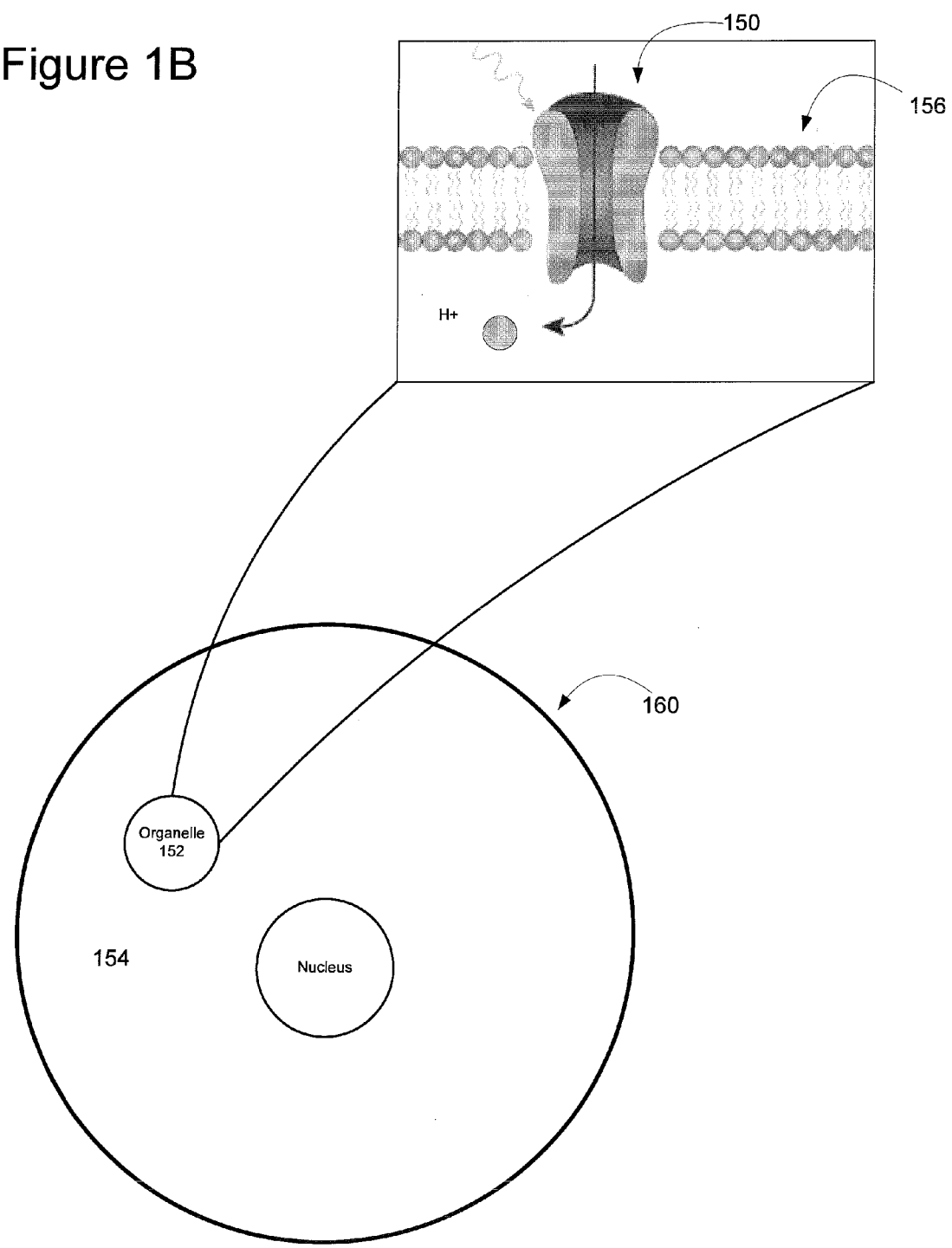
FIG. 1B shows an ion pump in a cell membrane.

FIG. 1B shows an alternative embodiment of the present invention where a light responsive ion-passing molecule 150 is expressed within membranes that are internal to a cell. Many of the internal components of the cell have membranes similar to the cell membrane that encloses the cell. The membrane of organelle 152 contains naturally occurring ion pump/channels before introduction of a light responsive protein. Depending on the promoters introduced along with the exogenous light responsive protein, the light responsive protein can express as an ion pump/channel in the membrane of variety of different organelles, in the cell membrane, or a combination of different organelles and/or the cell membrane. In certain embodiments the light responsive ion-passing molecule 150 is a proton pump. In other embodiments the pump can be a pump/channel for a specific cation or a specific anion. The ion pump/channel 150 is located in the membrane 156 of the organelle.

The transfer of protons across a membrane in which the ion-passing molecule is expressed can be used to change the membrane potential of either or both membrane 156 and membrane 160. The transport of protons out of the cytoplasm can cause a cell to become hyperpolarized, resulting in inhibition of the cell.

In certain instances, the pump/channel 150 can be used to change the pH of the organelle 152 and the surrounding cytoplasm 154. In addition, the pH of the organelle in which the protein is expressed can be changed and/or controlled. Because most enzymes within a cell are pH sensitive, the pH of each organelle critically determines the coordinated biochemical reactions occurring along the endocytic and secretory pathways. Aberrations of the normal organellar pH homeostasis can lead to significant functional changes. Depending on the level of expression of the light responsive protein, and the location (i.e. which organelle) various functions of the cell may be enhanced or retarded. At high enough levels of expression the cell may be killed. This can be desirable in unwanted (i.e. cancer) cells. For instance, cells can be locally transfected at a cancerous tumor location and then carefully directed light pulses can be used to shrink or eliminate the tumor.

Figure 2A:
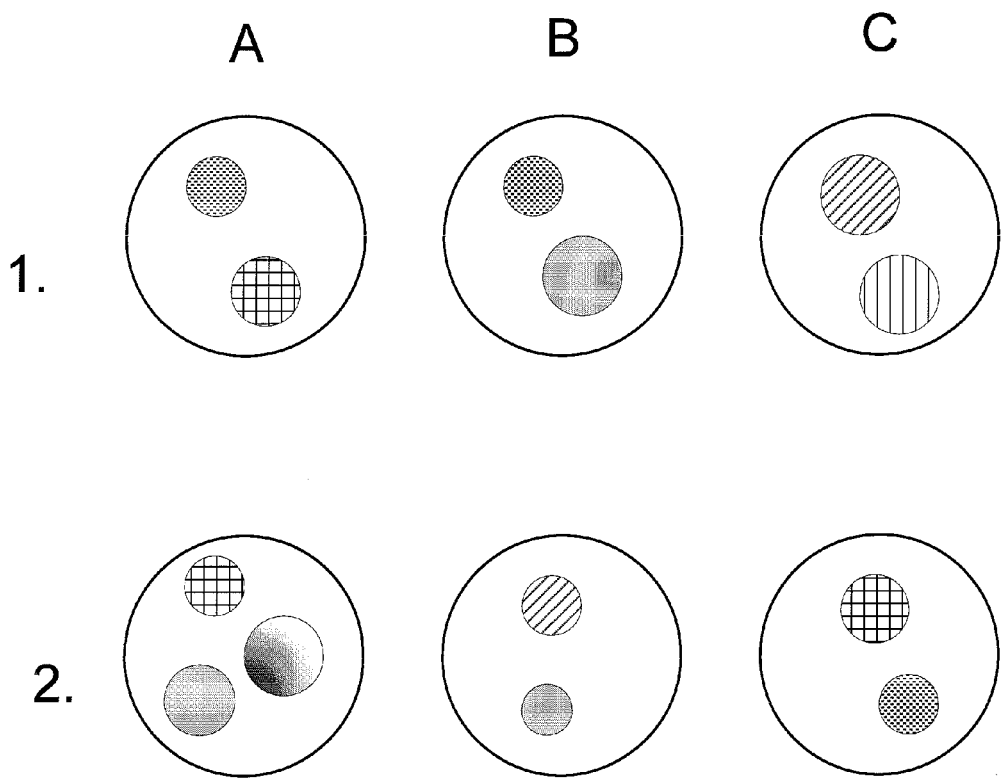
FIG. 2A shows cell populations expressing combinations of light responsive proteins.

FIG. 2A shows two examples of the use of light responsive proteins, each example including three cell populations, A, B, and C. As discussed briefly above, two or more light responsive proteins can be introduced into the same cell populations. The light responsive proteins introduced can cause the same response or different response when activated. The different proteins can also have different reaction times, or strengths of reactions. Two proteins of the same polarity can be activated at the same time causing an additive effect. Two depolarizing proteins, for example, may be alternatively stimulated. This can allow for an increase in frequency of firing. In example 1, cell populations A and B express the same inhibiting protein, but different excitatory proteins. Cell population C has an excitatory protein which reacts to light around the same wavelength as the inhibiting protein of cell populations A and B. The inhibitor of cell population C reacts to a wavelength similar to the excitatory protein of cell population A. This arrangement allows for a variety of combinations of cell population reactions to the light provided to stimulate the cell populations. As example 1 is set up, cell population B may be excited without exciting or inhibiting either of the other two populations. However, cell populations A and C react in almost an inverse way to the light provided.

Example 2 includes cell population A with three light responsive proteins and cell populations B and C with two light responsive proteins. Cell population A includes two excitatory proteins which react to different light wavelengths, and one inhibitory protein. Cell populations B and C each have one of the excitatory proteins of cell population A and an inhibitory protein which responses to wavelengths in the same spectrum as the excitatory protein present in the other cell population (B or C). This arrangement allows for the combination of cell populations A and B to be excited, or cell populations B and C to be excited, while the third cell population is inhibited. It allows for cell population A to be inhibited without affecting either cell population B or C, and for cell population A to be excited while both cell populations B and C are inhibited. The example combination of FIG. 2A are not meant to be limiting, but to illustrate some of the many combinations of light responsive proteins in both a single cell population, and the combinations across cell populations.

Consistent with another example embodiment of the present invention, target cells are neurons located in the brain of a mammal. The target cells are genetically modified to express photosensitive bio-molecular arrangement, for example, DChR ion channels. Light can then be used to stimulate the neurons. Depending upon a number of factors, such as the location within the brain and the frequency and length of stimulation, different objectives can be achieved. For instance, current techniques for deep brain stimulus (DBS) use electrodes to apply a current directly to the targeted area of the brain. The frequency of the electrical stimulus is sometimes referred to as either low-frequency DBS or high-frequency DBS. Studies have suggested that high-frequency DBS inhibits the generation of impulses from the stimulated cells, while low-frequency DBS facilitates the generation of impulses from the stimulated cells. The frequencies that produce the effects of high-frequency of low-frequency DBS have also been shown to vary depending upon the specific area of the brain being stimulated. According to one example of high-frequency DBS, the neurons are stimulated using electrodes supplying current pulses at frequencies around 100 Hz or more. Such a frequency has been shown to be effective in certain applications, as discussed further herein.

In various cell populations, similar to those illustrated in FIG. 2A, two or more light responsive proteins may be present. Some (or all) of the two or more light responsive proteins can direct the same action (i.e., excitation or inhibition) within the cell population. For example cell population A of example 2 includes two excitatory light responsive proteins, DChR and VChR1. FIG. 2B shows a stimulus profile for use with certain embodiments in which two or more types of light responsive proteins, for example DChR and VChR1, may be introduced into the same cell population. Each ion-passing molecule has a respective stimulus frequency limit, which can be partially responsive to environmental factors like pH. This limit reflects the recovery time necessary for the molecule to transition between active and inactive states. The use of two types of light-responsive proteins, each responding to different optical wavelengths, can allow for each type of protein to be controlled separately. The respective ion channels can be activated alternatively, allowing for an increased frequency of stimulation of the brain.

For instance, example 3 shows that light pulses (solid vertical lines) of a first wavelength and provided at a frequency F. This wavelength is selected to activate a first type of molecule (triangles). A second set of light pulses (dotted vertical lines) of a second wavelength can also be provided at a frequency F. This second set of light pulses can be used to activate a second type of molecule (squares). The resulting activation frequency for both cells is thus twice the frequency of activation for each individual ion-passing molecule. Of course, the frequencies need not be identical between the two types of molecules and can be varied over time.

In another implementation, shown in example 4, a first type of ion-passing molecule can be activated for a time period followed by activation of a second type of ion-passing molecule. This can be particularly useful for allowing each of the ion-passing molecules to be inactive for the time period during which the other ion-passing molecule is being activated. In certain instances, this can facilitate recovery and sustained use of the ion-passing molecules. Moreover, the different current types, densities and ion-passing capabilities can be considered when deciding on the specific stimulation profile to create the desired response.

A specific example of DBS is used for the treatment of Parkinson's disease. In this application, DBS is often applied to the globus pallidus interna, or the subthalamic nucleus within a patient's brain. By implanting a biological arrangement that modifies the cells to respond to light, a light flashing light can be used in place of electrodes. Thus, the targeted neuron cells and external electrical signal need not be directly applied to the targeted cells. Moreover, light can often travel from its point of origin farther than electricity, thereby increasing the effective area relative to the stimulation source and only those neurons that have been photosensitized are stimulated.

As with the electrode-based DBS methods, one embodiment of the present invention can be implemented using high-frequency DBS to inhibit neuron generated impulses. While high-frequency DBS has been accomplished at frequencies around 100 Hz, high-frequency DBS using various embodiments of the present invention may not necessarily require the same frequency. For instance, it may be possible to reproduce the inhibiting effects of high-frequency DBS at lower frequencies (e.g., 50 Hz) when using light activated techniques. For example, activation of the GtR3 pump intrinsically favors hyperpolarization and resistance to action potential generation. Various frequencies can be used depending upon the particular application (e.g., the targeted portion of the brain and the desired effect), and the stimulation modality being applied.

Consistent with another example embodiment of the present invention, gene transfer vectors inducing the expression of photosensitive bio-molecules are used to target a specific type of cell. For instance, viral-based proteins (e.g., lentiviruses, adeno-associated viruses or retroviruses) can be created to target specific types of cells, based upon the proteins that they uniquely express. The targeted cells are then infected by the viral-based gene-transfer proteins, and begin to produce a new type of ion channel (for example DChR), thereby becoming photosensitive. This can be particularly useful for stimulating the targeted cells without stimulating other cells that are in proximity to the targeted cells. For example, neurons of disparate length, diameter, chronaxie, other membrane properties, electrical insulation, neurotransmitter output, and overall function, lie in close proximity to one another, and thus, can be inadvertently stimulated when using electrodes to provide the stimulation of the neurons. For further details on the generation of viral vectors and the in vivo modification and stimulation of neural cells, reference may be made to U.S. patent application Ser. No. 11/459,636 filed on Jul. 24, 2006, "An optical neural interface: in vivo control of rodent motor cortex with integrated fiber optic and optogenetic technology" by Alexander M. Aravanis, et al, Journal Neural Engineering 4 (2007) S143-S156, "Neural substrates of awakening probed with optogenetic control of hypocretin neurons" by Antoine R. Adamantidis, et al, Nature, (Nov. 15, 2007) Vol. 450: 420-424, "Targeting and Readout Strategies for Fast Optical Neural Control In Vitro and In Vivo" by Viviana Gradinaru, et al, The Journal of Neuroscience, (Dec. 26, 2007) 27(52):14231-14238, "Multimodal fast optical interrogation of neural circuitry" by Feng Zhang, et al, Nature (Apr. 5, 2007) Vol. 446: 633-639, "Circuit-breakers: optical technologies for probing neural signals and systems" by Feng Zhang, et al, Nature Reviews Neuroscience (August 2007) Vol. 8: 577-581, which are each fully incorporated herein by reference.

A specific embodiment of the present invention employs an implantable arrangement for in vivo use. A light-emitting diode, laser or similar light source is included for generating light (as shown, for example, light generator 104 in FIG. 3). A biological portion that modifies target cells to include light responsive molecules which facilitate stimulation of the target cells in response to light generated by the light source.

Figure 4:
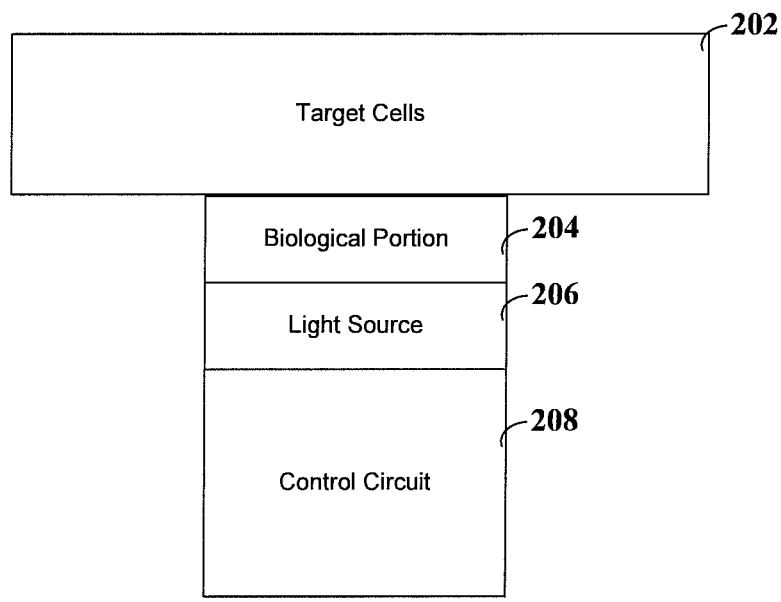
FIG. 4 shows a block diagram of an implantable device for stimulating target cells, according to an example embodiment of the present invention.

Another embodiment of the present invention employs an arrangement for stimulating target cells using a photosensitive protein that allows the target cells to be stimulated in response to light. A biological delivery device, such as those discussed in connection with biological portion 204 of FIG. 4, is used for implanting vectors that modify the target cells to include the photosensitive protein. An implantation component, such as that discussed in connection with biological portion 204, the mesh of FIG. 7 or viral matrix of FIG. 8, is used for implanting a light generating device near the target cells. A control device, such as that discussed in connection control circuit 208, is used for activating the light generating device to generate light to be received by the target cells, thereby stimulating the target cells in response to the generated light.

Figure 3:
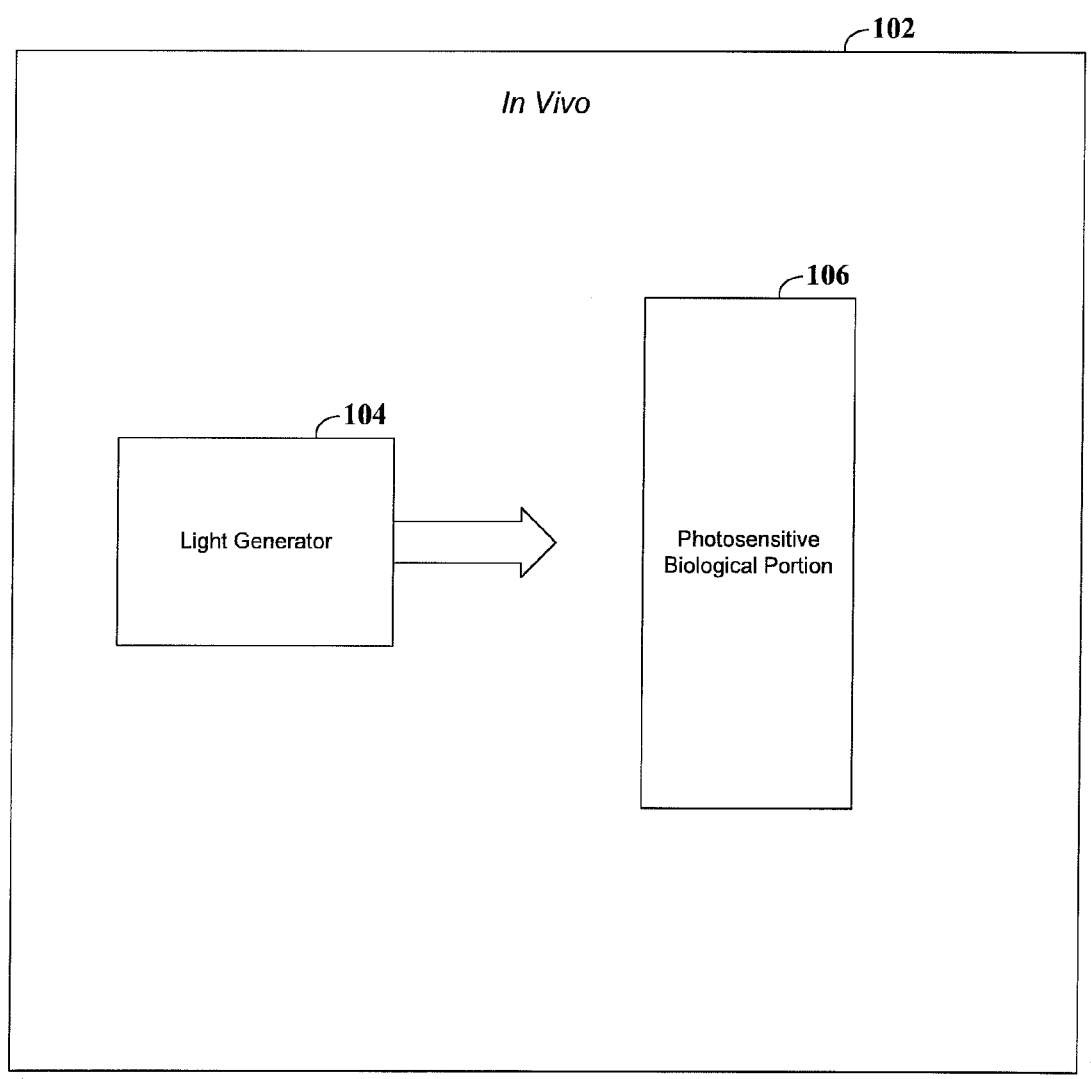
FIG. 3 shows a block diagram of a system for stimulating target cells, according to an example embodiment of the present invention.

Returning now to the figures, FIG. 3 shows a block diagram of a system for stimulating target cells, according to an example embodiment of the present invention. Block 102 represents a location internal to an organism (e.g., a mammal), as shown by the in vivo designation. Light generator 104 is an implantable device that generates light in vivo. The photosensitive biological portion 106 affects the target cells such that generated light strikes causes stimulation of the target. In one instance, the light generator 104 is a small electronic device on the order of a few millimeters in size. The small size is particularly useful for minimizing the intrusiveness of the device and associated implantation procedure. In another instance, the light generator 104 may include a fiber optic device that can be used to transmit light from an external source to the target cells.

In one embodiment of the present invention, the target cells are modified to contain light-activated proton pump/channel proteins. A specific example of such protein is GtR3, which is a product based upon the cryptophytes *Guillardia theta*. Characterization of the action spectra for GtR3 suggests that the absorption maxima are around 490 nm. Another specific example is DChR from *Dunaliella salina*. The action maxima for DChR are around 500 nm.

These light sensitive proteins can be implanted using a number of different methods. Example methods include, but are not limited to, the use of various delivery devices, such as gelatin capsules, liquid injections and the like. Such methods also include the use of stereotactic surgery techniques such as frames or computerized surgical navigation systems to implant or otherwise access areas of the body. For further details on delivery of such proteins, reference may be made to U.S. patent application Ser. No. 11/459,636 filed on Jul. 24, 2006 and entitled "Light-Activated Cation Channel and Uses Thereof", which is fully incorporated herein by reference.

FIG. 4 shows a block diagram of an implantable device for stimulating target cells, according to an example embodiment of the present invention. The figure includes control circuit 208, light source 206, biological portion 204 and target cells 202. Biological portion 204 affects the target cells 202 such that the target cells are stimulated in response to light In one embodiment of the present invention, biological portion 204 may be composed of target cells 202 that have been modified to be photosensitive. In another embodiment of the present invention, biological portion 204 may contain biological elements such as gene transfer vectors, which cause target cells 202 to become sensitive to light. An example of this is lentiviruses carrying the gene for DChR expression. In this manner, the stimulation of target cells 202 can be controlled by the implantable device. For example, the control circuit 208 can be arranged to respond to an external signal by activating, or deactivating light source 206, or by charging the battery that powers light source 206. In one instance, the external signal is electromagnetic radiation that is received by control circuit 208. For example, radio frequency (RF) signals can be transmitted by an external RF transmitter and received by control circuit 208. In another example, a magnetic field can be used to activate and/or power the control circuit.

Control circuit 208 can be implemented using varying degrees of complexity. In one instance, the circuit is a simple coil that when exposed to a magnetic field generates a current. The current is then used to power light source 206. Such an implementation can be particularly useful for limiting the size and complexity as well as increasing the longevity of the device. In another instance, control circuit 208 can include an RF antenna. Optionally, a battery or similar power source, such as a capacitive element, can be used by control circuit 208. While charged, the power source allows the circuitry to continue to operate without need for concurrent energy delivery from outside the body. This can be particularly useful for providing precise control over the light emitted by light source 206 and for increased intensity of the emitted light. In one embodiment of the present invention, light source 206 is implemented using a light-emitting-diode (LED). LEDs have been proven to be useful for low power applications and also to have a relatively fast response to electrical signals.

In another embodiment of the present invention, biological portion 204 includes a gelatin or similar substance that contains gene transfer vectors which genetically code the target cells for photosensitivity. In one instance, the vectors are released once implanted into the body. This can be accomplished, for example, by using a containment material that allows the vectors to be released into aqueous solution (e.g., using dehydrated or water soluble materials such as gelatins). The release of the vectors results in the target cells being modified such that they are simulated in response to light from light source 206.

In another embodiment of the present invention, the biological portion 204 includes a synthetic mesh that contains the photosensitive cells. In one instance, the cells are neurons that have been modified to be photosensitive. The synthetic mesh can be constructed so as to allow the dendrites and axons to pass through the mess without allowing the entire neuron (e.g., the cell body) to pass. One example of such a mesh has pores that are on the order of 3-7 microns in diameter and is made from polyethylene terephthalate. In another example embodiment, the biological portion 204 includes an injection mechanism as discussed in further detail herein.

Figure 5:
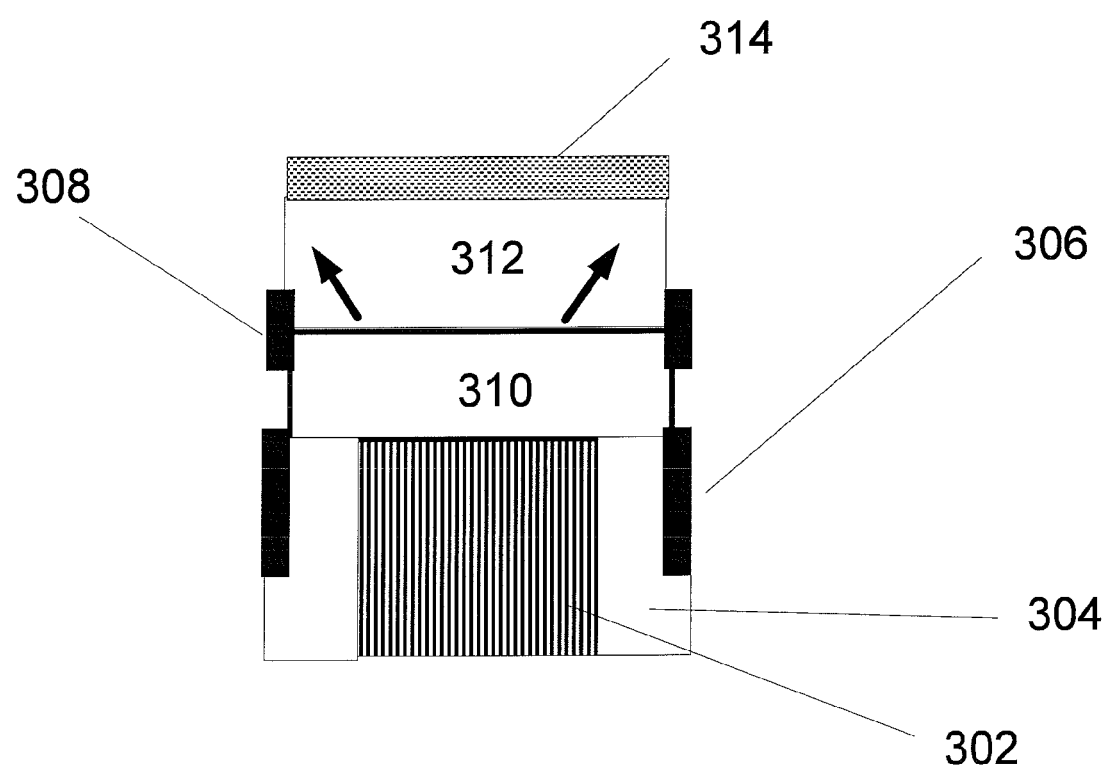
FIG. 5 shows a block diagram of an implantable device, according to an example embodiment of the present invention.

FIG. 5 shows a block diagram of an implantable device, according to an example embodiment of the present invention. The implantable device of FIG. 3 is responsive to a field magnetic. More specifically, an inductor constructed from windings 302 and core 304 generates a current/voltage in response to a magnetic field. The current is passed to control circuit 310 through conductive path 306. In response, control circuit 310 activates light source 312 using conductive path 308. Light source 312 illuminates biological portion 314 in order to stimulate the target cells. In one instance, biological portion 314 includes a gelatin, synthetic mesh or injection mechanism as discussed in further detail herein.

In one embodiment of the present invention, the control portion can be a simple electrical connection, resistive element, or can be removed completely. In such an embodiment, the intensity, duration and frequency of light generated would be directly controlled by the current generated from a magnetic field. This can be particularly useful for creating inexpensive, long lasting and small devices. An example of such an embodiment is discussed further in connection with FIG. 6A and FIG. 6B.

In another embodiment of the present invention, the control portion can be implemented as a more complex circuit. For instance the control circuit may include and otherwise implement different rectifier circuits, batteries, pulse timings, comparator circuits and the like. In a particular example, the control circuit includes an integrated circuit (IC) produced using CMOS or other processes. Integrated circuit technology allows for the use of a large number of circuit elements in a very small area, and thus, a relatively complex control circuit can be implemented for some applications.

In a particular embodiment of the present invention, the inductor (302 and 304 of FIG. 5) is a surface mount inductor, such as a 100 uH inductor part number CF1008-103K supplied by Gowanda Electronics Corp. The light generating portion is a blue LED, such as LEDs in 0603 or 0805 package sizes. A particular example is a blue surface mount LED having part number SML0805, available from LEDtronics, Inc (Torrance, Calif.). Connective paths 306 and 308 can be implemented using various electrical conductors, such as conductive epoxies, tapes, solder or other adhesive materials. LEDs emitting light in the amber spectrum (as applicable to NpHR channels) and other spectrums are available through commercial sources including this same manufacturer.

Figure 6A:
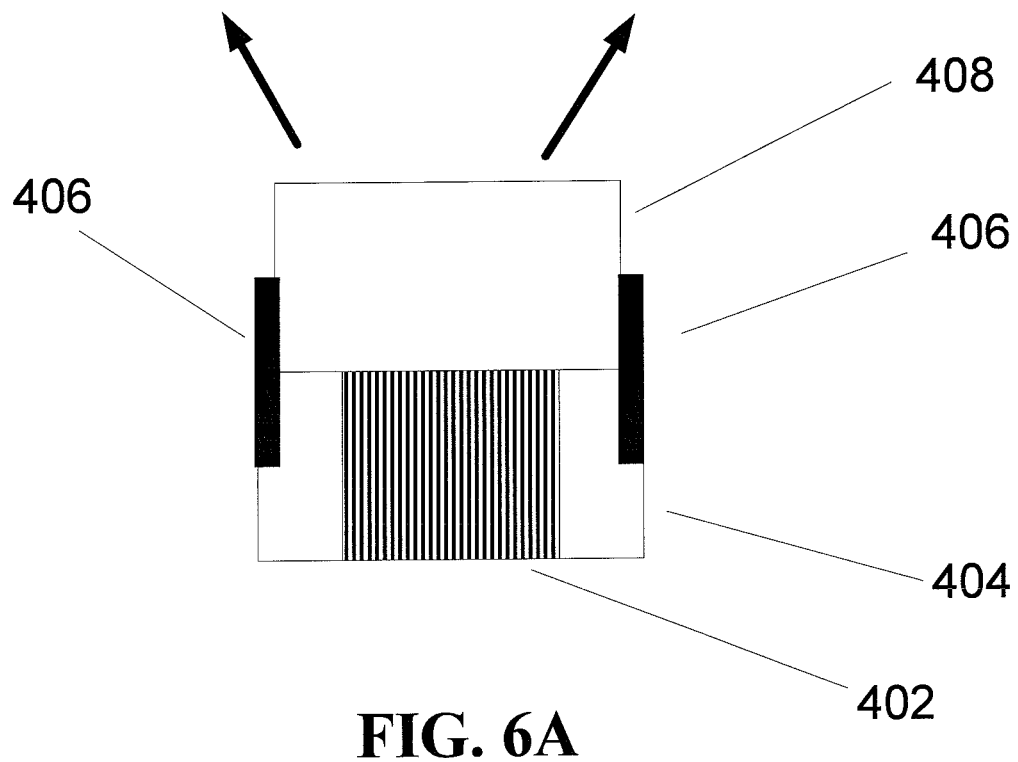
FIG. 6A shows a block diagram of an implantable device, according to an example embodiment of the present invention.
Figure 6B:
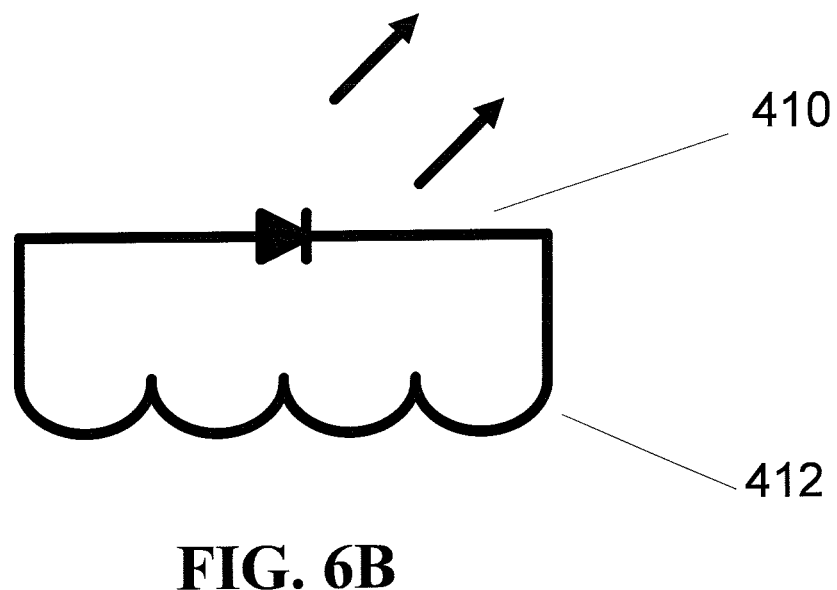
FIG. 6B shows a circuit diagram corresponding to the block diagram of FIG. 6A, according to an example embodiment of the present invention.

FIG. 6A shows a block diagram of an implantable device, according to an example embodiment of the present invention. FIG. 6A shows an inductor comprising coils 402 and core 404 connected to LED 408 using conductive paths shown by 406. FIG. 6B shows a circuit diagram corresponding to the block diagram of FIG. 6A. Inductor 412 is connected in parallel to LED 410. Thus, current and voltage generated by changing a magnetic field seen at inductor 412 causes LED 410 to produce light. The frequency and strength of the changing magnetic field can be varied to produce the desired amount and periodicity of light from LED 410.

Figure 7A:
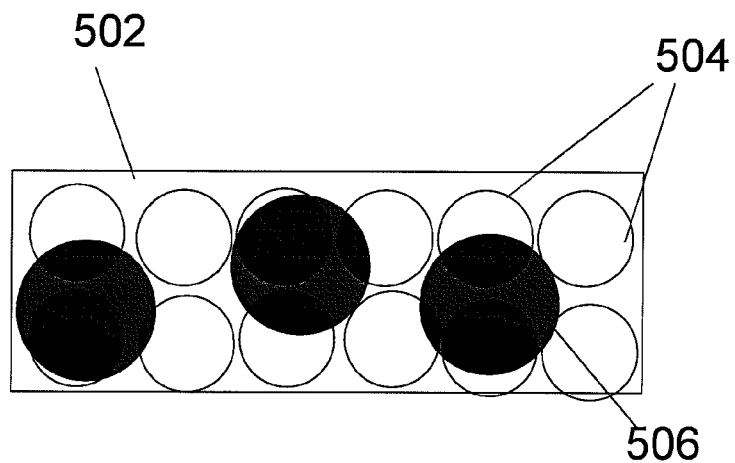
FIG. 7A and FIG. 7B show a diagram of a mesh for containing photosensitive bio-molecules, according to an example embodiment of the present invention.
Figure 7B:
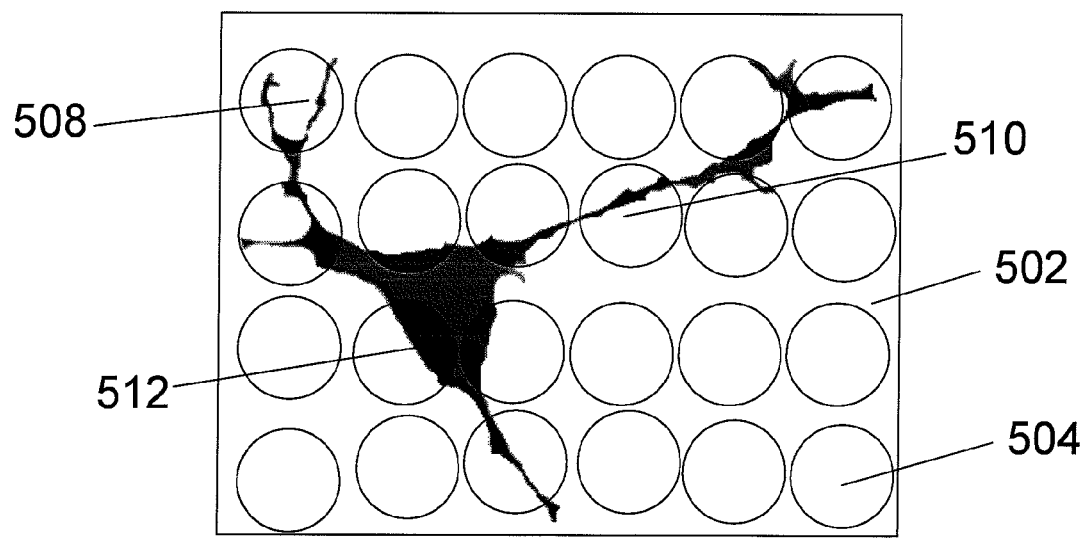

FIG. 7A and FIG. 7B show a diagram of a mesh for containing photosensitive bio-molecules, according to an example embodiment of the present invention. Mesh 502 is constructed having holes 504 of a size that allows illumination to pass but is small enough to prevent cells 506 to pass. This allows for cells 506 to be implanted while still receiving light from a light generator.

In one embodiment of the present invention, the cells 506 are stem cells that are modified to be photosensitive. The stem cells are allowed to mature as shown by FIG. 7B. In a particular instance, the stem cells mature into neurons having a cell body 512, axons/dendrites 508 and 510. The neurons are genetically modified to be photosensitive. Holes 504 are on the order of 3-7 microns in diameter. This size allows some axons and dendrites to pass through holes 504, while preventing the cell body 512 to pass.

FIG. 8A and FIG. 8B show a diagram of a viral matrix, according to an example embodiment of the present invention. The viral matrix includes structure 602, which contains viral vectors 604. In one instance, structure 602 includes a gel or fluid substance that contains viral vectors 604 until they are implanted in a mammal 606. Once viral vectors 604 are released, they infect target cells 608 in the vicinity of the implanted viral matrix as shown by FIG. 8B. Infected target cell 610 becomes photosensitive, and thus, light can be used to control the stimulation of target cell 610.

According to one embodiment of the present invention, structure 602 is a gelatin that has been impregnated, or otherwise sealed with viral vectors 604 contained within the gelatin. When structure 602 is implanted, the gelatin is hydrated and or dissolved, thereby releasing viral vectors 604. Standard commercially available gelatin mix may be used, in addition to compounds such as Matrigel by BD Biosciences division of Becton Dickenson and Company (Franklin Lakes, N.J.)

Figure 9:
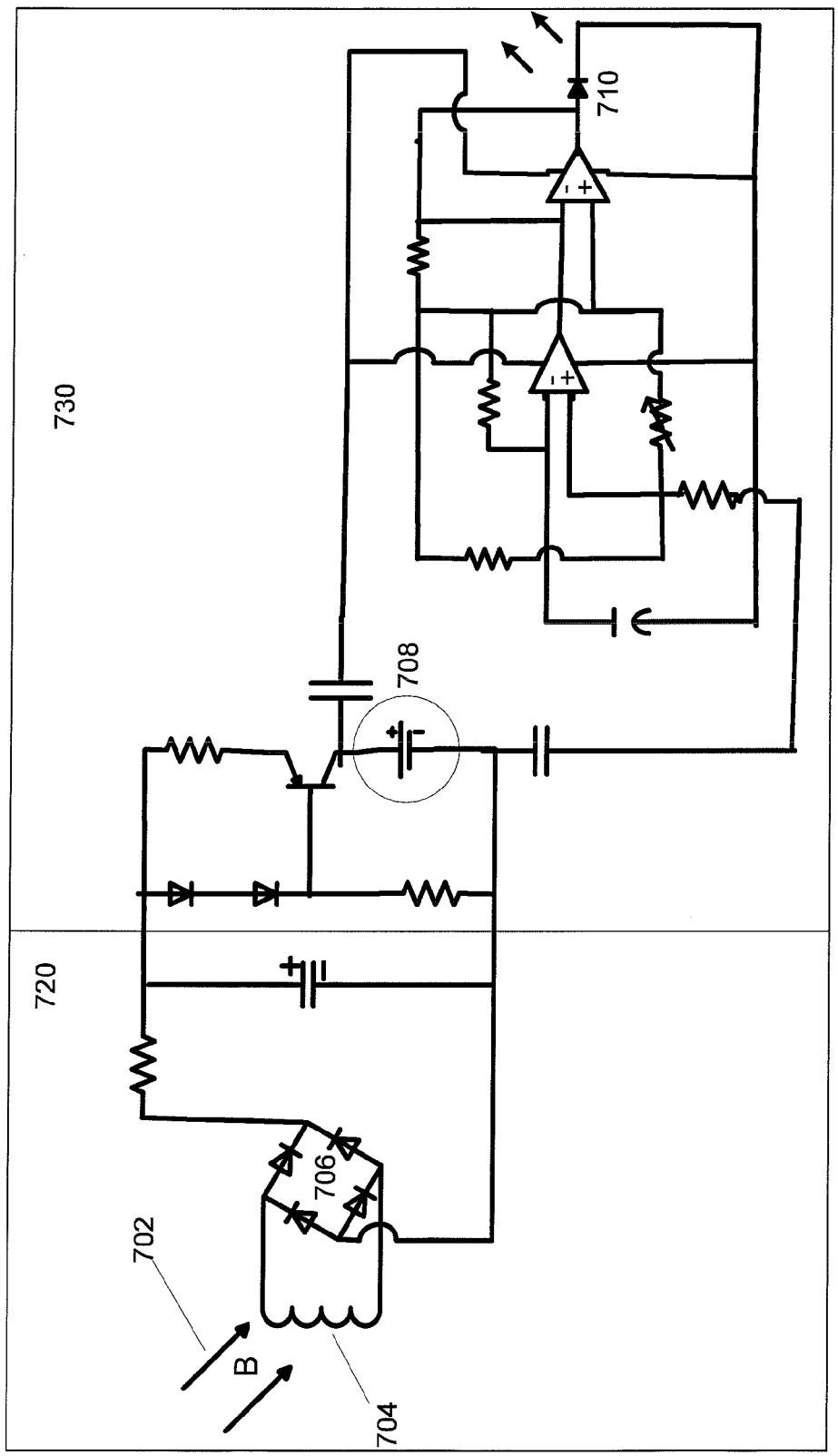
FIG. 9 shows a circuit diagram of a circuit that produces light in response to a magnetic field, according to an example embodiment of the present invention.

FIG. 9 shows a circuit diagram of a circuit that produces light in response to a magnetic field, according to an example embodiment of the present invention. FIG. 9 includes an input circuit 720 and an output circuit 730. Inductor 704 generates current in response to magnetic field 702. Due to properties of magnetic fields, the current produced by inductor 704 is an alternating current (AC) signal. Full-wave bridge rectifier 706 rectifies the AC signal and along with an RC circuit generates a relatively stable voltage from the AC signal. This generated voltage is responsive to magnetic field 702 and output circuit 730 which generates light when the generated voltage is at a sufficient level. More specifically, power from battery 708 is used to drive LED 710 in response to magnetic field 702. This is particularly useful for applications where the magnetic field 702 seen by inductor 704 is less powerful (e.g., due to the in vivo location of inductor 704).

Figure 10A:
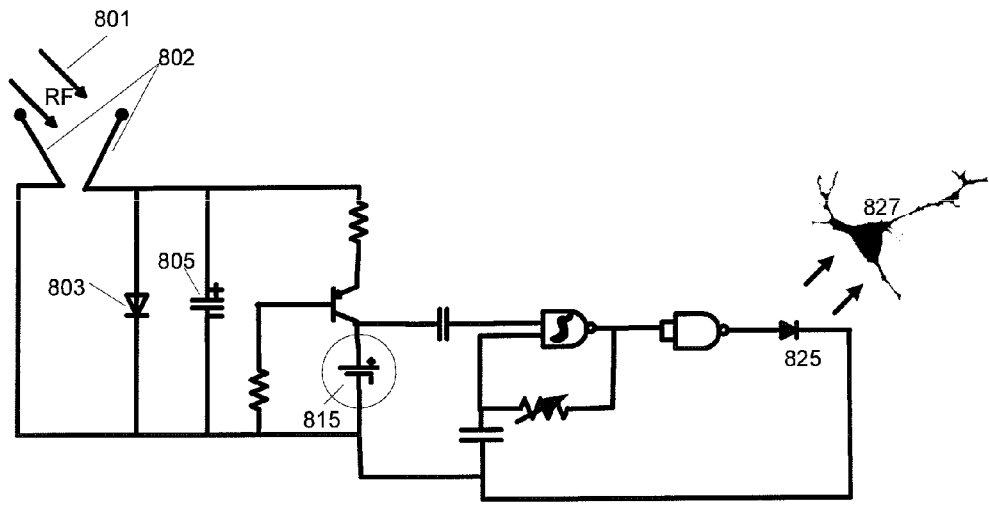
FIGS. 10A, 10B and 10C show a block diagram and circuits for the production of light in response to a RF signal, according to an example embodiment of the present invention.

FIG. 10A shows a circuit diagram of a circuit that produces light in response to RF signal 801, according to an example embodiment of the present invention. Antenna 802 is used to receive RF transmission 801 and convert the signal to electricity. The received transmission is rectified by diode 803 and further filtered by capacitor 805. In a one instance, diode 803 can be implemented using a diode having a low forward bias and fast switching capabilities, such as a Schottky diode.

In a particular embodiment of the present invention, RF transmission 801 contains a power component for charging battery 815 and a signal component for controlling LED 825. Capacitor 805 can be selected to separate these components for use by the circuit. For instance, the power component may be a relatively low-frequency, large-amplitude signal, while the signal component is a relatively high-frequency, small-amplitude signal. Capacitor 805 can be selected to filter the power component of the signal to create a corresponding voltage. The remaining high-frequency component of the RF transmission is added to this voltage. The power component of the transmission can then be used to charge the battery 815, and the signal component of the transmission is used to enable LED 825. The light generated by LED 825 triggers stimulus of the target cells 827.

Figure 10B:
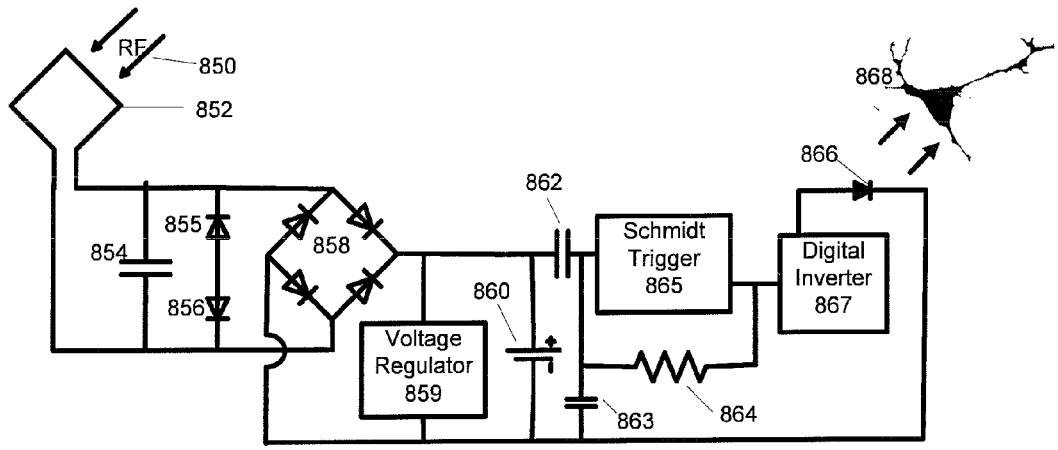

FIG. 10B illustrates an alternative embodiment radio-frequency energy accumulator, which charges a battery, which in turn, powers a digital pulse generator, which powers a LED. An electromagnetic signal 850 is received by loop antenna 852 generating a corresponding electrical signal. The voltage generated from loop antenna 852 is limited by the reverse bias voltage of the diodes 855 and 856 and stored in capacitor 854. In a particular instance these diodes have a low reverse bias voltage that is relatively precise, such as a Zener diode. Electromagnetic signal 850 is rectified via diode rectifier bridge 858 and filtered by voltage regulator 859 to produce a DC voltage. The DC can be used to charge power source 860.

Battery 860 is coupled to the input of Schmidt trigger 865 through capacitor 862. Feedback from the output of the Schmidt trigger is provided through resistor 864 relative to the charge on capacitor 863. Accordingly, the frequency of the square-wave output of Schmidt trigger 865 is determined by the values of the resistor-capacitor network including capacitor 863 and resistor 864. Resistor 864 and capacitor 863 may be fixed or variable. The output of Schmidt trigger 865 is fed through digital inverter 867 which powers LED 866. Light from LED 866 is transmitted to light-sensitive neurons 868 relative to the frequency of the square-wave output of Schmidt trigger 865.

Figure 10C:
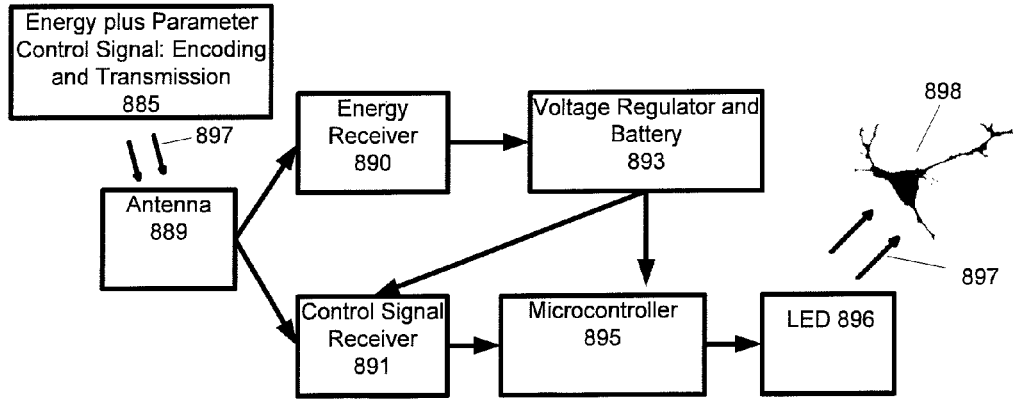

FIG. 10C illustrates block diagram for an electromagnetic field (EMF) energy accumulator and pulsing approach in which the received EMF 897 (for example radiofrequency energy) includes not only energy for accumulation, but also an encoded signal regarding instructions to microcontroller 895. In step 885 (Energy plus Parameter Control Signal: Encoding and transmission), a control instruction signal is encoded to ride upon the energy component by methods known in the art, for example, by frequency modulation. Energy receiver block 890 uses a portion of the EMF signal to provide power to block 893. Control signal receiver block 891 uses a portion of the EMF signal to provide control instructions to microcontroller block 895.

The control instruction can be used to transmit information regarding the various parameters of the generated light, such as frequency, strength, duration, color, and the like. These instructions can be decoded and processed using a microcontroller or logic circuitry as shown by block 895. Block 895 can generate control signal(s) in response to the decoded instructions. Accordingly, the frequency (and other parameters) of the light generated by LED 896 rate need not be fixed for the given implanted device. Antenna 889 delivers input to the Energy Receiver 890 (providing power to voltage regulator and battery circuitry 893). Concurrently, antenna 889 delivers encoded data to Control Signal Receiver 891, which provides control input to microcontroller 895 that drives LED 896. Selected wavelength light 897 is then delivered to electrically excitable cell 898. The battery in the voltage regulator and battery circuitry 893 provides power to the microcontroller 895 and the Control Signal Receiver 891.

The circuit diagrams of FIG. 9 and FIGS. 10A, 10B and 10C are merely illustrative of a few particular embodiments of the present invention, and various other implementations are envisioned. For example, particular embodiments implement a light source that uses a blue LED; however, other colors and light sources can be implemented depending upon the particular application. In other particular embodiments the light source includes more than one color light source. The circuitry controls not only when light is provided, but which color, depending on whether the instructions require inhibition or excitation of the cell. For example, in a specific example the target cell express both an inhibitor (e.g., GtR3) and an exciter (e.g., VChR1), which respond to different wavelengths of light. The system can also control the level at which the cells are excited or inhibited. This can be done by including multiple light responsive proteins in the target cells that excite (or inhibit) and programming the instructions to provide more than one light wavelength at a single time.

Figure 11A:
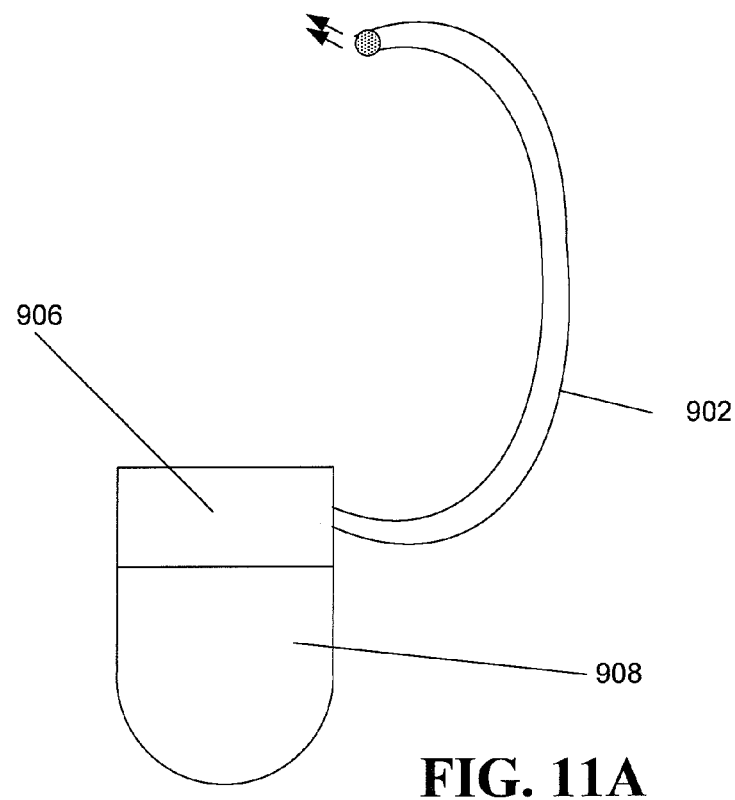
FIG. 11A and FIG. 11B each show a diagram of a fiber-optic device, according to an example embodiment of the present invention.
Figure 11B:
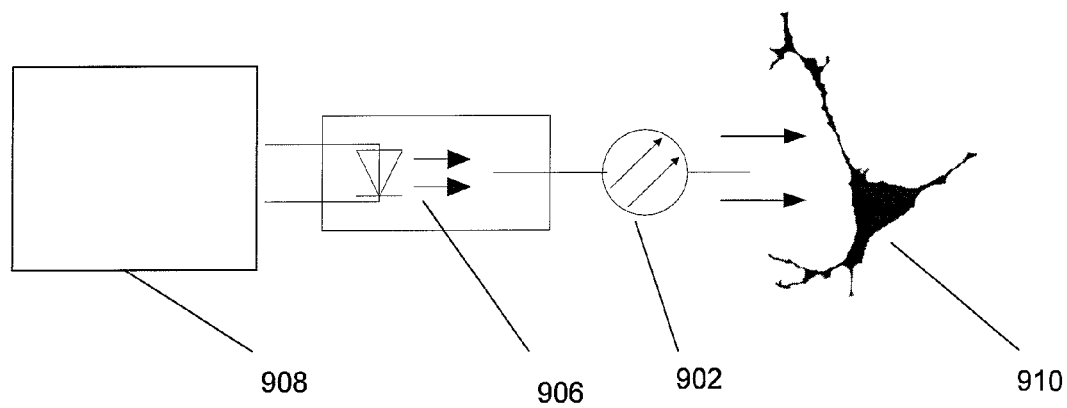

FIG. 11A and FIG. 11B each show a diagram of a fiber-optic device, according to an example embodiment of the present invention. The fiber-optic device includes a control portion 908, a light generator 906 and a fiber optic cable 902.

Fiber optic cable 902 can be positioned near a photosensitive biological portion, such as a viral matrix or synthetic mesh as discussed herein. This allows for control portion 908 and light generator 906 to be located at a distance from the target cells 910 (e.g., at a distance corresponding to the length of fiber-optic cable 902). This can be particularly useful for minimizing the size of the portion of the implanted device that is near the target cells, for example, where the target cells are located at or near a sensitive location within the brain. In some instances, the remote location of portions 908 and 906 also facilitates modifications of the device, including, but not limited to, replacement of various components (e.g., batteries), changes in stimulation frequency and length.

Control portion 908 can be configured to respond to an external signal, such as magnetic field or RF signals. Alternatively, control portion 908 can be configured to enable light generator 906 according to a programmed schedule or a combination of an external signal and a programmed response.

Figure 12A:
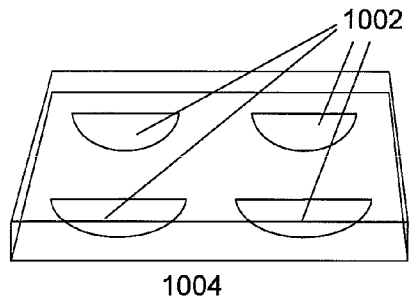
FIGS. 12A, 12B, 12C and 12D depict various stages in the production of a photosensitive biological portion, according to an example embodiment of the present invention.

FIGS. 12A-12D depicts various stages in the production of a photosensitive biological portion, according to an example embodiment of the present invention. More specifically, FIG. 12A shows molding structure 1004 having several molds 1002. Molds 1002 are constructed to various sizes depending upon the particular application. In one such application, the molds are a few millimeters or less in diameter.

Figure 12B:
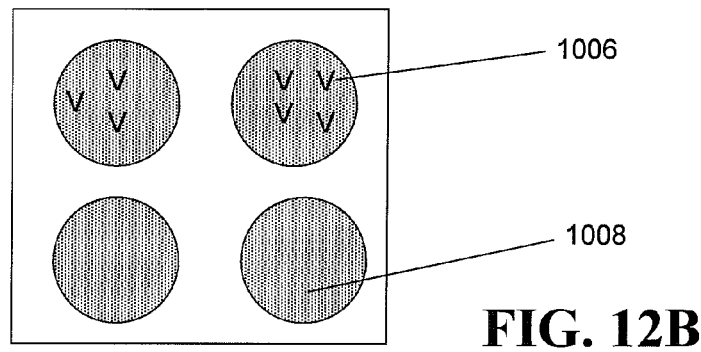

FIG. 12B shows the molds 1002 from FIG. 12A after applying a layer of gelatin or similar substance as shown by 1006 and 1008. Moreover, viral vectors (shown by 'v') are in the upper two molds. These viruses may be suspended within media 1012, which may be a liquid or gelatinous media. Such liquids include normal saline, HEPES-buffered saline and other known viral substances and transfer media. Suitable gelatinous media includes Matrigel (BD Biosciences, San Jose Calif.). These viral vectors are designed transfer genes for light-sensitization to the membranes of targeted cells after implantation.

Figure 12C:
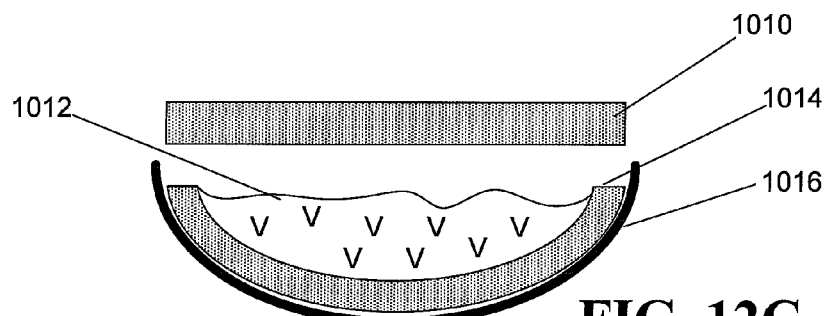

FIG. 12C shows a side view of mold 1006. 1016 represents the molding structure that forms the shape of gelatin layer 1014. Gelatin layer 1014 traps viral vectors contained within media 1012. A top gelatin layer 1010 is applied to fully contain the viral vectors.

Figure 12D:
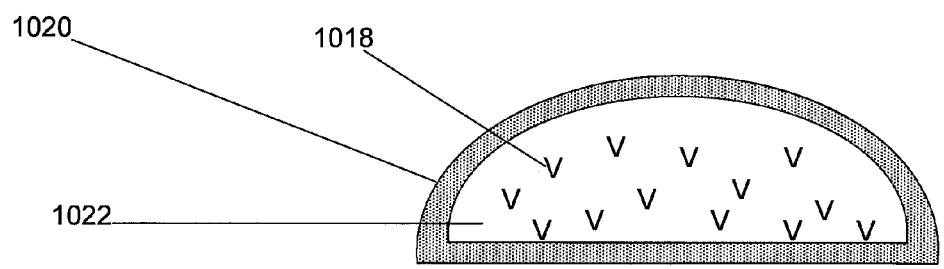

FIG. 12D shows the resulting viral vector capsule. The viral vectors 1018 are contained within area 1022 by casing 1020. Casing 1020 can be designed to dissolve or otherwise allow viral vectors 1018 to disseminate towards the target cells once implanted. In one instance, the capsule is constructed of a water soluble material, for example, gelatin, so that upon implantation the viral vectors are allowed to escape into the body. Water soluble capsule materials are well known in the pharmaceutical industry.

Figure 13:
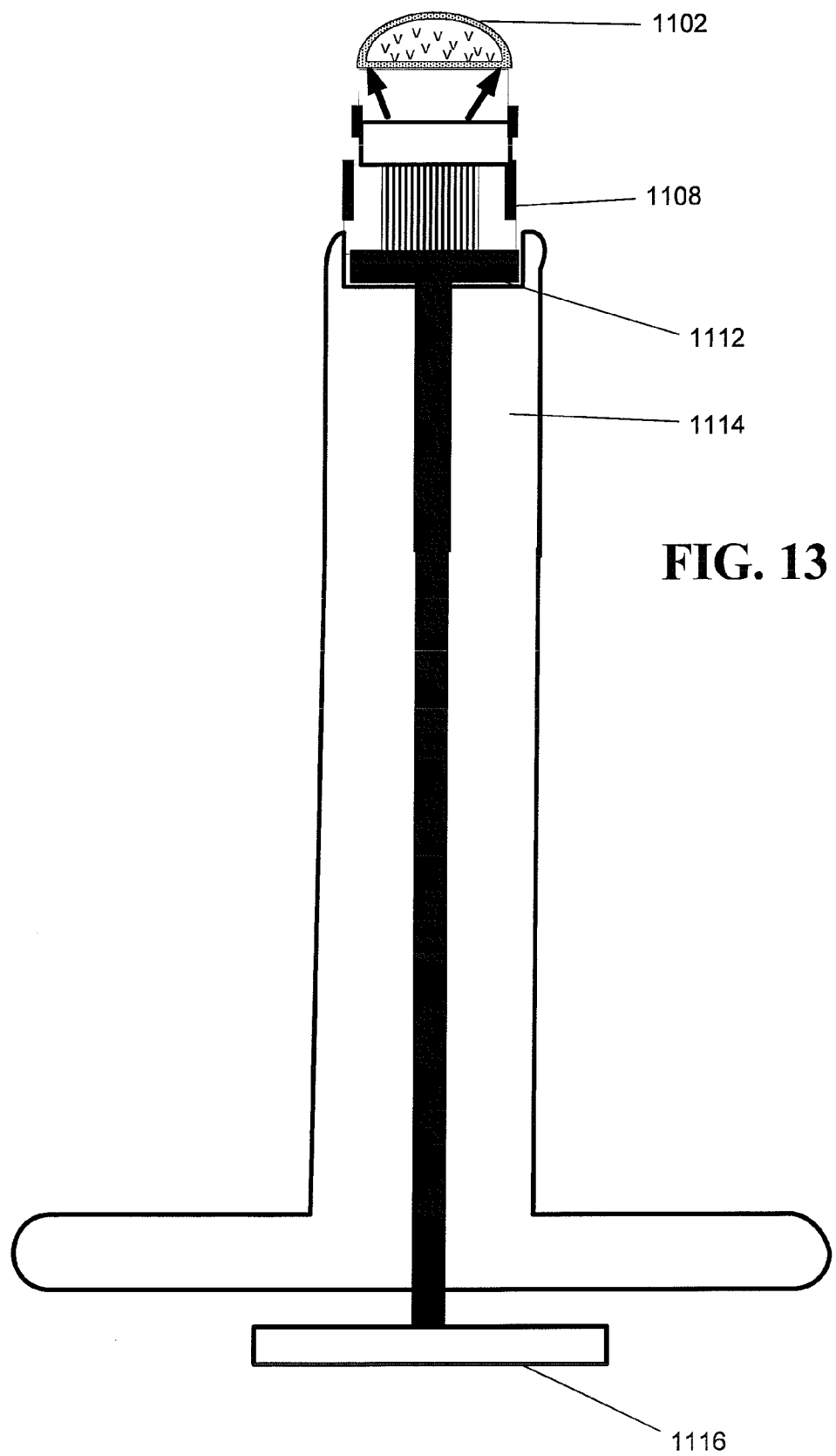
FIG. 13 shows an implantation device, according to an example embodiment of the present invention.

FIG. 13 shows an implantation device, according to an example embodiment of the present invention. Biological portion 1102 and light generation device 1108 are implanted using the implantation device. For example, the shaft of the device 1114 is positioned near the target cells. Next, a user of the device presses on portion 1116 which causes portion 1112 to place biological portion 1102 and light generation device 1108 near the target cells. The implantation device can then be removed.

Figure 14A:
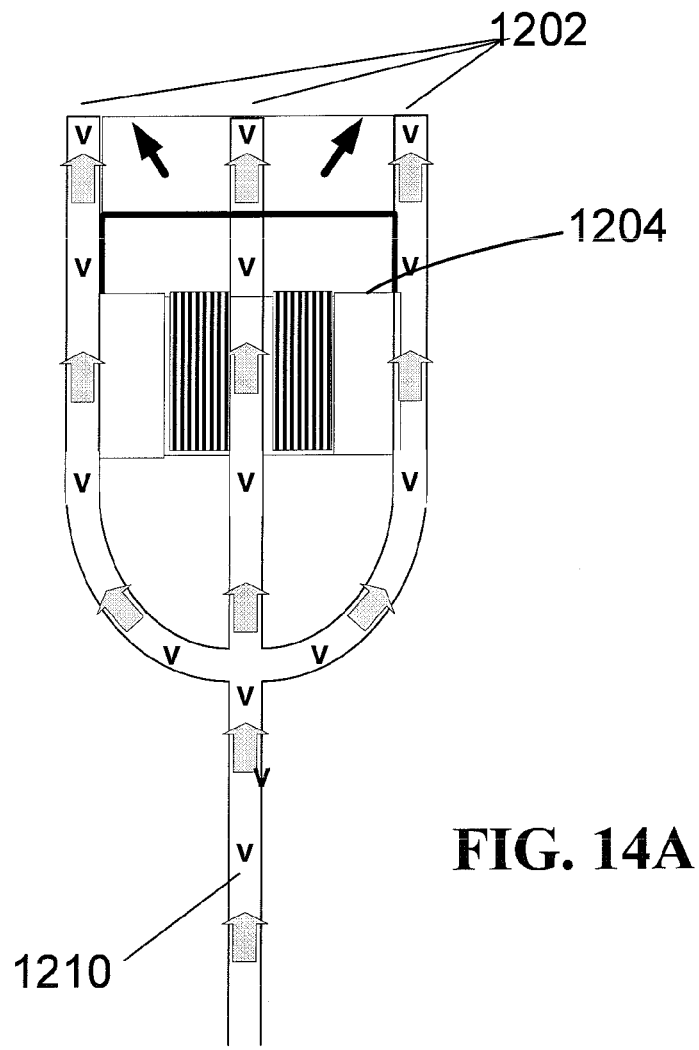
FIG. 14A and FIG. 14B show a diagram for another implantation device, according to an example embodiment of the present invention.
Figure 14B:
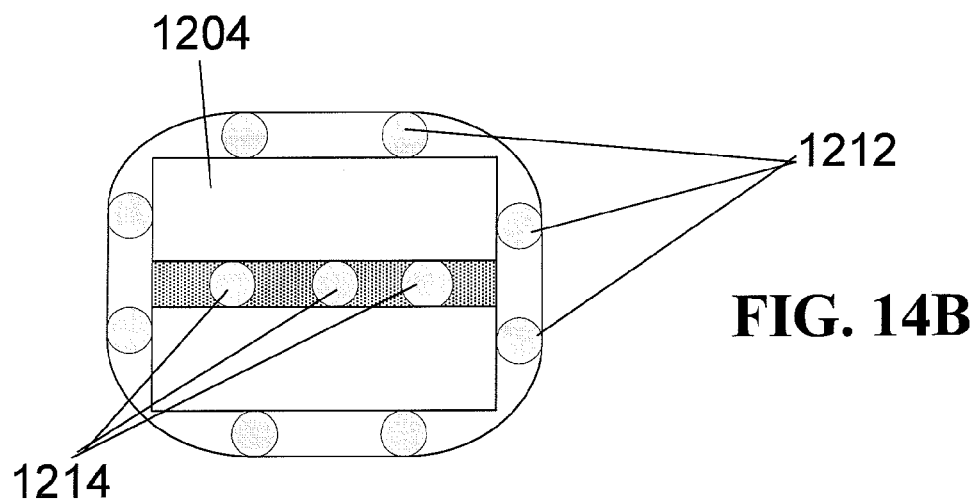

FIG. 14A and FIG. 14B show a diagram for another implantation device, according to an example embodiment of the present invention. Implantable light generating device 1204 is surrounded by, and permeated by fluid channels 1202. Fluid channels 1202 allow a solution 1210 containing biomolecular material (e.g., photosensitizing viral vectors) to be injected immediately proximal to light generating device 1204 and the target cells. The fluid channels can be located outside of device 1204 and/or within device 1204, as shown by 1212 and 1214 respectively. In this manner, the viral vectors can be injected in large quantities or over a period of time. For instance, cells infected by viral vectors can revert back to their pre-infection state after a period of time. Using the device of FIG. 12A, the viral vectors can be periodically reintroduced to the target cells. Alternatively, different viral vectors can be introduced through the fluid channels, allowing for targeting of different cells at the implantation site. This can be particularly useful for staged treatment through stimulation of different types of cells.

A specific embodiment of the present invention relates to a method for genetically modifying neurons to express light-sensitive ion channel DChR. In this method, pulses of blue light causes DChR neurons to fire action potentials corresponding to each pulse. Depolarization and repolarization occur on a millisecond timescale making this method consistent with normal network neurophysiology.

Specific targeted neurons are modified using viral vectors for gene transfer. For further details on the generation of viral vectors, reference can be made to Boyden et al. 2005, Zhang et al. 2006 entitled "Channelrhodopsin-2 and Optical Control of Excitable Cells," *Nature Methods* Vol. 3, No. 10, which is fully incorporated herein by reference. This transfection results in the introduction of a gene for a single protein, a cell membrane ion channel, known as "DChR". In nature, DChR resides on the cellular membrane of *Dunaliella salina*. Upon absorption of blue/green light (500 nm), this ion channel briefly opens, allowing cation influx. When transfected into a mammalian nerve cell, affected nerves become photosensitive, producing light-triggered action potentials.

A neuronal-type specific feature which is also a robust promoter is inserted adjacent to the DChR code within the virus, and the line is propagated by calcium-phosphate cotransfection of 293FT cells. The supernatant is then centrifuged into viral pellets, which are placed within phosphate-buffered saline.

In a particular instance, application of a DChR is used for photo stimulation. The amino-acid residues comprising DChR channelrhodopsin from *Dunaliella salina* can be used to impart fast photosensitivity upon mammalian nerve cells, by using a viral vector to insert the gene for DChR into targeted nerve cells which may subsequently express this gene. Upon illumination with approximately 500 nm blue/green light, ATR isomerizes and triggers a conformational change to open the channel pore. As DChR is a light-sensitive ion channel, it allows an inward current to be evoked.

In another instance, application GtR3 (derived from *Guillardia theta*) is used for photostimulation. This proton pump can be imparted upon mammalian nerve cells by using a viral vector to insert the gene for GtR3 into targeted nerve cells, which may subsequently express this gene. Upon illumination with approximately 472 nm blue light, active pumping of protons out of the neuronal cytoplasm results in hyperpolarization of the cell.

Since sensitivity to blue light via DChR or GtR3 is induced when a viral vector inserts the respective gene into a previously normal cell, the insertion may be genetically targeted to the products expressed by specific cellular subtypes. For example, it might be advantageous to cause only dopaminergic neurons, and not cholinergic neurons to react to blue light.

As discussed above, certain embodiments of the present invention involves the use of an optically responsive ion pump or ion channel that is expressed in a cell. In a particular instance, the cell is either a neural cell or a stem cell. A specific embodiment involves in vivo animal cells expressing an ion pump. Certain aspects of the present invention are based on the identification and development of a proton pump, derived from *Guillardia Theta*, for example, for temporally-precise optical inhibition of neural activity. The pump allows both knockout of single action potentials within rapid spike trains and sustained blockade of spiking over many minutes.

According to an example embodiment of the present invention, an optically responsive ion pump and/or channel is expressed in one or more stem cells, progenitor cells, or progeny of stem or progenitor cells. Optical stimulation is used to activate expressed pumps/channels. The activation can be used to control the proton concentration in the cells. It may also be used to control the pH of particular subcellular organelles. This can be particularly useful for affecting the survival, proliferation, differentiation, de-differentiation, or lack of differentiation in the cells. Thus, optical stimulus is implemented to provide control over the (maturation) of stem or progenitor cells.

According to other example embodiments of the present invention, methods for generating an inhibitory neuron-current flow involve, in a neuron, engineering a protein that responds to light by producing an inhibitory current to dissuade depolarization of the neuron. In one such method, the protein is GtR3 is an exogenous molecule in the neuron, and in another method the protein is an inhibitory protein that uses an endogenous cofactor.

In another example embodiment, a method for controlling action potential of a neuron involves the following step: engineering a first light responsive protein in the neuron; producing, in response to light, an inhibitory current in the neuron and from the first light responsive protein; engineering a second light responsive protein in the neuron; and producing, in response to light, an excitation current in the neuron from the second light responsive protein. The combination of light responsive proteins may depend on the light sensitivity of the protein, the reaction time of the protein, and defined action of the protein, for example. Multiple light responsive proteins of the same type (inhibitory vs. excitatory) may be used in the same cell population to allow for, for example, long term blockage of action potential or single action potential inhibition depending on the light wavelength used.

In another method for controlling a voltage level across a cell membrane of a cell, the method comprises: engineering a first light responsive protein in the cell; measuring the voltage level across the cell membrane; and producing, in response to light of a first wavelength and using the first light responsive protein, a current across the cell membrane that is responsive to the measured voltage level.

Another aspect of the present invention is directed to a system for controlling an action potential of a neuron in vivo. The system includes a delivery device, a light source, and a control device. The delivery device introduces a light responsive protein to the neuron, with the light responsive protein producing an inhibitory current. The light source generates light for stimulating the light responsive protein, and the control device controls the generation of light by the light source. In a particular embodiment the light source is a blue light source and the light responsive protein is responsive to blue light.

In more detailed embodiments, such a system is further adapted such that the delivery device introduces the light responsive protein by one of transfection, transduction and microinjection, and/or such that the light source introduces light to the neuron via one of an implantable light generator and fiber-optics.

Another aspect of the present invention is directed to a method for treatment of a disorder. The method targets a group of neurons associated with the disorder; and in this group, the method includes engineering an inhibitory proteins that use an endogenous cofactor to respond to light by producing an inhibitory current to dissuade depolarization of the neurons, and exposing the neurons to light, thereby dissuading depolarization of the neurons.

In another aspect of the present invention, GtR3 is optimized for mammalian expression. A light responsive protein is isolated from *Guillardia theta*. The isolated protein has a C-terminus and an N-terminus. An endoplasmic reticulum (ER) export signal promoter is added to the C-terminus of the isolated protein, creating an enhanced light responsive protein. In various embodiments the promoter added to the isolated GtR3 varies depending on the desired location of expression.

Figure 15:
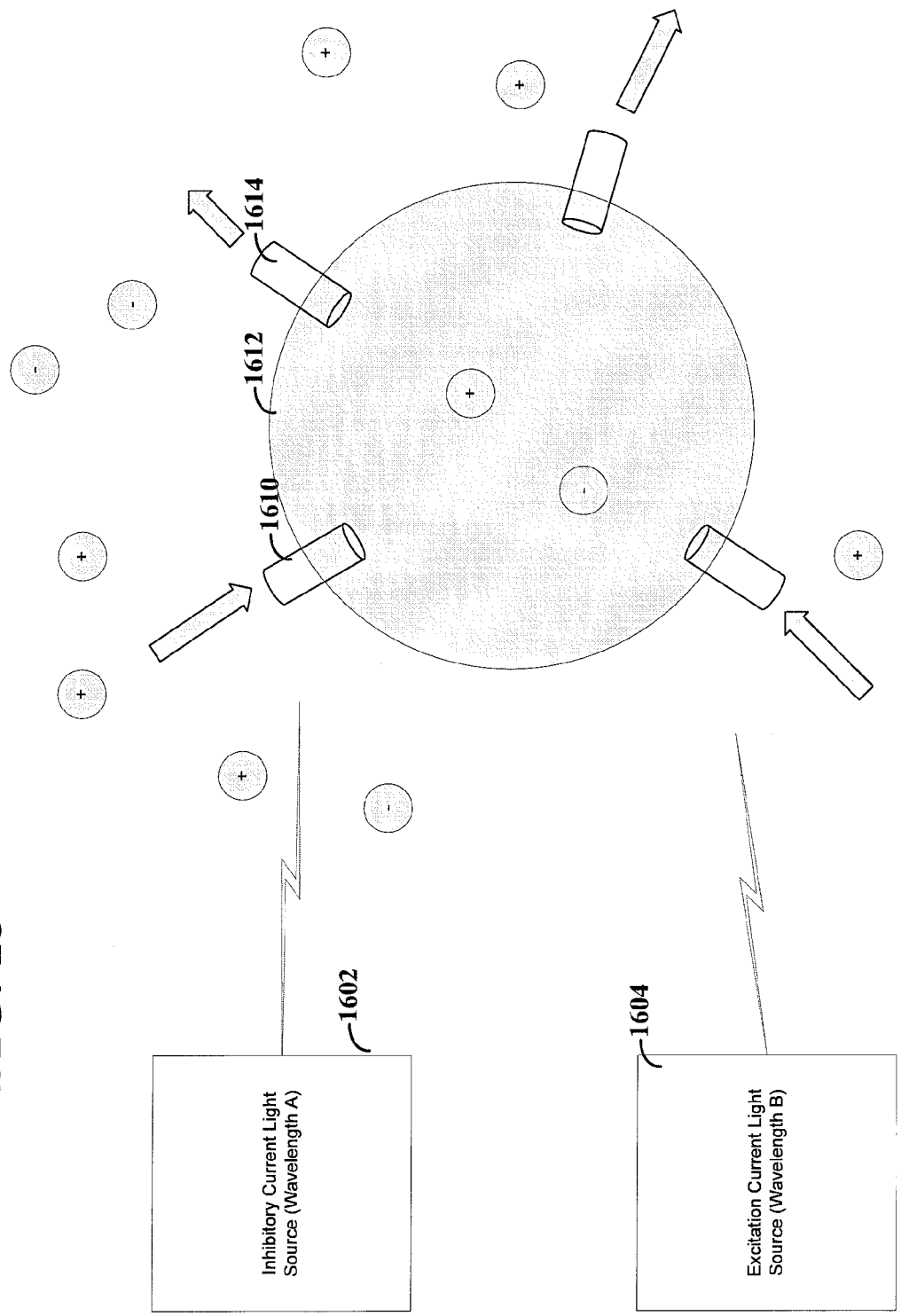
FIG. 15 depicts an arrangement with multiple light sources, according to an example embodiment of the present invention.

FIG. 15 depicts an arrangement with multiple light sources, according to an example embodiment of the present invention. FIG. 15 shows light sources 1602 and 1604 that illuminate proteins 1610 and 1614. The proteins 1610 and 1614 are engineered within cell 1612 to control current across the cell membrane in response to light from light sources 1602 and 1604, respectively. In one instance, the first protein 1610 functions to dissuade action potential firing, while the second protein 1614 functions to encourage action potential firing. Each of proteins 1610 and 1614 are responsive to light. In a particular instance, the first protein is responsive to light from light source 1602 having a wavelength A and the second protein is responsive to light from light source 1604 having a wavelength B. Thus, the light sources can be used to control each protein independently. This can be useful for both encouraging and dissuading action potentials in the cell. In another instance, having both types of proteins allows for both positive and negative control of the cell membrane voltage. Thus, the different light sources and proteins could be used to control the voltage or current level (e.g., clamping) of the cell membrane.

One method of determining responsiveness involves quantifying the responsiveness in terms of the intensity of light required to produce a given response. In some instances, the first or second protein can still be responsive to the alternate wavelength of light although the responsiveness of the protein may be less than that of the primary wavelength. Accordingly, a protein of a first type may have some responsiveness to the wavelength corresponding to the other type of protein while still maintaining sufficient independence of operation. In one such instance, control of the cell can be implemented by shifting either the wavelength of light or the intensity of the light. For instance, the wavelength can be shifted between A and B to induce a corresponding increase or decrease of the membrane voltage potential. Alternatively, multiple proteins having similar actions, but different activation wavelength may be introduced into the same cell. The response may vary as the wavelength is shifted, in some places the combination of the two responses create a greater response than from an individual protein.

According to one embodiment of the present invention, pump 1614 can optionally be implemented for purposes other than dissuading action potential firing, such as controlling the voltage level of cell 1612. More specifically, a sensor can be used provide feedback to the light source 1602. For instance, this feedback could be a measurement of the voltage or current across the cell membrane. Thus, the light source could be configured to maintain a constant current or voltage (e.g., clamp) across the cell. Moreover, the amount of responsiveness can be controlled by modifying one or more of the intensity and wavelength of the light.

Figure 16:
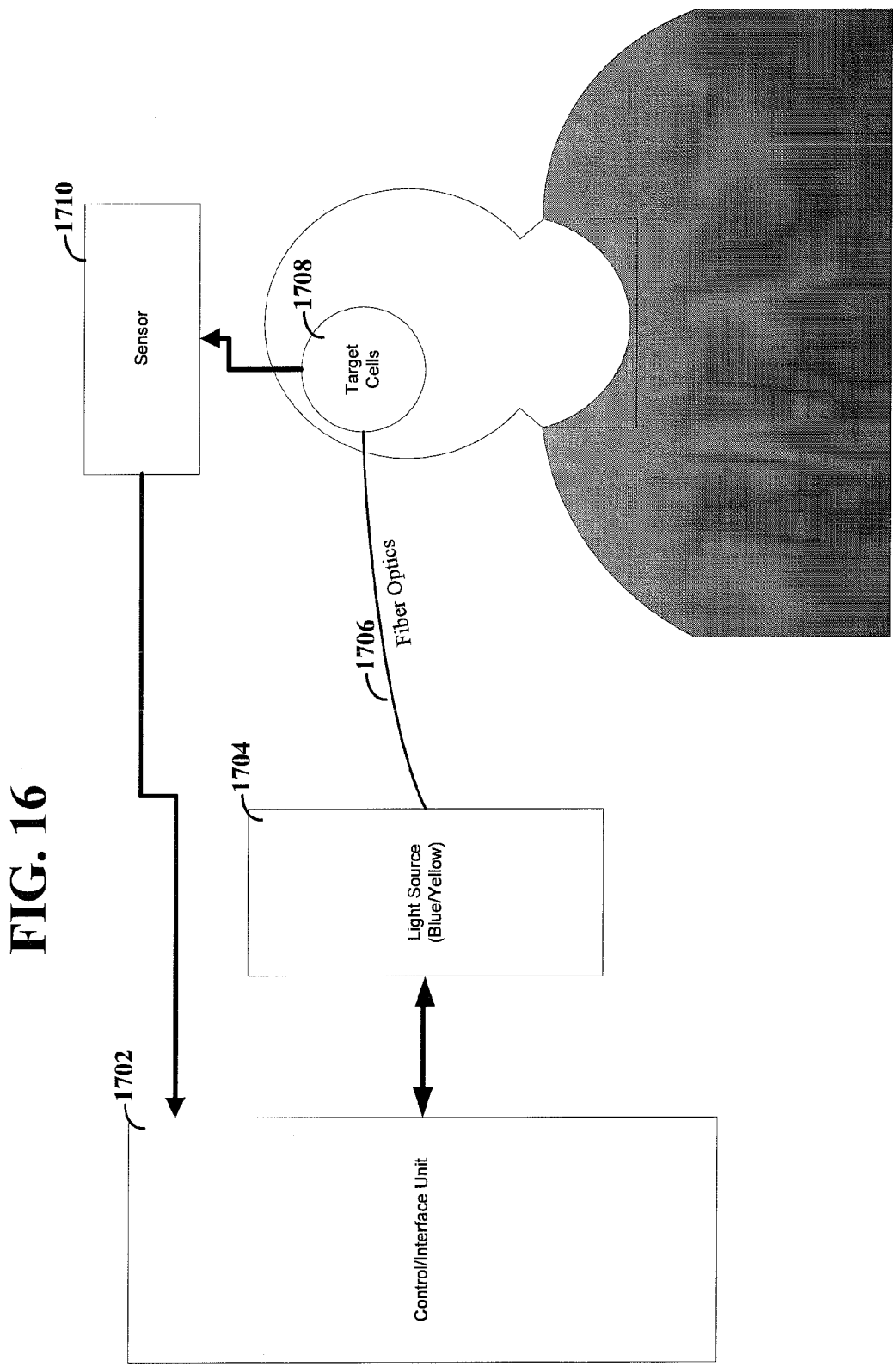
FIG. 16 shows a system for controlling electrical properties of one or more cells in vivo, according to an example embodiment of the present invention.

FIG. 16 shows a system for controlling electrical properties of one or more cells in vivo, according to an example embodiment of the present invention. Control/Interface unit 1702 enables/disables light source 1704 to illuminate target cells 1708. A delivery mechanism, such as fiber optic cable 1706, routes or otherwise directs the light to target cells 1708. Fiber optic cable 1706 may include a bundle of optical cables, each capable of carrying and directing light independently. Thus, fiber optic cable 1706 can be configured to deliver light having one or more wavelengths to multiple locations. Sensor 1710 can be implemented e.g., as an optical device such as an optical scope or as a voltmeter, to provide feedback to control unit 1702. In a particular instance, the feedback includes optical imaging of the target cells or of other related cells. In another instance, the feedback could monitor the voltage response of the target cells, including the amount of action potential firing.

Figure 17:
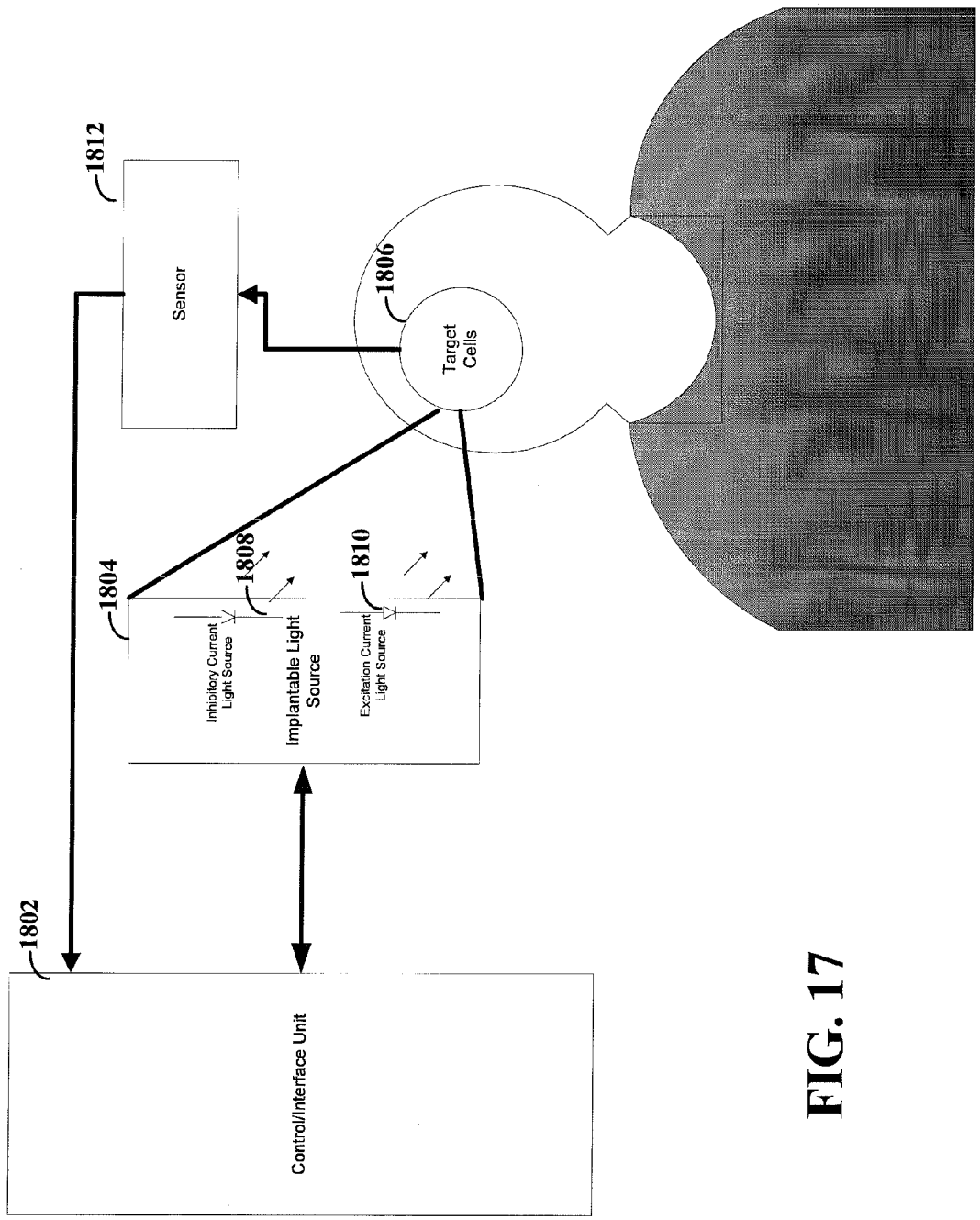
FIG. 17 shows a system for controlling electrical properties of one or more cells in vivo, according to an example embodiment of the present invention

FIG. 17 shows a system for controlling electrical properties of one or more cells in vivo, according to an example embodiment of the present invention. Control/Interface unit 1802 enables/disables implantable light source 1804, which in turn illuminates target cells 1806. Light source 1804 is shown with two light source, inhibitory current light source 1808 and excitation current light source 1810. Light source 1808 produces light at a wavelength and intensity that an inhibitory protein is responsive to, while light source 1810 produces light at a wavelength and intensity that an excitation protein is responsive to. One skilled in the art would recognize that various configurations of light source 1810 are possible, including a single inhibitory light source or an array of light sources having one or more wavelengths. Control/Interface unit 1802 communicates with light source 1804 through any suitable communication mechanisms, such as wired communications or wireless communications using radio-frequency signals, magnetic signals and the like. As discussed above in connection with FIG. 16, sensor 1812 can optionally be implemented for providing feedback to control unit 1802.

Certain embodiments of the present invention can be useful in drug screening. The various light-sensitive proteins, serving to regulate membrane voltage using ion switches that, when activated (or deactivated) in response to light, function as channels or pumps and are referred to hereafter as light-responsive ion switches or light-activated membrane potential switches (LAMPS).

Consistent with one example embodiment of the present invention, a system screens for ion-channel and ion-pump affecting compounds. The system introduces one or more drug candidates that could either block or enhance the activity of ion-channels or ion-pumps to cells that were made optically responsive by the addition of a combination of the above mentioned proteins (ChR2, DChR and NpHR among others), for the purpose of screening the drug candidates. Light triggers optically responsive ion channels in the cells causing a change in the voltage seen across the cell membrane. The voltage change stimulates voltage-gated ion channels in the cells which will then cause a change in ion concentrations that can be read as optical outputs. These optical signals are detected and used to determine what effect, if any, the drug candidates have on the voltage-gated ion channels. In a more specific embodiment a protein expressing a proton pump is introduced into the cell.

In one instance, the system allows for different drug candidates to be screened without necessitating extensive setup between screenings. For example, an assay may be performed using optics both to stimulate the optically responsive cells and to detect the effectiveness of the drug. The use of optics instead of manual contacts, e.g., using a whole-cell patch clamp, can be particularly useful in increasing the throughput of the assay screening process. For instance, the time between screenings can be reduced by minimizing or eliminating physical manipulations otherwise necessary to stimulate or detect ion flow in the target cells. The cells can also be prepared prior to the screening process because the test equipment need only be optically coupled to the prepared cells. In another instance, throughput may be increased by screening a number of different drugs simultaneously using, for example, an array of photo detectors and a corresponding array of modified cells exposed to different drugs.

A cell line based approach is not limited to a particular ion channel. For example, cell lines can be created for voltage-gated sodium (e.g., $Na_v1.1$ through $Na_v1.9$), potassium (e.g., $K_v$ such as hERG, TASK1, Shaker, or KvLQT1), or chloride conducting channels/pumps (e.g., members of the CLC family of chloride channels). The methods of introducing such genes into the cell line are known in the art and may include, for example liposomal transfection, or viral gene transfer. For further information in this regard, reference may be made to one or more of the following references:

Warren Pear, *Transient Transfection Methods for Preparation of High-Titer Retroviral Supernatants*, Supplement 68, Current Protocols in Molecular Biology, 9.11.1-9.11.18, John Wiley & Sons, Inc. (1996).

R. E. Kingston, C. A. Chen, H. Okayama, and J. K. Rose, *Transfection of DNA into Eukarotic Cells*. Supplement 63, Current Protocols in Molecular Biology, 9.1.1-9.1.11, John Wiley & Sons, Inc. (1996).

R. Mortensen, J. D. Chesnut, J. P. Hoeffler, and R. E. Kingston, *Selection of Transfected Mammalian Cells*, Supplement 62, Current Protocols in Molecular Biology, 9.5.1-09.5.19, John Wiley & Sons, Inc. (1997).

H. Potter, *Transfection by Electroporation*, Supplement 62, Current Protocols in Molecular Biology, 9.3.1-9.3.6, John Wiley & Sons, Inc. (1996).

T. Gulick, *Transfection using DEAE-Dextran*, Supplement 40, Current Protocols in Molecular Biology, 9.2.1-9.2.10, John Wiley & Sons, Inc. (1997).

R. E. Kingston, C. A. Chen, H. Okayama, *Transfection and Expression of Cloned DNA*, Supplement 31, Current Protocols in Immunology (CPI), 10.13.1-10.13.9, John Wiley & Sons, Inc.

Each of the above references is incorporated by reference in its entirety.

These and other transfer vectors may be generated using various genetic engineering techniques. For instance, the transfer vectors may be derived from a provirus clone of a retrovirus, such as an immunodeficiency virus (e.g., HIV-1 or HIV-2, or SIV). For further details on the use of 293T cells and transfection thereof, reference can be made to U.S. Pat. No. 6,790,657 (entitled, Lentivirus Vector System, to Arya), which is fully incorporated herein by reference.

In one embodiment of the invention, optical stimulation of the modified cells may be altered to determine specific properties of an introduced drug candidate. For example, the intensity of the optical stimulus may be modified to change the corresponding level of depolarization. The level of desired depolarization can be tuned to further characterize the effectiveness of the drug under test. In another example, the optical stimulus may include rapid pulsing of the light. By correlating the temporal relationship between the optical stimulus and the resultant detected fluorescence, the drug may be further characterized in terms of a kinetic response. Thus, the drug may be characterized for a variety of different aspects including, but not limited to, the steady state effect on ion concentrations, a change in the level of depolarization necessary to trigger the voltage gated ion channels and the effect on repeated depolarization.

In one embodiment, the system allows for simple calibration of the optical stimulation and/or detection. The modified cells may be optically stimulated prior to introduction of the drug candidate. The ion channel responsiveness is detected and recorded. The recorded values may be used as a baseline for comparison to the ion channel responsiveness of the same modified cells after the introduction of the drug under test. The recorded values may also be used to modify the optical stimulus or the sensitivity of the optical detector. Such modifications may be applied to an individual test sample or an array of test samples. For such an array of test samples, each test sample may be individually calibrated by adjusting the corresponding optical stimulus. Similarly, each corresponding photo detector may be individually adjusted.

Figure 18A:
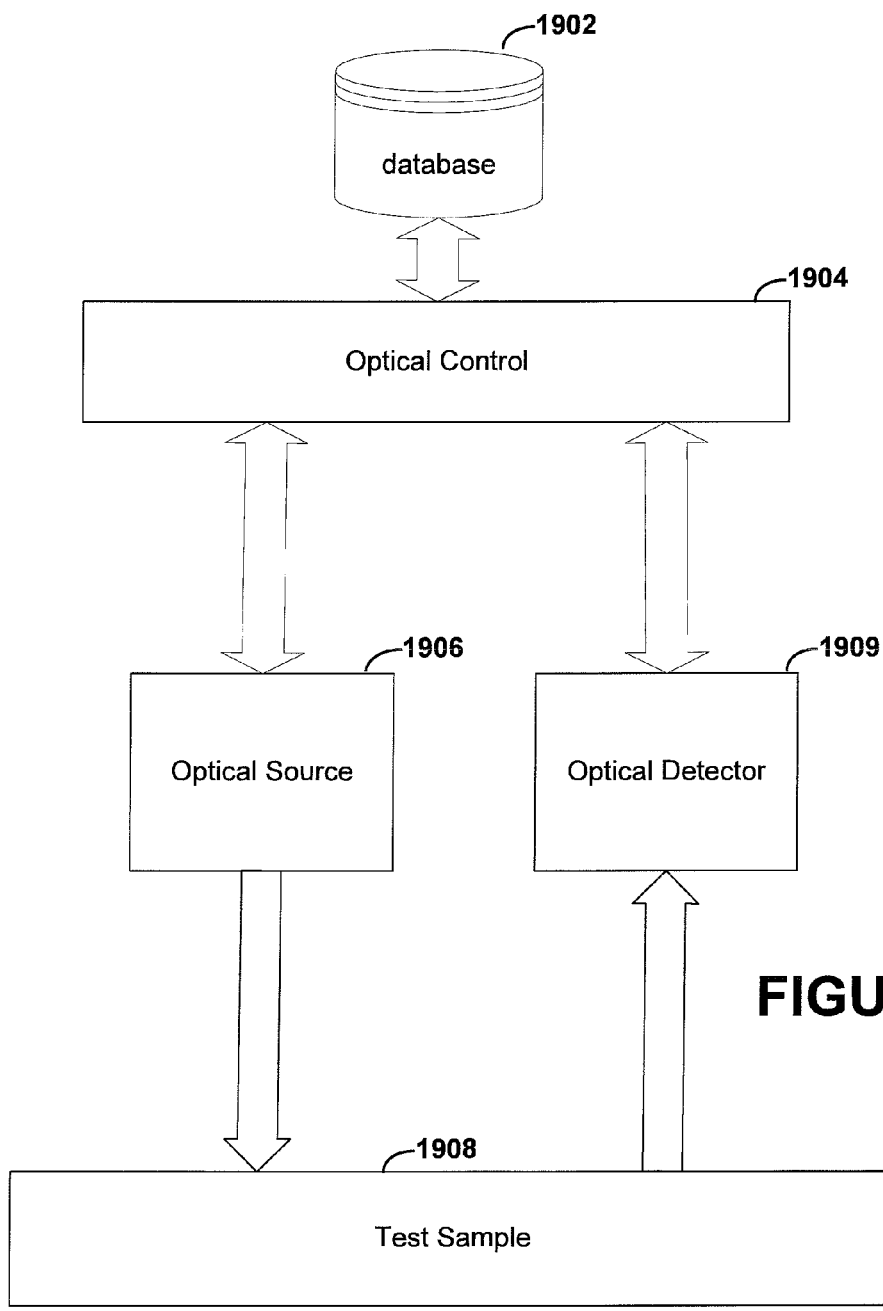
FIG. 18A shows a block diagram of a system for optical drug screening, according to an example embodiment of the present invention.

FIG. 18A shows a basic block diagram of a system for screening for ion-channel affecting drugs, according to an embodiment of the invention. Optical control 1904 communicates with database 1902, optical source 1906 and optical detector 1909. Optical source 1906 provides optical stimulus to test sample 1908. Test sample 1908 includes the drug under test, cells with optically responsive ion channels, and a voltage/ion indicator. In one instance, the indicator fluoresces in response to light from optical source 1906. Optical control 1904 may also include a reconfigurable readout, so that as different LAMPS and different LEIAs are used, the same control system can be readily adapted to each paradigm. Optical detector 1909 produces a signal responsive to such florescence, and optical control 1904 receives the produced signal. The optical control 1904 stores data obtained from the signal in database 1902. The information stored may include factors such as the intensity, duration and wavelength of the detected light. In a particular instance, the stored data can be compared against baseline data, where the baseline data corresponds to data recorded prior to the introduction of the drug to the test sample 1908. In another instance, optical source 1906 may vary the intensity, duration or other parameters related to the control of optical source 1906. These and other parameters may be stored in database 1902.

It should be apparent that optical source 1906 may be implemented using a single light source, such as a light-emitting diode (LED), or using several light sources. Similarly, optical detector 1909 may use one or more detectors and database 1902 may be implemented using any number of suitable storage devices.

Figure 18B:
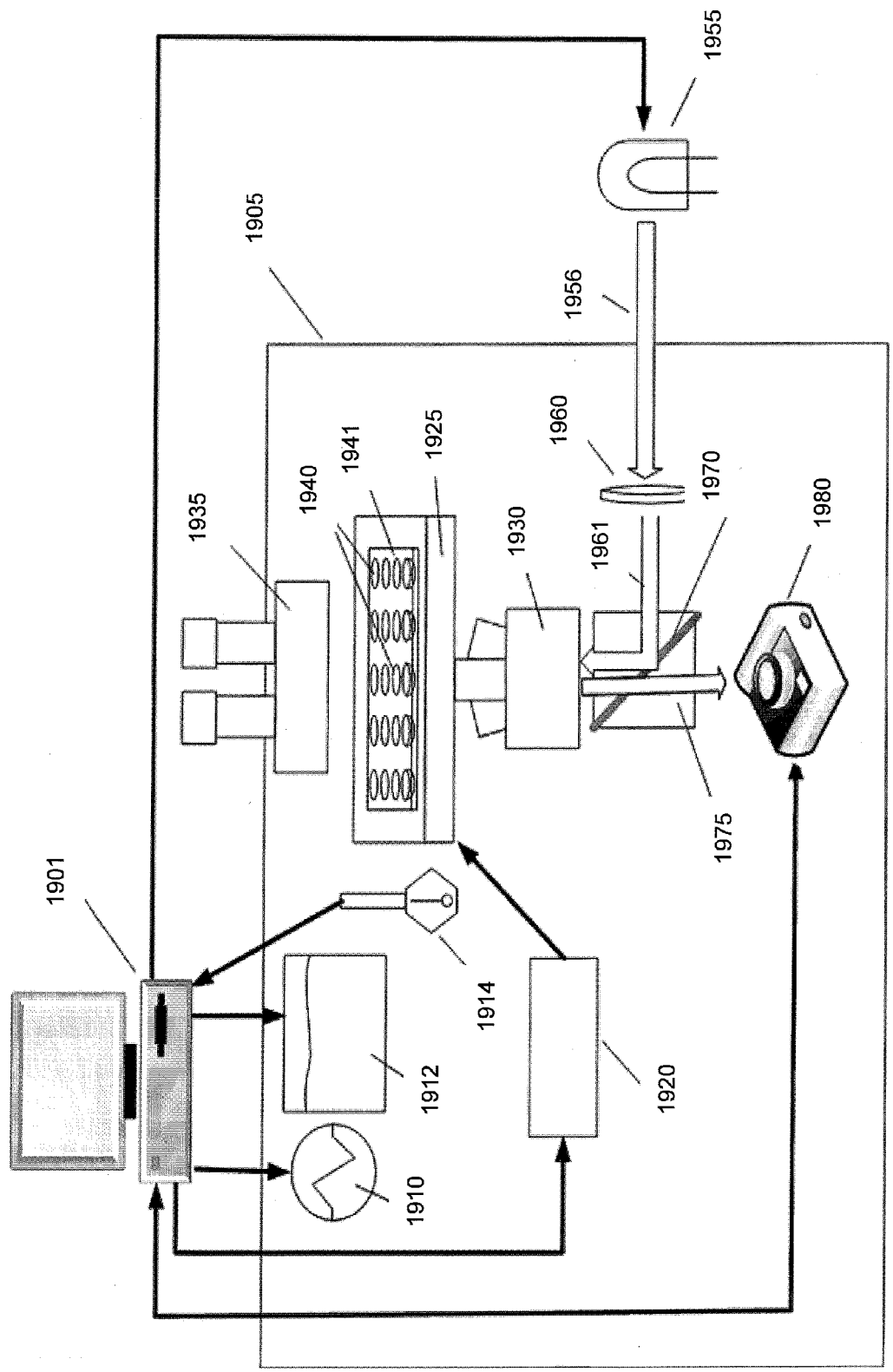
FIG. 18B shows a specific system diagram of a large-format, quasi-automated system for drug screening in accordance with the present methodology, according to an example embodiment of the present invention.

FIG. 18B shows a system diagram of a large-format, quasi-automated system for drug screening in accordance with a specific embodiment of the invention. Control device 1901 (e.g., a computer or control logic) controls various processes, and serves as the central point of system input/output functions. The environment may be maintained at an appropriate temperature, humidity, carbon dioxide level and ambient light level within the walls of the climate control chamber 1905, with the help of one or more sensors 1914 (e.g., thermostat, carbon dioxide sensor and humidity sensor), carbon dioxide and humidifier apparatus 1912, and heater 1910. Multi-well tray 1941 contains test wells 1940 for holding cultured cells, drugs, and other ingredients needed for each test. Tray 1941 rests upon X-Y-Z table 1925, the movement of which is carried out by table actuators 1920, under control of computer 1901. Xenon lamp 1955 emits high-intensity white light 1956, which is passed through color filter 1960. In the case that DChR is used for stimulating the cells within wells 1940, color filter 1960 is blue, causing blue light 1961 to exit the filter, and strike dichroic mirror 1970. Blue light 1961 then passes upward, through microscope objective lens apparatus 1930, and through bottom of transparent tray 1941. In this fashion, the contents of wells 1940, with their transparent undersides, are illuminated. When a separate wavelength of light is required to stimulate a fluorescent light-emitting indicator of cellular activity, a filter of the appropriate specification may be substituted for the previous filter 160, causing light of the proper wavelength for this latter task to be piped toward well 1940. If the cells within well 1940 have been light-sensitized, and if the drug being tested in each of these wells does not suppress the process, a light-emitting indicator of cellular activity (LEIA), which has also been added to each well or expressed by the cells via genetic modification, will emit light in accordance with the voltage change caused by the effect of the light. This second wavelength of light, which may be much smaller in magnitude than the stimulation light, is collected by microscope turret 1935, and will also be passed through dichroic mirror 1975, onto the lens of (CCD) camera 1980.

Dichroic mirror 1970 allows for upward reflection of both the wavelength required to stimulate the optical gating of the membrane (e.g., blue-green for DChR), and the wavelength required by any LEIA used (e.g., ultraviolet for FURA-2). This dichroic mirror may be arranged to allow passage of the output spectrum of the LEIA (e.g., blue-green for FURA-2) with minimal reflection or absorption.

Figure 19:
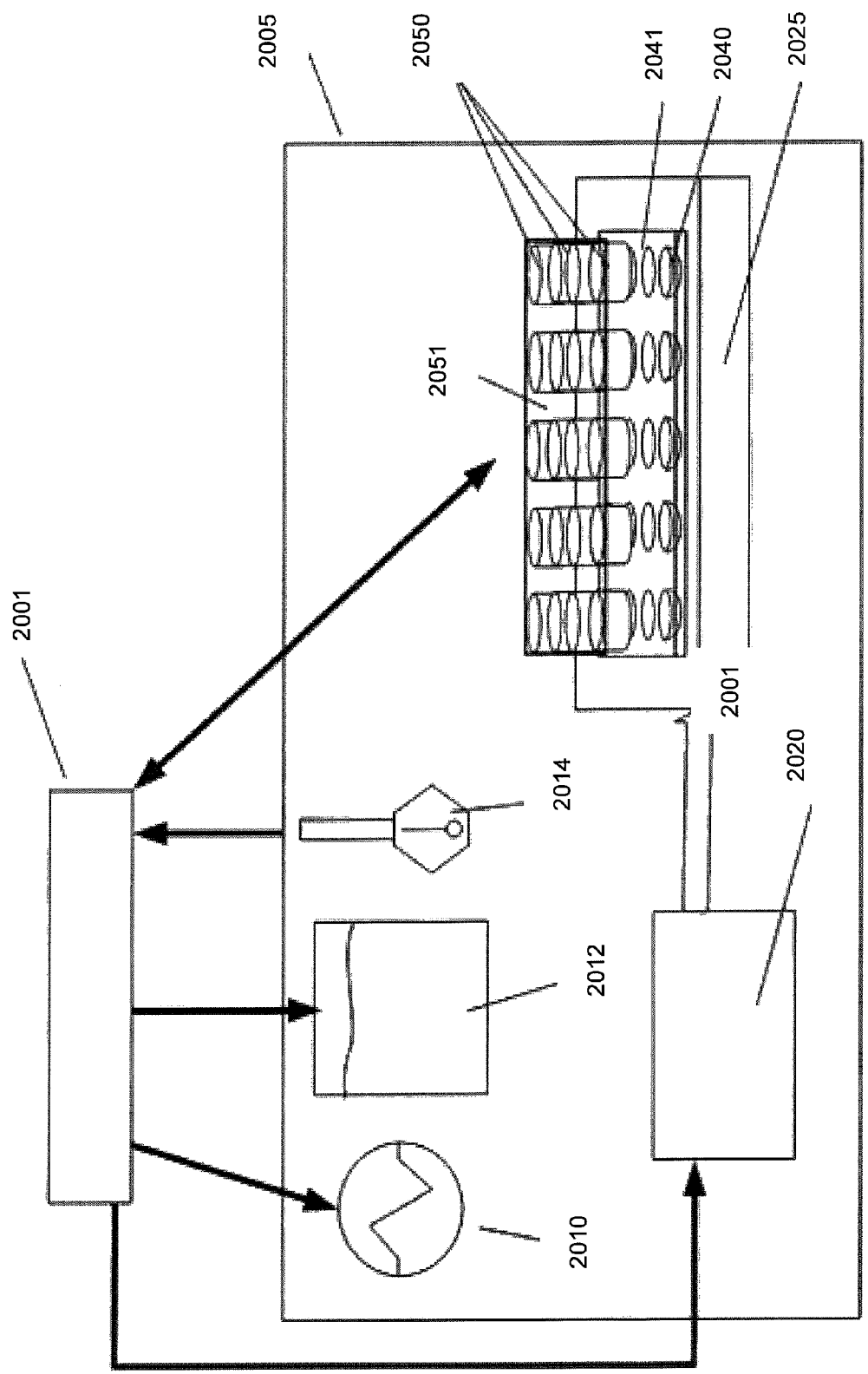
FIG. 19 shows a system diagram of a small-format, fully automated drug screening system which operates in accordance with the invented methodology, according to an example embodiment of the present invention.

FIG. 19 is a system diagram of an automated-drug-screening system, according to an example embodiment of the invention. Emitter/detector units 2050 make up the emitter/detector array 2051. Emitter/detector array 2051 matches the number, size, and layout of the wells on tray 2040. Tray holding device 2025 permits tray swapping mechanism 2020 to rapidly move a new tray into position once testing of a given tray has been completed. The entire process may be automated, and under the control of device 2001. Device 2001 can be implemented using a computer, control logic, programmable logic arrays, discreet logic and the like. The introduction of the drug candidates under test can also be automated using a machine that provides a reservoir for storing the drugs and a dispensing nozzle for injecting the drugs into the tray. In a manner similar to that shown by FIG. 18, the environment within the walls of the climate control chamber 2005 may be maintained at an appropriate temperature, humidity, carbon dioxide level and ambient light level, with the help of thermostat, carbon dioxide sensor and humidity sensor 2014, carbon dioxide and humidifier apparatus 2012, and heater 2010. The use of multiple stimulator/detector elements simultaneously and in parallel, can be particularly useful for augmenting the speed of the overall process. Low cost elements may be used to make multiple parallel detectors (e.g., the components detailed below in description of FIGS. 20A and 20B); the multiple parallel emitter/detector units may also be quite economically feasible.

Figure 20A:
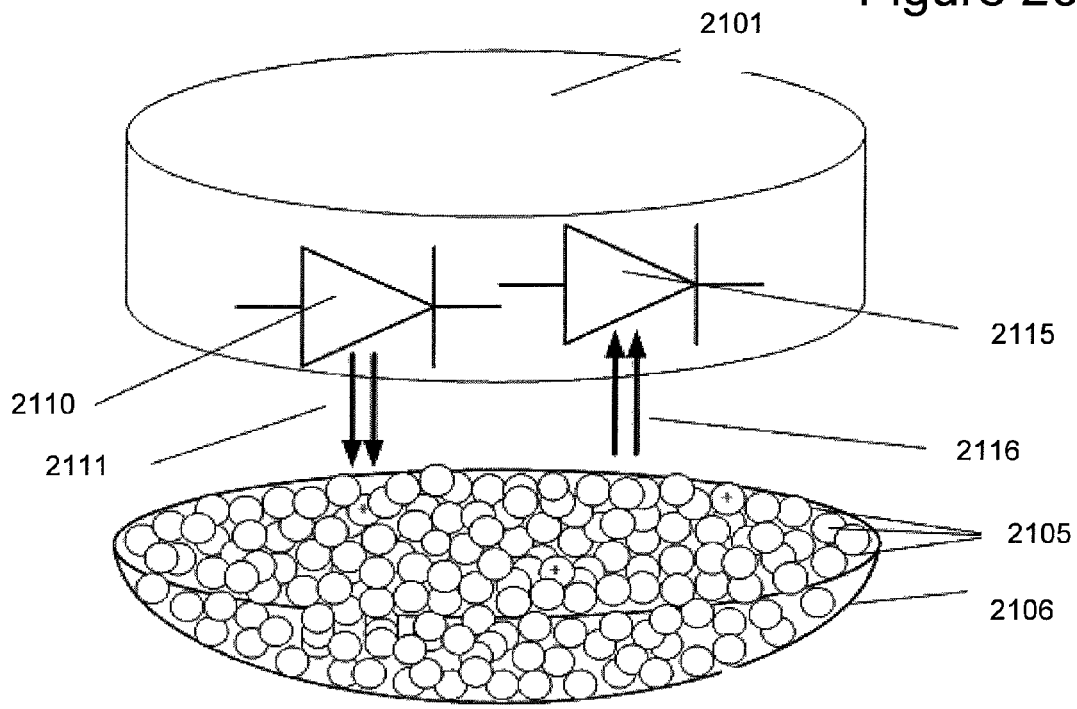
FIG. 20A depicts the workings of an example of emitter/detector units, according to an example embodiment of the present invention.

FIG. 20A depicts the workings of emitter/detector units, such as those shown in FIG. 19, according to an example embodiment of the invention. An LED stimulates light-sensitive ion channels of cells located within a well, and a photodiode detects the response of a LEIA. In this embodiment, device 2101 includes LED 2110, which produces light pulses 2111, at the proper wavelength, pulse frequency and intensity, so as to stimulate light-sensitive transgenic cells 2105 in culture within well 2106. Due to the presences of an LEIA (e.g., a voltage-sensitive dye or a calcium dye), light 2116 is returned from cells 2105, and is detected by photodiode 2115. In the case that RH 1691 being used, red light is fluoresced and detected by photodiode 2115. In the absence of cellular depolarization, no fluorescence is detected by photodiode 2115. Other light detecting technologies may also be used instead of a photodiode including phototransistors, and CCD elements.

The combination of photostimulation with optical imaging techniques of LEIAs may be useful for a number of different reasons. For example, photostimulation may simplify the study of excitable cells by reducing the need to use mechanical electrodes for stimulation. Several commercially available LEIAs are suitable for photogrammetrically indicating the activation of electrically excitable cells. One such LEIA is calcium dye Fura-2, which may be stimulated with violet/ultraviolet light around 340 nm, and whose fluorescent output is detectable as blue-green light around 535 nm. Another example is voltage sensitive dye RH 1691, which may be stimulated with green light at about 550 nm, and whose fluorescent output is detectable as red light at about 70 nm. Another example is voltage sensitive dye di-4-ANEPPS, which is stimulated by blue light at about 560 nm, and whose fluorescent output is detectable as red light at about 640 nm.

Figure 20B:
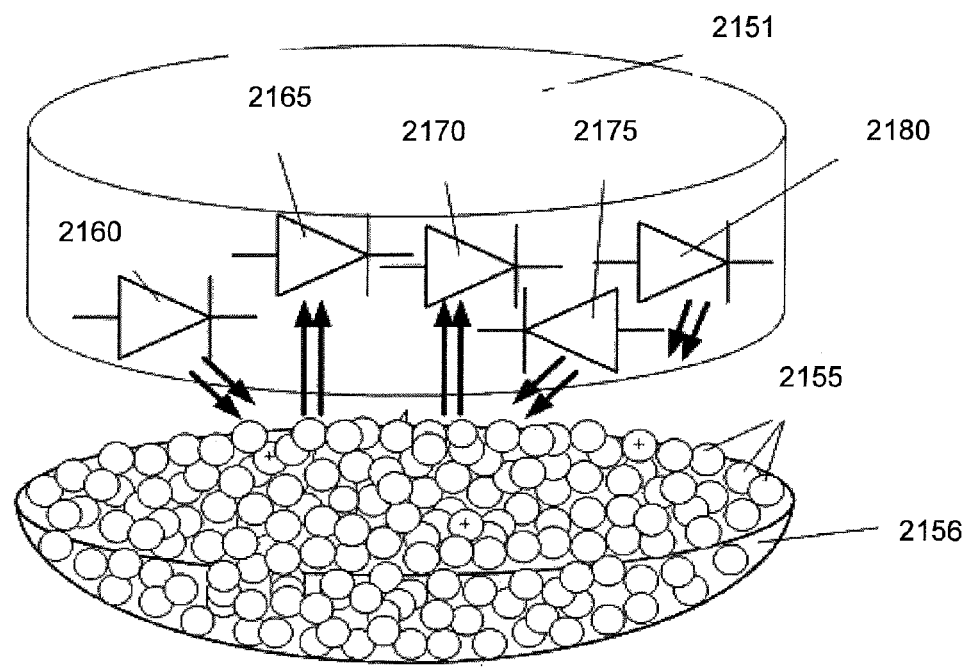
FIG. 20B depicts the workings of another embodiment of emitter/detector units, according to an example embodiment of the present invention.

FIG. 20B depicts the workings of another embodiment of the emitter/detector units shown in the FIG. 19, in which multiple effects are tested within the context of a single well. For example, the cells 2155 in the wells 2156 may express both GtR3 and VChR1, and hence be sensitive to both the hyperpolarizing effects of blue light, and the depolarizing effects of amber light. Device 2151 includes LED 2160, which is used for the stimulation of the targeted proton pump (e.g., GtR3) of light-sensitive transgenic cells 2155. Additional LED 2175 may be used to stimulate a second targeted ion channel or pump (e.g., VChR1). Yet another LED 2180 may be used to stimulate a voltage sensitive dye (e.g., RH1691 or calcium dye, such as Fura-2). Each LED may be arranged to output specific wavelengths and intensities for stimulus of respective targeted compounds. In one instance, an LED may affect more than one target, depending upon the specific sensitivities of each compound used. Photodiode 2165 detects the fluorescence of a selected voltage dye, while photodiode 2170 is sensitive to the spectrum fluoresced by a selected calcium dye. The use of multiple LEDs for the same cell allows for the stimulation of LEIAs at different wavelengths. Multiple LEDs may also be used to detect different light wavelengths emitted by the LEIA.

FIG. 21A depicts an electronic circuit mechanism for activating the LED emitters used within the emitter/detector units, according to an example embodiment of the invention. Control device 2201 generates a "light on signal" 2202 to transistor base 2205. This light on signal 2202 will remain on for the duration of a light flash desired, or alternatively may turn on and off in order to produce rhythmic light flashes at a specified frequency. Light on signal 2202 permits (conventional) current to flow from power source 2210, through resister 2211, and through transistor collector 2207 and transistor emitter 2212, to ground 2213. Current is also thereby permitted to pass through resistor 2215, and into LED 2220. LED 2220 emits light 2221, which falls upon well 2225. In a particular instance, the transistor functions as transconductance amplifier of signal 2202. In this manner, light of the appropriate wavelength, intensity and frequency is delivered to cells within the well 2225, so as to cause them to stimulate the particular channel (e.g. DChR) or pump (e.g., GtR3), or other photoactive membrane structure being used to regulate the activity of electrically excitable cells. Various other circuits are also possible. For example, other circuits can be used in place of circuit 2206 to control LED 2220 including, but not limited to, replacing the transistor with an operational amplifier, a field-effect-transistor, a resistor divider network, transistor-transistor logic, push-pull driver circuits and switches.

FIG. 21B depicts an example electronic circuit mechanism for light detection by the emitter/detector units, according to one embodiment of the invention. Control device 2250 may (optionally, depending upon specific implementation) provide power to photodiode 2255. Photodiode 2255 receives fluoresced (emitted) light 2256 from the LEIA on the cells within well 2257. The received light results in an output signal. This output passes through resistor 2260, and is input to Schmitt triggered hex inverter 2270, which conditions the signal, providing a clean "high" or "low value" to be input to computer 2250.

Operation of the photodetector is shown in photovoltaic mode, but the element may also be used in the photoconductive mode of operation. Of course, many other light-detection devices and methods may also be used, including phototransistors, photothyristors, and charged-coupled device (CCD) elements, or arrays of elements.

Alternatively, the circuit of FIG. 21B can be used without Schmitt-triggered hex inverter 2270, permitting a continuum of signal intensities to be transmitted directly to an analog input to computer 2250 or to an analog-to-digital converter. Various other signal conditioning circuits are also possible.

Figure 22:
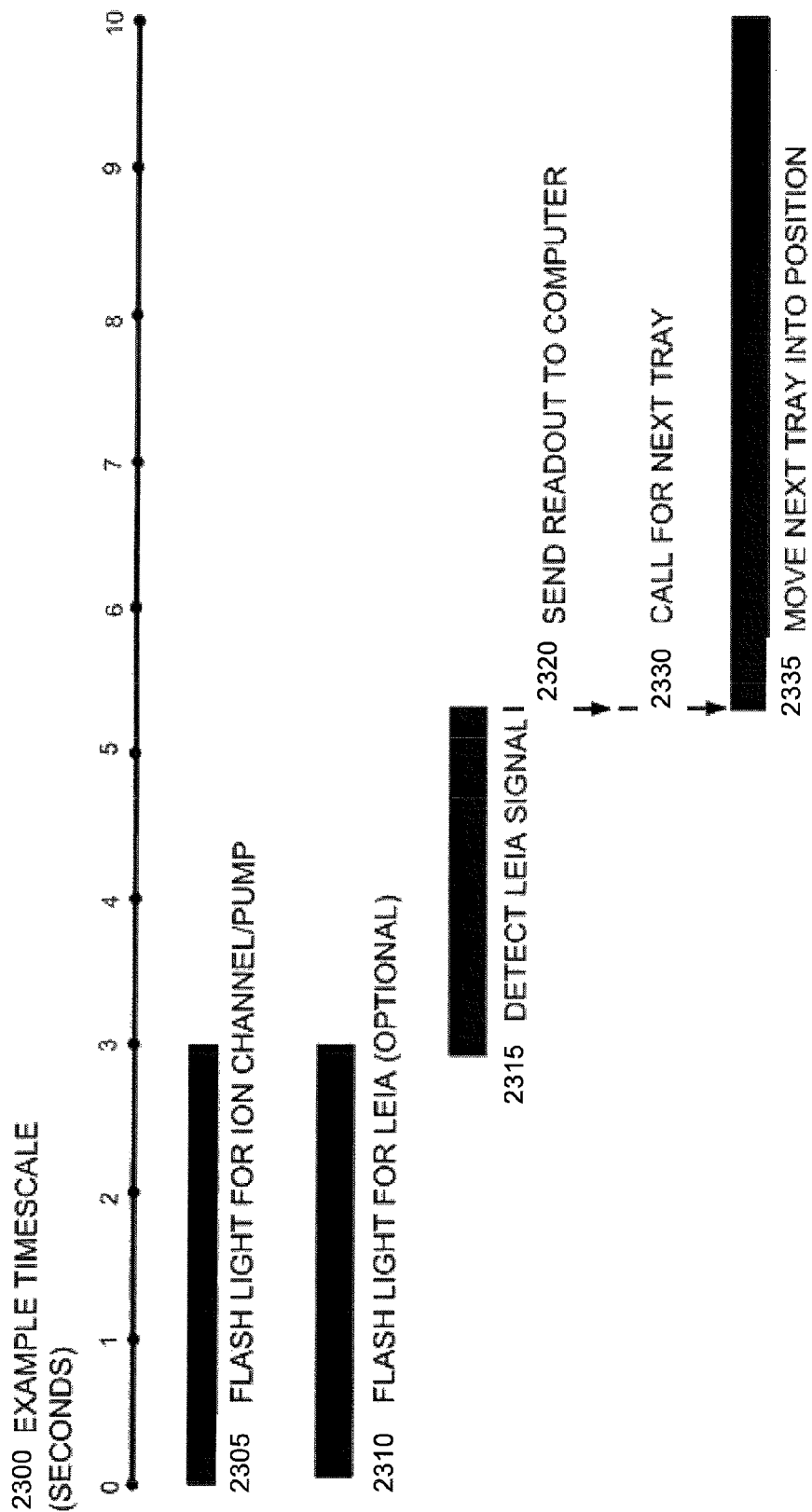
FIG. 22 shows a timeline for a sequence of events in the context of an example screening process, according to an example embodiment of the present invention.

FIG. 22 shows a sequence of steps using the embodiment shown in FIGS. 19, 20 and 21, in the context of projected high-throughput process time course 2300 and in accordance with one embodiment of the invention. In step 2305, light of the appropriate wavelength and intensity for the targeted ion channel is flashed-in this case for approximately three seconds. Concurrently, a LEIA stimulation flash 2310 may optionally be triggered, depending upon the specific voltage or calcium dye, etc. being used. This LEIA compound may have been previously added to the well, or may be (artificially) genetically imparted upon the cells such that the chemical is produced/expressed by the cells. In step 2315, the light signal produced by the LEIA is detected by the photodetector element (e.g., photodiode). For example, RH1691, fluoresces red light at about 70 nm.

In step 2320, the signal resulting from the impingement of light onto the photodetector element is sent back to the computer. This may be a binary (e.g., "high" versus "low" signal intensity), or may be graded to reflect a continuum of activation levels. In the case that multiple photodetectors are used to determine energies at different wavelengths, the individual readings of these photodetectors may be logged in parallel or in sequence for appropriate interpretation in a later stage of the automated process. In step 2330, the system calls for the next tray to be placed by the automated system. The next tray is moved into position at step 2335 and the process may be repeated until all trays in a batch have been processed.

The amount of time allotted for light delivery may vary, and depends on factors including the level of light-gated proton or ion channel/pump expression, and the density and characteristics of other proton/ionic channel characteristics of that cell population. The amount of time allotted for light receipt may vary, and depends upon factors including the degree of accuracy required for the screening session. The amount of time allotted for well-plate (tray) changing may vary, and depends upon factors including the mechanical speed of the automated apparatus. If fast neurons are used as the cells being tested, the cellular stimulation and LEIA detection process may be accomplished in milliseconds.

The process above may be repeated under varying conditions. For example, a given set of cells may be tested with no drug present, and subsequently with one or more drugs present. The response of electrically-excitable cells under those conditions may be thereby documented, compared and studied. If the invention is implemented with at least one emitter/detector for each well on a tray and at least two concurrently operating devices, continuous operation may be maintained for extended periods of time.

Figure 23:
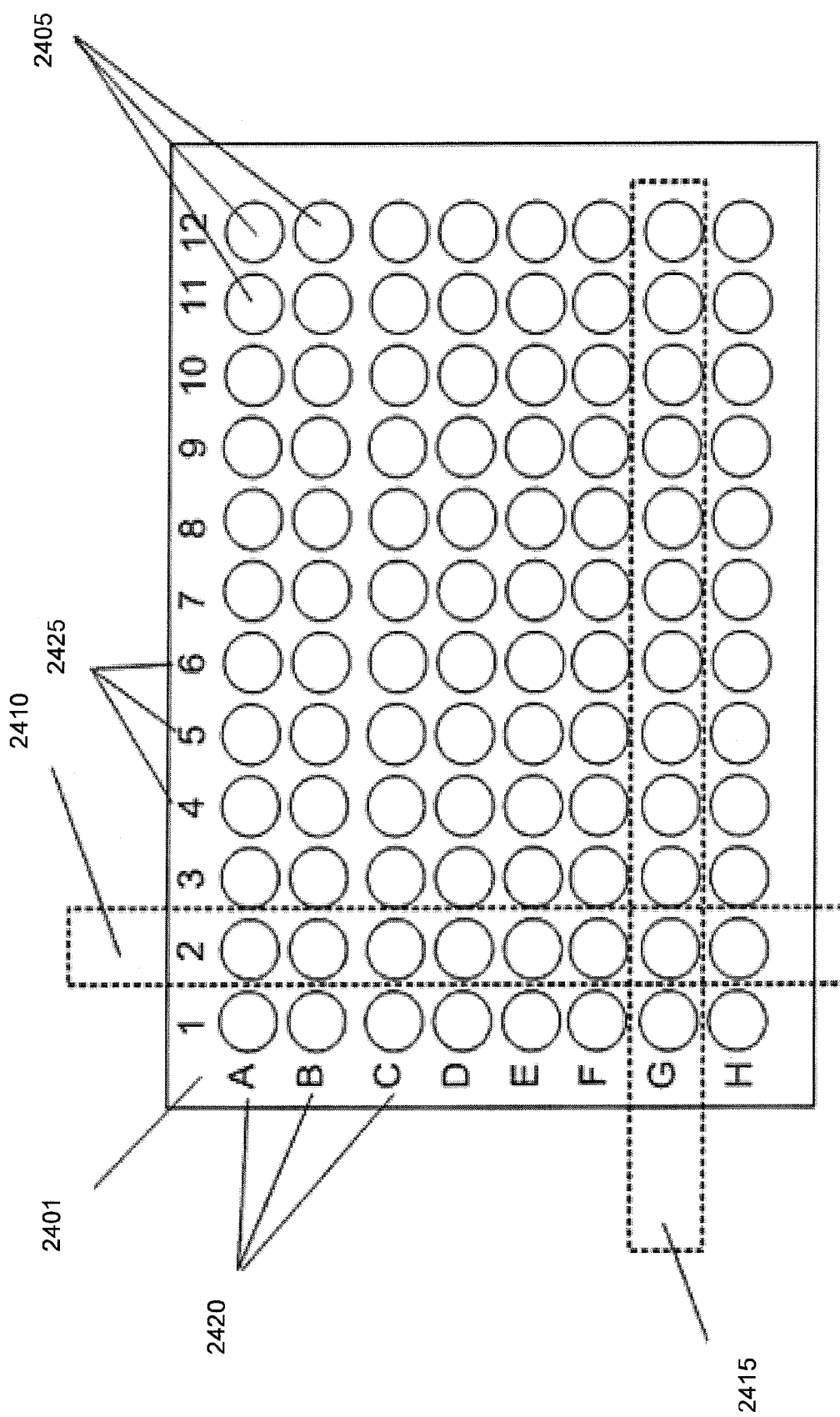
FIG. 23 illustrates an example of a layout of cell and drug samples within the wells of a well-plate, according to an example embodiment of the present invention.

FIG. 23 illustrates an example of a layout of cell and drug samples within the wells of a well-plate which is suitable for use within an embodiment of the invention. In this figure, well-plate 2401 (also referred to herein as a "tray") contains wells 2405 (examples), which are organized into columns 2425, labeled with numbers 1-12 and rows 2420, labeled with letters A-H. More specifically, an example column and row are defined by 2410 and 2415 respectively.

As an example of a functional layout of contents introduced into these wells, rows A-H of a single plate might be used for the testing of two different drugs. To represent a baseline condition, column 1 might contain optically gated cells, an endogenous or exogenous LEIA, but no drug. Columns 2-6 might be used for five different concentrations of Drug X, one concentration level per column. Likewise, columns 7-11 might be use for five different concentrations of Drug Y, one concentration per column. Column 12, while fully usable, is left unused in this particular example.

Variables in the various wells might include the type of cell being tested, the type of ion channel being tested for, the type of drug placed in the cell, the concentration of the drug placed in the well, the specific LEIA used, and the optical gating stimulation parameters (e.g., wavelength, intensity, frequency, duration) applied to Inc cells in that well.

Figure 24:
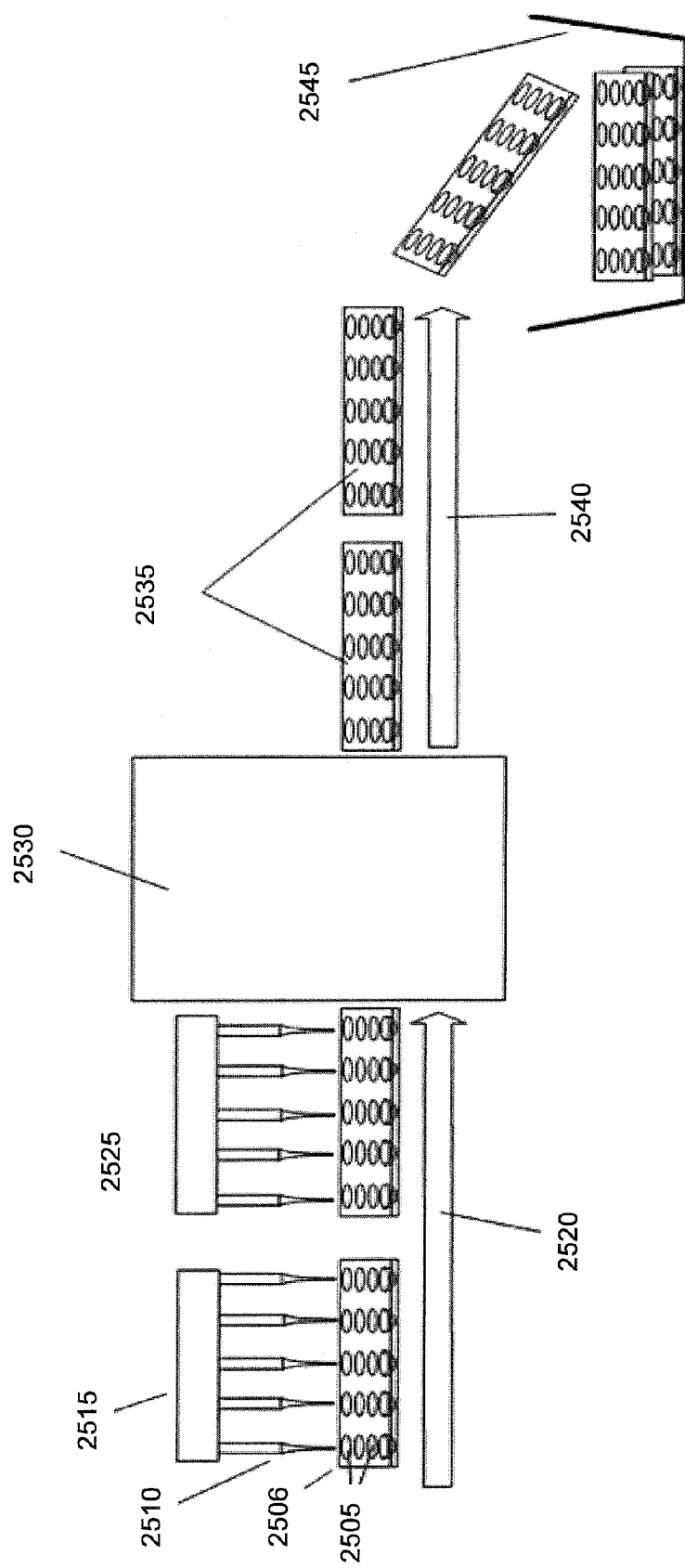
FIG. 24 illustrates the context in which the disclosed invention may be employed within a larger system that facilitates high-throughput drug screening, according to an example embodiment of the present invention.

FIG. 24 illustrates the context in which the disclosed invention may be employed within a larger system which facilitates high-throughput drug screening. Well-plate 2506 contains wells 2505. These are carried forward by conveyer 2520, which may be a device such as a conveyor belt, robotic transporter or other delivery mechanism. Pipettes 2510 are held in array by robotic member 2515, and serve to inject the proper number of cultured cells and media into wells 2505. Subsequently, well-plate 2506 is moved down conveyer 2520, where robotic member 2525, analogous to robotic member 2515 and also containing pipettes, injects the proper amount of a LEIA into wells 2505. Conveyer 2520 then brings well-plate 2505 into screening chamber 2530. An emitter/detector apparatus, such as those described in connection with FIG. 17, FIG. 18A, FIG. 18B, FIG. 19A, and FIG. 19B, is located within chamber 2530. Additionally, portions of the processes described in FIG. 20A and FIG. 20B may occur within this chamber. Subsequently, well-plates 2535 is moved out of screening chamber 2530 by conveyor 2540, and discarded at 2545. In an alternative embodiment, one or more robotic devices may move pipettes 2510, screening chamber 2530, etc. to the locations of well-plate 2506, rather than vice-versa.

Consistent with the above discussion, example screening methods could include the collection of multiple data points without having to switch samples. Because control over the samples is reversible in the same sample preparation by simply turning the activating light on and off with fast shutters, the same samples can be reused. Further, a range of patterns of stimulation can be provided to the same cell sample so that testing can be performed for the effect of drugs without concern with regards to differences across different sample preparations. By modulating the level of excitation (e.g., by ramping the level from no light to a high or maximum intensity), the effect of the drug across a range of membrane potentials can be tested. This permits for the identification of drugs that are efficacious during hyperpolarized, natural, or depolarized membrane potentials.

The cell lines described herein may be a particularly useful for detailed characterization of drug candidates in a high-throughput manner Optical control is relatively fast, thereby allowing for the testing the drug's activity under more physiological forms of activation. For example, different frequencies of depolarization and/or hyperpolarization may be used to determine how a drug interacts with the channel under physiological forms of neural activity. In some instances, the process may be accomplished without the application of expensive chemical dyes to the cell lines.

In conjunction with the various properties discussed herein, the use of various embodiments of the invention may be particularly useful for improving screening throughput by eliminating the need for cumbersome mechanical manipulation and liquid handling. Various embodiments may also be useful for repeatable the screening assay using the same samples, reducing screening cost by eliminating the need for chemically-based fluorescence reports, producing high temporal precision and low signal artifact (due to the optical nature of the voltage manipulation), modulating the level of depolarization by attenuating the light intensity used for stimulation, and ascertaining the kinetics of the drug's modulation on the ion channel through the use of pulsed light patterns.

The existence of multiple independently controllable excitation proteins and inhibition proteins opens the door for a variety of applications including, but not limited to, applications for treatment of a variety of disorders and the use of a plurality of light responsive proteins that can be selected so as to respond to a plurality of respective optical wavelengths. Although not always expressly stated, inhibition can be used in combination with, in addition to, or in place of excitation in the applications. The family of single-component proteins has been shown to respond to multiple wavelengths and intensities of light. Aspects of the invention allow for further mutations and/or searches for sequences that allow for additional optical wavelengths and/or individually controllable protein channels. Variations on the optical stimulus (e.g., a wavelength, intensity or duration profile) can also be used. For instance, stimulation profiles may exploit overlaps in the excitation wavelengths of two different ion channel proteins to allow excitation of both proteins at the same time. In one such instance, the proteins may have different levels of responsibility. Thus, in a neural application, one set of ion channels may produce spiking at a different success percentage relative to a second set of ion channels. Similarly, the overlaps in inhibition wavelengths of two different ion channels (or pumps) allows for inhibition of both proteins at the same time. Alternatively, multiple light sources may be used allowing for stimulations of the light responsive proteins in the combination desired, while leaving other proteins unstimulated.

Many human applications of the present invention require governmental approval prior to their use. For instance, human use of gene therapy may require such approval. However, similar gene therapies in neurons (non-proliferative cells that are non-susceptible to neoplasms) are proceeding rapidly, with active, FDA-approved clinical trials already underway involving viral gene delivery to human brains. This is likely to facilitate the use of various embodiments of the present invention for a large variety of applications. The following is a non-exhaustive list of a few examples of such applications and embodiments.

Addiction is associated with a variety of brain functions, including reward and expectation. Additionally, the driving cause of addiction may vary between individuals. According to one embodiment, addiction, for example nicotine addiction, may be treated with optogenetic stabilization of small areas on the insula. Optionally, functional brain imaging, for example cued-state PET or fMRI, may be used to locate a hyper metabolic focus in order to determine a precise target spot for the intervention on the insula surface.

Optogenetic excitation of the nucleus accumbens and septum may provide reward and pleasure to a patient without need for resorting to use of substances, and hence may hold a key to addiction treatment. Conversely, optogenetic stabilization of the nucleus accumbens and septum may be used to decrease drug craving in the context of addiction. In an alternative embodiment, optogenetic stabilization of hyper metabolic activity observed at the genu of the anterior cingulate (BA32) can be used to decrease drug craving. Optogenetic stabilization of cells within the arcuate nucleus of the medial hypothalamus which contain peptide products of pro-opiomelanocortin (POMC) and cocaine-and-amphetamine-regulating transcript (CART) can also be used to decrease drug addiction behavior. For further information in this regard, reference may be made to: Naqvi N H, Rudrauf D, Damasio H, Bechara A. "Damage to the insula disrupts addiction to cigarette smoking." Science. 2007 Jan. 26; 315(5811): 531-534, which is fully incorporated herein by reference.

Optogenetic stimulation of neuroendocrine neurons of the hypothalamic periventricular nucleus that secrete somatostatin can be used to inhibit secretion of growth hormone from the anterior pituitary, for example in acromegaly. Optogenetic stabilization of neuroendocrine neurons that secrete somatostatin or growth hormone can be used to increase growth and physical development. Among the changes that accompany "normal" aging, is a sharp decline in serum growth hormone levels after the $4^{th}$ and $5^{th}$ decades. Consequently, physical deterioration associated with aging may be lessened through optogenetic stabilization of the periventricular nucleus.

Optogenetic stabilization of the ventromedial nucleus of the hypothalamus, particularly the pro-opiomelanocortin (POMC) and cocaine-and-amphetamine-regulating transcript (CART) of the arcuate nucleus, can be used to increase appetite, and thereby treat anorexia nervosa. Alternatively, optogenetic stimulation of the lateral nuclei of the hypothalamus can be used to increase appetite and eating behaviors.

Optogenetic excitation in the cholinergic cells of affected areas including the temporal lobe, the NBM (Nucleus basalis of Meynert) and the posterior cingulate gyrus (BA 31) provides stimulation, and hence neurotrophic drive to deteriorating areas. Because the affected areas are widespread within the brain, an analogous treatment with implanted electrodes may be less feasible than an opto-genetic approach.

Anxiety disorders are typically associated with increased activity in the left temporal and frontal cortex and amygdala, which trends toward normal as anxiety resolves. Accordingly, the affected left temporal and frontal regions and amygdala may be treated with optogenetic stabilization, so as to dampen activity in these regions.

In normal physiology, photosensitive neural cells of the retina, which depolarize in response to the light that they receive, create a visual map of the received light pattern. Optogenetic ion channels can be used to mimic this process in many parts of the body, and the eyes are no exception. In the case of visual impairment or blindness due to damaged retina, a functionally new retina can be grown, which uses natural ambient light rather than flashing light patterns from an implanted device. The artificial retina grown may be placed in the location of the original retina (where it can take advantage of the optic nerve serving as a conduit back to the visual cortex). Alternatively, the artificial retina may be placed in another location, such as the forehead, provided that a conduit for the depolarization signals are transmitted to cortical tissue capable of deciphering the encoded information from the optogenetic sensor matrix. Cortical blindness could also be treated by simulating visual pathways downstream of the visual cortex. The stimulation would be based on visual data produced up stream of the visual cortex or by an artificial light sensor.

Treatment of tachycardia may be accomplished with optogenetic stimulation to parasympathetic nervous system fibers including CN X or Vagus Nerve. This causes a decrease in the SA node rate, thereby decreasing the heart rate and force of contraction. Similarly, optogenetic stabilization of sympathetic nervous system fibers within spinal nerves T1 through T4, serves to slow the heart. For the treatment of pathological bradycardia, optogenetic stabilization of the Vagus nerve, or optogenetic stimulation of sympathetic fibers in T1 through T4 will serve to increase heart rate. Cardiac disrhythmias resulting from aberrant electrical foci that outpace the sinoatrial node may be suppressed by treating the aberrant electrical focus with moderate optogenetic stabilization. This decreases the intrinsic rate of firing within the treated tissue, and permits the sinoatrial node to regain its role in pacing the heart's electrical system. In a similar way, any type of cardiac arrhythmia could be treated. Degeneration of cardiac tissue that occurs in cardiomyopathy or congestive heart failure could also be treated using this invention; the remaining tissue could be excited using various embodiments of the invention.

Optogenetic excitation stimulation of brain regions including the frontal lobe, parietal lobes and hippocampi, may increase processing speed, improve memory, and stimulate growth and interconnection of neurons, including spurring development of neural progenitor cells. As an example, one such application of the present invention is directed to optogenetic excitation stimulation of targeted neurons in the thalamus for the purpose of bringing a patient out of a near-vegetative (barely-conscious) state. Growth of light-gated ion channels or pumps in the membrane of targeted thalamus neurons is affected. These modified neurons are then stimulated (e.g., via optics which may also gain access by the same passageway) by directing a flash of light thereupon so as to modulate the function of the targeted neurons and/or surrounding cells. For further information regarding appropriate modulation techniques (via electrode-based treatment) or further information regarding the associated brain regions for such patients, reference may be made to: Schiff N D, Giacino J T, Kalmar K, Victor J D, Baker K, Gerber M, Fritz B, Eisenberg B, O'Connor J O, Kobylarz E J, Farris S, Machado A, McCagg C, Plum F, Fins J J, Rezai A R "Behavioral improvements with thalamic stimulation after severe traumatic brain injury," Nature, Vol. 448, Aug. 2, 2007, pp. 600-604.

In an alternative embodiment, optogenetic excitation may be used to treat weakened cardiac muscle in conditions such as congestive heart failure. Electrical assistance to failing heart muscle of CHF is generally not practical, due to the thin-stretched, fragile state of the cardiac wall, and the difficulty in providing an evenly distributed electrical coupling between an electrodes and muscle. For this reason, preferred methods to date for increasing cardiac contractility have involved either pharmacological methods such as Beta agonists, and mechanical approaches such as ventricular assist devices. In this embodiment of the present invention, optogenetic excitation is delivered to weakened heart muscle via light emitting elements on the inner surface of a jacket surround the heart or otherwise against the affected heart wall. Light may be diffused by means well known in the art, to smoothly cover large areas of muscle, prompting contraction with each light pulse.

Optogenetic stabilization in the subgenual portion of the cingulate gyrus (Cg25), yellow light may be applied with an implanted device. The goal would be to treat depression by suppressing target activity in manner analogous to what is taught by Mayberg H S et al., "Deep Brain Stimulation for Treatment-Resistant Depression," Neuron, Vol. 45, 651-660, Mar. 3, 2005, pp. 651-660, which is fully incorporated herein by reference. In an alternative embodiment, an optogenetic excitation stimulation method is to increase activity in that region in a manner analogous to what is taught by Schlaepfer et al., "Deep Brain stimulation to Reward Circuitry Alleviates Anhedonia in Refractory Major Depression," Neuropsychopharmacology 2007, pp. 1-10, which is fully incorporated herein by reference.

In yet another embodiment, the left dorsolateral prefrontal cortex (LDPFC) is targeted with an optogenetic excitation stimulation method. Pacing the LDLPFC at 5-20 Hz serves to increase the basal metabolic level of this structure which, via connecting circuitry, serves to decrease activity in Cg 25, improving depression in the process. Suppression of the right dorsolateral prefrontal cortex (RDLPFC) is also an effective depression treatment strategy. This may be accomplished by optogenetic stabilization on the RDLPFC, or suppression may also be accomplished by using optogenetic excitation stimulation, and pulsing at a slow rate (e.g., 1 Hz or less) improving depression in the process. Vagus nerve stimulation (VNS) may be improved using an optogenetic approach. Use of optogenetic excitation may be used in order to stimulate only the vagus afferents to the brain, such as the nodose ganglion and the jugular ganglion. Efferents from the brain would not receive stimulation by this approach, thus eliminating some of the side-effects of VNS including discomfort in the throat, a cough, difficulty swallowing and a hoarse voice. In an alternative embodiment, the hippocampus may be optogenetically excited, leading to increased dendritic and axonal sprouting, and overall growth of the hippocampus. Other brain regions implicated in depression that could be treated using this invention include the amygdala, accumbens, orbitofrontal and orbitomedial cortex, hippocampus, olfactory cortex, and dopaminergic, serotonergic, and noradrenergic projections. Optogenetic approaches could be used to control spread of activity through structures like the hippocampus to control depressive symptoms.

So long as there are viable alpha and beta cell populations in the pancreatic islets of Langerhans, the islets can be targeted for the treatment of diabetes. For example, when serum glucose is high (as determined manually or by closed loop glucose detection system), optogenetic excitation may be used to cause insulin release from the beta cells of the islets of Langerhans in the pancreas, while optogenetic stabilization is used to prevent glucagon release from the alpha cells of the islets of Langerhans in the pancreas. Conversely, when blood sugars are too low (as determined manually or by closed loop glucose detection system), optogenetic stabilization may be used to stop beta cell secretion of insulin, and optogenetic excitation may be used to increase alpha-cell secretion of glucagon.

For treatment of epilepsy, quenching or blocking epileptogenic activity is amenable to optogenetic approaches. Most epilepsy patients have a stereotyped pattern of activity spread resulting from an epileptogenic focus. Optogenetic stabilization could be used to suppress the abnormal activity before it spreads or truncated it early in its course. Alternatively, activation of excitatory tissue via optogenetic excitation stimulation could be delivered in a series of deliberately asynchronous patterns to disrupt the emerging seizure activity. Another alternative involves the activation of optogenetic excitation stimulation in GABAergic neurons to provide a similar result. Thalamic relays may be targeted with optogenetic stabilization triggered when an abnormal EEG pattern is detected.

Another embodiment involves the treatment of gastrointestinal disorders. The digestive system has its own, semi-autonomous nervous system containing sensory neurons, motor neurons and interneurons. These neurons control movement of the GI tract, as well as trigger specific cells in the gut to release acid, digestive enzymes, and hormones including gastrin, cholecystokinin and secretin. Syndromes that include inadequate secretion of any of these cellular products may be treated with optogenetic stimulation of the producing cell types, or neurons that prompt their activity. Conversely, optogenetic stabilization may be used to treat syndromes in which excessive endocrine and exocrine products are being created. Disorders of lowered intestinal motility, ranging from constipation (particularly in patients with spinal cord injury) to megacolan may be treated with optogenetic excitation of motor neurons in the intestines. Disorders of intestinal hypermotility, including some forms of irritable bowel syndrome may be treated with optogenetic stabilization of neurons that control motility. Neurogenic gastric outlet obstructions may be treated with optogenetic stabilization of neurons and musculature in the pyloris. An alternative approach to hypomobility syndromes would be to provide optogenetic excitation to stretch-sensitive neurons in the walls of the gut, increasing the signal that the gut is full and in need of emptying.

In this same paradigm, an approach to hypermobility syndromes of the gut would be to provide optogenetic stabilization to stretch receptor neurons in the lower GI, thus providing a "false cue" that the gut was empty, and not in need of emptying. In the case of frank fecal incontinence, gaining improved control of the internal and external sphincters may be preferred to slowing the motility of the entire tract. During periods of time during which a patient needs to hold feces in, optogenetic excitation of the internal anal sphincter will provide for retention. Providing optogenetic stimulation to the external sphincter may be used to provide additional continence. When the patient is required to defecate, the internal anal sphincter, and then external anal sphincter should be relaxed, either by pausing the optogenetic stimulation, or by adding optogenetic stabilization.

Conductive hearing loss may be treated by the use of optical cochlear implants. Once the cochlea has been prepared for optogenetic stimulation, a cochlear implant that flashes light may be used. Sensorineural hearing loss may be treated through optical stimulation of downstream targets in the auditory pathway.

Another embodiment of the present invention is directed toward the treatment of blood pressure disorders, such as hypertension. Baroreceptors and chemoreceptors in regions such as the aorta (aortic bodies and paraaortic bodies) and the carotid arteries ("carotid bodies") participate in the regulation of blood pressure and respiration by sending afferents via the vagus nerve (CN X), and other pathways to the medulla and pons, particularly the solitary tract and nucleus. Optogenetic excitation of the carotid bodies, aortic bodies, paraortic bodies, may be used to send a false message of "hypertension" to the solitary nucleus and tract, causing it to report that blood pressure should be decreased. Optogenetic excitation or stabilization directly to appropriate parts of the brainstem may also be used to lower blood pressure. The opposite modality causes the optogenetic approach to serve as a pressor, raising blood pressure. A similar effect may also be achieved via optogenetic excitation of the Vagus nerve, or by optogenetic stabilization of sympathetic fibers within spinal nerves T1-T4. In an alternative embodiment, hypertension may be treated with optogenetic stabilization of the heart, resulting in decreased cardiac output and lowered blood pressure. According to another embodiment, optogenetic stabilization of aldosterone-producing cells within the adrenal cortex may be used to decrease blood pressure. In yet another alternative embodiment, hypertension may be treated by optogenetic stabilization of vascular smooth muscle. Activating light may be passed transcutaneously to the peripheral vascular bed.

Another example embodiment is directed toward the treatment of hypothalamic-pituitary-adrenal axis disorders. In the treatment of hypothyroidism, optogenetic excitation of parvocellular neuroendocrine, neurons in the paraventricular and anterior hypothalamic nuclei can be used to increase secretion of thyrotropin-releasing hormone (TRH). TRH, in turn, stimulates anterior pituitary to secrete TSH. Conversely, hyperthyroidism may be treated with optogenetic stabilization of the provocellular neuroendocrine neurons. For the treatment of adrenal insufficiency, or of Addison's disease, optogenetic excitation of parvocellular neuroendocrine neurons in the supraoptic nucleus and paraventricular nuclei may be used to increase the secretion of vasopressin, which, with the help of corticotropin-releasing hormone (CRH), stimulate anterior pituitary to secrete ACTH. Cushing syndrome, frequently caused by excessive ACTH secretion, may be treated with optogenetic stabilization of the parvocellular neuroendocrine neurons of supraoptic nucleus via the same physiological chain of effects described above. Neuroendocrine neurons of the arcuate nucleus produce dopamine, which inhibits secretion of prolactin from the anterior pituitary.

Hyperprolactinemia can therefore be treated via optogenetic excitation, while hypoprolactinemia can be treated with optogenetic stabilization of the neuroendocrine cells of the arcuate nucleus.

In the treatment of hyperautonomic states, for example anxiety disorders, optogenetic stabilization of the adrenal medulla may be used to reduce norepinephrine output. Similarly, optogenetic stimulation of the adrenal medulla may be used in persons with need for adrenaline surges, for example those with severe asthma, or disorders that manifest as chronic sleepiness.

Optogenetic stimulation of the adrenal cortex will cause release of chemicals including cortisol, testosterone, and aldosterone. Unlike the adrenal medualla, the adrenal cortex receives its instructions from neuroendocrine hormones secreted from the pituitary and hypothalamus, the lungs, and the kidneys. Regardless, the adrenal cortex is amenable to optogenetic stimulation. Optogenetic stimulation of the cortisol-producing cells of the adrenal cortex may be used to treat Addison's disease. Optogenetic stabilization of cortisol-producing cells of the adrenal cortex may be used to treat Cushing's disease. Optogenetic stimulation of testosterone-producing cells may be used to treat disorders of sexual interest in women: Optogenetic stabilization of those same cells may be used to decrease facial hair in women. Optogenetic stabilization of aldosterone-producing cells within the adrenal cortex may be used to decrease blood pressure. Optogenetic excitation of aldosterone-producing cells within the adrenal cortex may be used to increase blood pressure.

Optogenetic excitation stimulation of specific affected brain regions may be used to increase processing speed, and stimulate growth and interconnection of neurons, including spurring the maturation of neural progenitor cells. Such uses can be particularly useful for treatment of mental retardation.

According to another embodiment of the present invention, various muscle diseases and injuries can be treated. Palsies related to muscle damage, peripheral nerve damage and to dystrophic diseases can be treated with optogenetic excitation to cause contraction, and optogenetic stabilization to cause relaxation. This latter relaxation via optogenetic stabilization approach can also be used to prevent muscle wasting, maintain tone, and permit coordinated movement as opposing muscle groups are contracted. Likewise, frank spasticity can be treated via optogenetic stabilization.

In areas as diverse as peripheral nerve truncation, stroke, traumatic brain injury and spinal cord injury, there is a need to foster the growth of new neurons, and assist with their integration into a functional network with other neurons and with their target tissue. Re-growth of new neuronal tracts may be encouraged via optogenetic excitation, which serves to signal stem cells to sprout axons and dendrites, and to integrate themselves with the network. Use of an optogenetic technique (as opposed to electrodes) prevents receipt of signals by intact tissue, and serves to ensure that new target tissue grows by virtue of a communication set up with the developing neurons, and not with an artificial signal like current emanating from an electrode.

Obesity can be treated with optogenetic excitation to the ventromedial nucleus of the hypothalamus, particularly the pro-opiomelanocortin (POMC) and cocaine-and-amphetamine-regulating transcript (CART) of the arcuate nucleus. In an alternative embodiment, obesity can be treated via optogenetic stabilization of the lateral nuclei of the hypothalamus. In another embodiment, optogenetic stimulation to leptin-producing cells or to cells with leptin receptors within the hypothalamus may be used to decrease appetite and hence treat obesity.

Destructive lesions to the anterior capsule and analogous DBS to that region are established means of treating severe, intractable obsessive-compulsive disorder 48 (OCD48). Such approaches may be emulated using optogenetic stabilization to the anterior limb of the internal capsule, or to regions such as BA32 and Cg24 which show metabolic decrease as OCD remits.

Chronic pain can be treated using another embodiment of the present invention. Electrical stimulation methods include local peripheral nerve stimulation, local cranial nerve stimulation and "sub threshold" motor cortex stimulation. Reasonable autogenic approaches include optogenetic stabilization at local painful sites. Attention to promoter selection would ensure that other sensory and motor fibers would be unaffected. Selective optogenetic excitation of interneurons at the primary motor cortex also may provide effective pain relief. Also, optogenetic stabilization at the sensory thalamus, (particularly medial thalamic nuclei), periventricular grey matter, and ventral raphe nuclei, may be used to produce pain relief. In an alternative embodiment, optogenetic stabilization of parvalbumin-expressing cells targeting as targeting strategy, may be used to treat pain by decreasing Substance P production. The release of endogenous opiods may be accomplished by using optogenetic excitation to increase activity in the nucleus accumbens. In an alternative embodiment, when POMC neurons of the arcuate nucleus of the medial hypothalamus are optogenetically excited, beta endorphin are increased, providing viable treatment approaches for depression and for chronic pain.

Certain personality disorders, including the borderline and antisocial types, demonstrate focal deficits in brain disorders including "hypofrontality." Direct or indirect optogenetic excitation of these regions is anticipated to produce improvement of symptoms. Abnormal bursts of activity in the amygdala are also known to precipitate sudden, unprompted flights into rage: a symptom of borderline personality disorder, as well as other conditions, which can benefit from optogenetic stabilization of the amygdala. Optogenetic approaches could improve communication and synchronization between different parts of the brain, including amygdala, striatum, and frontal cortex, which could help in reducing impulsiveness and improving insight.

The amygdalocentric model of post-traumatic-stress disorder (PTSD) proposes that it is associated with hyperarousal of the amygdala and insufficient top-down control by the medial prefrontal cortex and the hippocampus. Accordingly, PTSD may be treated with optogenetic stabilization of the amygdale or hippocampus.

Schizophrenia is characterized by abnormalities including auditory hallucinations. These might be treated by suppression of the auditory cortex using optogenetic stabilization. Hypofrontality associated with schizophrenia might be treated with optogenetic excitation in the affected frontal regions. Optogenetic approaches could improve communication and synchronization between different parts of the brain which could help in reducing misattribution of self-generated stimuli as foreign.

Optogenetic stabilization of cells within the arcuate nucleus of the medial hypothalamus, which contain peptide products of pro-opiomelanocortin (POMC) and cocaine-and-amphetamine-regulating transcript (CART), can be used to reduce compulsive sexual behavior. Optogenetic excitation of cells within the arcuate nucleus of the medial hypothalamus which contain peptide products of pro-opiomelanocortin (POMC) and cocaine-and-amphetamine-regulating transcript (CART) may be used to increase sexual interest in the treatment of cases of disorders of sexual desire. In the treatment of disorders of hypoactive sexual desire testosterone production by the testes and the adrenal glands can be increased through optogenetic excitation of the pituitary gland. Optogenetic excitation of the nucleus accumbens can be used for the treatment of anorgasmia.

The suprachiasmatic nucleus secretes melatonin, which serves to regulate sleep/wake cycles. Optogenetic excitation to the suprachiasmic nucleus can be used to increase melatonin production, inducing sleep, and thereby treating insomnia. Orexin (hypocretin) neurons strongly excite numerous brain nuclei in order to promote wakefulness. Optogenetic excitation of orexin-producing cell populations can be used to treat narcolepsy, and chronic daytime sleepiness.

Optogenetic stimulation of the supraoptic nucleus may be used to induce secretion of oxytocin, can be used to promote parturition during childbirth, and can be used to treat disorders of social attachment.

Like muscular palsies, the motor functions that have been de-afferented by a spinal cord injury may be treated with optogenetic excitation to cause contraction, and optogenetic stabilization to cause relaxation. This latter relaxation via optogenetic stabilization approach may also be used to prevent muscle wasting, maintain tone, and permit coordinated movement as opposing muscle groups are contracted. Likewise, frank spasticity may be treated via optogenetic stabilization. Re-growth of new spinal neuronal tracts may be encouraged via optogenetic excitation, which serves to signal stem cells to sprout axons and dendrites, and to integrate themselves with the network.

Stroke deficits include personality change, motor deficits, sensory deficits, cognitive loss, and emotional instability. One strategy for the treatment of stroke deficits is to provide optogenetic stimulation to brain and body structures that have been deafferented from excitatory connections. Similarly, optogenetic stabilization capabilities can be imparted on brain and body structures that have been deafferented from inhibitory connections.

Research indicates that the underlying pathobiology in Tourette's syndrome is a phasic dysfunction of dopamine transmission in cortical and subcortical regions, the thalamus, basal ganglia and frontal cortex. In order to provide therapy, affected areas are preferably first identified using techniques including functional brain imaging and magnetoencephalography (MEG). Whether specifically identified or not, optogenetic stabilization of candidate tracts may be used to suppress motor tics. Post-implantation empirical testing of device parameters reveals which sites of optogenetic stabilization, and which are unnecessary to continue.

In order to treat disorders of urinary or fecal incontinence optogenetic stabilization can be used to the sphincters, for example via optogenetic stabilization of the bladder detrussor smooth muscle or innervations of that muscle. When micturation is necessary, these optogenetic processes are turned off, or alternatively can be reversed, with optogenetic stabilization to the (external) urinary sphincter, and optogenetic excitation of the bladder detrussor muscle or its innervations. When a bladder has been deafferentated, for example, when the sacral dorsal roots are cut or destroyed by diseases of the dorsal roots such as tabes dorsalis in humans, all reflex contractions of the bladder are abolished, and the bladder becomes distended. Optogenetic excitation of the muscle directly can be used to restore tone to the detrussor, prevent kidney damage, and to assist with the micturition process. As the bladder becomes "decentralized" and hypersensitive to movement, and hence prone to incontinence, optogenetic stabilization to the bladder muscle can be used to minimize this reactivity of the organ.

In order to selectively excite/inhibit a given population of neurons, for example those involved in the disease state of an illness, several strategies can be used to target the optogenetic proteins/molecules to specific populations.

For various embodiments of the present invention, genetic targeting may be used to express various optogenetic proteins or molecules. Such targeting involves the targeted expression of the optogenetic proteins/molecules via genetic control elements such as promoters (e.g., Parvalbumin, Somatostatin, Cholecystokinin, GFAP), enhancers/silencers (e.g., Cytomaglovirus Immediate Early Enhancer), and other transcriptional or translational regulatory elements (e.g., Woodchuck Hepatitis Virus Post-transcriptional Regulatory Element). Permutations of the promoter+enhancer+regulatory element combination can be used to restrict the expression of optogenetic probes to genetically-defined populations.

Various embodiments of the present invention may be implemented using spatial/anatomical targeting. Such targeting takes advantage of the fact that projection patterns of neurons, virus or other reagents carrying genetic information (DNA plasmids, fragments, etc), can be focally delivered to an area where a given population of neurons project to. The genetic material will then be transported back to the bodies of the neurons to mediate expression of the optogenetic probes. Alternatively, if it is desired to label cells in a focal region, viruses or genetic material may be focally delivered to the interested region to mediate localized expression.

Various gene delivery systems are useful in implementing one or more embodiments of the present invention. One such delivery system is Adeno-Associated Virus (AAV). AAV can be used to deliver a promoter+optogenetic probe cassette to a specific region of interest. The choice of promoter will drive expression in a specific population of neurons. For example, using the CaMKIIa promoter will drive excitatory neuron specific expression of optogenetic probes. AAV will mediate long-term expression of the optogenetic probe for at least one year or more. To achieve more specificity, AAV may be pseudotyped with specific serotypes 1, 2, 3, 4, 5, 6, 7, and 8, with each having different trophism for different cell types. For instance, serotype 2 and 5 is known to have good neuron-specific trophism.

Another gene delivery mechanism is the use of a retrovirus. HIV or other lentivirus-based retroviral vectors may be used to deliver a promoter+optogenetic probe cassette to a specific region of interest. Retroviruses may also be pseudo-typed with the Rabies virus envelope glycoprotein to achieve retrograde transport for labeling cells based on their axonal projection patterns. Retroviruses integrate into the host cell's genome, therefore are capable of mediating permanent expression of the optogenetic probes. Non-lentivirus based retroviral vectors can be used to selectively label dividing cells.

Gutless Adenovirus and Herpes Simplex Virus (HSV) are two DNA-based viruses that can be used to deliver promoter+ optogenetic probe cassette into specific regions of the brain as well. HSV and Adenovirus have much larger packaging capacities and therefore can accommodate much larger promoter elements and can also be used to deliver multiple optogenetic probes or other therapeutic genes along with optogenetic probes.

Focal Electroporation can also be used to transiently transfect neurons. DNA plasmids or fragments can be focally delivered into a specific region of the brain. By applying mild electrical current, surrounding local cells will receive the DNA material and expression of the optogenetic probes.

In another instance, lipofection can be used by mixing genetic material with lipid reagents and then subsequently injected into the brain to mediate transfection of the local cells.

Various embodiments involve the use of various control elements. In addition to genetic control elements, other control elements (particularly promoters and enhancers whose activities are sensitive to chemical, magnetic stimulation or infrared radiation) can be used to mediate temporally-controlled expression of the optogenetic probes. For example, a promoter whose transcriptional activity is subject to infrared radiation allows one to use focused radiation to fine tune the expression of optogenetic probes in a focal region at only the desired time.

Parkinson's Disease can be treated by expressing optogenetic stabilization in the glutamatergic neurons in either the subthalamic nucleus (STN) or the globus pallidus interna (GPi) using an excitatory-specific promoter such as CaMKIIα, and apply optogenetic stabilization. Unlike electrical modulation in which all cell-types are affected, only glutamatergic STN neurons would be suppressed.

Aspects of the present invention are directed towards testing a model of a neural circuit or disease. The model can define output response of the circuit as a function of input signals. The output response can be assessed using a number of different measurable characteristics. For instance, characteristics can include an electrical response of downstream neurons and/or behavioral response of a patient. To test the model, optogenetic probes are expressed at an input position for the model. The optogenetic probes are stimulated and the output characteristics are monitored and compared to an output predicted by the model.

In certain implementations, the use of optogenetic probes allows for fine tuning of models defined using electrical probes. As electrical probes provide only limited ability to direct the stimulus and thus are not well suited for stimulus of certain areas without also directly stimulating nearby areas. Optogenetic probes disclosed herein provide a mechanism for more precise selection of the stimulus location. For instance, the stimulus from the optogenetic probes can be directed to very specific types of circuits/cells, such as afferent fibers. The following description provides an example implementation consistent with such an embodiment and is meant to show the feasibility and wide-ranging applicability for aspects of present invention.

According to one embodiment of the present invention, the invention may be used in animal models of DBS, for example in Parkinsonian rats, to identify the target cell types responsible for therapeutic effects (an area of intense debate and immense clinical importance). This knowledge alone may lead to the development of improved pharmacological and surgical strategies for treating human disease.

One such application involves long-term potentiation (LTP) and/or long-term depression (LTD) between two neural groups. By targeting the expression of VChR1 and ChR2 to different neural populations and stimulating each with a different frequency of light, LTP or LTD can be accomplished between the two groups. Each group can be individually controlled using the respective wavelength of light. This can be particularly useful for applications in which the spatial arrangement of the two groups presents issues with individual control using the same wavelength of light. Thus, the light delivery device(s) are less susceptible to exciting the wrong neural group and can be less reliant upon precise spatial location of the optical stimulus.

The delivery of the proteins to cells in vivo can be accomplished using a number of different deliver devices, methods and systems. On such delivery device is an implantable device that delivers a nucleotide sequence for modifying cells in vivo, such as a viral-vector. The implantable device can also include a light delivery mechanism. The light delivery can be accomplished using, for example, light-emitting diodes (LEDs), fiber optics and/or Lasers.

Another embodiment of the present invention involves the use of VChR1 in affecting stem cell fate including survival/death, differentiation and replication. The modulation of electrical properties has been shown to control stem cell fate. Various techniques can be used to provide stimulus patterns that modify stem cell fate. A specific example is consistent with the techniques explained in Deisseroth, K. et al. "Excitation-neurogenesis coupling in adult neural stem/progenitor cells," Neuron 42, pp. 535-552 (2004), which is fully incorporated herein by reference.

Another embodiment of the present invention is directed to the use of DChR and/or GtR3 to assess the efficacy of treatments. This can include, but is not limited to, drug screening, treatment regimens or modeling of treatments/disorders. In a specific embodiment, DChR is used as the primary optically responsive protein in such assessments. In alternate embodiments, DChR is used with other types of optically responsive proteins (e.g., VCHR1, GtR3, ChR2 and/or NpHR) that respond to different wavelengths.

Also provided herein are methods of identifying transsynaptic connection between neuronal cells in an animal or a tissue, comprising: a) administering a first viral vector encoding a Cre recombinase fused to a transcellular tracer protein to neuronal cells in region A of the animal or tissue; b) administering a second viral vector encoding a light-activated protein to neuronal cells in region B of the animal or tissue, wherein the expression of the light-activated protein depends on the presence of the Cre recombinase; and c) identifying neuronal cells expressing the light-activated protein in region B, wherein the expression of the light-activated protein in the neuronal cells indicating that these cells are in transsynaptic connection with the cells in region A.

Also provided herein are methods of generating optical control of targeted neuronal cells in an animal or tissue, comprising: a) administering a first viral vector expressing a Cre recombinase fused to a transcellular tracer protein to region A of the animal or tissue; b) administering a second viral vector encoding a light-activated protein to region B of the animal or tissue, wherein the expression of the light-activated protein depends on the presence of the Cre recombinase, and wherein the neuronal cells in region A and in region B are in transsynaptic connected; and c) controlling action potential of a neuronal cell in region B with light that activates the protein.

Also provided herein are methods of controlling action potential of a neuron in an animal, comprising activating a light-activated protein in the neuron with light to generate action potential change, wherein expression of the light-activated protein in the neuron is generated by a) administering a first viral vector expressing a Cre recombinase fused to a transcellular tracer protein to region A of the animal, b) administering a second viral vector encoding a light-activated protein to region B of the animal which contains the neuron, wherein the expression of the light-activated protein depends on the presence of the Cre recombinase, wherein the neurons in region A and region B are in transsynaptic connection.

In some embodiments, the viral vector is a viral vector selected from the group consisting of AAV, HSV, and lentivirus. In some embodiments, the transcellular tracer protein is wheat germ agglutinin (WGA) or tetanus toxin-fragment C (TTC).

It is to be understood that one, some, or all of the properties of the various embodiments described herein may be combined to form other embodiments of the present invention. These and other aspects of the invention will become apparent to one of skill in the art.

It is understood that aspect and variations of the invention described herein include "consisting" and/or "consisting essentially of" aspects and variations.

As used herein and in the appended claims, the singular forms "a," "an," and "the" include plural reference unless the context clearly indicates otherwise. For example, reference to an "animal cell" is a reference to from one to many cells.

An "isolated" polynucleotide is one which has been identified and separated and/or recovered from a component of its natural environment.

Reference to "about" a value or parameter herein includes (and describes) variations that are directed to that value or parameter per se. For example, description referring to "about X" includes description of "X". The term "about" has its normal meaning of approximately. In some embodiments, "about" means±10% or ±5%.

TABLE 3

Sequence for GtR3

>GtR3
(SEQ ID NO: 6)
ATGGACTACGGAGGAGCACTGTCTGCTGTGGGCCGTGAATTACTCTTTGTGACCAATCCAGTCGTTGTA
AATGGGAGCGTCCTGGTGCCGGAGGATCAATGCTACTGCGCCGGTTGGATTGAAAGCAGAGGCACGA
ATGGGGCCTCATCCTTCGGCAAGGCCCTACTGGAGTTTGTCTTCATCGTCTTCGCGTGTATCACATTACT
GTTGGGAATTAACGCTGCGAAATCAAAGGCTGCATCTAGGGTGCTGTTTCCCGCTACTTTCGTCACTGG
AATCGCAAGTATCGCATATTTTCCATGGCAAGCGGCGGCGGGTGGGTGATTGCCCCTGACTGTCGGC
AGCTCTTTGTGGCCCGCTATCTGGACTGGCTCATTACTACACCACTTCTACTCATAGATTTGGGTCTGGT
TGCAGGGGTCAGTCGGTGGGATATAATGGCCCTCTGCCTGTCTGATGTCCTGATGATTGCTACGGGTG
CTTTCGGGAGCCTGACAGTGGGTAACGTGAAGTGGGTGTGGTGGTTCTTTGGAATGTGTTGGTTTCTT
CACATAATCTTCGCGCTTGGGAAAAGTTGGGCAGAAGCAGCCAAGGCCAAGGGCGGCGACTCTGCTTC
TGTGTACTCCAAAATCGCCGGCATCACCGTGATTACATGGTTCTGTTATCCCGTGGTATGGGTCTTCGCT
GAGGGCTTCGGAAACTTTTCCGTAACCTTCGAAGTTCTCATCTATGGAGTGTTGGATGTTATTTCAAAG
GCCGTTTTTGGCCTTATACTGATGTCAGGGGCCGCCACCGGATACGAGTCCATT

Translation Map

GtR3
```
  1 ATGGACTACGGAGGAGCACTGTCTGCTGTGGGCCGTGAATTACTCTTTGTGACCAATCCA
  1 M  D  Y  G  G  A  L  S  A  V  G  R  E  L  L  F  V  T  N  P

61 GTCGTTGTAAATGGGAGCGTCCTGGTGCCGGAGGATCAATGCTACTGCGCCGGTTGGATT
 21 V  V  V  N  G  S  V  L  V  P  E  D  Q  C  Y  C  A  G  W  I

121 GAAAGCAGAGGCACGAATGGGGCCTCATCCTTCGGCAAGGCCCTACTGGAGTTTGTCTTC
 41 E  S  R  G  T  N  G  A  S  S  F  G  K  A  L  L  E  F  V  F

181 ATCGTCTTCGCGTGTATCACATTACTGTTGGGAATTAACGCTGCGAAATCAAAGGCTGCA
 61 I  V  F  A  C  I  T  L  L  L  G  I  N  A  A  K  S  K  A  A

241 TCTAGGGTGCTGTTTCCCGCTACTTTCGTCACTGGAATCGCAAGTATCGCATATTTTCC
 81 S  R  V  L  F  P  A  T  F  V  T  G  I  A  S  I  A  Y  F  S

301 ATGGCAAGCGGCGGCGGGTGGGTGATTGCCCCTGACTGTCGGCAGCTCTTTGTGGCCCGC
101 M  A  S  G  G  G  W  V  I  A  P  D  C  R  Q  L  F  V  A  R

361 TATCTGGACTGGCTCATTACTACACCACTTCTACTCATAGATTTGGGTCTGGTTGCAGGG
121 Y  L  D  W  L  I  T  T  P  L  L  L  I  D  L  G  L  V  A  G

421 GTCAGTCGGTGGGATATAATGGCCCTCTGCCTGTCTGATGTCCTGATGATTGCTACGGGT
141 V  S  R  W  D  I  M  A  L  C  L  S  D  V  L  M  I  A  T  G

481 GCTTTCGGGAGCCTGACAGTGGGTAACGTGAAGTGGGTGTGGTGGTTCTTTGGAATGTGT
161 A  F  G  S  L  T  V  G  N  V  K  W  V  W  W  F  F  G  M  C

541 TGGTTTCTTCACATAATCTTCGCGCTTGGGAAAAGTTGGGCAGAAGCAGCCAAGGCCAAG
181 W  F  L  H  I  I  F  A  L  G  K  S  W  A  E  A  A  K  A  K

601 GGCGGCGACTCTGCTTCTGTGTACTCCAAAATCGCCGGCATCACCGTGATTACATGGTTC
201 G  G  D  S  A  S  V  Y  S  K  I  A  G  I  T  V  I  T  W  F

661 TGTTATCCCGTGGTATGGGTCTTCGCTGAGGGCTTCGGAAACTTTTCCGTAACCTTCGAA
221 C  Y  P  V  V  W  V  F  A  E  G  F  G  N  F  S  V  T  F  E

721 GTTCTCATCTATGGAGTGTTGGATGTTATTTCAAAGGCCGTTTTTGGCCTTATACTGATG
241 V  L  I  Y  G  V  L  D  V  I  S  K  A  V  F  G  L  I  L  M

781 TCAGGGGCCGCCACCGGATACGAGTCCATT    (SEQ ID NO: 6)
261 S  G  A  A  T  G  Y  E  S  I     (SEQ ID NO: 5)
```

TABLE 3-continued

Sequence for GtR3

Restriction Sites

| Name | Seq. | Locations |
| --- | --- | --- |
| AatI | AGGCCT | none |
| AccI | GTMKAC | none |
| AflII | CTTAAG | none |
| AgeI | ACCGGT | none |
| AlwI | GGATC | 92 |
| AlwNI | CAGNNNCTG | none |
| ApaI | GGGCCC | none |
| ApaLI | GTGCAC | none |
| AscI | GGCGCGCC | none |
| AseI | ATTAAT | none |
| AvaI | CYCGRG | none |
| AvaII | GGWCC | none |
| AvrII | CCTAGG | none |
| BamHI | GGATCC | none |
| BbsI | GAAGAC | 174(c), 183(c), 678(c) |
| BbvI | GCAGC | 341, 585, 219(c), 234(c) |
| BclI | TGATCA | none |
| BglI | GCCNNNNNGGC | none |
| BglII | AGATCT | none |
| BlpI | GCTNAGC | none |
| BsaI | GGTCTC | none |
| BsmAI | GTCTC | none |
| BsmBI | CGTCTC | none |
| BstEII | GGTNACC | none |
| BstXI | CCANNNNNNTGG | none |
| ClaI | ATCGAT | none |
| DraIII | CACNNNGTG | none |
| EagI | CGGCCG | none |
| EarI | CTCTTC | none |
| EcoRI | GAATTC | none |
| EcoRV | GATATC | none |
| FokI | GGATG | 740, 145(c) |
| FseI | GGCCGGCC | none |
| HindIII | AAGCTT | none |
| KasI | GGCGCC | none |
| KpnI | GGTACC | none |
| MluI | ACGCGT | none |

TABLE 3-continued

Sequence for GtR3

| NarI | GGCGCC | none |
|---|---|---|
| NcoI | CCATGG | 298 |
| NdeI | CATATG | none |
| NheI | GCTAGC | none |
| NotI | GCGGCCGC | none |
| NsiI | ATGCAT | none |
| PacI | TTAATTAA | none |
| PciI | ACATGT | none |
| PmeI | GTTTAAAC | none |
| PstI | CTGCAG | none |
| PvuI | CGATCG | none |
| PvuII | CAGCTG | none |
| SacI | GAGCTC | none |
| SacII | CCGCGG | none |
| SalI | GTCGAC | none |
| SapI | GCTCTTC | none |
| SfiI | GGCCNNNNNGGCC | none |
| SgrAI | CRCCGGYG | none |
| SmaI | CCCGGG | none |
| SpeI | ACTAGT | none |
| SphI | GCATGC | none |
| SspI | AATATT | none |
| StuI | AGGCCT | none |
| SwaI | ATTTAAAT | none |
| TliI | CTCGAG | none |
| XbaI | TCTAGA | none |
| XhoI | CTCGAG | none |
| XmaI | CCCGGG | none |
| XmnI | GAANNNNTTC | 697 |
| AvaIII | atgcat | none |
| AfeI | AGCGCT | none |
| AvrII | CCTAGG | none |
| BspEI | TCCGGA | none |
| BsrGI | TGTACA | none |

TABLE 4

Sequence for DChR

>DChR
(SEQ ID NO: 7)
```
ATGCGTAGAAGGGAGTCTCAGCTCGCATACCTTTGCCTGTTCGTTTTGATCGCTGGCTGGGCCCCACGT
CTGACTGAAAGCGCCCCTGATCTAGCCGAGCGGCGGCCTCCCTCCGAGCGAAACACCCCTTACGCCAAT
ATTAAAAAGGTGCCCAATATAACTGAACCCAACGCCAATGTGCAACTTGATGGGTGGGCTCTGTACCA
GGATTTTTACTACCTGGCTGGTTCAGATAAGGAATGGGTCGTTGGCCCTAGCGACCAGTGTTACTGCCG
AGCATGGTCTAAATCACACGGCACCGACAGAGAGGGCGAGGCGGCTGTGGTGTGGGCGTACATCGTA
TTCGCCATTTGTATCGTACAACTGGTTTATTTCATGTTTGCCGCTTGGAAGGCAACGGTCGGATGGGAG
GAAGTCTACGTAACATCATTGAGCTGGTGCACATTGCCCTGGTGATTTGGGTCGAGTTCGATAAACCC
GCCATGCTCTACCTTAACGACGGTCAGATGGTTCCATGGTTGCGCTATAGTGCATGGCTCCTTTCCTGCC
CAGTCATCCTAATTCACCTGAGCAACTTAACAGGGCTAAAGGGGACTATAGTAAGAGAACCATGGGG
CTTTTGGTCTCTGACATCGGAACCATAGTGTTTGGTACAAGCGCCGCACTCGCTCCGCCAAACCATGTC
AAAGTCATCTTATTTACAATTGGGTTGCTGTATGGACTCTTCACTTTTTTCACGGCAGCGAAGGTATATA
TTGAGGCCTACCACACCGTTCCAAAAGGCCAATGTAGAAACCTCGTGAGGGCTATGGCCTGGACTTATT
TCGTAAGTTGGGCGATGTTCCCCATCCTGTTTATCCTGGGAAGAGAGGGTTTTGGCCATATTACATATTT
TGGCTCATCCATCGGACACTTCATACTGGAGATATTTTCAAAAAATCTGTGGAGTCTACTGGGCCACGG
ATTACGGTATCGCATAAGGCAGCATATCATCATTCATGGCAATTTGACAAAGAAGAATAAGATTAATAT
CGCAGGGGACAACGTCGAAGTGGAAGAGTACGTGGATTCTAACGACAAGGACAGCGACGTT
```

Translation Map

```
DChR
    1 ATGCGTAGAAGGGAGTCTCAGCTCGCATACCTTTGCCTGTTCGTTTTGATCGCTGGCTGG
    1 M  R  R  R  E  S  Q  L  A  Y  L  C  L  F  V  L  I  A  G  W

61 GCCCCACGTCTGACTGAAAGCGCCCCTGATCTAGCCGAGCGGCGGCCTCCCTCCGAGCGA
   21 A  P  R  L  T  E  S  A  P  D  L  A  E  R  R  P  P  S  E  R

121 AACACCCCTTACGCCAATATTAAAAAGGTGCCCAATATAACTGAACCCAACGCCAATGTG
   41 N  T  P  Y  A  N  I  K  K  V  P  N  I  T  E  P  N  A  N  V

181 CAACTTGATGGGTGGGCTCTGTACCAGGATTTTTACTACCTGGCTGGTTCAGATAAGGAA
   61 Q  L  D  G  W  A  L  Y  Q  D  F  Y  Y  L  A  G  S  D  K  E

241 TGGGTCGTTGGCCCTAGCGACCAGTGTTACTGCCGAGCATGGTCTAAATCACACGGCACC
   81 W  V  V  G  P  S  D  Q  C  Y  C  R  A  W  S  K  S  H  G  T

301 GACAGAGAGGGCGAGGCGGCTGTGGTGTGGGCGTACATCGTATTCGCCATTTGTATCGTA
  101 D  R  E  G  E  A  A  V  V  W  A  Y  I  V  F  A  I  C  I  V

361 CAACTGGTTTATTTCATGTTTGCCGCTTGGAAGGCAACGGTCGGATGGGAGGAAGTCTAC
  121 Q  L  V  Y  F  M  F  A   A  W  K  A  T  V  G  W  E  E  V  Y

421 GTGAACATCATTGAGCTGGTGCACATTGCCCTGGTGATTTGGGTCGAGTTCGATAAACCC
  141 V  N  I  I  E  L  V  H  I  A  L  V  I  W  V  E  F  D  K  P

481 GCCATGCTCTACCTTAACGACGGTCAGATGGTTCCATGGTTGCGCTATAGTGCATGGCTC
  161 A  M  L  Y  L  N  D  G  Q  M  V  P  W  L  R  Y  S  A  W  L

541 CTTTCCTGCCCAGTCATCCTAATTCACCTGAGCAACTTAACAGGGCTAAAGGGGACTAT
  181 L  S  C  P  V  I  L  I  H  L  S  N  L  T  G  L  K  G  D  Y

601 AGTAAGAGAACCATGGGGCTTTTGGTCTCTGACATCGGAACCATAGTGTTTGGTACAAGC
  201 S  K  R  T  M  G  L  L  V  S  D  I  G  T  I  V  F  G  T  S

661 GCCGCACTCGCTCCGCCAAACCATGTCAAAGTCATCTTATTTACAATTGGGTTGCTGTAT
  221 A  A  L  A  P  P  N  H  V  K  V  I  L  F  T  I  G  L  L  Y

721 GGACTCTTCACTTTTTTCACGGCAGCGAAGGTATATATTGAGGCCTACCACACCGTTCCA
  241 G  L  F  T  F  F  T  A  A  K  V  Y  I  E  A  Y  H  T  V  P

781 AAAGGCCAATGTAGAAACCTCGTGAGGGCTATGGCCTGGACTTATTTCGTAAGTTGGGCG
  261 K  G  Q  C  R  N  L  V  R  A  M  A  W  T  Y  F  V  S  W  A

841 ATGTTCCCCATCCTGTTTATCCTGGGAAGAGAGGGTTTTGGCCATATTACATATTTTGGC
  281 M  F  P  I  L  F  I  L  G  R  E  G  F  G  H  I  T  Y  F  G

901 TCATCCATCGGACACTTCATACTGGAGATATTTTCAAAAAATCTGTGGAGTCTACTGGGC
  301 S  S  I  G  H  F  I  L  E  I  F  S  K  N  L  W  S  L  L  G

961 CACGGATTACGGTATCGCATAAGGCAGCATATCATCATTCATGGCAATTTGACAAAGAAG
  321 H  G  L  R  Y  R  I  R  Q  H  I  I  I  H  G  N  L  T  K  K

1021 AATAAGATTAATATCGCAGGGGACAACGTCGAAGTGGAAGAGTACGTGGATTCTAACGAC
  341 N  K  I  N  I  A  G  D  N  V  E  V  E  E  Y  V  D  S  N  D

1081 AAGGACAGCGACGTT
  361 K  D  S  D  V
```

TABLE 4-continued

Sequence for DChR

Restriction Sites

| Name | Seq. | Locations |
|---|---|---|
| AatI | AGGCCT | 760 |
| AccI | GTMKAC | 414, 949 |
| AflII | CTTAAG | none |
| AgeI | ACCGGT | none |
| AlwI | GGATC | none |
| AlwNI | CAGNNNCTG | none |
| ApaI | GGGCCC | 58 |
| ApaLI | GTGCAC | 438 |
| AscI | GGCGCGCC | none |
| AseI | ATTAAT | 1026 |
| AvaI | CYCGRG | none |
| AvaII | GGWCC | none |
| AvrII | CCTAGG | none |
| BamHI | GGATCC | none |
| BbsI | GAAGAC | none |
| BbvI | GCAGC | 741, 983 |
| BclI | TGATCA | none |
| BglI | GCCNNNNNGGC | none |
| BglII | AGATCT | none |
| BlpI | GCTNAGC | none |
| BsaI | GGTCTC | 623 |
| BsmAI | GTCTC | 14, 624 |
| BsmBI | CGTCTC | none |
| BstEII | GGTNACC | none |
| BstXI | CCANNNNNNTGG | none |
| ClaI | ATCGAT | none |
| DraIII | CACNNNGTG | none |
| EagI | CGGCCG | none |
| EarI | CTCTTC | 723, 865(c), 1056(c) |
| EcoRI | GAATTC | none |
| EcoRV | GATATC | none |
| FokI | GGATG | 402, 554(c), 848(c), 901(c) |
| FseI | GGCCGGCC | none |
| HindIII | AAGCTT | none |
| KasI | GGCGCC | none |
| KpnI | GGTACC | none |
| MluI | ACGCGT | none |

TABLE 4-continued

| Sequence for DChR | | |
|---|---|---|
| NarI | GGCGCC | none |
| NcoI | CCATGG | 513, 610 |
| NdeI | CATATG | none |
| NheI | GCTAGC | none |
| NotI | GCGGCCGC | none |
| NsiI | ATGCAT | none |
| PacI | TTAATTAA | none |
| PciI | ACATGT | none |
| PmeI | GTTTAAAC | none |
| PstI | CTGCAG | none |
| PvuI | CGATCG | none |
| PvuII | CAGCTG | none |
| SacI | GAGCTC | none |
| SacII | CCGCGG | none |
| SalI | GTCGAC | none |
| SapI | GCTCTTC | none |
| SfiI | GGCCNNNNNGGCC | none |
| SgrAI | CRCCGGYG | none |
| SmaI | CCCGGG | none |
| SpeI | ACTAGT | none |
| SphI | GCATGC | none |
| SspI | AATATT | 135 |
| StuI | AGGCCT | 760 |
| SwaI | ATTTAAAT | none |
| TliI | CTCGAG | none |
| XbaI | TCTAGA | none |
| XhoI | CTCGAG | none |
| XmaI | CCCGGG | none |
| XmnI | GAANNNNTTC | none |
| AvaIII | atgcat | none |
| AfeI | AGCGCT | none |
| AvrII | CCTAGG | none |
| BspEI | TCCGGA | none |
| BsrGI | TGTACA | none |

Provided herein is an animal cell including, but not limited to, neural cells, cell lines and muscle cells, the animal cell comprising: an integrated exogenous molecule which expresses a proton pump responsive to blue light, the exogenous molecule derived from *Guillardia theta*.

Also provided herein is a method comprising: modifying a light responsive protein derived from *Guillardia theta* to add an endoplasmic reticulum (ER) export signal at the C-Terminus of the light responsive protein.

Also provided herein is a system for controlling an action potential of a neuron in vivo, the system comprising: a delivery device that introduces a protein to the neuron, the protein being responsive to blue light, wherein the produces an inhibitory current a blue light source that generates light for stimulation of the blue light responsive protein; and a control device that controls the generation of light by the light source.

Also provided herein are systems, methods, arrangements, or kits directed toward: optical stimulation of a cell expressing a GtR3 proton pump.

Also provided herein are systems, methods, arrangements, or kits directed toward control of subcellular processes using GtR3 and/or DChR.

Also provided herein are systems, methods, arrangements, or kits directed toward the use of GtR3 and DChR in different cell populations of a common cellular network.

Also provided herein are systems, methods, arrangements, or kits directed toward DChR.

Also provided herein is a protein consistent with any of the sequences described herein (e.g., sequences shown in Table 1).

Also provided herein are systems, methods, arrangements, or kits directed toward combinations of DChR or GtR3 with other light-responsive opsin types, which can be based on reaction profiles thereof.

Also provided herein are systems, methods, arrangements, or kits directed toward combinations of three or more light-responsive opsin types.

Also provided herein are methods for providing tiered-levels of activity using multiple opsin types in same cell but reactive to different light.

Also provided herein are methods for providing tiered-levels of activity using multiple opsin types in same cell to provide increase frequency of channel function through alternating stimulation of each opsin type.

Also provided herein are systems, methods, arrangements, or kits directed toward muscle control.

Also provided herein are systems, methods, arrangements, or kits directed toward combination control of several different cell groups, each group having a different combination of opsins so that each groups be controlled independently of at least one other group.

Also provided herein is a system comprising a feedback loop for control of a cell (or cell population) with the cell(s) having multiple light-responsive proteins types expressed therein.

Also provided herein are therapeutic applications including, but not limited to, treatment of Parkinson's disease.

Also provided herein are systems, methods, arrangements, or kits directed toward implantation in retinal cells/retraining brain to respond to intensity of multiple wavelengths.

Also provided herein are systems, methods, arrangements, or kits directed toward drug testing.

Also provided herein are systems, methods, arrangements, or kits directed toward the use of GtR3 and/or DChR with transgenic animals.

Also provided herein are systems, methods, arrangements, or kits directed toward control of pH levels in cells including, but not limited to, control over pH levels in an organelle, which can be implemented, without limitation, to encourage or inhibit functions thereof or to kill or maim the cell.

EXAMPLES

According to certain embodiments, subcellular and transcellular trafficking strategies now permit (1) optical regulation at the far-red/infrared border and extension of optogenetic control across the entire visible spectrum; (2) increased potency of optical inhibition without increased light power requirement (nanoampere-scale chloride-mediated photocurrents that maintain the light sensitivity and reversible, step-like kinetic stability of earlier tools); and (3) generalizable strategies for targeting cells based not only on genetic identity, but also on morphology and tissue topology, to allow versatile targeting when promoters are not known or in genetically intractable organisms. These results illustrate the use of cell-biological principles to enable expansion of the versatile fast optogenetic technologies suitable for intact-systems biology and behavior.

Specific aspects of the present disclosure are directed to applications of molecular trafficking strategies, to derive a panel of tools that both quantitatively and qualitatively enhance the power of optogenetics and open distinct avenues of investigation. In particular, tools are developed that allow targeting of cells solely by virtue of their topological relationships within tissue and that extend the reach of optical control to the infrared border, with effector function enhanced beyond the other known tools and covering the entire visible spectrum.

According to the present disclosure, examination of eNpHR2.0-expressing hippocampal neurons revealed the absence of globular ER accumulations with persistent intracellular labeling and poor membrane localization, suggesting that additional modifications subsequent to the ER export step are important. Examination of primary-sequence differences between two forms of an inward rectifier potassium channel with differential membrane localization (Kir2.1 and Kir2.4) revealed differences not only in C-terminal ER export motifs but also in N-terminal Golgi export signals and in C-terminal trafficking signals (Hofherr et al., 2005). Surprisingly, provision of the Golgi export signal did not significantly affect surface expression, but that addition of the trafficking signal from Kir2.1 either between eNpHR and the EYFP fusion, or at the C terminus of the fusion protein, dramatically reduced intracellular labeling and increased apparent surface membrane expression and also improved labeling of cellular processes. Indeed, high-resolution confocal imaging revealed marked localization in processes, with identifiable labeled membranes spanning intracellular regions apparently devoid of the opsin-EYFP fusion protein, in a pattern never previously observed with NpHR or its derivatives.

Figure 25:
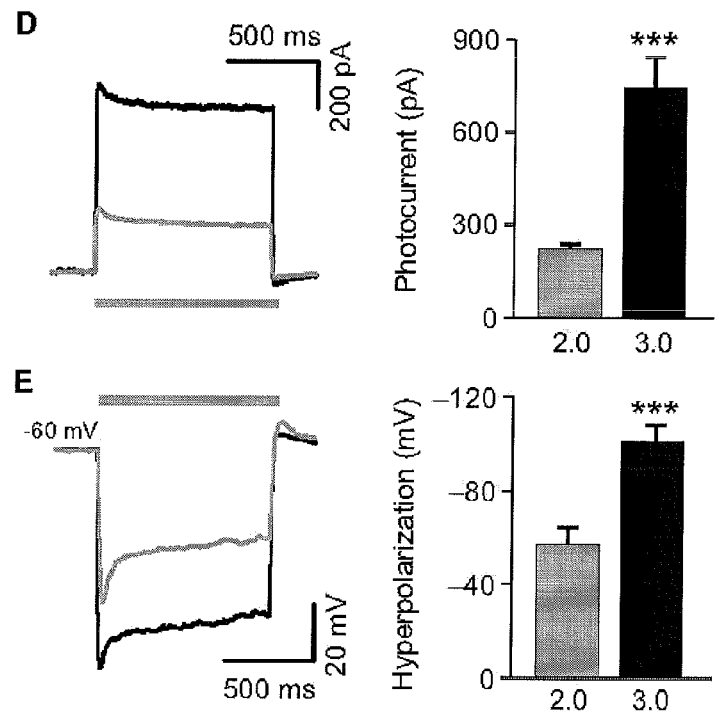
FIG. 25D shows representative photocurrent traces showing in cells transduced with eNpHR3.0 and cells transduced with eNpHR2.0, and summary plots thereof.
FIG. 25E shows representative hyperpolarization voltage traces showing in cells transduced with eNpHR3.0 and cells transduced with eNpHR2.0, and summary plots thereof.

We examined photocurrents, using whole-cell patch clamp recordings to quantify bona fide functional plasma membrane localization of halorhodopsin pump molecules. Photocurrents were indeed profoundly increased (to a level ~20-fold larger than the initially described NpHR currents; mean±standard error of the mean [SEM], photocurrent 747.2±93.9 pA in lentivirally transduced hippocampal pyramidal neurons under the human synapsin I promoter; n=10). FIG. 25D shows representative traces in the left portion of the figure, and summary plots in the right portion of the figure. The representative traces and summary plots of FIG. 25D shows the average photocurrent levels in cells expressing eNPHR3.0 (747.2±93.9 pA), shown in black, and eNpHR2.0, shown in gray, (214.1±24.7 pA; unpaired t test p, 0.0005; n=10). Membrane input resistance was similar for all neurons patched (eNpHR: 193.1±36.6 MΩ; eNpHR3.0: 151.6±28.5 MΩ; unpaired t test p=0.37). At action spectrum peak described below, nanoampere-scale mean outward currents were readily observed with 3.5 mW/mm² yellow light, an order of magnitude lower intensity than required by proton pumps to attain this level of photocurrent (maintaining low light intensities becomes an important issue only for in vivo experiments, wherein safe control of significant tissue volumes is paramount) (Aravanis et al., 2007; Adamantidis et al., 2007; Chow et al., 2010). FIG. 25E shows representative voltage traces, in the left portion of the figure, and summary plots, in the right portion, of eNpHR3.0 (black) and eNpHR2.0 (gray). In virally transduced neurons, light-induced hyperpolarizations by >100 mV were routinely achievable, at the same modest light power levels, as shown in FIG. 25E (mean hyperpolarization in cells expressing eNpHR3.0: 101.0±24.7 mV, n=10; and eNpHr2.0: 57.2±6.8 mV, unpaired t test p, 0.0005, n=10). Membrane potential changes of this new magnitude represent a functionally distinct advance in optogenetic inhibition, and we accordingly designate this third-generation NpHR as eNpHR3.0 (the *Natronomonas* halorhodopsin was named NpHR in 2005 [Sato et al., 2005], and the first trafficking-enhanced version developed by Gradinaru et al. [2008] is now referred to as eNpHR2.0). As expected from prior work (Zhang et al., 2007a) showing that NpHR photocurrents were step-like and exhibited little inactivation over more than 10 min of continuous illumination (indeed, NpHR was selected for this reason, as described in Zhang et al. [2007a]), the eNpHR3.0 photocurrents were also step-like, resistant to inactivation, and highly stable over multiple light pulses and long (behaviorally relevant) timescales (Zhang et al., 2007a).

Figure 30:
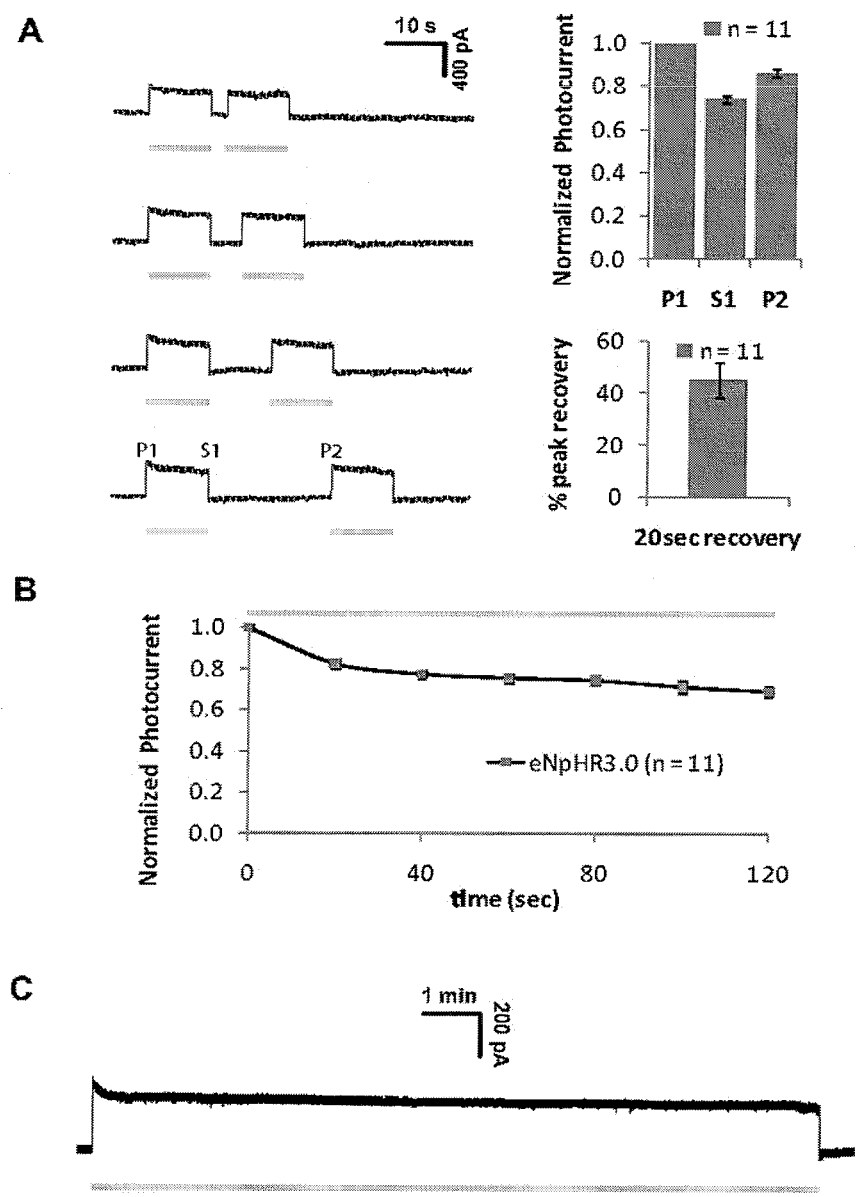
FIG. 30A shows stability and recovery of potent photocurrents in cells expressing eNpHR3.0 when exposed to pairs of 10 second long yellow light pulses separated in time by: 2.5 seconds, 5 seconds, 10 seconds, and 20 seconds.
FIG. 30B shows a timecourse of eNpHR3.0 normalized photocurrents for long-term continuous light exposure.
FIG. 30C shows stability of outward current of eNpHR3.0 over greater than 10 minutes.

FIG. 30A shows stability and recovery for eNpHR3.0 over a short time scale. The representative traces in the left portion of FIG. 30A show photocurrents in cells expressing eNpHR3.0 when exposed to pairs of 10 second long yellow light pulses separated in time by, from the top to bottom of FIG. 30A: 2.5 seconds, 5 seconds, 10 seconds, and 20 seconds. The upper right portion of FIG. 30A shows the summary plot for pulses 20 second apart displaying normalized average photocurrent levels in cells expressing eNpHR3.0 (P1=first pulse peak, 1.00, S1=first pulse steady state, 0.74±0.01; P2=second pulse peak, 0.86±0.02; n=11). The lower right portion of FIG. 30A shows the summary plot for pulses 20 seconds apart displaying approximately 50% peak recovery (P2-S1)/(P1-S1). After 20 seconds, the peak recovers to (45.2±6.6) %. FIG. 30B shows the timecourse of NpHR3.0 normalized photocurrents for long-term continuous light exposure (n=11; various plotted are mean±SEM). FIG. 30C shows the outward current of eNpHR3.0 stability over 10 minutes (light deliver of 593 nm is indicated by the solid bar; output power density: 2.5 mW/mm²).

Figure 26:
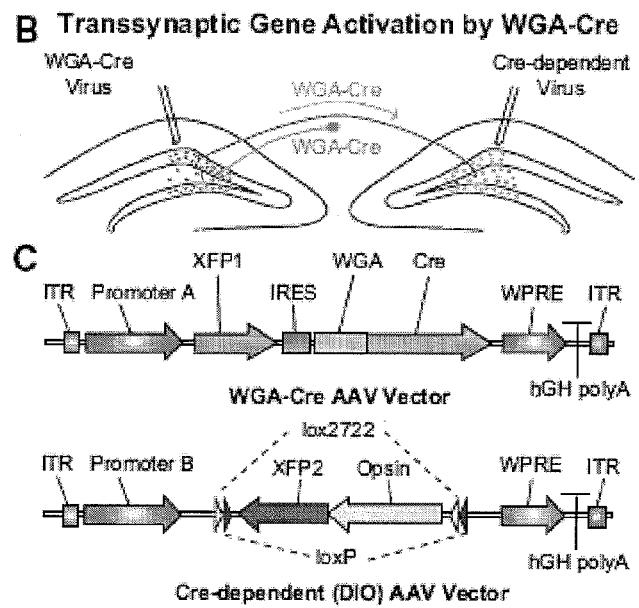
FIG. 26B shows a model of trans-synaptic gene activation by WGA-Cre-fusion. The schematic depicts two injection sites (one with WGA-Cre-fusion gene and another with Cre-dependent opsin virus) and long range projections; Cre can be trans-synaptically delivered from transduced cells to activate distant gene expression only in synaptically connected neurons that have received the Cre-dependent virus.
FIG. 26C shows construct design for the WGA-Cre and Cre-dependent AAV vectors optimized with mammalian codons.

To address whether the robust improved expression is preserved in the mammalian brain in vivo, we injected lentiviral vectors delivering the novel opsin gene under control of the CaMKIIα promoter to the CA1 region of the hippocampal formation in adult mice and examined distribution of the expressed EYFP fusion. As in cultured cells, strong expression was observed not only in dendrites but also in axons in vivo with both eNpHR3.0 and eNpHR3.1 (a shorter version of eNpHR3.0 with equivalent functionality but the N-terminal signal peptide removed). A major in vivo opportunity for systems neurobiology is controlling not just a projection from region A to region B, but a cell type itself that has (among its connections) a projection from A to B. This fundamentally distinct result requires multiplexing of optical control with other targeting methods. Such control would be of great value in systems neurobiology; for example, cortical excitatory pyramidal neurons form a genetically and anatomically defined class of cell, but within this class are cells that each project to multiple different areas of the brain (e.g., thalamus, spinal cord, striatum, and other cortical areas) and therefore have fundamentally distinct roles (Lein et al., 2007; Yoshimura et al., 2005). It is unlikely that genetic tools will advance far enough to separate all of these different cell classes, pointing to the need to inhibit or excite cells defined by connection topology (FIG. 26B). One way to achieve this goal is to capitalize on transcellular trafficking: to introduce into the local cell-body location a Cre-dependent virus conditionally expressing the microbial opsin gene of choice (e.g., Tsai et al., 2009), and rather than additionally employing a Cre-drive mouse line, to instead introduce into a distant target structure (chosen to define the cells of interest by anatomical connectivity) a virus expressing Cre recombinase fused to a transcellular tracer protein, e.g., wheat germ agglutinin (WGA) (FIG. 26B) or tetanus toxin-fragment C (TTC) (Kissa et al., 2002; Maskos et al., 2002; Perreault et al., 2006; Sano et al., 2007; Sugita and Shiba, 2005). Cre recombinase in the fusion protein would be transported by presumed endosomal trafficking mechanisms along with the tracer to the local cell-body location if anatomically connected and activate opsin expression in the subset of local cells defined by this connectivity (FIG. 26B) (Gradinaru et al., 2007, 2009; Petreanu et al., 2007, 2009). Note that this approach does not require any specific promoter fragment or genetic definition of target cells (a clear advantage for use in less-genetically tractable species such as rats and primates); but, if needed, such additional genetic refinements can be readily added (for example, both the WGA-Cre- and the Cre-dependent opsin could be delivered under control of cell type-specific promoters where available), creating a versatile means for addressing cells defined at the intersection of connectivity, location, and genetics.

This concept was first validated in the rat by devising a strategy to selectively introduce eNpHR3.0 into those primary motor cortex (M1) microcircuits that are involved in cortico-cortical connections with primary sensory cortex (S1) (Colechio and Alloway, 2009). To do this, we injected the previously described Cre-dependent AAV, now conditionally expressing eNpHR3.0 into motor cortex, and injected a novel WGA-Cre-expressing AAV (AAV2-EF1α-mCherry-IRES-WGA-Cre) remotely into primary somatosensory cortex. Robust eNpHR3.0-EYFP expression was indeed observed in a distributed subset of the motor cortex neurons at 5 weeks after injection, despite the remoteness of the Cre recombinase AAV injection; in control animals without Cre recombinase, no expression is observed from these Cre-dependent AAVs (Tsai et al., 2009; Sohal et al., 2009). FIG. 26C shows the construct design for the WGA-Cre and Cre dependent AAV vectors, wherein the WGA and Cre genes are both optimized with mammalian codons. Consistent with the anticipated mode of trans-synaptic or transcellular transport of Cre, no mCherry-positive cell bodies were observed in motor cortex, and no EYFP-positive cell bodies were observed in S1 sensory cortex. Cre can be trans-synaptically delivered from transduced cells to activate distant gene expression only in synaptically connected neurons that have received the Cre-dependent virus, and not in others. The expected EYFP-eNpHR3.0 axon terminals arising from M1 were present in S1. Simultaneous optrode stimulation/recording (Gradinaru et al., 2007) was conducted to validate functionality of eNpHR3.0 under the WGA system; indeed, robust inhibition was readily observed in M1, as expected from the intense fluorescence of the XFP-opsin fusion protein. These data indicate that neurons involved in cortico-cortical connections can indeed be addressed and targeted not simply as a projection, but as a cell type defined by connectivity.

To independently validate this targeting technology in a distinct circuit and with a different opsin, we next targeted hippocampal formation dentate gyrus neurons involved in interhemispheric projections. Within the dentate hilus, the only known monosynaptic contralateral projection arises from the hilar mossy cells, which terminate on granule cells of the contralateral dentate, in dendrites of the molecular layer (Freund and Buzsáki, 1996; Ratzliff et al., 2004). The WGA-Cre AAV was unilaterally injected into one dentate gyrus, while the Cre-dependent AAV was injected into the contralateral dentate gyrus of the same animal. Strikingly, opsin expression was observed only in hilar cells of the contralateral side. Indeed, in this case and at this time point, accumulation of Cre was retrograde and monosynaptic to the contralateral hilar cells, as no EYFP labeling was observed in the contralateral granule cell layer; moreover, pointing to lack of direct transduction of axon terminals with this AAV serotype, no mCherry was observed in the contralateral dentate. The only EYFP-expressing circuit elements in the ipsilateral dentate, affording precise opportunities for optical control, were axonal fibers observed to terminate in the molecular layer of the granule cell layer, precisely as expected for fibers arising from the contralateral dentate hilus. Indeed, in vivo optrode recordings confirmed the functionality of WGA/Cre-activated ChR2 in driving light-triggered spikes both at the opsin-expressing cell bodies and in neurons downstream to the axonal projections of ChR2-expressing cells, in the contralateral hemisphere; in line with previous optogenetic studies (Zhang et al., 2007a, 2007b), 470 nm light pulses at 30 Hz (5 ms pulse width) delivered through the optical fiber reliably drove neuronal firing in vivo.

The utility of these targeting strategies for engineered opsins within intact tissue raised the question of whether additional advantages might accrue with regard to volume of tissue modulatable in vivo. While membrane trafficking modifications alone will not shift the action spectrum, the capability to control neurons in the far red is a long-sought goal of optogenetics, as this will allow use of light that penetrates much more deeply into scattering biological tissues (as with the far-red utility recently demonstrated for fluorescent proteins) (Shu et al., 2009), and therefore will allow recruitment of larger volumes (Aravanis et al., 2007; Adamantidis et al., 2007; Gradinaru et al., 2009). The massive photocurrents observed for eNpHR3.0 (~20× those initially reported for NpHR, which itself is capable of blocking spiking in response to 589 nm amber light), suggested optogenetic control with far-red light might be achieved. We therefore explored optical control in the far red with the trafficking-enhanced eNpHR3.0.

Figure 27:
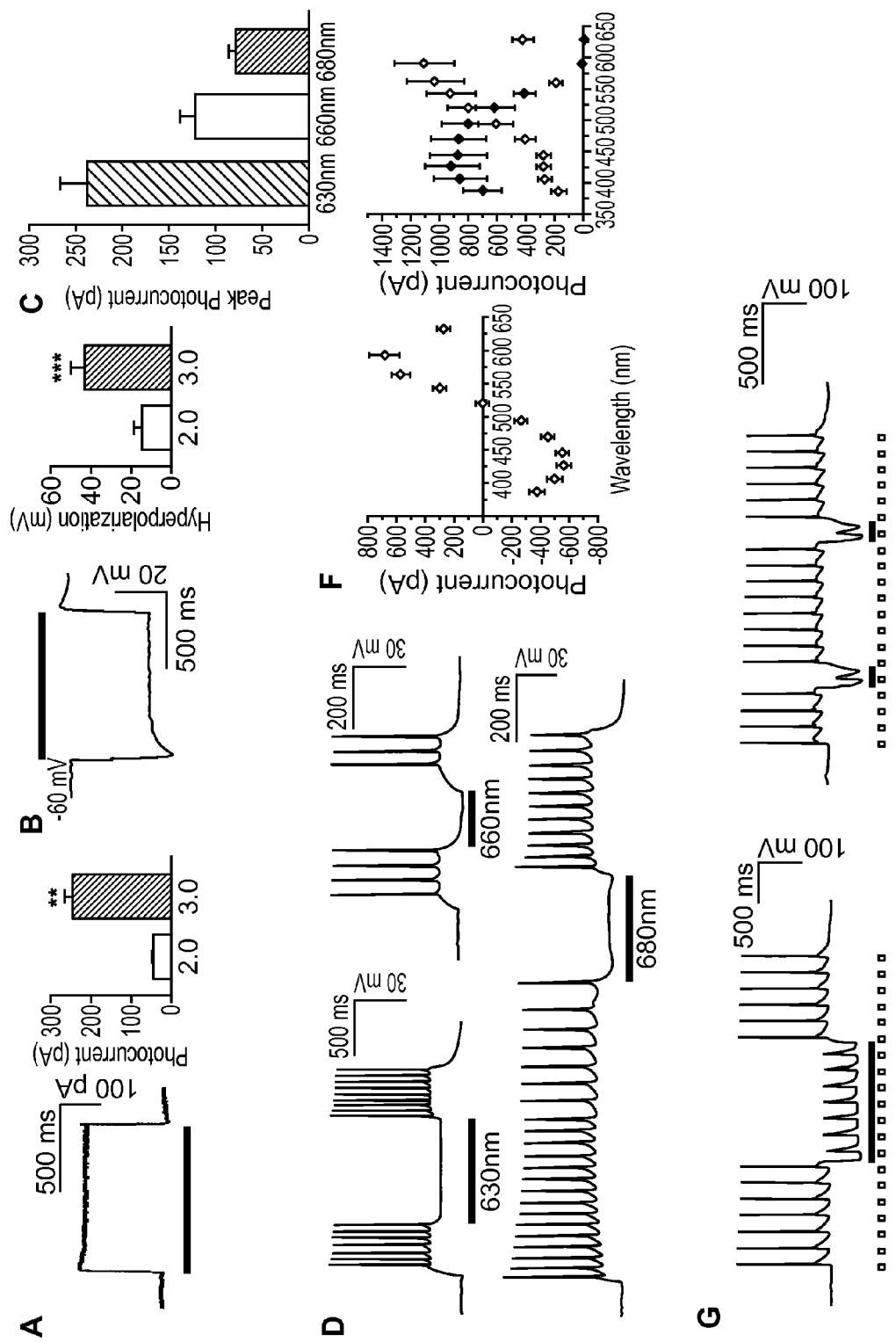
FIG. 27A shows that six hundred thirty nanometer light evokes robust photocurrents in neurons transduced with eNpHR3.0 (representative voltage clamp trace at left). Summary plot comparing eNpHR2.0- and eNpHR3.0-expressing neurons (at right); eNpHR2.0, 42.7±4.5 pA; eNpHR3.0, 239.4±28.7 pA; unpaired t test p=0.00004; n=10).
FIG. 27B shows that six hundred thirty nanometer illumination evoked robust hyperpolarization (representative voltage clamp trace at left). Summary plot comparing eNpHR2.0- and eNpHR3.0-expressing neurons (right); 15.6±3.2 mV for eNpHR2.0 and 43.3±6.1 mV for eNpHR3.0; unpaired t test p=0.00116; n=10).
FIG. 27C shows a summary of outward photocurrents evoked by different wavelengths of red and far-red/infrared border illumination: 630 nm, 239.4±28.7 pA (left, n=10); 660 nm, 120.5±16.7 pA (middle, n=4); and 680 nm: 76.3±9.1 pA (right, n=4). Power density: 3.5 mW/mm$^2$ (630 nm) and 7 mW/mm$^2$ (660 nm, 680 nm).
FIG. 27D shows that illumination with red and far-red/infrared border light inhibited spiking induced by current injection in neurons expressing eNpHR3.0. Typical current-clamp traces show optical inhibition at 630 nm (top left), 660 nm (top right), and 680 nm (bottom). Power density: 3.5 mW/mm$^2$ (630 nm) and 7 mW/mm$^2$ (660 nm, 680 nm).
FIG. 27G shows that blue light (445 nm, 5 ms pulses) drove spiking at 20 Hz (left) and 10 Hz (right), while simultaneous application of yellow light (590 nm) inhibited spikes.
FIG. 27F shows activation spectrums for eNPAC, ChR2 (H134R), and eNpHR3.0 alone.

Even in response to true-red (630 nm) light of only 3.5 mW/mm$^2$, we observed potent ~250 pA outward photocurrents in virally transduced cells-still more than 6-fold larger than the first observed NpHR currents with yellow light (FIG. 27A), and maintaining the characteristic step-like, stable kinetics typical of NpHR (eNpHR3.0-expressing and eNpHR2.0 expressing neurons: eNpHR3.0: 239.4±28.7 pA; eNpHR2.0: 42.7±4.5 pA; unpaired t test p=0.00004; n=10) (Zhang et al., 2007a). Moreover, we found that these photocurrents evoked by red light could be used to trigger large (>40 mV) hyperpolarizations in hippocampal pyramidal neurons (FIG. 27B) (eNpHR3.0-expressing and eNpHR2.0 expressing neurons: eNpHR3.0: 43.3±6.1 mV; eNpHR2.0: 15.6±3.2 mV; unpaired t test p=0.00116; n=10). We therefore explored even further red-shifted light. We continued to observe robust photocurrents in the deep red with 660 nm light and at the red/infrared border with 680 nm light (FIG. 27C). At 680 nm, the photocurrents (~75 pA) were still larger than peak (yellow light) eNpHR2.0 currents previously reported at 7 mW/mm$^2$. Importantly, at all of the red and far-red wavelengths tested, eNpHR3.0 photocurrents readily blocked action potentials induced by current injection (FIG. 27D) with 7 mW/mm$^2$ or less, validating the extension of optogenetic control channels to far-red light. The outward photocurrents evoked by different wavelengths of red and far-red/infrared border illumination are: 239.4±28.7 pA (n=10) at 630 nm; 120.5±16.7 pA (n=4) at 660 nm; and 76.3±8.1 pA (n=4) at 680 nm.

One important feature of NpHR is its spectral compatibility with ChR2: the two opsins have largely separable action spectra and operate with similar light power density requirements, allowing bidirectional control of optical activity (Zhang et al., 2007a) in vitro or in vivo despite a small region of spectral overlap. To test whether eNpHR3.0 had become too potent, given the spectral overlap, to use in combination with ChR2 in the same cell, we created a bicistronic vector containing eNpHR3.0; analogous 2A-based combination vectors (Ryan and Drew, 1994) have been employed with earlier tools, and channelrhodopsin currents with this method have ranged from 150 to 240 pA and halorhodopsin currents from 11 to 40 pA (Tang et al., 2009, Han et al., 2009b). We transfected the eNpHR3.0-2A-ChR2 construct (abbreviated eNPAC) into hippocampal pyramidal neurons. With these experiments, trafficking of both opsin gene products to cellular processes was observed. To verify that independent excitation and inhibition was still possible despite the increased currents from eNpHR3.0, we mapped out the steady-state photocurrent action spectrum in detail for eNPAC and for ChR2(H134R) (Gradinaru et al., 2007) and eNpHR3.0 alone. FIG. 27F, shows the activation spectrums for eNPAC, the left portion of FIG. 27F, and for ChR2 (H124R) and eNpHR3.0, on the right portion of FIG. 27F. In the right portion of FIG. 27F, the activation spectrum of ChR2 is shown in dark gray, and the activation spectrum of eNpHR3.0 is shown in light gray. Maximal eNPAC steady-state excitatory and inhibitory currents were both approximately 60% of that observed when each opsin was expressed individually, yielding maximal photocurrents of >550 pA in each direction (FIGS. 27F-G); the modestly overlapping action spectra may provide a feature, in that potent shunting inhibition combined with hyperpolarizing inhibition is likely possible with this combination approach. More specifically, maximum eNPAC steady-state excitation was 567±49 pA at 427 nm (n=9), 62% of the value for ChR2(H134R) alone (916±185 pA, n=5). Similarly, maximum eNPAC inhibition was 679±109 pA at 590 nm (n=9), 61% of the value for eNpHR3.0 alone (1110±333 pA; n=4). Output power density for peak current values was 3.5-5 mW/mm$^2$ (3.5 mW/mm$^2$ at 590 nm). Validation in vivo will require demonstration that the specific P2A method (or other linker approach) is functional in a particular circuit or cell type (yet to be determined); however, these data in cultured hippocampal neurons demonstrate that potent bidirectional photocurrents of >500 pA each can be achieved within a single cell, without incapacitating interference of the trafficking-enhanced opsin.

The known wide action spectrum of the microbial opsins poses challenges with regard to achieving multiple independent channels of control; interestingly, eNpHR3.0 becomes not only a potent far-red optical control tool, but also the most potent known blue light-driven opsin-based inhibitor (>400 pA at 472 nm). Indeed, the membrane trafficking strategies delineated here may form a generalizable strategy for adapting diverse microbial opsins with unique properties for optogenetic control purposes. In a final series of experiments, we explored whether these and other enhanced membrane trafficking principles could enable the addition of genetically and functionally distinct components to the optogenetic toolbox.

While a very large number of microbial opsins genes exist in nature, we and others have thus far found none that outperform eNpHR3.0 (as described herein) with regard to photocurrent size, light requirements, or kinetics (Zhang et al., 2007a; Han and Boyden, 2007; Chow et al., 2010). It is important to continue to expand the optogenetic toolbox, but we have found that most microbial opsins traffic poorly in mammalian cells. However, application of the trafficking principles for microbial opsin engineering outlined here may enable optogenetics to continue the genomics progress over the past few years (Zhang et al., 2008), capitalizing on the immense natural diversity of microbial opsins (Zhang et al., 2008; Chow et al., 2010). We sought to test the adaptability of the membrane trafficking principle with the best-characterized microbial opsin, bacteriorhodopsin (BR) (Stoeckenius and Bogomolni, 1982), from *H. salinarum*, a green light-activated regulator of transmembrane ion conductance (Marti et al., 1991).

Figure 28:
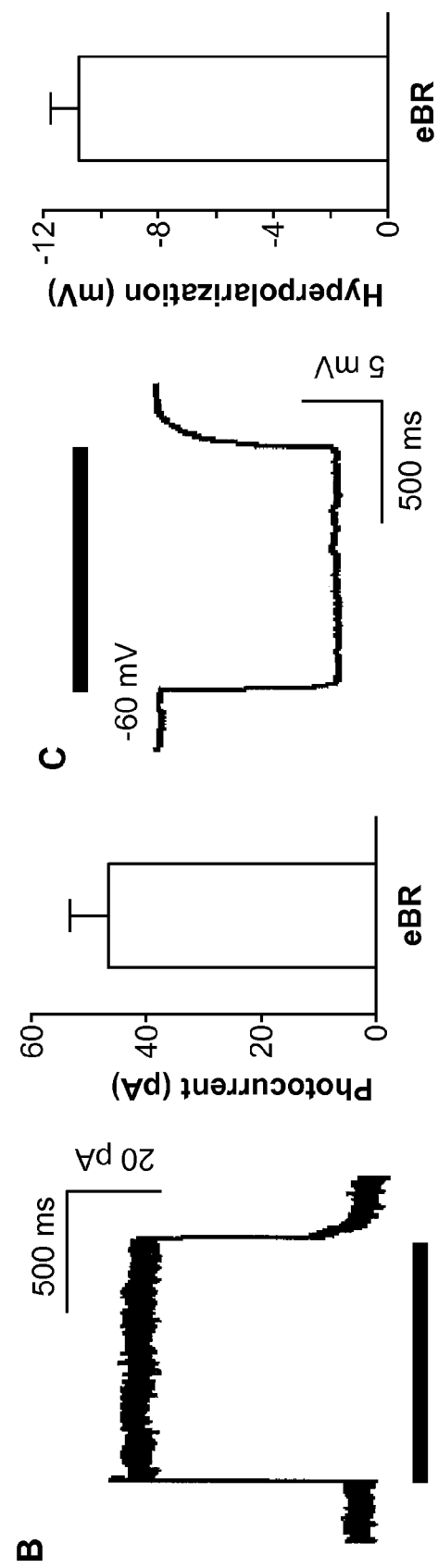
FIG. 28B shows five hundred sixty nanometer light induced outward photocurrents in eBR cells, and the corresponding sample trace in voltage clamp.
FIG. 28C shows five hundred sixty nanometer light induced hyperpolarizations in eBR cells, and the corresponding sample trace in current clamp.

We found that expressed in unmodified form, prominent intracellular accumulations were observed, similar to those seen when the *Natronomonas* halorhodopsin is expressed at high levels, and no photocurrents were observed. However, addition of the trafficking signal (TS, as employed for eNpHR3.0) between BR and EYFP substantially improved membrane and process localization, with smaller persistent ER-like accumulations that were eliminated with further C-terminal addition of the ER export signal FCYENEV (SEQ ID NO: 12). The resulting construct (eBR, doubly engineered for optimal membrane trafficking) was well tolerated in cultured neurons, with marked membrane localization and process targeting. Validation of functional plasma membrane targeting revealed that eBR could typically deliver −50 pA of outward photocurrent and ~10 mV hyperpolarizations that sufficed to block spiking in hippocampal pyramidal neurons when exposed to the optimal wavelength light of 560 run, thereby providing another channel for optogenetic control and illustrating the potential generalizeability of the microbial opsin membrane trafficking approach. More specifically, as seen in FIG. 28B, five hundred sixty nanometer light induced outward photocurrents of 46.4±7.2 pA in eBR cells (mean±SEM is plotted, n=12). The membrane input resistance was similar for all neurons patched (131.6±19.5 mQ). The light power density at sample was 7 mW/mm². As seen in FIG. 28C, the light induced hyperpolarizations were 10.8±1.0 mV (mean±SEM plotted, n=12).

We also continued genomic strategies similar to those that allowed our identification of the red-shifted excitatory opsin VChR1 from *Volvox carter i* (Zhang et al., 2008); indeed, a number of microbes have been reported to display light sensitivities from violet to near infrared. We accordingly continued our broad genomic mining approach in environmental sequencing databases, plant/microbial expressed sequence tag (EST) libraries, and whole-genome shotgun (WGS) sequencing repositories to search for new rhodopsins with channel or pump properties and novel light sensitivities (Zhang et al., 2008). Using the primary amino acid sequences for ChRs, HRs, and BRs as the template sequence, we continued the search among evolutionarily distant species (Zhang et al., 2008; Chow et al., 2010). Among other candidate sequences from diverse hosts (*Cryptomonas, Guillardia, Mesostigma, Dunaliella, Gloeobacter*, etc.), one of these from *Guillardia theta*. was different from the previously reported GtR1 and GtR2 (Sineshchekov et al., 2005) and showed high amino acid homology to ChR2. We designated this new protein as *G. theta* rhodopsin-3 (GtR3), optimized the codon bias of GtR3 for mammalian expression, and delivered the GtR3-EYFP fusion gene to hippocampal pyramidal neurons. In an emerging theme, GtR3 showed intracellular accumulations and no photocurrents. Provision of the TS signal between GtR3 and EYFP only mildly reduced accumulations, but, together with addition of the ER export signal FCYENEV (SEQ ID NO: 12) to the C terminus, accumulations were abolished and increased surface and process localization observed.

Figure 31:
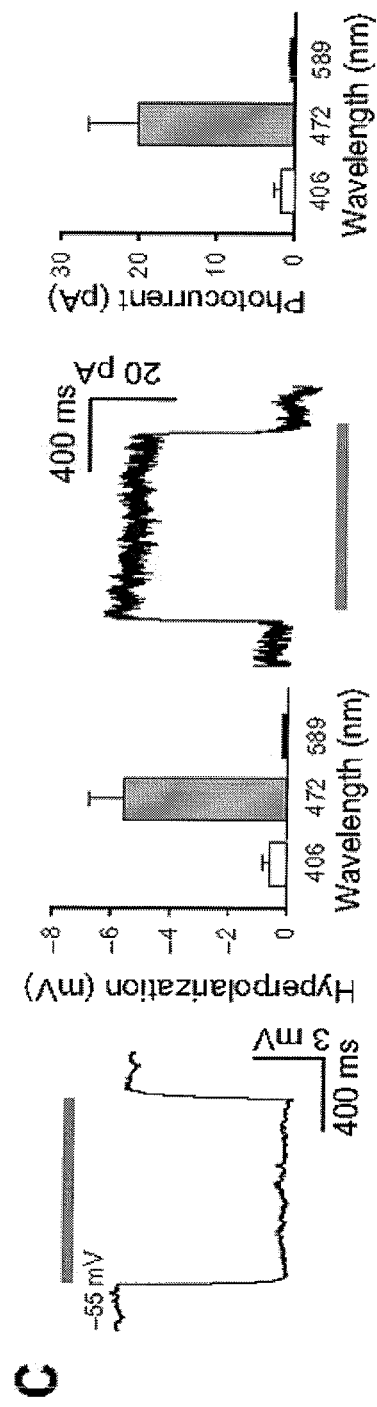
FIG. 31C shows sample current clamp and voltage clamp traces and summary data of GtR3 function under 472 nm light.

The resulting modified GtR3 hyperpolarizes hippocampal neurons in response to 472 nm blue light, albeit with smaller currents than eBR, and could inhibit spiking as well. We also achieved blue inhibition of spiking with an opsin (AR) from *Acetabularia acetabulum* (Tsunoda et al., 2006; Chow et al., 2010) engineered for improved trafficking; AR generates little current alone but was initially aggregate free and required only addition of the TS signal between AR and EYFP for functional membrane localization and spike inhibition. Sample current clamp and voltage clamp traces and summary data show GtR3 function under 472 nm light (18.5 mW/mm²) are shown in the left and right portions, respectively, of FIG. 31C. A light induced outward photocurrent summary is shown in the left bar graph of FIG. 31C, and the corresponding hyperpolarization summary for a blue light peak is shown in the right bar graph. Corresponding photocurrents and hyperpolarization were: 0.5±0.4 pA and 0.12±0.09 mV for yellow light (589 nm; 7.5 mW/mm²); 20.0±6.7 pA and 5.6±1.2 mV for blue light (472 nm; 18.5 mW/mm²); 1.7±0.9 pA and 0.6±0.3 mV for purple light (406 nm; 3 mW/mm²) (mean±SEM plotted; n=10; input resistance was similar for all neurons: 113.5±24.2 mΩ).

Figure 29:
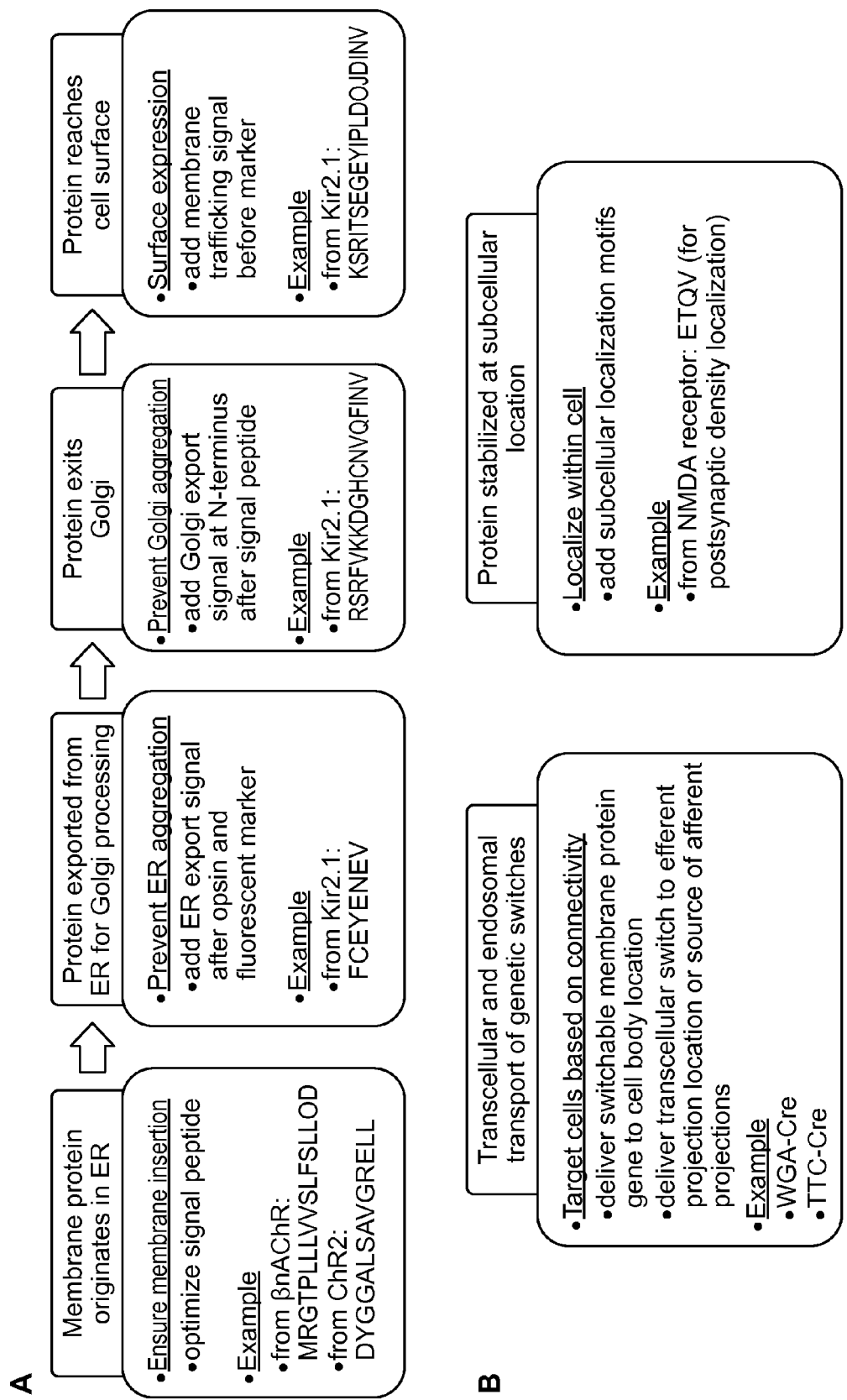
FIG. 29A shows general subcellular targeting strategies for adapting microbial opsin genes to metazoan intact-systems biology. MRGTPLLLWSLFSLLQD (SEQ ID NO:15); DYGGALSAVGRELL (SEQ ID NO:16); FCEYENEV (SEQ ID NO:12); RSRFVKKDGHCNVQFINV (SEQ ID NO:17); and KSRITSEGEYIPLDQIDINV (SEQ ID NO:11).
FIG. 29B shows refinement of targeting at the tissue and subcellular levels.

While these and other published microbial opsin-derived inhibitors are not yet as potent as eNpHR3.0 (and for this reason we continue with eNpHR3.0 for optogenetic applications), the improved functionality achieved here by membrane trafficking modifications point to the potential versatility of this approach in unlocking the full potential of ecological diversity, and to the individualized strategies that will be indicated for different microbial opsin genes. FIG. 29A shows general subcellular targeting strategies for adapting microbial opsin genes to metazoan intact-systems biology. FIG. 29B shows refinement of targeting at the tissue and subcellular levels (subcellular opsin targeting methods have been previously described, see Gradinaru et al. [2007] and Lewis et al., [2009]; tissue/transcellular opsin targeting methods are described herein).

Optogenetic approaches previously have found substantial utility in the control of biological processes and behavior in freely moving mammals (Adamantidis et al., 2007; Airan et al., 2009; Gradinaru et al., 2009; Petreanu et al., 2007, 2009; Sohal et al., 2009; Tsai et al., 2009) and other animals (Douglass et al., 2008; Hwang et al., 2007; Lerchner et al., 2007; Zhang et al., 2007a), with the high temporal precision that is important for intact-systems biology. We have found that engineering specific membrane-trafficking capabilities for microbial proteins is an important step in generating diverse optogenetic technologies for intact-systems biology. Not all trafficking strategies will be suitable for all microbial opsins, with different motifs required for opsins that encounter trafficking difficulty at different stages; therefore, careful subcellular analysis with rational selection of proper modifications together constitute a directed and principled strategy that may be applicable to all opsins of nonmammalian origin, thereby enabling systematic generation of novel optogenetic tools from genomic resources.

We have previously observed that inhibition with NpHR and NpHR2.0, while useful for many applications (Gradinaru et al., 2009; Sohal et al., 2009; Tønnesen et al., 2009; Arrenberg et al., 2009), can in some cases be overcome by very strong excitation (Sohal et al., 2009). Hyperpolarizations by greater than 100 mV with eNpHR3.0 provide a substantial step forward in the potency of optical inhibition. The inhibition now provided with eNpHR3.0, more than 20-fold stronger than the initial NpHR, remains tunable with light intensity or duty-cycle adjustments, as with any of the optogenetic tools. At the action spectrum peak, nanoampere-scale mean outward currents readily resulted with only 3.5 mW/mm$^2$ yellow light (10-fold less light power than required for approaching similar currents with previously described proton pumps). At the same time, eNpHR3.0 preserved the step-like kinetics, fast recovery, and resistance to inactivation over long timescales of NpHR (Zhang et al., 2007a).

eNpHR3.0 is particularly well suited for in vivo applications, as the most red-shifted and potent optogenetic inhibitor to date, but further strategies to enhance potency of this and other tools will no doubt emerge, and membrane trafficking work as described here may enable even more potent inhibitors in the future. When employing eNpHR3.0, inhibition can be readily dialed down if needed by using weaker promoters, shorter expression times, or reduced light levels, while maintaining access to new wavelengths ~100 nm red-shifted from previous reports (680 nm versus 589 nm) to enable operating at the infrared border with deeper-penetrating and safer photons. Of course, not only the opsin gene and light source selected, but also the strategy for circuit element targeting, may determine effectiveness; for example, optogenetic work on Parkinsonian models (Gradinaru et al., 2009) showed that therapeutically effective deep brain stimulation (DBS) in the subthalamic nucleus (STN) is likely initiated by action on afferent axons (which in turn then modulate both downstream and upstream networks). While direct fiber-optic-based inhibition of local cell bodies in the STN did not show behavioral effects comparable to those observed with direct modulation of afferent axons, these results do not mean that inhibition of the STN is not important (indeed, optogenetic axonal modulation in the STN results in inhibition of STN spiking, as noted by Gradinaru et al. [2009]). Rather, these results informed the long-standing clinical significant questions surrounding the mechanism and target of DBS by showing that axonal modulation constitutes the likely therapeutic mechanism and a highly efficient means for a point source such as a DBS electrode (or optical fiber) to control a structure or network in diseased neural circuitry (Gradinaru et al., 2009). In addition to these circuit element targeting considerations, the light intensity and wavelength, promoter choice, virus titer, virus tropism, time of opsin expression, target cell biophysics, and local patterns of endogenous activity and modulation will all affect optogenetic inhibition efficacy and should be carefully considered for each experimental system (Cardin et al., 2010).

To enable control of cell types on the basis of connectivity properties, we leveraged transcellular delivery of a Cre recombinase. First, in rat, we selectively targeted those M1 neurons that are involved in cortico-cortical connections with S1, and second, we targeted hippocampal formation dentate gyms neurons involved in interhemispheric projections; in both cases, cells were targeted defined only by connectivity, without use of cell type-specific promoter fragments or transgenic animals. In each system, this approach must be validated for directionality (antero- or retrograde) and extent of Cre transport, which may depend on cell-specific endosomal dynamics and experimental timepoint; this strategy may also work only with viruses rather than mouse transgenesis, allowing Cre access to episomal DNA. This approach is best served by vectors that do not directly transduce axon terminals, which may not be the case for all AAV serotypes (as we and others have in some circuits observed [Paterna et al., 2004]). Any direct transduction of axon terminals may be detected or ruled out with appropriate XFP markers, and direct transduction of axon terminals in some cases may be desirable and can be achieved with HSVs, some AAV serotypes, and pseudotyped lentiviruses; however, such an approach (unlike the present strategy) does not allow selection of the cell type postsynaptic to the transduced terminals and is not as efficient with certain AAVs that are the vector of choice for many applications due to high titer, tissue penetration, safety, and tolerability.

The cell-process targeting enabled by membrane trafficking modification allows for control of cells that are defined topologically—that is, by the essential character of their connections within tissue. At present, it is not guaranteed that transport is synaptic or monosynaptic (as in the hippocampal circuit experiments, such properties will need to be validated in each system); therefore, the term "topological targeting" rather than synaptic targeting is here used to underscore the deformation independence of the fundamental character of the connection—an axonal connection can take any path from A to B, and as long as the connection is present, the topological targeting strategy remains valid. This property is important in genetically less-tractable organisms, but also of substantial value even in animals such as mice, where genetic targeting tools are in many cases inadequate. Of course, genetic targeting strategies may be multiplexed with topological targeting; for example, expression from the Cre-dependent vector and the Cre-fusion vector may each be governed by specific genetic targeting sequences if available. Moreover, the availability of multiple channels of optical control opens the door to combinatorial topological targeting strategies.

Like ChR2, NpHR, and VChR1, we note that most microbial opsins can benefit from substantial protein engineering to achieve new kinds of functionality. Indeed, we and others have previously demonstrated molecular strategies for eliciting from microbial opsins increased light sensitivity (Berndt et al., 2009), increased photocurrent magnitude (Gradinaru et al., 2007, 2008; Zhao et al., 2008), faster kinetics (Gunaydin et al., 2010; Lin et al., 2009), and bistable switching behavior (Berndt et al., 2009). Other possibilities such as shifted action spectrum (Zhang et al., 2008; Gunaydin et al., 2010), increased two-photon responsivity, and altered ion permeability (e.g., for Ca2+) may also be achieved in the future.

While ion conductance-regulating opsins have been the most versatile for ready translation (employing a common electrical language), biochemical control with light in defined cell types is also possible (but with a different set of approaches, given that microbial signal transduction employs principles distinct from metazoan signaling). Indeed, optogenetic control of well-defined biochemical signaling pathways was recently achieved both in cultured cells and in freely moving mammals, using the optoXR method for optical control of specified G protein-coupled receptor signaling (Airan et al., 2009). A photoactivatable adenylyl cyclase has been studied from Euglena, although with high dark activity that limits in vivo application (Schröder-Lang et al., 2007), and subsequent work on light-sensitive PAS or LOV domains (Levskaya et al., 2009; Wu et al., 2009) may open up new ways to control protein-protein association if these approaches can be made to operate in living animals.

We have found that in the nervous system, optogenetic tools can be applied to probe the neural circuit underpinnings of information transmission, oscillations, locomotion, awakening, and reward, as well as to probe the operation of neural circuits important in a number of brain diseases including Parkinson's disease and epilepsy (Adamantidis et al., 2007; Airan et al., 2009; Cardin et al., 2009; Gradinaru et al., 2009; Sohal et al., 2009; Tønnesen et al., 2009; Tsai et al., 2009). Moreover, results thus far point to substantial versatility of the optogenetic approach across animal species (Adamantidis et al., 2007; Airan et al., 2009; Aravanis et al., 2007; Arenkiel et al., 2007; Bi et al., 2006; Boyden et al., 2005; Chow et al., 2010; Douglass et al., 2008; Gradinaru et al., 2008, 2009; Hägglund et al., 2010; Han et al., 2009a; Huber et al., 2008; Hwang et al., 2007; Ishizuka et al., 2006; Li et al., 2005; Nagel et al., 2003, 2005; Petreanu et al., 2007, 2009; Tsai et al., 2009; Wang et al., 2007; Zhang et al., 2006, 2007a; Zhang and Oertner, 2007; Zhao et al., 2008). Together with fiberoptic (Adamantidis et al., 2007; Aravanis et al., 2007) and integrated fiberoptic-electrode "optrode" assemblies (Gradinaru et al., 2007), even cells located deep within large, dense organs can be readily accessed and interrogated in freely moving mammals. The additional resources defined here arise from the application of molecular, cellular, and genomic strategies to enable expansion of the capabilities of optical control, and, as this toolbox rapidly grows, optogenetics may come to play an increasingly potent and versatile role in intact-systems biology for the fast control of defined cells within functioning tissues.

Experimental Procedures

Constructs

All NpHR variants were produced by PCR amplification of the NpHR-EYFP construct previously published (Zhang et al., 2007b). All opsins described here have been optimized for mammalian expression by changing each gene's codon usage to conform to human codon usage distribution. Updated maps and vectors are available and freely distributed from the Deisseroth laboratory (affiliated with Stanford University, Stanford, Calif.) and described at 2010 Scientific American, "Method of the Year," December 2010 (http://www.optogenetics.org/), the contents of which are hereby incorporated by reference in their entirety.

The Amino Acid Sequence of GtR3 without the Signal Peptide Sequence

```
                                      (SEQ ID NO: 1)
A S S F G K A L L E F V F I V F A C I T
L L L G I N A A K S K A A S R V L F P A
T F V T G I A S I A Y F S M A S G G G W
V I A P D C R Q L F V A R Y L D W L I T
T P L L L I D L G L V A G V S R W D I M
A L C L S D V L M I A T G A F G S L T V
G N V K W V W W F F G M C W F L H I I F
A L G K S W A E A A K A K G G D S A S V
Y S K I A G I T V I T W F C Y P V V W V
F A E G F G N F S V T F E V L I Y G V L
D V I S K A V F G L I L M S G A A T G Y
E S I
```

The Amino Acid Sequence of GtR3 with the Signal Peptide Sequence from ChR2

```
                                      (SEQ ID NO: 5)
M D Y G G A L S A V G R E L L F V T N P
V V V N G S V L V P E D Q C Y C A G W I
E S R G T N G A S S F G K A L L E F V F
I V F A C I T L L L G I N A A K S K A A
S R V L F P A T F V T G I A S I A Y F S
M A S G G G W V I A P D C R Q L F V A R
Y L D W L I T T P L L L I D L G L V A G
V S R W D I M A L C L S D V L M I A T G
A F G S L T V G N V K W V W W F F G M C
W F L H I I F A L G K S W A E A A K A K
G G D S A S V Y S K I A G I T V I T W F
C Y P V V W V F A E G F G N F S V T F E
V L I Y G V L D V I S K A V F G L I L M
S G A A T G Y E S I
```

The Amino Acid Sequence of DChR

```
                                      (SEQ ID NO: 2)
M R R R E S Q L A Y L C L F V L I A G W
A P R L T E S A P D L A E R R P P S E R
N T P Y A N I K K V P N I T E P N A N V
Q L D G W A L Y Q D F Y Y L A G S D K E
W V V G P S D Q C Y C R A W S K S H G T
D R E G E A A V V W A Y I V F A I C I V
Q L V Y F M F A A W K A T V G W E E V Y
V N I I E L V H I A L V I W V E F D K P
A M L Y L N D G Q M V P W L R Y S A W L
L S C P V I L I H L S N L T G L K G D Y
S K R T M G L L V S D I G T I V F G T S
A A L A P P N H V K V I L F T I G L L Y
G L F T F F T A A K V Y I E A Y H T V P
K G Q C R N L V R A M A W T Y F V S W A
M F P I L F I L G R E G F G H I T Y F G
S S I G H F I L E I F S K N L W S L L G
H G L R Y R I R Q H I I I H G N L T K K
N K I N I A G D N V E V E E Y V D S N D
K D S D V
```

The Amino Acid Sequence of NpHR

```
                                      (SEQ ID NO: 3)
M T E T L P P V T E S A V A L Q A E V T Q R E L
F E F V L N D P L L A S S L Y I N I A L A G L S
I L L F V F M T R G L D D P R A K L I A V S T I
L V P V V S I A S Y T G L A S G L T I S V L E M
P A G H F A E G S S V M L G G E E V D G V V T M
W G R Y L T W A L S T P M I L L A L G L L A G S
```

```
                                       (SEQ ID NO: 4)
N A T K L F T A I T F D I A M C V T G L A A A L

T T S S H L M R W F W Y A I S C A C F L V V L Y

I L L V E W A Q D A K A A G T A D M F N T L K L

L T V V M W L G Y P I V W A L G V E G I A V L P

V G V T S W G Y S F L D I V A K Y I F A F L L L

N Y L T S N E S V V S G S I L D V P S A S G T P

A D D
```

The Amino Acid Sequence of BR

```
                                       (SEQ ID NO: 4)
M L E L L P T A V E G V S Q A Q I T G R P E W I

W L A L G T A L M G L G T L Y F L V K G M G V S

D P D A K K F Y A I T T L V P A I A F T M Y L S

M L L G Y G L T M V P F G G E Q N P I Y W A R Y

A D W L F T T P L L L L D L A L L V D A D Q G T

I L A L V G A D G I M I G T G L V G A L T K V Y

S Y R F V W W A I S T A A M L Y I L Y V L F F G

F T S K A E S M R P E V A S T F K V L R N V T V

V L W S A Y P V V W L I G S E G A G I V P L N I

E T L L F M V L D V S A K V G F G L I L L R S R

A I F G E A E A P E P S A G D G A A A T S D
```

Hippocampal Cultures

Primary cultured hippocampal neurons were prepared from P0 Spague-Dawley rat pups. The CA1 and CA3 regions were isolated, digested with 0.4 mg/ml papain (Worthington, Lakewood, N.J.), and plated onto glass coverslips precoated with 1:30 Matrigel (Beckton Dickinson Labware, Bedford, Mass.) at a density of 65,000/cm². Hippocampal cultures grown on coverslips were transfected or transduced at 4 days in vitro (DIV) with titer-matched viruses for all constructs (final dilution $10^4$ infectious units (i.u.)/ml in neuronal growth medium). Whole-cell patch clamp recordings were performed as previously described (Zhang et al., 2007b). Primary hippocampal cultures were infected at 4 DIV with titer-matched virus (final dilution 104 i.u./ml in neuronal growth medium). At 14 DIV, cultures were fixed for 30 min with ice-cold 4% paraformaldehyde and then permeabilized for 30 min with 0.4% saponin in 2% normal donkey serum (NDS). Primary antibody incubations were performed overnight at 4° C.; Cy3-conjugated secondary antibodies (Jackson Laboratories, West Grove, Pa.) were applied in 2% NDS for 1 hr at room temperature. Images were obtained on a Leica confocal microscope with a 63×/1.4 NA oil objective.

Stereotactic Injection into the Rodent Brain and Optrode Recordings

Adult mice and Long-Evans rats were housed according to the approved protocols at Stanford. All surgeries were performed under aseptic conditions. The animals were anesthetized with intraperitoneal injections of a ketamine (80 mg/kg)/xylazine (15-20 mg/kg) cocktail (Sigma). The virus was delivered via a 10 µl syringe and a thin 34 gauge metal needle; the injection volume and flow rate (1 µl at 0.1 µl/min) were controlled with an injection pump from World Precision Instruments (Sarasota, Fla.). For validation of opsin functionality, simultaneous optical stimulation and electrical recording in living rodents was conducted as described previously (Gradinaru et al., 2007) with an optrode composed of an extracellular tungsten electrode (1 MΩ, ~125 µm) attached to an optical fiber (~200 µm) with the tip of the electrode deeper (~0.4 mm) than the tip of the fiber to ensure illumination of the recorded neurons. The optical fiber was coupled to a 473 nm (for ChR2) or 560 nm (for eNpHR3.0) laser diode (10 mW fiber output) from CrystaLaser. Optrode recordings were conducted in rodents anesthetized with 1.5% isoflurane, and the optrode was placed through small craniotomies created above target regions. pClamp 10 and a Digidata 1322A board were used to both collect data and generate light pulses through the fiber. The recorded signal was band-pass filtered at 300 Hz low/5 kHz high (1800 Microelectrode AC Amplifier).

Tissue Slice Preparation

For preparation of brain slices, mice or rats were sacrificed 4 to 5 weeks after viral injection. Rodents were perfused with 20 ml ice-cold PBS, followed by 20 ml 4% paraformaldehyde. The brains were then fixed overnight in 4% paraformaldehyde and transferred to 30% sucrose solution for 2 days. Brains were frozen and coronal slices (40 µm) were prepared with a Leica SM2000R cryostat and preserved in 4° C. in cryoprotectant (25% glycerol and 30% ethylene glycol in PBS). Slices (DAPI stain 1:50,000) were mounted with PVA-DABCO on microscope slides, and single confocal optical sections (e.g., through dorsal CA1 region, ~1-2.5 mm posterior to bregma or the dorsal subiculum, 2.7-3 mm posterior to bregma) were acquired using a 10× air and 40×/1.4 NA oil objectives on a Leica confocal microscope.

Extended Experimental Procedures

Opsin Sources

All opsins described here have been optimized for mammalian expression by changing each gene's codon usage to conform to human codon usage distribution (http://www.kazusa.or.jp/codon/cgi-bin/showcodon.cgi?species=9606). The GenBank accession code for the original AR, BR, and GtR3 sequences are DQ074124, M11720, and EG722553.

DNA Constructs

All NpHR variants were produced by PCR amplification of the NpHR-EYFP construct previously published (Zhang et al., 2007b) and cloned in-frame into the AgeI and EcoRI restriction sites of a lentivirus carrying the CaMKIIa or Synapsin-1 promoters according to standard molecular biology protocols. A similar strategy was used for BR and AR. GtR3 was identified through genomic searches. All opsins described here have been optimized for mammalian expression by changing each gene's codon usage to conform to human codon usage distribution (http://www.kazusa.or.jp/codon/cgi-bin/showcodon.cgi?species=9606), and the optimized sequence was custom synthesized (DNA2.0, Inc., Menlo Park, Calif.). The GenBank accession codes for the original AR, BR, and GtR3 sequences are DQ074124, M11720, and EG722553. pAAV-EF1a-mCherry-IRES-WGA-Cre vector was constructed using standard molecular biology protocols. Codons for the WGA and Cre genes were optimized for expression in mammalian cells. The genes were synthesized by DNA2.0 (Menlo Park, Calif.). Cre was fused in-frame to the C-term of WGA, which in turn was fused to IRES. The mCherry-IRES-WGA-Cre bicistronic expression cassette was designed using the EMCV IRES sequence. The pAAV-EF1a plasmid backbone is the same as described previously (Sohal et al., 2009; Tsai et al., 2009). pAAV-hSyn-eNpHR3.0-EFYP-P2A-ChR2H134R-mCherry was constructed with a 120-mer primer (5'caagttctgctacgagaacgaggtgggctccggagccacgaacttctctctgttaaa gcaag-
cagg agacgtggaagaaaaccccggtcccatggactatggcggcgctttgtct-
gccg 3' (SEQ ID NO:18)) that contained the p2A region with
the ER export sequence at the 5' end and 20 bases of the start
of hChR2 at the 3' end. First, the ChR2(H134R)-mCherry
fragment was amplified using the 120-mer as the forward
primer and 5'-atatcgaattctcattacttgtacagctcgt-3' (SEQ ID
NO:19) as the reverse primer. Second, this amplified product
was used as a reverse primer along with the forward primer
5'-ccggatccccgggtaccggtaggccaccatgacagagaccctgcct-3'
(SEQ ID NO:20) to fuse eNpHR 3.0-EYFP to ChR2
(H134R)-mCherry with the p2A region interposed. The 3.4
Kb fragment was then purified and cloned into the BamHI and
EcoRI sites of the pAAV-hSyn vector. All constructs were
fully sequenced for accuracy of cloning; updated maps are
available online at http://www(dot)optogenetics(dot)org, the
contents of which are hereby incorporated by reference in
their entirety.

Lentivirus Preparation and Titering

Lentiviruses for cultured neuron infection and for in vivo
injection were produced as previously described (Zhang et
al., 2007b). Viral titering was performed in HEK293 cells that
were grown in 24-well plates and inoculated with 5-fold serial
dilutions in the presence of polybrene (8 μg/ml). After 4 days,
cultures were resuspended in PBS and sorted for EYFP fluo-
rescence on a FACScan flow cytometer (collecting 20,000
events per sample) followed by analysis using FlowJo soft-
ware (Ashland, Oreg.). The titer of the virus was determined
as follows: [(% of infected cells)×(total number of cells in
well)×(dilution factor)]/(volume of inoculum added to cells)
=infectious units/ml. The titer of viruses for culture infection
was $10^5$ i.u./ml. The titer of concentrated virus for in vivo
injection was $10^{10}$ i.u./ml.

Hippocampal Cultures

Primary cultured hippocampal neurons were prepared
from P0 Spague-Dawley rat pups. The CA1 and CA3 regions
were isolated, digested with 0.4 mg/mL papain (Worthington,
Lakewood, N.J.), and plated onto glass coverslips precoated
with 1:30 Matrigel (Beckton Dickinson Labware, Bedford,
Mass.) at a density of 65,000/cm². Cultures were maintained
in a 5% $CO_2$ humid incubator with Neurobasal-A medium
(Invitrogen Carlsbad, Calif.) containing 1.25% FBS (Hy-
clone, Logan, Utah), 4% B-27 supplement (GIBCO, Grand
Island, N.Y.), 2 mM Glutamax (GIBCO), and FUDR (2
mg/ml, Sigma, St. Louis, Mo.).

Calcium Phosphate Transfection 6-10 div hippocampal neurons were grown at 65,000 cells/
well in a 24-well plate. DNA/CaC $CI_2$ mix for each well:
1.5-3 μg DNA (QIAGEN endotoxin-free preparation)+1.875
μl 2M CaC $CI_2$ (final $Ca^{2+}$ concentration 250 mM) in 15 μl
total $H_2O$. To DNA/$CaCI_2$ was added 15 μl of 2×HEPES-
buffered saline (pH 7.05), and the final volume was mixed
well by pipetting. After 20 min at RT, the 30 μl DNA/$CaCI_2$/
HBS mixture was dropped into each well (from which the
growth medium had been temporarily removed and replaced
with 400 μl warm MEM) and transfection allowed to proceed
at 37 C for 45-60 min. Each well was then washed with 3×1
mL warm MEM and the growth medium replaced. Opsin
expression was generally observed within 20-24 hr.

Electrophysiology

Hippocampal cultures grown on coverslips were trans-
duced at 4 div with titer-matched viruses for all constructs
(final dilution $10^4$ i.u./ml in neuronal growth medium) and
allowed to express for one week. Whole-cell patch clamp
recordings were performed as previously described (intracel-
lular solution: 129 mM K-gluconate, 10 mM HEPES, 10 mM
KCl, 4 mM MgATP, 0.3 mM $Na_3GTP$, titrated to pH 7.2;
extracellular Tyrode: 125 mM NaCl, 2 mM KCl, 3 mM
CaCl2, 1 mM $MgCl_2$, 30 mM glucose, and 25 mM HEPES,
titrated to pH 7.3). For voltage clamp recordings cells were
held at −70 mV. Light in the visible range was delivered from
a 300 W DG-4 lamp (Sutter Instruments, Novato, Calif.)
through filters of different wavelength selectivity (Semrock,
Rochester, N.Y.) and a Leica 40×/0.8 NA water objective.
Filters, except for power spectra, (given here as wavelength in
nm/bandwidth in nm/output power in mW/mm²) were: 406/
15/3; 472/30/18.5; 560/14/7; 589/15/7.5; 593/40/15.5; 630/
20/3.5. Far-red and near-infrared light delivery: light (7
mW/mm2) for 660 nm inhibition was delivered using a light
emitting diode and a 40×/0.8 NA water objective. Light (7
mW/mm²) for 680 nm inhibition was delivered using the
X-Cite 120 W halogen light source through a 680±13 nm
filter and a 40×/0.8 NA water objective. Light delivery for
eNPAC, ChR2(H134R), and eNpHR3.0 power spectra was
delivered from a 300 W DG-4 lamp fitted with a Lambda 10-3
filter wheel (Sutter Instruments) with a 10-position wheel for
25-mm filters of different wavelengths and a 40×/0.8 NA
water objective. Filters (given here as wavelength in
nm/bandwidth in nm/output power in mW/mm²) were: 387/
10/3.5; 406/15/3.5; 427/10/4.0; 445/20/4.0; 470/22/4.0; 494/
20/4.5; 520/15/4.5; 542/27/5.0; 560/20/5.0; 590/20/3.5; 630/
20/3.5. For FIGS. 1, 3A-3D, and 4 and FIG. S2 (see, Table 5
below), confocal images and whole-cell patch clamp data are
from cultured hippocampal neurons either transfected (con-
focal data) or transduced (patch data) with lentiviral NpHR,
BR, GtR3 and AR-based constructs, and allowed to express
for one week. Expression was driven by the human Synapsin
I promoter and visualized by fusion to EYFP.

Table 5 shows additional trafficking-enhanced tools for
blue inhibition, and a new opsin sequence: *G. theta* rhodop-
sin-3 or GtR3.

TABLE 5

```
ChR2  MDYGGALSAVGRELLFVTNPVVVNGSVLVPEDQCYCAGWIESRGTNGAQTASNVLQWLAA  60

Gtr3  ------------------------------EGAKLDVHGCKTVDMASSFGKALLEFVF  60
                                                        ━━TM1━━

ChR2  GFSILLLMFYAYQTWKSTCGWEEIYVCAIEMVKVILEFFFEFKNPSMLYLATGHRVQQWLR  120

GtR3  IVFACITLLLGINAAKSKAASRVLFPATFVTGIASIAYFSMASGGGWVIAPDCRQLFVAR  120
      ━━━━━━━TM2━━━━━━━
```

TABLE 5-continued

```
ChR2  YAEWLLTCPVILIHLSNLTGLSNDYSRRTMGLLVSDIGTIVWGATSAMATGYVKVIFFCL    180

GtR3  YLDWLITTPLLLIDLGLVAGVS---RWDIMALCLSDVLMIATGAFGSLTVGNVKWVWWFF    177
            ━━━TM3━━━━                 ━━━━━TM4━━━━

ChR2  GLCYGANTFFHAAKAYIEGYHTVPKGRCRQVVTGMAWLFFVSWGMFPILFILGPEGFGVL    240

GtR3  GMCWFLHIIFALGKSWAEAAKAK-GGDSASVYSKIAGITVITWFCYPVVWVFA-EGFGNF    235
         ━━━━TM5━━━━             ━━━━━━TM5━━━━

ChR2  SVYGSTVGHTIIDLMSKNCWGLLGHYLRVLIHEHILIHGDIRKTTKLNIGGTEIEVETLV    300

GtR3  SVTFEVLIYGVLDVISKAVFGLILMSGAATGYESI--------------------------    270
           ━━━━TM7━━━━

ChR2  EDKEAEAGAVP  310    (SEQ ID NO: 9)
GtR3  -----------         (SEQ ID NO: 8)
```

New opsin sequence: *G. theta* rhodopsin-3 or GtR3. The EST sequence included all seven transmembrane halices; the 5' amino acid sequence was provided from ChR2 (transmembrane motifs: bars; conserved residues: highlighted; truncation site for peptide: *; signal peptide provided from ChR2: gray.

Immunohistochemistry

Primary hippocampal cultures were infected at 4 div with titer matched virus (final dilution $10^4$ i.u./ml in neuronal growth medium). At 14 div cultures were fixed for 30 min with ice-cold 4% paraformaldehyde and then permeabilized for 30 min with 0.4% saponin in 2% normal donkey serum (NDS). Primary antibody incubations were performed overnight at 4° C. using a monoclonal marker of endoplasmic reticulum recognizing endogenous ER-resident proteins containing the KDEL (SEQ ID NO:13) retention signal (KDEL (SEQ ID NO:13) 1:200, Abeam, Cambridge, Mass.). Cy3-conjugated secondary antibodies (Jackson Laboratories, West Grove, Pa.) were applied in 2% NDS for 1 hr at room temperature. Images were obtained on a Leica confocal microscope using a 63×/1.4 NA oil objective.

Stereotactic Injection into the Rodent Brain

Adult mice and Long-Evans rats were housed according to the approved protocols at Stanford. All surgeries were performed under aseptic conditions. The animals were anesthetized with intraperitoneal injections of a ketamine (80 mg/kg)/xylazine (15-20 mg/kg) cocktail (Sigma). The head was placed in a stereotactic apparatus (Kopf Instruments, Tujunga, Calif.; Olympus stereomicroscope). Ophthalmic ointment was applied to prevent eye drying. A midline scalp incision was made and a small craniotomy was performed using a drill mounted on the stereotactic apparatus (Fine Science Tools, Foster City, Calif.). The virus was delivered using a 10 µl syringe and a thin 34 gauge metal needle; the injection volume and flow rate (1 µl at 0.1 $CI_2$ l/min) was controlled with an injection pump from World Precision Instruments (Sarasota, Fla.). After injection the needle was left in place for 5 additional minutes and then slowly withdrawn. The skin was glued back with Vetbond tissue adhesive. The animal was kept on a heating pad until it recovered from anesthesia. Buprenorphine (0.03 mg/kg) was given subcutaneously following the surgical procedure to minimize discomfort. For the experiment in FIG. 2A, to cover a large area in dorsal CA1, 1 µl of concentrated lentivirus ($10^{10}$ i.u./ml) carrying eNpHR3.1 (a shorter form of eNpHR3.0 with the N-terminal signal peptide, the first 17 amino acids of original NpHR, removed) under the CaMKIIα promoter was microinjected into 2 sites in each hippocampus (site one: anteroposterior −1.5 mm from bregma; lateral, ±1 mm; ventral, 1.5 mm; site two: AP, −2.5 mm from bregma; lateral, ±2 mm; ventral, 1.5 mm). For FIGS. 2D and 2E, two different adeno-associated viruses (AAVs) (virus titer $2×10^{12}$ g.c./mL), were stereotactically injected during the same surgery with an injection speed of 0.15 ul/min High-titer ($2×10^{12}$ g.c./mL) AAV was produced by the UNC Vector Core. For FIG. 2D, double-floxed cre-dependent AAV5 carrying eNpHR3.0-EYFP (AAV5-Ef1a-DIO-eNpHR3.0-EYFP) was injected into M1, and AAV2-Ef1α-mCherry-IRESWGA-Cre was injected into 51 of adult Long-Evans rats. 1 µl of virus was delivered at five different sites defined by the following coordinates: M1 injection I: AP, +1 mm from bregma; lateral, 1.5 mm; ventral, 2 mm; M1 injection II: AP, +2 mm; lateral, 1.5 mm; ventral, 2 mm; 51 injection I: AP, −0.3 mm; lateral, 3.4 mm; ventral, 2 mm; S1 injection II: AP, −1.3 mm; lateral, 3 mm; ventral, 2 mm; S1 injection III: AP, −2.12 mm; lateral, 3 mm; ventral, 2 mm. For FIG. 2E, 1 µl of virus was injected bilaterally into the dentate gyms (DG) of adult BL6 mice. AAV8-EF1a-DIO-ChR2-EYFP was injected in the right DG and of AAV2-EF1a-mCherry-IRES-WGA-Cre was injected in the left DG with the following coordinates: AP, −2.1 from bregma; lateral, ±1.05 mm; ventral, 2.1 mm.

In Vivo Optrode Recordings

To validate opsin functionality in the WGA-Cre system simultaneous optical stimulation and electrical recording in living rodents was conducted as described previously (Gradinaru et al., 2007) using an optrode composed of an extracellular tungsten electrode (1 MΩ, ~125 µm) attached to an optical fiber (~200 µm) with the tip of the electrode deeper (~0.4 mm) than the tip of the fiber to ensure illumination of the recorded neurons. The optical fiber was coupled to a 473 nm (for ChR2) or 560 nm (for eNpHR3.0) laser diode (10 mW fiber output) from CrystaLaser. Optrode recordings were conducted in rodents anesthetized with 1.5% isoflurane and the optrode was placed through small craniotomies created above target regions. pClamp 10 and a Digidata 1322A board were used to both collect data and generate light pulses through the fiber. The recorded signal was band pass filtered at 300 Hz low/5 kHz high (1800 Microelectrode AC Amplifier). For precise placement of the fiber/electrode pair, stereotactic instrumentation was used.

Tissue Slice Preparation

For preparation of brain slices, mice or rats were sacrificed 4 to 5 weeks after viral injection. Rodents were perfused with 20 ml of ice-cold PBS, followed by 20 ml of 4% paraformaldehyde. The brains were then fixed overnight in 4% paraformaldehyde, and transferred to 30% sucrose solution for 2 days. Brains were frozen and coronal slices (40 μm) were prepared using a Leica SM2000R cryostat, and preserved in 4° C. in cryoprotectant (25% glycerol, 30% ethylene glycol, in PBS). Slices (DAPI stain 1:50,000) were mounted with PVA-DABCO on microscope slides, and single confocal optical sections (e.g., through dorsal CA1 region, ~1-2.5 mm posterior to bregma or the dorsal subiculum, 2.7-3 mm posterior to bregma) were acquired using a 10× air and 40×/1.4 NA oil objectives on a Leica confocal microscope.

For further details and discussion of the above-noted embodiments, reference can be made to "Molecular and Cellular Approaches for Diversifying and Extending Optogenetics" by Viviana Gradinaru et al., Cell 141, 154-165, Apr. 2, 2010, which is fully incorporated herein by reference.

REFERENCES

Adamantidis, A. R., Zhang, F., Aravanis, A. M., Deisseroth, K., and de Lecea, L. (2007). Neural substrates of awakening probed with optogenetic control of hypocretin neurons. Nature 450, 420-424.

Airan, R. D., Thompson, K. R., Fenno, L. E., Bernstein, H., and Deisseroth, K. (2009). Temporally precise in vivo control of intracellular signalling. Nature 458, 1025-1029.

Aravanis, A. M., Wang, L. P., Zhang, F., Meltzer, L. A., Mogri, M. Z., Schneider, M. B., and Deisseroth, K. (2007). An optical neural interface: in vivo control of rodent motor cortex with integrated fiberoptic and optogenetic technology. J. Neural Eng. 4, S143-S156.

Arenkiel, B. R., Peca, J., Davison, I. G., Feliciano, C., Deisseroth, K., Augustine, G. J., Ehlers, M. D., and Feng, G. (2007). In vivo light-induced activation of neural circuitry in transgenic mice expressing channelrhodopsin-2. Neuron 54, 205-218.

Arrenberg, A. B., Del Bene, F., and Baier, H. (2009). Optical control of zebrafish behavior with halorhodopsin. Proc. Natl. Acad. Sci. USA 106, 17968-17973.

Berndt, A., Yizhar, O., Gunaydin, L. A., Hegemann, P., and Deisseroth, K. (2009). Bi-stable neural state switches. Nat. Neurosci. 12, 229-234. Bi, G. Q., and Poo, M. M. (1998). Synaptic modifications in cultured hippocampal neurons: dependence on spike timing, synaptic strength, and postsynaptic cell type. J. Neurosci. 18, 10464-10472.

Bi, A., Cui, J., Ma, Y. P., Olshevskaya, E., Pu, M., Dizhoor, A. M., and Pan, Z. H. (2006). Ectopic expression of a microbial-type rhodopsin restores visual responses in mice with photoreceptor degeneration. Neuron 50, 23-33.

Boyden, E. S., Zhang, F., Bamberg, E., Nagel, G., and Deisseroth, K. (2005). Millisecond-timescale, genetically targeted optical control of neural activity. Nat. Neurosci. 8, 1263-1268.

Cardin, J. A., Carlén, M., Meletis, K., Knoblich, U., Zhang, F., Deisseroth, K., Tsai, L. H., and Moore, C. I. (2009). Driving fast-spiking cells induces gamma rhythm and controls sensory responses. Nature 459, 663-667.

Cardin, J. A., Carlén, M., Meletis, K., Knoblich, U., Zhang, F., Deisseroth, K., Tsai, L. H., and Moore, C. I. (2010). Targeted optogenetic stimulation and recording of neurons in vivo using cell-type-specific expression of Channelrhodopsin-2. Nat. Protoc. 5, 247-254.

Chow, B. Y., Han, X., Dobry, A. S., Qian, X., Chuong, A. S., Li, M., Henninger, M. A., Belfort, G. M., Lin, Y., Monahan, P. E., and Boyden, E. S. (2010) High-performance genetically targetable optical neural silencing by lightdriven proton pumps. Nature 463, 98-102.

Colechio, E. M., and Alloway, K. D. (2009). Differential topography of the bilateral cortical projections to the whisker and forepaw regions in rat motor cortex. Brain Struct. Funct. 213, 423-439.

Deisseroth, K., Feng, G., Majewska, A. K., Miesenböck, G., Ting, A., and Schnitzer, M. J. (2006). Next-generation optical technologies for illuminating genetically targeted brain circuits. J. Neurosci. 26, 10380-10386.

Douglass, A. D., Kraves, S., Deisseroth, K., Schier, A. F., and Engert, F. (2008). Escape behavior elicited by single, channelrhodopsin-2-evoked spikes in zebrafish somatosensory neurons. Curr. Biol. 18, 1133-1137.

Fleischmann, A., Shykind, B. M., Sosulski, D. L., Franks, K. M., Glinka, M. E., Mei, D. F., Sun, Y., Kirkland, J., Mendelsohn, M., Albers, M. W., and Axel, R. (2008). Mice with a "monoclonal nose": perturbations in an olfactory map impair odor discrimination. Neuron 60, 1068-1081.

Freund, T. F., and Buzsáki, G. (1996). Interneurons of the hippocampus. Hippocampus 6, 347-470.

Gradinaru, V., Thompson, K. R., Zhang, F., Mogri, M., Kay, K., Schneider, M. B., and Deisseroth, K. (2007). Targeting and readout strategies for fast optical neural control in vitro and in vivo. J. Neurosci. 27, 14231-14238.

Gradinaru, V., Thompson, K. R., and Deisseroth, K. (2008). eNpHR: a Natronomonas halorhodopsin enhanced for optogenetic applications. Brain Cell Biol. 36, 129-139.

Gradinaru, V., Mogri, M., Thompson, K. R., Henderson, J. M., and Deisseroth, K. (2009). Optical deconstruction of parkinsonian neural circuitry. Science 324, 354-359.

Gunaydin, L. A., Yizhar, O., Berndt, A., Sohal, V. S., Deisseroth, K., and Hegemann, P. (2010). Ultrafast optogenetic control. Nat. Neurosci. 13, 387-392.

Hägglund, M., Borgius, L., Dougherty, K. J., and Kiehn, O. (2010). Activation of groups of excitatory neurons in the mammalian spinal cord or hindbrain evokes locomotion. Nat. Neurosci. 13, 246-252.

Han, X., and Boyden, E. S. (2007). Multiple-color optical activation, silencing, and desynchronization of neural activity, with single-spike temporal resolution. PLoS ONE 2, e299.

Han, X., Qian, X., Bernstein, J. G., Zhou, H. H., Franzesi, G. T., Stern, P., Bronson, R. T., Graybiel, A. M., Desimone, R., and Boyden, E. S. (2009a). Millisecond-timescale optical control of neural dynamics in the nonhuman primate brain. Neuron 62, 191-198.

Han, X., Qian, X., Stern, P., Chuong, A. S., and Boyden, E. S. (2009b). Informational lesions: optical perturbation of spike timing and neural synchrony via microbial opsin gene fusions. Front Mol Neurosci 2, 12.

Hofherr, A., Fakler, B., and Mocker, N. (2005). Selective Golgi export of Kir2.1 controls the stoichiometry of functional Kir2.x channel heteromers. J. Cell Sci. 118, 1935-1943.

Huber, D., Petreanu, L., Ghitani, N., Ranade, S., Hromádka, T., Mainen, Z., and Svoboda, K. (2008). Sparse optical microstimulation in barrel cortex drives learned behaviour in freely moving mice. Nature 451, 61-64.

Hwang, R. Y., Zhong, L., Xu, Y., Johnson, T., Zhang, F., Deisseroth, K., and Tracey, W. D. (2007). Nociceptive neurons protect Drosophila larvae from parasitoid wasps. Curr. Biol. 17, 2105-2116.

Ishizuka, T., Kakuda, M., Araki, R., and Yawo, H. (2006). Kinetic evaluation of photosensitivity in genetically engineered neurons expressing green algae light-gated channels. Neurosci. Res. 54, 85-94.

Kalaidzidis, I. V., Kalaidzidis, Y. L., and Kaulen, A. D. (1998). Flash-induced voltage changes in halorhodopsin from *Natronobacterium pharaonis*. FEBS Lett. 427, 59-63.

Kissa, K., Mordelet, E., Soudais, C., Kremer, E. J., Demeneix, B. A., Brûlet, P., and Coen, L. (2002). In vivo neuronal tracing with GFP-TTC gene delivery. Mol. Cell. Neurosci. 20, 627-637.

Lanyi, J. K., and Oesterhelt, D. (1982). Identification of the retinal-binding protein in halorhodopsin. J. Biol. Chem. 257, 2674-2677.

Lein, E. S., Hawrylycz, M. J., Ao, N., Ayres, M., Bensinger, A., Bernard, A., Boe, A. F., Boguski, M. S., Brockway, K. S., Byrnes, E. J., et al. (2007). Genome-wide atlas of gene expression in the adult mouse brain. Nature 445, 168-176.

Lerchner, W., Xiao, C., Nashmi, R., Slimko, E. M., van Trigt, L., Lester, H. A., and Anderson, D. J. (2007). Reversible silencing of neuronal excitability in behaving mice by a genetically targeted, ivermectin-gated Cl− channel. Neuron 54, 35-49.

Levskaya, A., Weiner, O. D., Lim, W. A., and Voigt, C. A. (2009). Spatiotemporal control of cell signalling using a light-switchable protein interaction. Nature 461, 997-1001.

Lewis, T. L., Jr., Mao, T., Svoboda, K., and Arnold, D. B. (2009). Myosindependent targeting of transmembrane proteins to neuronal dendrites. Nat. Neurosci. 12, 568-576.

Li, X., Gutierrez, D. V., Hanson, M. G., Han, J., Mark, M. D., Chiel, H., Hegemann, P., Landmesser, L. T., and Herlitze, S. (2005). Fast noninvasive activation and inhibition of neural and network activity by vertebrate rhodopsin and green algae channelrhodopsin. Proc. Natl. Acad. Sci. USA 102, 17816-17821.

Lin, J. Y., Lin, M. Z., Steinbach, P., and Tsien, R. Y. (2009). Characterization of engineered channelrhodopsin variants with improved properties and kinetics. Biophys. J. 96, 1803-1814.

Lozier, R. H., Bogomolni, R. A., and Stoeckenius, W. (1975). Bacteriorhodopsin: a light-driven proton pump in *Halobacterium Halobium*. Biophys. J. 15, 955-962.

Marti, T., Otto, H., Mogi, T., Rösselet, S. J., Heyn, M. P., and Khorana, H. G. (1991). Bacteriorhodopsin mutants containing single substitutions of serine or threonine residues are all active in proton translocation. J. Biol. Chem. 266, 6919-6927.

Maskos, U., Kissa, K., St Cloment, C., and Brûlet, P. (2002). Retrograde trans-synaptic transfer of green fluorescent protein allows the genetic mapping of neuronal circuits in transgenic mice. Proc. Natl. Acad. Sci. USA 99, 10120-10125.

Nagel, G., Szellas, T., Huhn, W., Kateriya, S., Adeishvili, N., Berthold, P., Ollig, D., Hegemann, P., and Bamberg, E. (2003). Channelrhodopsin-2, a directly light-gated cation-selective membrane channel. Proc. Natl. Acad. Sci. USA 100, 13940-13945.

Paterna, J. C., Feldon, J., and Büeler, H. (2004). Transduction profiles of recombinant adeno-associated virus vectors derived from serotypes 2 and 5 in the nigrostriatal system of rats. J. Virol. 78, 6808-6817.

Perreault, M. C., Bernier, A. P., Renaud, J. S., Roux, S., and Glover, J. C. (2006). C fragment of tetanus toxin hybrid proteins evaluated for muscle-specific transsynaptic mapping of spinal motor circuitry in the newborn mouse. Neuroscience 141, 803-816.

Petreanu, L., Huber, D., Sobczyk, A., and Svoboda, K. (2007). Channelrhodopsin-2-assisted circuit mapping of long-range callosal projections. Nat. Neurosci. 10, 663-668.

Petreanu, L., Mao, T., Sternson, S. M., and Svoboda, K. (2009). The subcellular organization of neocortical excitatory connections. Nature 457, 1142-1145.

Ratzliff, A. H., Howard, A. L., Santhakumar, V., Osapay, I., and Soltesz, I. (2004). Rapid deletion of mossy cells does not result in a hyperexcitable dentate gyrus: implications for epileptogenesis. J. Neurosci. 24, 2259-2269.

Ryan, M. D., and Drew, J. (1994). Foot-and-mouth disease virus 2A oligopeptide mediated cleavage of an artificial polyprotein. EMBO J. 13, 928-933.

Sano, H., Nagai, Y., and Yokoi, M. (2007). Inducible expression of retrograde transsynaptic genetic tracer in mice. Genesis 45, 123-128.

Sato, M., Kubo, M., Aizawa, T., Kamo, N., Kikukawa, T., Nitta, K., and Demura, M. (2005). Role of putative anion-binding sites in cytoplasmic and extracellular channels of *Natronomonas pharaonis* halorhodopsin. Biochemistry 44, 4775-4784.

Schröder-Lang, S., Schwärzel, M., Seifert, R., Strünker, T., Kateriya, S., Looser, J., Watanabe, M., Kaupp, U. B., Hegemann, P., and Nagel, G. (2007). Fast manipulation of cellular cAMP level by light in vivo. Nat. Methods 4, 39-42.

Shu, X., Royant, A., Lin, M. Z., Aguilera, T. A., Lev-Ram, V., Steinbach, P. A., and Tsien, R. Y. (2009). Mammalian expression of infrared fluorescent proteins engineered from a bacterial phytochrome. Science 324, 804-807.

Silberberg, G., Wu, C., and Markram, H. (2004). Synaptic dynamics control the timing of neuronal excitation in the activated neocortical microcircuit. J. Physiol. 556, 19-27.

Simon, S. M., and Blobel, G. (1993). Mechanisms of translocation of proteins across membranes. Subcell. Biochem. 21, 1-15.

Sineshchekov, O. A., Govorunova, E. G., Jung, K. H., Zauner, S., Maier, U. G., and Spudich, J. L. (2005). Rhodopsin-mediated photoreception in cryptophyte flagellates. Biophys. J. 89, 4310-4319.

Sohal, V. S., Zhang, F., Yizhar, O., and Deisseroth, K. (2009). Parvalbumin neurons and gamma rhythms enhance cortical circuit performance. Nature 459, 698-702.

Stoeckenius, W., and Bogomolni, R. A. (1982). Bacteriorhodopsin and related pigments of halobacteria. Annu. Rev. Biochem. 51, 587-616.

Sugita, M., and Shiba, Y. (2005). Genetic tracing shows segregation of taste neuronal circuitries for bitter and sweet. Science 309, 781-785.

Tang, W., Ehrlich, I., Wolff, S. B., Michalski, A. M., Wölfl, S., Hasan, M. T., Lüthi, A., and Sprengel, R. (2009). Faithful expression of multiple proteins via 2A-peptide self-processing: a versatile and reliable method for manipulating brain circuits. J. Neurosci. 29, 8621-8629.

Tengholm, A., and Gylfe, E. (2009). Oscillatory control of insulin secretion. Mol. Cell. Endocrinol. 297, 58-72.

Tønnesen, J., Sørensen, A. T., Deisseroth, K., Lundberg, C., and Kokaia, M. (2009). Optogenetic control of epileptiform activity. Proc. Natl. Acad. Sci. USA 106, 12162-12167.

Tsai, H. C., Zhang, F., Adamantidis, A., Stuber, G. D., Bonci, A., de Lecea, L., and Deisseroth, K. (2009). Phasic firing in dopaminergic neurons is sufficient for behavioral conditioning. Science 324, 1080-1084.

Tsunoda, S. P., Ewers, D., Gazzarrini, S., Moroni, A., Gradmann, D., and Hegemann, P. (2006). H+-pumping rhodopsin from the marine alga *Acetabularia*. Biophys. J. 91, 1471-1479.

Wang, H., Peca, J., Matsuzaki, M., Matsuzaki, K., Noguchi, J., Qiu, L., Wang, D., Zhang, F., Boyden, E., Deisseroth, K., et al. (2007). High-speed mapping of synaptic connectivity using photostimulation in Channelrhodopsin-2 transgenic mice. Proc. Natl. Acad. Sci. USA 104, 8143-8148.

Wu, Y. I., Frey, D., Lungu, O. I., Jaehrig, A., Schlichting, I., Kuhlman, B., and Hahn, K. M. (2009). A genetically encoded photoactivatable Rac controls the motility of living cells. Nature 461, 104-108.

Yooseph, S., Sutton, G., Rusch, D. B., Halpern, A. L., Williamson, S. J., Remington, K., Eisen, J. A., Heidelberg, K. B., Manning, G., Li, W., et al. (2007). The Sorcerer II Global Ocean Sampling expedition: expanding the universe of protein families. PLoS Biol. 5, e16.

Yoshimura, Y., Dantzker, J. L., and Callaway, E. M. (2005). Excitatory cortica neurons form fine-scale functional networks. Nature 433, 868-873.

Zhang, Y. P., and Oertner, T. G. (2007). Optical induction of synaptic plasticity using a light-sensitive channel. Nat. Methods 4, 139-141.

Zhang, F., Wang, L. P., Boyden, E. S., and Deisseroth, K. (2006). Channelrhodopsin-2 and optical control of excitable cells. Nat. Methods 3, 785-792.

Zhang, F., Wang, L. P., Brauner, M., Liewald, J. F., Kay, K., Watzke, N., Wood, P. G., Bamberg, E., Nagel, G., Gottschalk, A., and Deisseroth, K. (2007a). Multimodal fast optical interrogation of neural circuitry. Nature 446, 633-639.

Zhang, F., Aravanis, A. M., Adamantidis, A., de Lecea, L., and Deisseroth, K. (2007b). Circuit-breakers: optical technologies for probing neural signals and systems. Nat. Rev. Neurosci. 8, 577-581.

Zhang, F., Prigge, M., Beyrière, F., Tsunoda, S. P., Mattis, J., Yizhar, O., Hegemann, P., and Deisseroth, K. (2008). Red-shifted optogenetic excitation: a tool for fast neural control derived from *Volvox carteri*. Nat. Neurosci. 11, 631-633.

Zhao, S., Cunha, C., Zhang, F., Liu, Q., Gloss, B., Deisseroth, K., Augustine, G. J., and Feng, G. (2008). Improved expression of halorhodopsin for light-induced silencing of neuronal activity. Brain Cell Biol. 36, 141-154.

All references, publications, and patent applications disclosed herein are hereby incorporated by reference in their entirety.

The various embodiments described above are provided by way of illustration only and should not be construed to limit the invention. Based on the above discussion and illustrations, those skilled in the art will readily recognize that various modifications and changes may be made to the present invention without strictly following the exemplary embodiments and applications illustrated and described herein. For instance, such changes may include the use of digital logic or microprocessors to control the emitted light. Such modifications and changes do not depart from the true spirit and scope of the present invention, which is set forth in the following claims. As discussed above, specific applications and background details relative to the present invention are discussed above, in the description below and throughout the references cited herein. The embodiments in the Appendices may be implemented in connection with one or more of the above-described embodiments and implementations, as well as with those shown in the figures and described below. Reference may be made to the Appendices (A, B and C) which were filed in the underlying provisional application and incorporated herein by reference.

---

What is claimed is:

1. A light-activated protein comprising, in order from amino terminus (N-terminus) to carboxyl terminus (C-terminus):
 a) a core amino acid sequence at least 95% identical to the sequence shown in SEQ ID NO:3, SEQ ID NO:1, SEQ ID NO:2, or SEQ ID NO:4;
 b) an endoplasmic reticulum (ER) export signal; and
 c) a membrane trafficking signal.

2. The light-activated protein of claim 1, wherein the ER export signal comprises the amino acid sequence FCEYENEV (SEQ ID NO:12).

3. The light-activated protein of claim 1, wherein the membrane trafficking signal comprises the amino acid sequence KSRITSEGEYIPLDQIDINV (SEQ ID NO:11).

4. The light-activated protein of claim 1, wherein the core amino acid sequence is at least 95% identical to amino acids 25-265 of SEQ ID NO:2.

5. The light-activated protein of claim 1, wherein the core amino acid sequence is at least 95% identical to SEQ ID NO:3.

6. The light-activated protein of claim 1, wherein the core amino acid sequence is at least 95% identical to SEQ ID NO:4.

7. An isolated polynucleotide comprising a nucleotide sequence encoding the light-activated protein of claim 1.

8. The polynucleotide of claim 7, wherein the light-activated protein-encoding nucleotide sequence is operably linked to a promoter.

9. The polynucleotide of claim 7, wherein the promoter is a CaMKIIa promoter.

10. The polynucleotide of claim 7, wherein the promoter is a synapsin I promoter.

11. The polynucleotide of claim 7, wherein the polynucleotide is in an expression vector.

12. The polynucleotide of claim 11, wherein the expression vector is a viral vector.

13. The polynucleotide of claim 12, wherein the viral vector is an adenoassociated virus vector, a retroviral vector, an adenoviral vector, a herpes simplex virus vector, or a lentiviral vector.

* * * * *

SEQUENCE LISTING

```
<160> NUMBER OF SEQ ID NOS: 20

<210> SEQ ID NO 1
<211> LENGTH: 223
<212> TYPE: PRT
<213> ORGANISM: Artificial sequence
<220> FEATURE:
<223> OTHER INFORMATION: Synthetic sequence

<400> SEQUENCE: 1

Ala Ser Ser Phe Gly Lys Ala Leu Leu Glu Phe Val Phe Ile Val Phe
1               5                   10                  15

Ala Cys Ile Thr Leu Leu Leu Gly Ile Asn Ala Ala Lys Ser Lys Ala
            20                  25                  30

Ala Ser Arg Val Leu Phe Pro Ala Thr Phe Val Thr Gly Ile Ala Ser
        35                  40                  45

Ile Ala Tyr Phe Ser Met Ala Ser Gly Gly Gly Trp Val Ile Ala Pro
    50                  55                  60

Asp Cys Arg Gln Leu Phe Val Ala Arg Tyr Leu Asp Trp Leu Ile Thr
65                  70                  75                  80

Thr Pro Leu Leu Leu Ile Asp Leu Gly Leu Val Ala Gly Val Ser Arg
                85                  90                  95

Trp Asp Ile Met Ala Leu Cys Leu Ser Asp Val Leu Met Ile Ala Thr
            100                 105                 110

Gly Ala Phe Gly Ser Leu Thr Val Gly Asn Val Lys Trp Val Trp Trp
        115                 120                 125

Phe Phe Gly Met Cys Trp Phe Leu His Ile Ile Phe Ala Leu Gly Lys
    130                 135                 140

Ser Trp Ala Glu Ala Ala Lys Ala Lys Gly Gly Asp Ser Ala Ser Val
```

```
                  145                 150                 155                 160
            Tyr Ser Lys Ile Ala Gly Ile Thr Val Ile Thr Trp Phe Cys Tyr Pro
                                165                 170                 175

Val Val Trp Val Phe Ala Glu Gly Phe Gly Asn Phe Ser Val Thr Phe
                                180                 185                 190

Glu Val Leu Ile Tyr Gly Val Leu Asp Val Ile Ser Lys Ala Val Phe
                                195                 200                 205

Gly Leu Ile Leu Met Ser Gly Ala Ala Thr Gly Tyr Glu Ser Ile
                                210                 215                 220

<210> SEQ ID NO 2
<211> LENGTH: 365
<212> TYPE: PRT
<213> ORGANISM: Artificial sequence
<220> FEATURE:
<223> OTHER INFORMATION: Synthetic sequence

<400> SEQUENCE: 2

Met Arg Arg Arg Glu Ser Gln Leu Ala Tyr Leu Cys Leu Phe Val Leu
1               5                   10                  15

Ile Ala Gly Trp Ala Pro Arg Leu Thr Glu Ser Ala Pro Asp Leu Ala
                20                  25                  30

Glu Arg Arg Pro Pro Ser Glu Arg Asn Thr Pro Tyr Ala Asn Ile Lys
            35                  40                  45

Lys Val Pro Asn Ile Thr Glu Pro Asn Ala Asn Val Gln Leu Asp Gly
        50                  55                  60

Trp Ala Leu Tyr Gln Asp Phe Tyr Tyr Leu Ala Gly Ser Asp Lys Glu
65                  70                  75                  80

Trp Val Val Gly Pro Ser Asp Gln Cys Tyr Cys Arg Ala Trp Ser Lys
                85                  90                  95

Ser His Gly Thr Asp Arg Glu Gly Glu Ala Ala Val Val Trp Ala Tyr
                100                 105                 110

Ile Val Phe Ala Ile Cys Ile Val Gln Leu Val Tyr Phe Met Phe Ala
                115                 120                 125

Ala Trp Lys Ala Thr Val Gly Trp Glu Glu Val Tyr Val Asn Ile Ile
            130                 135                 140

Glu Leu Val His Ile Ala Leu Val Ile Trp Val Glu Phe Asp Lys Pro
145                 150                 155                 160

Ala Met Leu Tyr Leu Asn Asp Gly Gln Met Val Pro Trp Leu Arg Tyr
                165                 170                 175

Ser Ala Trp Leu Leu Ser Cys Pro Val Ile Leu Ile His Leu Ser Asn
                180                 185                 190

Leu Thr Gly Leu Lys Gly Asp Tyr Ser Lys Arg Thr Met Gly Leu Leu
                195                 200                 205

Val Ser Asp Ile Gly Thr Ile Val Phe Gly Thr Ser Ala Ala Leu Ala
            210                 215                 220

Pro Pro Asn His Val Lys Val Ile Leu Phe Thr Ile Gly Leu Leu Tyr
225                 230                 235                 240

Gly Leu Phe Thr Phe Phe Thr Ala Ala Lys Val Tyr Ile Glu Ala Tyr
                245                 250                 255

His Thr Val Pro Lys Gly Gln Cys Arg Asn Leu Val Arg Ala Met Ala
                260                 265                 270

Trp Thr Tyr Phe Val Ser Trp Ala Met Phe Pro Ile Leu Phe Ile Leu
            275                 280                 285

Gly Arg Glu Gly Phe Gly His Ile Thr Tyr Phe Gly Ser Ser Ile Gly
```

```
                   290                 295                 300
His Phe Ile Leu Glu Ile Phe Ser Lys Asn Leu Trp Ser Leu Gly
305                 310                 315                 320

His Gly Leu Arg Tyr Arg Ile Arg Gln His Ile Ile His Gly Asn
                325                 330                 335

Leu Thr Lys Lys Asn Lys Ile Asn Ile Ala Gly Asp Asn Val Glu Val
                340                 345                 350

Glu Glu Tyr Val Asp Ser Asn Asp Lys Asp Ser Asp Val
            355                 360                 365

<210> SEQ ID NO 3
<211> LENGTH: 291
<212> TYPE: PRT
<213> ORGANISM: Artificial sequence
<220> FEATURE:
<223> OTHER INFORMATION: Synthetic sequence

<400> SEQUENCE: 3

Met Thr Glu Thr Leu Pro Pro Val Thr Glu Ser Ala Val Ala Leu Gln
1               5                   10                  15

Ala Glu Val Thr Gln Arg Glu Leu Phe Glu Phe Val Leu Asn Asp Pro
                20                  25                  30

Leu Leu Ala Ser Ser Leu Tyr Ile Asn Ile Ala Leu Ala Gly Leu Ser
                35                  40                  45

Ile Leu Leu Phe Val Phe Met Thr Arg Gly Leu Asp Asp Pro Arg Ala
            50                  55                  60

Lys Leu Ile Ala Val Ser Thr Ile Leu Val Pro Val Val Ser Ile Ala
65                  70                  75                  80

Ser Tyr Thr Gly Leu Ala Ser Gly Leu Thr Ile Ser Val Leu Glu Met
                85                  90                  95

Pro Ala Gly His Phe Ala Glu Gly Ser Ser Val Met Leu Gly Gly Glu
                100                 105                 110

Glu Val Asp Gly Val Val Thr Met Trp Gly Arg Tyr Leu Thr Trp Ala
            115                 120                 125

Leu Ser Thr Pro Met Ile Leu Leu Ala Leu Gly Leu Leu Ala Gly Ser
130                 135                 140

Asn Ala Thr Lys Leu Phe Thr Ala Ile Thr Phe Asp Ile Ala Met Cys
145                 150                 155                 160

Val Thr Gly Leu Ala Ala Ala Leu Thr Thr Ser Ser His Leu Met Arg
                165                 170                 175

Trp Phe Trp Tyr Ala Ile Ser Cys Ala Cys Phe Leu Val Val Leu Tyr
            180                 185                 190

Ile Leu Leu Val Glu Trp Ala Gln Asp Ala Lys Ala Ala Gly Thr Ala
            195                 200                 205

Asp Met Phe Asn Thr Leu Lys Leu Leu Thr Val Val Met Trp Leu Gly
210                 215                 220

Tyr Pro Ile Val Trp Ala Leu Gly Val Glu Gly Ile Ala Val Leu Pro
225                 230                 235                 240

Val Gly Val Thr Ser Trp Gly Tyr Ser Phe Leu Asp Ile Val Ala Lys
                245                 250                 255

Tyr Ile Phe Ala Phe Leu Leu Leu Asn Tyr Leu Thr Ser Asn Glu Ser
                260                 265                 270

Val Val Ser Gly Ser Ile Leu Asp Val Pro Ser Ala Ser Gly Thr Pro
                275                 280                 285

Ala Asp Asp
```

-continued

290

<210> SEQ ID NO 4
<211> LENGTH: 262
<212> TYPE: PRT
<213> ORGANISM: Artificial sequence
<220> FEATURE:
<223> OTHER INFORMATION: Synthetic sequence

<400> SEQUENCE: 4

Met Leu Glu Leu Leu Pro Thr Ala Val Glu Gly Val Ser Gln Ala Gln
1               5                   10                  15

Ile Thr Gly Arg Pro Glu Trp Ile Trp Leu Ala Leu Gly Thr Ala Leu
            20                  25                  30

Met Gly Leu Gly Thr Leu Tyr Phe Leu Val Lys Gly Met Gly Val Ser
        35                  40                  45

Asp Pro Asp Ala Lys Lys Phe Tyr Ala Ile Thr Thr Leu Val Pro Ala
    50                  55                  60

Ile Ala Phe Thr Met Tyr Leu Ser Met Leu Leu Gly Tyr Gly Leu Thr
65                  70                  75                  80

Met Val Pro Phe Gly Gly Glu Gln Asn Pro Ile Tyr Trp Ala Arg Tyr
                85                  90                  95

Ala Asp Trp Leu Phe Thr Thr Pro Leu Leu Leu Leu Asp Leu Ala Leu
            100                 105                 110

Leu Val Asp Ala Asp Gln Gly Thr Ile Leu Ala Leu Val Gly Ala Asp
        115                 120                 125

Gly Ile Met Ile Gly Thr Gly Leu Val Gly Ala Leu Thr Lys Val Tyr
    130                 135                 140

Ser Tyr Arg Phe Val Trp Trp Ala Ile Ser Thr Ala Ala Met Leu Tyr
145                 150                 155                 160

Ile Leu Tyr Val Leu Phe Phe Gly Phe Thr Ser Lys Ala Glu Ser Met
                165                 170                 175

Arg Pro Glu Val Ala Ser Thr Phe Lys Val Leu Arg Asn Val Thr Val
            180                 185                 190

Val Leu Trp Ser Ala Tyr Pro Val Val Trp Leu Ile Gly Ser Glu Gly
        195                 200                 205

Ala Gly Ile Val Pro Leu Asn Ile Glu Thr Leu Leu Phe Met Val Leu
    210                 215                 220

Asp Val Ser Ala Lys Val Gly Phe Gly Leu Ile Leu Leu Arg Ser Arg
225                 230                 235                 240

Ala Ile Phe Gly Glu Ala Glu Ala Pro Glu Pro Ser Ala Gly Asp Gly
                245                 250                 255

Ala Ala Ala Thr Ser Asp
            260

<210> SEQ ID NO 5
<211> LENGTH: 270
<212> TYPE: PRT
<213> ORGANISM: Artificial sequence
<220> FEATURE:
<223> OTHER INFORMATION: Synthetic sequence

<400> SEQUENCE: 5

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

```
Gln Cys Tyr Cys Ala Gly Trp Ile Glu Ser Arg Gly Thr Asn Gly Ala
             35                  40                  45

Ser Ser Phe Gly Lys Ala Leu Leu Glu Phe Val Phe Ile Val Phe Ala
 50                  55                  60

Cys Ile Thr Leu Leu Leu Gly Ile Asn Ala Ala Lys Ser Lys Ala Ala
 65                  70                  75                  80

Ser Arg Val Leu Phe Pro Ala Thr Phe Val Thr Gly Ile Ala Ser Ile
                 85                  90                  95

Ala Tyr Phe Ser Met Ala Ser Gly Gly Trp Val Ile Ala Pro Asp
                100                 105                 110

Cys Arg Gln Leu Phe Val Ala Arg Tyr Leu Asp Trp Leu Ile Thr Thr
            115                 120                 125

Pro Leu Leu Leu Ile Asp Leu Gly Leu Val Ala Gly Val Ser Arg Trp
        130                 135                 140

Asp Ile Met Ala Leu Cys Leu Ser Asp Val Leu Met Ile Ala Thr Gly
145                 150                 155                 160

Ala Phe Gly Ser Leu Thr Val Gly Asn Val Lys Trp Val Trp Trp Phe
                165                 170                 175

Phe Gly Met Cys Trp Phe Leu His Ile Ile Phe Ala Leu Gly Lys Ser
            180                 185                 190

Trp Ala Glu Ala Ala Lys Ala Lys Gly Gly Asp Ser Ala Ser Val Tyr
        195                 200                 205

Ser Lys Ile Ala Gly Ile Thr Val Ile Thr Trp Phe Cys Tyr Pro Val
210                 215                 220

Val Trp Val Phe Ala Glu Gly Phe Gly Asn Phe Ser Val Thr Phe Glu
225                 230                 235                 240

Val Leu Ile Tyr Gly Val Leu Asp Val Ile Ser Lys Ala Val Phe Gly
                245                 250                 255

Leu Ile Leu Met Ser Gly Ala Ala Thr Gly Tyr Glu Ser Ile
            260                 265                 270

<210> SEQ ID NO 6
<211> LENGTH: 810
<212> TYPE: DNA
<213> ORGANISM: Artificial sequence
<220> FEATURE:
<223> OTHER INFORMATION: Synthetic sequence

<400> SEQUENCE: 6
atggactacg gaggagcact gtctgctgtg ggccgtgaat tactctttgt gaccaatcca      60
gtcgttgtaa atgggagcgt cctggtgccg gaggatcaat gctactgcgc cggttggatt     120
gaaagcagag gcacgaatgg ggcctcatcc ttcggcaagg ccctactgga gtttgtcttc     180
atcgtcttcg cgtgtatcac attactgttg gaattaacg ctgcgaaatc aaaggctgca     240
tctagggtgc tgtttcccgc tactttcgtc actggaatcg caagtatcgc atatttttcc     300
atggcaagcg gcggcgggtg ggtgattgcc cctgactgtc ggcagctctt tgtggcccgc     360
tatctggact ggctcattac tacaccactt ctactcatag atttgggtct ggttgcaggg     420
gtcagtcggt gggatataat ggccctctgc ctgtctgatg tcctgatgat tgctacgggt     480
gctttcggga gcctgacagt gggtaacgtg aagtgggtgt ggtggttctt tggaatgtgt     540
tggtttcttc acataatctt cgcgcttggg aaaagttggg cagaagcagc caaggccaag     600
ggcggcgact tgcttctgt gtactccaaa atcgccggca tcaccgtgat tacatggttc     660
tgttatcccg tggtatgggt cttcgctgag ggcttcggaa acttttccgt aaccttcgaa     720
```

```
gttctcatct atggagtgtt ggatgttatt tcaaaggccg ttttggcct tatactgatg    780 tcagggccg ccaccggata cgagtccatt                                     810
```

<210> SEQ ID NO 7
<211> LENGTH: 1095
<212> TYPE: DNA
<213> ORGANISM: Artificial sequence
<220> FEATURE:
<223> OTHER INFORMATION: Synthetic sequence

<400> SEQUENCE: 7

```
atgcgtagaa gggagtctca gctcgcatac ctttgcctgt tcgttttgat cgctggctgg     60
gccccacgtc tgactgaaag cgcccctgat ctagccgagc ggcggcctcc ctccgagcga    120
aacacccctt acgccaatat taaaaaggtg cccaatataa ctgaacccaa cgccaatgtg    180
caacttgatg ggtgggctct gtaccaggat ttttactacc tggctggttc agataaggaa    240
tgggtcgttg gccctagcga ccagtgttac tgccgagcat ggtctaaatc acacggcacc    300
gacagagagg gcgaggcggc tgtggtgtgg gcgtacatcg tattcgccat ttgtatcgta    360
caactggttt atttcatgtt tgccgcttgg aaggcaacgg tcggatggga ggaagtctac    420
gtgaacatca ttgagctggt gcacattgcc ctggtgattt gggtcgagtt cgataaaccc    480
gccatgctct accttaacga cggtcagatg gttccatggt tgcgctatag tgcatggctc    540 cttttcctgcc cagtcatcct aattcacctg agcaacttaa cagggctaaa ggggggactat    600 agtaagagaa ccatgggggct tttggtctct gacatcggaa ccatagtgtt tggtacaagc    660
gccgcactcg ctccgccaaa ccatgtcaaa gtcatcctta ttacaattgg gttgctgtat    720
ggactcttca cttttttcac ggcagcgaag gtatatattg aggcctacca caccgttcca    780
aaaggccaat gtagaaacct cgtgagggct atggcctgga cttatttcgt aagttgggcg    840
atgttcccca tcctgtttat cctgggaaga gagggttttg gccatattac atattttggc    900
tcatccatcg gacacttcat actggagata ttttcaaaaa atctgtggag tctactgggc    960
cacggattac ggtatcgcat aaggcagcat atcatcattc atggcaattt gacaaagaag   1020
aataagatta tatcgcagg ggacaacgtc gaagtggaag agtacgtgga ttctaacgac   1080
aaggacagcg acgtt                                                    1095
```

<210> SEQ ID NO 8
<211> LENGTH: 238
<212> TYPE: PRT
<213> ORGANISM: Artificial sequence
<220> FEATURE:
<223> OTHER INFORMATION: Synthetic sequence

<400> SEQUENCE: 8

```
Glu Gly Ala Lys Leu Asp Val His Gly Cys Lys Thr Val Asp Met Ala
1               5                   10                  15

Ser Ser Phe Gly Lys Ala Leu Leu Glu Phe Val Phe Ile Val Phe Ala
            20                  25                  30

Cys Ile Thr Leu Leu Gly Ile Asn Ala Ala Lys Ser Lys Ala Ala
        35                  40                  45

Ser Arg Val Leu Phe Pro Ala Thr Phe Val Thr Gly Ile Ala Ser Ile
    50                  55                  60

Ala Tyr Phe Ser Met Ala Ser Gly Gly Gly Trp Val Ile Ala Pro Asp
65                  70                  75                  80

Cys Arg Gln Leu Phe Val Ala Arg Tyr Leu Asp Trp Leu Ile Thr Thr
                85                  90                  95
```

```
Pro Leu Leu Leu Ile Asp Leu Gly Leu Val Ala Gly Val Ser Arg Trp
            100                 105                 110

Asp Ile Met Ala Leu Cys Leu Ser Asp Val Leu Met Ile Ala Thr Gly
        115                 120                 125

Ala Phe Gly Ser Leu Thr Val Gly Asn Val Lys Trp Val Trp Trp Phe
130                 135                 140

Phe Gly Met Cys Trp Phe Leu His Ile Ile Phe Ala Leu Gly Lys Ser
145                 150                 155                 160

Trp Ala Glu Ala Lys Ala Lys Gly Gly Asp Ser Ala Ser Val Tyr
                165                 170                 175

Ser Lys Ile Ala Gly Ile Thr Val Ile Thr Trp Phe Cys Tyr Pro Val
            180                 185                 190

Val Trp Val Phe Ala Glu Gly Phe Gly Asn Phe Ser Val Thr Phe Glu
        195                 200                 205

Val Leu Ile Tyr Gly Val Leu Asp Val Ile Ser Lys Ala Val Phe Gly
    210                 215                 220

Leu Ile Leu Met Ser Gly Ala Ala Thr Gly Tyr Glu Ser Ile
225                 230                 235

<210> SEQ ID NO 9
<211> LENGTH: 310
<212> TYPE: PRT
<213> ORGANISM: Artificial sequence
<220> FEATURE:
<223> OTHER INFORMATION: Synthetic sequence

<400> SEQUENCE: 9

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Lys Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
50                  55                  60

Leu Leu Leu Met Phe Tyr Ala Tyr Gln Thr Trp Lys Ser Thr Cys Gly
65                  70                  75                  80

Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
210                 215                 220
```

```
Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
            245                 250                 255

Lys Asn Cys Trp Gly Leu Leu Gly His Tyr Leu Arg Val Leu Ile His
        260                 265                 270

Glu His Ile Leu Ile His Gly Asp Ile Arg Lys Thr Thr Lys Leu Asn
            275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 10
<211> LENGTH: 47
<212> TYPE: PRT
<213> ORGANISM: Artificial sequence
<220> FEATURE:
<223> OTHER INFORMATION: Synthetic sequence

<400> SEQUENCE: 10

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Gly Ser Arg Gly Thr Asn Gly
        35                  40                  45

<210> SEQ ID NO 11
<211> LENGTH: 20
<212> TYPE: PRT
<213> ORGANISM: Artificial sequence
<220> FEATURE:
<223> OTHER INFORMATION: Synthetic sequence

<400> SEQUENCE: 11

Lys Ser Arg Ile Thr Ser Glu Gly Glu Tyr Ile Pro Leu Asp Gln Ile
1               5                   10                  15

Asp Ile Asn Val
            20

<210> SEQ ID NO 12
<211> LENGTH: 7
<212> TYPE: PRT
<213> ORGANISM: Artificial sequence
<220> FEATURE:
<223> OTHER INFORMATION: Synthetic sequence

<400> SEQUENCE: 12

Phe Cys Tyr Glu Asn Glu Val
1               5

<210> SEQ ID NO 13
<211> LENGTH: 4
<212> TYPE: PRT
<213> ORGANISM: Artificial sequence
<220> FEATURE:
<223> OTHER INFORMATION: Synthetic sequence

<400> SEQUENCE: 13

Lys Asp Glu Leu
1
```

```
<210> SEQ ID NO 14
<211> LENGTH: 6
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any naturally occurring amino acid

<400> SEQUENCE: 14

Phe Xaa Tyr Glu Asn Glu
1               5

<210> SEQ ID NO 15
<211> LENGTH: 17
<212> TYPE: PRT
<213> ORGANISM: artificial sequence
<220> FEATURE:
<223> OTHER INFORMATION: synthetic peptide

<400> SEQUENCE: 15

Met Arg Gly Thr Pro Leu Leu Leu Trp Ser Leu Phe Ser Leu Leu Gln
1               5                   10                  15

Asp

<210> SEQ ID NO 16
<211> LENGTH: 14
<212> TYPE: PRT
<213> ORGANISM: artificial sequence
<220> FEATURE:
<223> OTHER INFORMATION: synthetic peptide

<400> SEQUENCE: 16

Asp Tyr Gly Gly Ala Leu Ser Ala Val Gly Arg Glu Leu Leu
1               5                   10

<210> SEQ ID NO 17
<211> LENGTH: 18
<212> TYPE: PRT
<213> ORGANISM: artificial sequence
<220> FEATURE:
<223> OTHER INFORMATION: synthetic peptide

<400> SEQUENCE: 17

Arg Ser Arg Phe Val Lys Lys Asp Gly His Cys Asn Val Gln Phe Ile
1               5                   10                  15

Asn Val

<210> SEQ ID NO 18
<211> LENGTH: 119
<212> TYPE: DNA
<213> ORGANISM: Artificial sequence
<220> FEATURE:
<223> OTHER INFORMATION: Synthetic primer

<400> SEQUENCE: 18
caagttctgc tacgagaacg aggtgggctc cggagccacg aacttctctc tgttaaagca      60
agcaggagac gtggaagaaa accccggtcc catggactat ggcggcgctt tgtctgccg     119

<210> SEQ ID NO 19
<211> LENGTH: 31
<212> TYPE: DNA
```

```
<213> ORGANISM: Artificial sequence
<220> FEATURE:
<223> OTHER INFORMATION: Synthetic primer

<400> SEQUENCE: 19
atatcgaatt ctcattactt gtacagctcg t                              31

<210> SEQ ID NO 20
<211> LENGTH: 46
<212> TYPE: DNA
<213> ORGANISM: Artificial sequence
<220> FEATURE:
<223> OTHER INFORMATION: Synthetic primer

<400> SEQUENCE: 20
ccggatcccc gggtaccggt aggccaccat gacagagacc ctgcct              46
```